United States Patent
Lellouche et al.

(10) Patent No.: US 12,391,944 B2
(45) Date of Patent: Aug. 19, 2025

(54) MAGNETIC INORGANIC IRON-BASED NANOPARTICLES

(71) Applicant: Bar-Ilan University, Ramat Gan (IL)

(72) Inventors: Jean-Paul Lellouche, Ashdod (IL); Shulamit Michaeli, Kiryat Ono (IL); Limor Liron Israel, Modiin (IL); Emmanuel Lellouche, Ramat Gan (IL); Yekaterina Kapilov-Buchman, Ramat Gan (IL)

(73) Assignee: Bar-Ilan University, Ramat Gan (IL)

( * ) Notice: Subject to any disclaimer, the term of this patent is extended or adjusted under 35 U.S.C. 154(b) by 3 days.

(21) Appl. No.: 18/090,884

(22) Filed: Dec. 29, 2022

(65) Prior Publication Data

US 2023/0287421 A1    Sep. 14, 2023

Related U.S. Application Data

(62) Division of application No. 14/778,060, filed as application No. PCT/IL2014/050064 on Jan. 19, 2014, now abandoned.

(60) Provisional application No. 61/802,750, filed on Mar. 18, 2013.

(51) Int. Cl.

| | | |
|---|---|---|
| C12N 15/113 | (2010.01) | |
| A61K 9/50 | (2006.01) | |
| A61K 9/51 | (2006.01) | |
| A61K 31/7088 | (2006.01) | |
| A61K 33/26 | (2006.01) | |
| A61K 47/52 | (2017.01) | |
| A61K 47/59 | (2017.01) | |
| A61K 47/69 | (2017.01) | |
| B01J 13/02 | (2006.01) | |
| B82Y 5/00 | (2011.01) | |
| B82Y 40/00 | (2011.01) | |
| C01G 49/06 | (2006.01) | |
| C12N 15/11 | (2006.01) | |
| C12N 15/87 | (2006.01) | |
| B82Y 15/00 | (2011.01) | |
| B82Y 30/00 | (2011.01) | |

(52) U.S. Cl.
CPC .......... *C12N 15/113* (2013.01); *A61K 9/5115* (2013.01); *A61K 31/7088* (2013.01); *A61K 33/26* (2013.01); *A61K 47/52* (2017.08); *A61K 47/59* (2017.08); *A61K 47/6923* (2017.08); *A61K 47/6929* (2017.08); *B01J 13/02* (2013.01); *B82Y 5/00* (2013.01); *C01G 49/06* (2013.01); *C12N 15/111* (2013.01); *A61K 9/5094* (2013.01); *B82Y 15/00* (2013.01); *B82Y 30/00* (2013.01); *B82Y 40/00* (2013.01); *C01P 2002/54* (2013.01); *C01P 2002/72* (2013.01); *C01P 2002/82* (2013.01); *C01P 2002/85* (2013.01); *C01P 2002/88* (2013.01); *C01P 2004/04* (2013.01); *C12N 15/87* (2013.01); *C12N 2310/113* (2013.01); *C12N 2310/14* (2013.01); *C12N 2310/141* (2013.01); *C12N 2310/351* (2013.01); *C12N 2320/32* (2013.01)

(58) Field of Classification Search
CPC .............. C12N 15/113; C12N 2310/14; C12N 2310/141; C12N 2310/351; C12N 2320/32; A61K 9/5115; A61K 31/7088; A61K 33/26; A61K 47/52
See application file for complete search history.

(56) References Cited

U.S. PATENT DOCUMENTS

| | | | | |
|---|---|---|---|---|
| 4,554,088 A | ‡ | 11/1985 | Whitehead | B01J 20/3433 427/127 |
| 7,402,262 B2 | ‡ | 7/2008 | Lellouche | B82Y 30/00 252/500 |
| 7,402,263 B2 | | 7/2008 | Lellouche | |

FOREIGN PATENT DOCUMENTS

| | | | | |
|---|---|---|---|---|
| WO | 2010093909 A1 | 2/2010 | | |
| WO | PCT-WO2010093909 A1 ‡ | 8/2010 | | B01J 13/02 |
| WO | WO-2010139603 A1 ‡ | 12/2010 | | C01B 33/18 |

OTHER PUBLICATIONS

Jaeyun Kim, Ji Eun Lee, Soo Hyeon Lee, Jung Ho Yu, Jung Hee Lee, Tae Gwan Park and Taeghwan Hyeon, "Designed Fabrication of a Multifunctional Polymer Nanomedical Platform for Simultaneous Cancer-Targeted Imaging and Magnetically Guided Drug Delivery", Advanced Materials, 2008, 20, 478-483. (Year: 2008).*
McKay et al., "Advances in multivariate analysis in pharmaceutical process development", Current Opinion in Drug Discovery & Development 2003, 966-977.‡
Forge et al., "Optimization of the Synthesis of Superparamagnetic Contrast Agents by the Design of Experiments Method", J. Phys. Chem. C 2008, 112, 19178-19185.‡
Cawse, "Experimental Strategies for Combinatorial and High-Throughput Materials Development", Acc. Chem.Res. 2001, 34, 213-221.‡

(Continued)

*Primary Examiner* — Mina Haghighatian
*Assistant Examiner* — Nathan W Schlientz
(74) *Attorney, Agent, or Firm* — The Roy Gross Law Firm, LLC; Roy Gross

(57) ABSTRACT

A nanoparticle, which has a metal oxide core and a cerium shell is provided. The weight ratio of the cerium within the shell to the metal oxide in the core is at least 1%. Additionally a method for delivering a ligand into a cell with the nanoparticle is provided. Processes for making the nanoparticle which include: sonicating an aqueous composition containing Ceric Ammonium Nitrate and a prefabricated nano particle suspension; and (b) adding a polycationic polymer to the mixture (for NP surface functionalization), are also described.

13 Claims, 82 Drawing Sheets

Specification includes a Sequence Listing.

(56) References Cited

OTHER PUBLICATIONS

Chapter 1, Handbook of Medical Imaging, vol. 1, Physics and Psychophysics, Eds. J. Beutel et al., SPIE Press, 2000.‡
Tartaj et al., "The preparation of magnetic nanoparticles for applications in biomedicine", J. Phys.D: Appl.Phys. 36 (2003) R182-R197.‡
Mahmoudi et al., "Optimal Design and Characterization of Superparamagnetic Iron Oxide Nanoparticles Coated with Polyvinyl Alcohol for Targeted Delivery and Imaging".‡
Lendrem et al., "DOE (Design of Experiments) in Development Chemistry: Potential Obstacles", Organic Process Research & Development 2001, 5, 324-327.‡
Castillo B. et al., "Intracellular Delivery of siRNA by PolycationicSuperparamagnetic Nanoparticles", Journal of Drug Delivery, vol. 2012, 2012, Article ID 218940, 12 Pages, (-Dec. 31, 2012.‡
Runowski M. et al., "Bifunctional luminescent and magnetic core/shell type nanostructures Fe304@CeF3:Tb3+/SiO2", Journal of Rare Earths, vol. 29, No. 12, Dec. 2011, pp. 1117-1122, ISSN: 1002-0721, Dec. 31, 2011.‡
Kennett et al., Modern Industrial Statistics with applications using R, MINITAB and JMP, May 6, 2013.‡
Scherer F. et al., "Magnetofection:enhancing and targeting gene delivery by magnetic force in vitro and in vivo", Gene Therapy, vol. 9, Issue 2, Jan. 2002, pp. 102-109, EISSN 1476-5462, Jan. 31, 2002.‡
International Search Report of PCT Application No. PCT/IL2014/050064.‡
Esman N. et al. "Magnetically responsive polypyrrole nanotubes using Ce(III)-stabilized maghemite nanoparticles", Nanotechnology, vol. 22, Issue 28, Article ID 285604, Online ISSN: 1361-6528, DOI: 10.1088/0957-4484/22/28/285604. filed Jun. 6, 2011.‡
Haviv A. H. et al., "Aggregation Control of Hydrophilic Maghemite (gamme-Fe2O3) Nanoparticles by Surface Doping Using Cerium Atoms", Journal of the American Chemical Society, vol. 132, Issue 36, pp. 12519-12521, Sep. 15, 2010, ISSN 0002-7863, DOI:10.1021/ja103283e. Aug. 24, 2010. The whole document.‡
Choudhury B. et al. "Extending photocatalytic activity of TiO2 nanoparticles to visible region of illumination by doping of cerium", Photochem Photobiol. Mar.-Apr. 2012;88(2):257-264. (8 pages).‡
Xueting Chang et al. "Solvothermal synthesis of Ce-doped tungsten oxide nanostructures as visible-light-driven photocatalysts", Nanotechnology, vol. 22, No. 26, May 17, 2011, p. 265603. (8 pages).‡
M. Comes Franchini et al. "Biocompatible nanocomposite for PET/MRI hybrid imaging of pancreatic cancer", International Journal of Nanomedicine, Dec. 1, 2012, p. 6021. (13 pages).‡
J. P. Lellouche et al., "[OA38] Surface doping of maghemite (gamma-Fe2O3) nanoparticles by Ce3/4+ metallic cations as an innovative ultra-small nanoparticulate delivery system for gene silencing", Third international conference on multifunctional, hybrid and nanomaterials. Mar. 7, 2013, retrieved from the internet : https://elsevier.conference-services.net/resources/247/3159/pdf/HYMA2013_1791.pdf (1 page).‡
Wang C. et al., "Preparation, characterization, photocatalytic properties of titania hollow sphere doped with cerium", Journal of Hazardous Materials, Elsevier, vol. 178, p. 517-521, 2010. (5 pages).‡
J.P. Lellouche, "Magnetic Core Conducting Polymer Shell Nanocomposites for DNA Attachment and Hybridization", Nanotechnologies for the Life Sciences, Challa S.S.R. Kumar (Ed.), 2007, 299-329. (Year: 2007).‡
Amit H. Haviv, Jean-Marc Greneche, and Jean-Paul Lellouche, "Aggregation Control of Hydrophilic Maghemite (-Fe2O3) Nanoparticles by Surface Doping Using Cerium Atoms", Journal of the American Chemical Society, 2010, 132, 12519-12521. (Year: 2010).‡
Tian Xia, Michael Kovochich, Monty Liong, Huan Meng, Sanaz Kabehie, Jeffrey I. Zink, and Andre E. Nel, "Polyethyleneimine Coating Enhances the Cellular Uptake of Mesoporous Silica Nanoparticles and Allows Safe Delivery of siRNA and DNA Constructs", ACS Nano, 2009, 3(10): 3273-3286. (Year: 2009).‡
Maria Arsianti, May Lim, Christopher P. Marquis, and Rose Amal, "Assembly of Polyethylenimine-Based Magnetic Iron Oxide Vectors: Insights into Gene Delivery", Langmuir, 2010, 26(10), 7314-7326. (Year: 2010).‡
PCT Search Report for International Application No. PCT/IL2014/050064, mailed Apr. 29, 2014, 4pp.
PCT Written Opinion for International Application No. PCT/IL2014/050064, mailed Apr. 29, 2014, 5pp.
PCT Preliminary Report on Patentability for International Application No. PCT/IL2014/050064, dated Sep. 22, 2015, 6pp.
Esman N. et al., "Magnetically responsive polypyrrole nanotubes using Ce(III)-stabilized maghemite nanoparticles.", Nanotechnology, (Jun. 6, 2011), vol. 22, No. Issue, XP020206963.
Haviv A.H. et al., "Aggregation Control of Hydrophilic Maghemite (gamma-Fe2O3) Nanoparticles by Surface Doping Using Cerium Atoms.", Journal of the American Chemical Society, (Sep. 15, 2010), vol. 132, No. ISSUE, pp. 12519-12521, XP055285862.
Runowski M. et al., "Bifunctional luminescent and magnetic core/shell type nanostructures Fe304@CeF3:Tb3+/Si02.", Journal of Rare Earths, vol. 29, No. 12, ISSN 1002-0721, (Dec. 31, 2011), pp. 1117-1122, URL: http://dx.doi.org/10.1016/S1002-0721(10)60609-6., XP055285857.
Castillo B. et al., "Intracellular Delivery of siRNA by Polycationic Superparamagnetic Nanoparticles.", Journal of Drug Delivery, vol. 2012, (Dec. 31, 2012), p. 12, URL: http://dx.doi.org/10.1155/2012/218940., XP055220818.
Scherer F. et al., "Magnetofection: enhancing and targeting gene delivery by magnetic force in vitro and in vivo.", Gene Therapy, (Jan. 2002), vol. 9, No. ISSUE, pp. 102-109, XP008132253.
J P Lellouche et al, "[OA38] Surface doping of maghemite (gamma-Fe 2 O 3 ) nanoparticles by Ce 3/4+ metallic cations as an innovative ultra-small nanoparticulate delivery system for gene silencing", (Mar. 7, 2013), Third International Conferenec on Multifunctional, Hybrid and Nanomaterials, Mar. 2013, URL: https://elsevier.conference-services.net/resources/247/3159/pdf/HYMA2013_1791.pdf, (Sep. 21, 2016), XP055304565.
Mauro Comes Franchini et al, "Biocompatible nanocomposite for PET/MRI hybrid imaging", International Journal of Nanomedicine, (Dec. 1, 2012), doi:10.2147/IJN.S38107, p. 6021, XP055304381.
Choudhury Biswajit et al, "Extending photocatalytic activity of TiO2 nanoparticles to visible region of illumination by doping of cerium.", Photochemistry and Photobiology Mar.-Apr. 2012, (Mar. 2012), vol. 88, No. 2, ISSN 1751-1097, pp. 257-264, XP002762196.
Xueting Chang et al, "Solvothermal synthesis of Ce-doped tungsten oxide nanostructures as visible-light-driven photocatalysts-;Solvothermal synthesis of Ce-doped tungsten oxide nanostructures as visible-light-driven photocatalysts", Nanotechnology, IOP, Bristol, GB, (May 17, 2011), vol. 22, No. 26, doi:10.1088/0957-4484/22/26/265603, ISSN 0957-4484, p. 265603, XP020206852.
Tian Xia, Michael Kovochich, Monty Liang, Huan Meng, Sanaz Kabehie, Jeffrey I. Zink, and Andre E. Nel, "Polyethyleneimine Coating Enhances the Cellular Uptake of Mesoporous Silica Nanoparticles and Allows Safe Delivery of siRNA and DNA Constructs", ACS Nano, 2009, 3(10): 3273-3286. (Year: 2009).

\* cited by examiner
‡ imported from a related application

Raman shift / cm-1

| Peak no. | Centre | Height | Width | Area | Absolute inten... | Low edge | High edge |
|---|---|---|---|---|---|---|---|
| 1 | 128.844 | 286.987 | 22.8424 | 3276 | 181.162 | 102.002 | 165.717 |
| 2 | 183.772 | 410.8684 | 23.3396 | 11098 | 140.938 | 167.401 | 216.719 |
| 3 | 486.447 | 806.2258 | 26.1177 | 46007.6 | 293.443 | 423.572 | 537.08 |
| 4 | 699.755 | 841.395 | 95.0802 | 122292 | 698.173 | 569.162 | 797.067 |
| 5 | 949.266 | 618.985 | 19.7204 | 44128.91 | 801.328 | 906.379 | 977.416 |
| 6 | 1333.77 | 510.0737 | 13.0805 | 53109.7 | 430.139 | 1227.87 | 1346.6 |
| 7 | 1808.02 | 386.1413 | 5.34836 | 1069.012 | 805.9557 | 1787.48 | 1889.32 |
| 8 | 2225.22 | 431.0599 | 10.9992 | 19440.03 | 188.766 | 2047.84 | 2238.84 |
| 9 | 2283.3 | 62.2054 | 6.14292 | 5281.26 | 133.695 | 2209.5 | 2243.19 |
| 10 | 2384.43 | 434.6403 | 20.2904 | 6648.48 | 121.753 | 2283.51 | 2487.94 |
| 11 | 1170.2 | | | | 189.034 | | |
| 12 | 1593.78 | | | | 351.3 | | |
| 13 | 3339.448 | | | | 289.613 | | |

Figure 9_continued

Figure 17B_continued

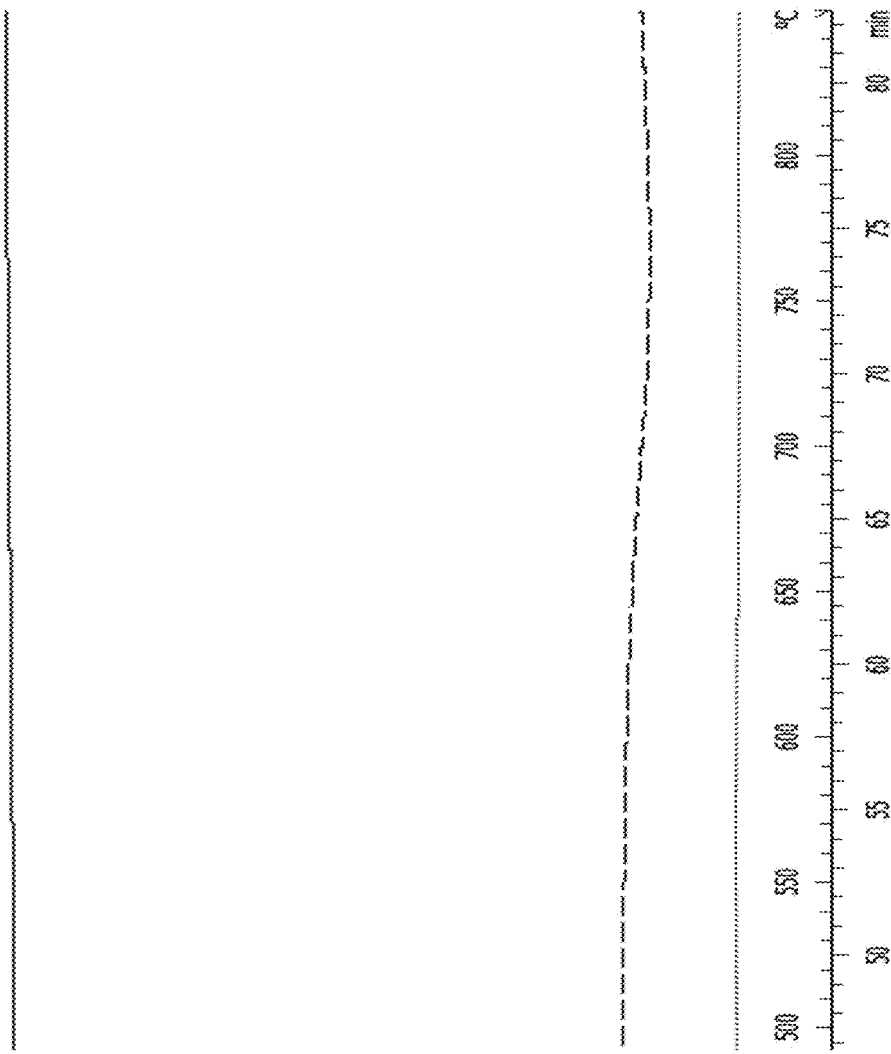
Figure 49_continued

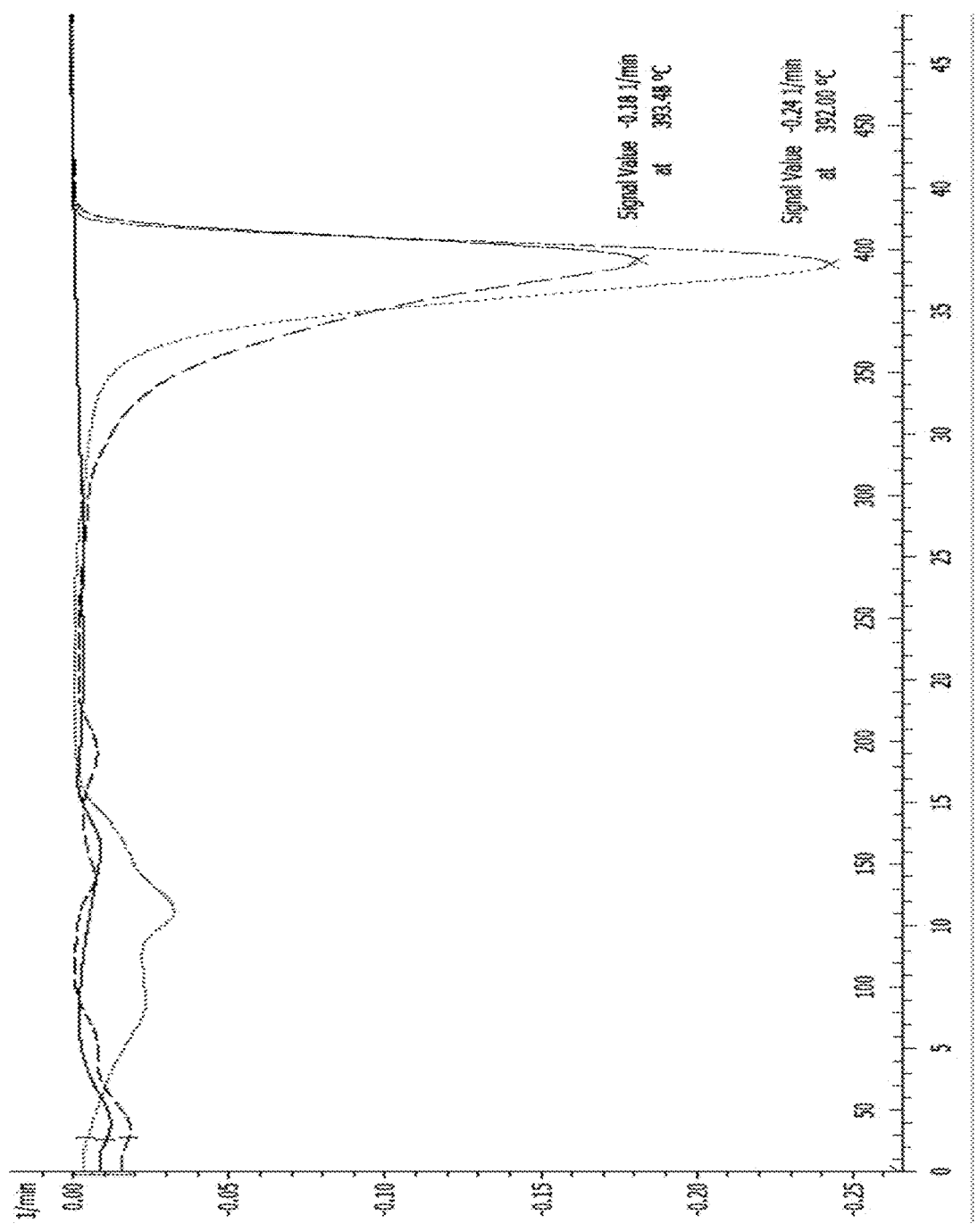
Figure 49_continued 1

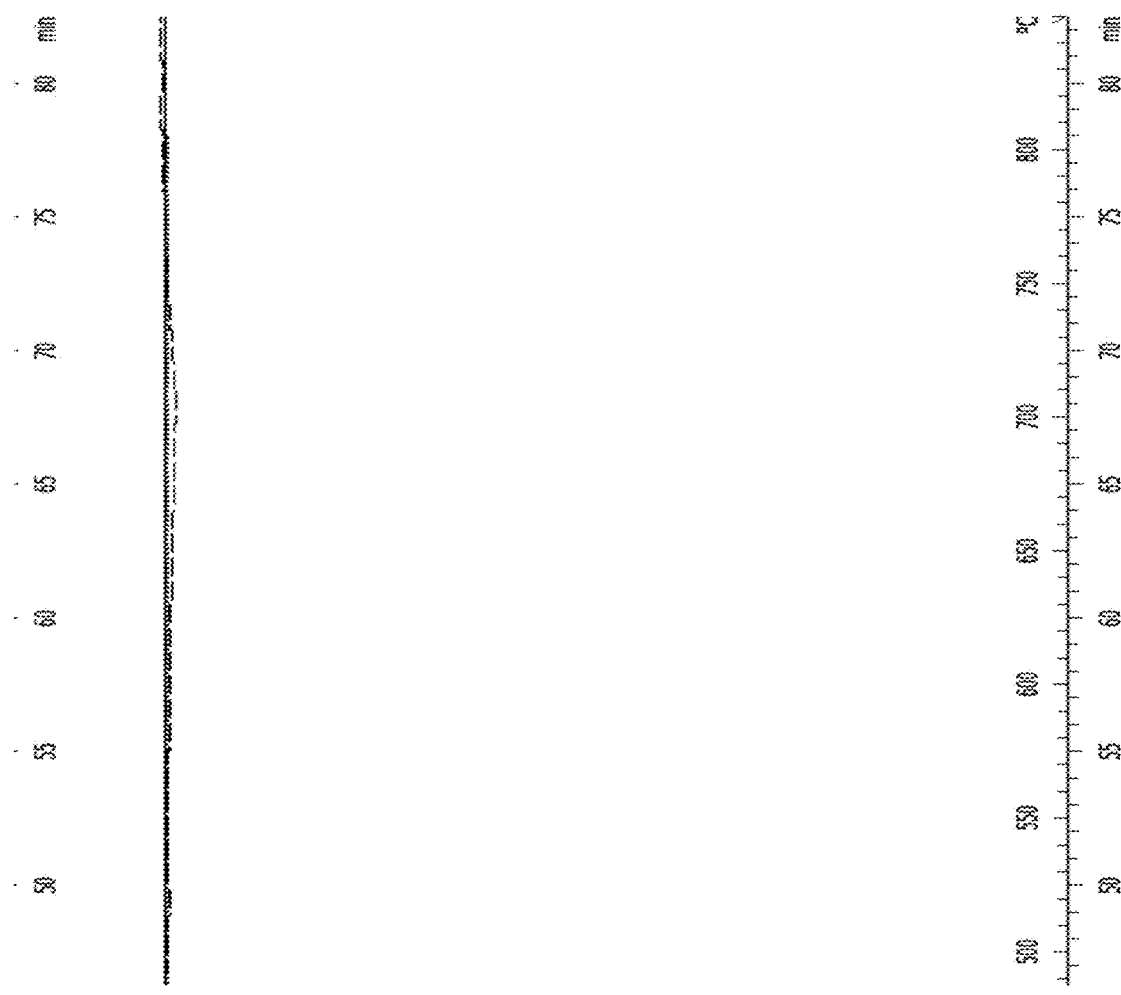
Figure 49_continued 2

MAGNETIC INORGANIC IRON-BASED NANOPARTICLES

CROSS REFERENCE TO RELATED APPLICATIONS

This application is a divisional of U.S. patent application Ser. No. 14/778,060 filed Sep. 17, 2015, which is a National Phase of PCT Patent Application No. PCT/IL2014/050064 filed Jan. 19, 2014, which claims the benefit of priority of U.S. Provisional Patent Application No. 61/802,750 filed Mar. 18, 2013, the contents of which are all incorporated herein by reference in their entirety.

REFERENCE TO AN ELECTRONIC SEQUENCE LISTING

The contents of the electronic sequence listing (BIU-P-015-US1.xml; Size: 2,800 bytes; and Date of Creation: May 30, 2023) is herein incorporated by reference in its entirety.

Both magnetically responsive magnetite ($Fe_3O_4$) and maghemite (gamma-$Fe_2O_3$)-based nanoscale particles are the subject of a current intense and sustained interest due to several attractive factors such as: (a) Crystalline spinel phases that can be readily prepared as nanoscale 3.0-100.0 nm-sized formulations using various quite effective fabrication methods and related variants. Basically, these nanofabrication methods mainly include hydrolytic (simultaneous $Fe^{2+}$ and $Fe^{3+}$ co-precipitation in basic media) and thermal decomposition processes of Fe-containing complexing organic species (beta-diketone complexes) that have been shown to be highly reproducible and easy to scale-up. These fabrication processes have been recently reviewed in addition to less common fabrication methods (laser vaporization for example: (Tartaj, Morales et al. 2003).

(b) Atom vacancies (surface defects) and polar amphoteric HO-decorating species enable easy surface chemical manipulation for post-nanoparticle fabrication surface engineering at $2^{nd}$ step functionalization levels. Such readily exploitable decoration processes strongly fueled the preparation of variously modified composite nanosized particles that might be surface tailored towards specific applications. For example, numerous polar amine, alcohol/thiol/phenol, carboxyl, and phosphate/phosphonate-containing species and organic/inorganic ($SiO_2$ phase) polymers as capping organic entities have been widely used towards the preparation of corresponding functional magnetite and maghemite nanocomposite particulate systems. Passivating silicate [$(EtO)_3Si$-linker-X, X: end functional group)]-based NP surface engineering is a quite good example of such versatile surface chemistries that might be tailored at will.

(c) Both magnetite and maghemite NPs are magnetically responsive (ferrimagnetic phases), i.e., enabling (i) distance manipulation of such particles/related composites by an external magnetic field (magnetically targeted drug delivery systems), (ii) anti-cancer local hyperthermia (heat-driven cancer ablation), (iii) internal tissue imaging when used as nanoscale contrast agents (magnetic resonance imaging), (iv) cell/ligand bio-separations, and (v) magnetic information storage (magnetic recording).

(d) Magnetite and maghemite NPs as well as relating dual phase iron oxide core-polymer shell nanocomposites are generally considered as safe minimally toxic particulate systems that have been authorized for in vivo clinic use (MRI contrast agents).

Beyond the NP surface enabling functionalization capability mentioned above, it should be noticed that the NP surface passivation using small functional ligands (poly (amidoamine) dendrimers, cyclodextrins), acidic and/or charged surfactants (cis-oleic acid, cis-oleyl amine and their mixtures) and/or polyfunctional polymers (polyacrylate or polymethacrylate acids, polyvinyl alcohol, dextran, chitosan) has also been deeply investigated to control (steric and/or charge control) the quite detrimental well-known irreversible NP aggregation phenomenon. Such organic modes of NP decoration/passivation by organic chemical species might cause (i) deterioration of magnetic properties (saturation magnetization $M_s$) as well as (ii) problematic issues concerning composite toxicity, and (iii) limitations of NP concentration ranges used for safe storage and transport.

siRNA/microRNA-mediated gene silencing—The mechanism of gene silencing inhibits the conversion of mRNA into protein. Briefly, dsRNA is recognized by an enzyme, i.e., Dicer that cleaves the RNA into small fragments of 21-23 nts known as siRNAs. siRNAs bind to a protein complex called RNA-induced silencing complex (RISC). The siRNA is composed of two strands, the passenger and the anti-sense (guide strand) ones with respect to the target mRNA. The passenger strand is cleaved and discarded while the guide strand is inducing the degradation of the mRNA via the Argonaute 2 that introduces an endonucleolytic cleavage into the target mRNA, leading to its degradation (Meister and Tuschl 2004). siRNAs are not present naturally in mammalian cells but can be designed such that these will efficiently incorporate into the RISC complex and induce the degradation of any mRNA at will. siRNAs can be designed to degrade only a mutated mRNA but not the wild type transcripts because the siRNA must exactly complement its target mRNA (Brummelkamp, Bernards et al. 2002; Hannon and Rossi 2004).

Mammalian cells as many metazoans possess miRNAs that are 21 nts RNA molecules that regulate gene expression by inducing the degradation of their target and inhibiting their translation. The interaction of the miRNA and its target does not require perfect complementarity. microRNAs are phylogenetically conserved and play an important role in cell survival, proliferation, differentiation, apoptosis, and angiogenesis. miRNA expression patterns differ depending upon cell, tissue, and disease types. Changes in these expression patterns have been implicated as an important player in carcinogenesis. Each microRNA is a master regulator and regulate the expression of hundreds of genes (Bartel and Chen 2004). Around 1,000 microRNAs are present in the human genome and these regulate almost every mRNA. Each mRNA is regulated by more than one microRNAs. Thus, silencing the expression of microRNAs dramatically change gene expression and even converts a cancer to normal cell (Baer, Claus et al. 2013).

Magnetic nanoscale carriers for DNA/RNA delivery and cell transfection—State of the Art—Iron oxide particles have many applications in biomedicine such as MRI, drug delivery, stem cell tracking, heat source hyperthermia, and more (Wahajuddin and Arora 2012). In particular, current advanced techniques in drug targeting use delicate surface modifications on these particles for the conjugation of anti-angiogenic and anti-cancer drugs (Cole, Yang et al. 2011). Very small iron oxide particles (in the size range of 30 nm) are commercially available. Numerous iron oxide NPs are already FDA-approved for use in the clinic as well as several more are undergoing clinical trials (Wahajuddin and Arora 2012). A recent review summarizes many in vitro toxicity studies with different iron oxide particles functionalized by variety of polymers such as Polyethylenimine (PEI), PVA, PLL, PDMA, as well as PEG (Petri-Fink and Hofmann 2007). Most studies claim that very high concentrations of these NPs showed a toxic effect but lower amounts of same materials were fully biocompatible. The toxicity varies much with the size and the surface chemistry of the particle. A more recent review summarizes the utility of iron oxide NPs as drug carriers (Cole, Yang et al. 2011).

Recently, the whole set of reported strategies to deliver siRNAs to cells was extensively reviewed. The majority of these studies utilize liposomes, dendrimers, and polymer particles for the delivery of siRNAs into cells in vivo and in vitro. NPs can enter tumor cells by the enhanced permeability and retention effect (EPR), but specific localization as well as enhanced internalization was also demonstrated upon binding of targeting moieties (Pecot, Calin et al. 2011). So far, there is not yet any report of using iron oxide particles for gene silencing of both mRNA and microRNAs. A recent study described the utility of super-magnetic nanoparticles for silencing of mRNAs (Castillo, Bromberg et al. 2012). Targeting of nanoparticles to cancer cells has been explored through the attachment of antibodies, small molecules (transferrin), aptamers, and well-established peptide ligands. However, these approaches are typically neither modular nor multifunctional and do not incorporate imaging moieties. Addition of a nanoparticle based-imaging agent to siRNA delivery strategies may be particularly advantageous as protein knockdown by RNAi is delayed (48 h or more after administration) and many fluorescent dyes are not stable for monitoring delivery over extended periods of time in vivo.

SUMMARY OF THE INVENTION

In one embodiment, this invention provides a composition comprising a metal oxide and cerium, wherein the weight ratio of the cerium to the metal oxide is at least 1%.

In a further embodiment, this invention provides a nanoparticle (NP), comprising a core and a shell, wherein the core comprises or consists a metal oxide and the shell comprises or consists cerium, wherein the weight ratio of the cerium within the shell to the metal oxide within the core is at least 1%.

In a further embodiment, this invention provides a nanoparticle (NP), comprising a ligand, a core, and a shell, wherein the core comprises a metal oxide and the shell comprises cerium, wherein the weight ratio of said cerium within said shell to said metal oxide within the core is at least 1%, wherein the ligand is bound to the shell. In a further embodiment, the ligand is a polyethyleneimine (PEI) polymer.

In a further embodiment, this invention provides a process for making a nanoparticle (NP), comprising a core and a shell, wherein the core comprises a metal oxide and the shell comprises cerium, wherein the weight ratio of the cerium within the shell to the metal oxide within the core is at least 1%, comprising the steps of: (a) Sonicating an aqueous composition comprising Ceric Ammonium Nitrate (CAN) and a prefabricated nanoparticle suspension, and obtaining a mixture; and (b) Adding a polycationic polymer to the mixture.

DETAILED DESCRIPTION OF THE INVENTION

Figure 1:
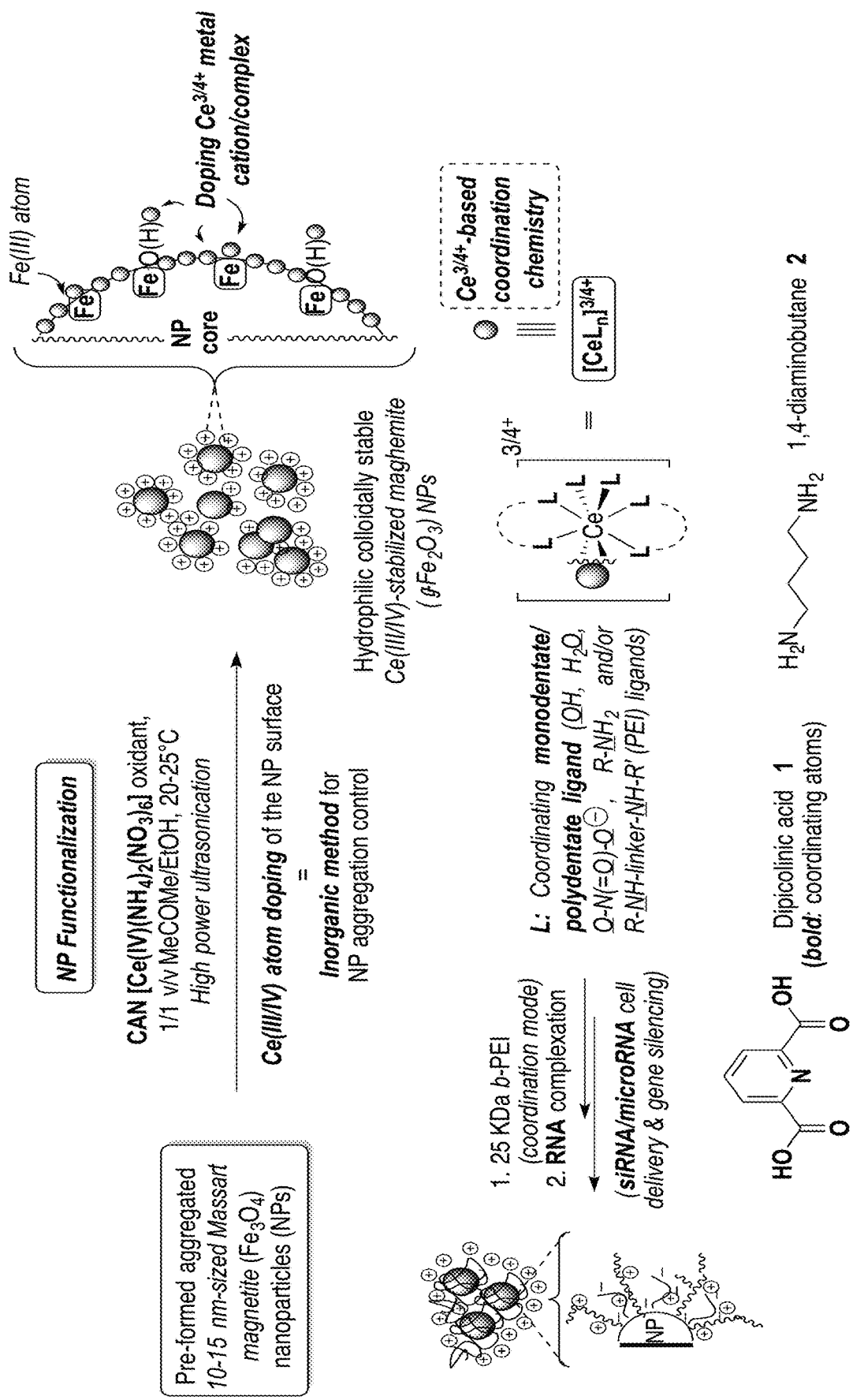
FIG. 1. is a schematic representation of the formation of PEI-chemically modified ultra-small $Ce^{3/4+}$-doped maghemite (gamma-$Fe_2O_3$) nanoparticles ($PEI_{25}$-CAN-gamma-$Fe_2O_3$ NPs) for RNA loading/gene silencing (cell transfection).

In one embodiment, the present invention provides a composition comprising a metal oxide and cerium, wherein the weight ratio of the cerium to the metal oxide is at least 1%. In one embodiment, the present invention provides a suspension comprising a metal oxide and cerium, wherein the weight ratio of the cerium to the metal oxide is at least 1%. In another embodiment, the weight ratio of the cerium to the metal oxide is at least 2%. In another embodiment, the weight ratio of the cerium to the metal oxide is at least 2.5%. In another embodiment, the weight ratio of the cerium to the metal oxide is at least 3%. In another embodiment, a composition as described herein is the basis for the process of making a nanoparticle as described herein. In another embodiment, the present invention provides that a composition comprising a metal oxide and cerium, wherein the weight ratio of the cerium to the metal oxide is at least 1% is used for the preparation of nanoparticles (NPs) as described hereinbelow.

In one embodiment, the term "comprises" includes or can be replaced with the term "consists".

In one embodiment, the term "cerium" includes or can be replaced with the term "cerium cations". In one embodiment, the term "cerium" includes or can be replaced with the term "cationic cerium species". In one embodiment, the term "cerium" includes or can be replaced with the term "cerium phase". In one embodiment, the term "cerium" includes or can be replaced with the term "cerium (III/IV) cations". In one embodiment, the term "cerium" includes or can be replaced with the term "cerium phase (cerium (III/IV) cations)".

In another embodiment, the present invention provides a suspension comprising a metal oxide and cerium, wherein the weight ratio of the cerium to the metal oxide is from 0.7% to 12%. In another embodiment, the present invention provides a suspension comprising a metal oxide and cerium, wherein the weight ratio of the cerium to the metal oxide is from 0.8% to 10%. In another embodiment, the present invention provides a suspension comprising a metal oxide and cerium, wherein the weight ratio of the cerium to the metal oxide is from 1% to 8%. In another embodiment, the present invention provides a suspension comprising a metal oxide and cerium, wherein the weight ratio of the cerium to the metal oxide is at least 1% (1% or more).

In another embodiment, the present invention provides a nanoparticle made from the composition or suspension as described herein. In another embodiment, the present invention provides a nanoparticle, comprising a core and a shell, wherein the core comprises a metal oxide and the shell comprises cerium, wherein the weight ratio of the cerium within the shell to the metal oxide within the core is at least 0.5%. In another embodiment, the present invention provides a nanoparticle, comprising a core and a shell, wherein the core comprises a metal oxide and the shell comprises cerium, wherein the weight ratio of the cerium within the shell to the metal oxide within the core is at least 0.7%. In another embodiment, the weight ratio of the cerium within the shell to the metal oxide within the core is at least 1%. In another embodiment, the weight ratio of the cerium within the shell to the metal oxide within the core is at least 2%. In another embodiment, the weight ratio of the cerium within the shell to the metal oxide within the core is at least 3%. In another embodiment, the weight ratio of the cerium within the shell to the metal oxide within the core is from 0.7% to 15%. In another embodiment, the weight ratio of the cerium within the shell to the metal oxide within the core is from 0.8% to 12%. In another embodiment, the weight ratio of the cerium within the shell to the metal oxide within the core is from 1% to 10%. In another embodiment, the weight ratio of the cerium within the shell to the metal oxide within the core is from 0.8% to 5%.

In one embodiment, the term "nanoparticle" refers to any particle having a diameter of less than 1000 nm. In one embodiment, a nanoparticle as described herein has a diameter of 100 to 1000 nm. In one embodiment, a nanoparticle as described herein has a diameter of 50 to 500 nm. In one embodiment, a nanoparticle as described herein has a diameter of 10 to 100 nm. In one embodiment, a nanoparticle as described herein has a diameter of 100 to 800 nm.

In some embodiments, a nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. In some embodiments, the nanoparticles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. In one embodiment, non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

In one embodiment, the invention provides a population of nanoparticles having a high surface-to-volume ratio. In one embodiment, a nanoparticle is crystalline. In one embodiment, a nanoparticle is amorphous. In another embodiment, the nanoparticle is in a crystalline spinel phase.

In another embodiment, the nanoparticle is a magnetic nanoparticle. In another embodiment, a magnetic nanoparticle includes but is not limited to, particles that are magnetic, super-paramagnetic, ferromagnetic, ferrimagnetic or paramagnetic.

In one embodiment, a single type (size, shape, and the like) of nanoparticle are used. In another embodiment, mixtures of different types of nanoparticles are used. In one embodiment, a homogeneously or non-homogeneously population of nanoparticles is used according to the teachings of the invention. In one embodiment, a homogenous population of nanoparticles is a population wherein the deviation in the diameter of at least 80% of the nanoparticles is 2-15%. In one embodiment, a homogenous population of nanoparticles is a population wherein the deviation in the diameter of at least 80% of the nanoparticles is up to 10%. In one embodiment, a homogenous population of nanoparticles is a population wherein the deviation in the diameter of at least 90% of the nanoparticles is up to 20%. In one embodiment, a homogenous population of nanoparticles is a population wherein the deviation in the diameter of at least 90% of the nanoparticles is up to 10%.

In another embodiment, repulsion forces exist between neighboring nanoparticles. In another embodiment, repulsion forces exist between the shells of neighboring nanoparticles. In another embodiment, repulsion forces exist between the cores of neighboring nanoparticles. In another embodiment, these repulsion forces contribute to a composition comprising the nanoparticles of the invention.

In one embodiment, the core is the nucleus. In another embodiment, the shell is the outer surface of the nanoparticle. In another embodiment, the shell continuously covers the core. In another embodiment, the outer surface of the nanoparticle comprises the shell. In some embodiments, the core can have more than one coating or shell. In some embodiments, the core has multiple layers of shells or coatings, which partially or fully encapsulate the core or a previous coating or shell. In some embodiments, a plurality of cores can cover the same shell. In one embodiment, a single shell covers all the cores present in the nanoparticle composition. In another embodiment, all the cores present in the nanoparticle are covered by two or more shells. In another embodiment, an individual shell comprises the same material or comprises two or more different materials. In some embodiments the core is covered with more than one shell. In another embodiment, the shell is of the same or of different material. In another embodiment, the outer surface of the nanoparticle comprises a shell and a ligand. In another embodiment, the outer surface of the nanoparticle comprises the shell and the ligand, wherein the ligand is bound directly or indirectly to the shell. In another embodiment, the outer surface of the nanoparticle comprises the shell and the ligand, wherein the ligand is bound directly or indirectly to the cerium in the shell. In another embodiment, the ligand is bound to the nucleus. In another embodiment, the outer surface of the nanoparticle comprises the shell and the ligand bound to the shell. In another embodiment, the shell is a single layer comprising cerium. In another embodiment, the shell is a single layer comprising cerium and a ligand bound thereto.

In one embodiment, the nanoparticle of the invention has enhanced anti-aggregation properties (at least partially due to the repulsion forces). In one embodiment, the nanoparticle of the invention has enhanced anti-aggregation properties derived from its charge. In one embodiment, an aggregate may include more than one nanoparticle in physical contact with one another, while agglomerates may include more than one aggregate in physical contact with one another. In some embodiments, a minimal number of nanoparticles are in an aggregated state so that less than 25% of nanoparticles are aggregated. In some embodiments, a minimal number of nanoparticles are in an aggregated state so that less than 15% of nanoparticles are aggregated. In some embodiments, a minimal number of nanoparticles are in an aggregated state so that less than 5% of nanoparticles are aggregated. In one embodiment, the core comprises an oxide of a metal. In one embodiment, the core comprises an oxide of a transition metal. As used herein, "transition metal" refers to elements from groups 3-12 of the Periodic Table. In one embodiment, "transition metal" is transition metal oxide. In certain embodiments, the core comprises one or more transition metal compounds, such as oxides, carbides, sulfides, nitrides, phosphides, borides, halides, selenides, and tellurides that contain one or more of these transition metal elements. In some embodiments a metal is a zero-valent metal; In other embodiments, a metal is a metallic or nonmetallic material that contains a transition metal element as a constituent.

In some embodiments, the nanoparticle comprises a single core. In some embodiments, the nanoparticle comprises a plurality of cores. In some embodiments where the nanoparticle comprises plurality of cores, the cores are the same or equal. In some embodiments, where the nanoparticle comprises plurality of cores, the cores are of different size or composition. In other embodiments, each of the nanoparticles comprises a single core.

In some embodiments, the core comprises a single transition metal compound. In another embodiment, the core comprises a mixture of two or more transition metal compounds. In some embodiments, transition metal element cations are of the same element or of two or more different elements. In one embodiment, the core may comprise a single metal compound, such as but not limited to tantalum oxide or iron oxide. In another embodiment, the core may comprise two or more different metal elements, for example tantalum oxide and hafnium oxide or tantalum oxide and hafnium nitride, or oxides of iron, zinc, magnesium, and manganese. In another embodiment, the core may comprise two or more compounds of the same metal element, for example tantalum oxide and tantalum sulfide.

In one embodiment, the core creates a contrast enhancement in X-ray or computed tomography (CT) imaging. A conventional CT scanner uses a broad spectrum of X-ray energy between about 10 keV and about 150 keV. Those skilled in the art will recognize that the amount of X-ray attenuation passing through a particular material per unit length is expressed as the linear attenuation coefficient. At an X-ray energy spectrum typical in CT imaging, the attenuation of materials is dominated by the photoelectric absorption effect and the Compton Scattering effect. Furthermore, the linear attenuation coefficient is well known to be a function of the energy of the incident X-ray, the density of the material (related to molar concentration), and the atomic number (Z) of the material. For molecular compounds or mixtures of different atoms the 'effective atomic number', $Z_{eff}$, can be calculated as a function of the atomic number of the constituent elements. The effective atomic number of a compound of known chemical formula is determined from the relationship: $Z_{eff}=[k=1 \ P \times w \ f \ k \times Z \ k \ \beta] \ 1/\beta$ (Eq.×1) where $Z_k$ is the atomic number of simple elements, P is the total quantity of simple elements, and $w_{f.sub.k}$ is the weight fraction of simple elements with respect to the total molecular weight of the molecule (related to the molar concentration). The optimal choice of the incident X-ray energy for CT imaging is a function of the size of the object to be imaged and is not expected to vary much from the nominal values. It is also well known that the linear attenuation coefficient of the contrast agent material is linearly dependent on the density of the material, i.e., the linear attenuation coefficient can be increased if the material density is increased or if the molar concentration of the contrast material is increased. However, the practical aspects of injecting contrast agent material into patients, and the associated toxicity effects, limit the molar concentration that can be achieved. Therefore it is reasonable to separate potential contrast agent materials according to their effective atomic number. Based on simulations of the CT contrast enhancement of typical materials for a typical CT energy spectrum with a molar concentration of approximately 50 mM, it is estimated that materials with effective atomic number greater than or equal to 34 may yield appropriate contrast enhancement of about 30 Hounsfield units (HU), or 3% higher contrast than water. Therefore, in certain embodiments the core comprises material having an effective atomic number greater than or equal to 34. See, e.g., Chapter 1 in Handbook of Medical Imaging, Volume 1. Physics and Psychophysics, Eds. J. Beutel, H. L. Kundel, R. L. Van Metter, SPIE Press, 2000.

In some embodiments, the core comprises transition metals with relatively high atomic number as described. In such embodiments, the core is substantially radiopaque, meaning that the core material prohibits significantly less X-ray radiation to pass through compared to materials that makeup living organisms, thus potentially giving the particles utility as contrast agents in X-ray imaging applications, such as computed tomography (CT). Examples of transition metal elements that may provide this property include tungsten, tantalum, hafnium, zirconium, molybdenum, silver, and zinc. Tantalum oxide is one particular example of a suitable core composition for use in X-ray imaging applications. In one or more embodiments, the core of the nanoparticle comprises tantalum oxide and the nanoparticle has a particle size up to about 6 nm. This embodiment may be particularly attractive for applications in imaging techniques that apply X-rays to generate imaging data, due to the high degree of radio-opacity of the tantalum-containing core and the small size that aids rapid renal clearance, for example.

In some embodiments, the core of the nanoparticle comprises at least about 30% transition metal material by weight. In certain embodiments, the core comprises at least about 50% transition metal material by weight. In still further embodiments, the core comprises at least about 75% transition metal material by weight. Having a high transition metal material content in the core provides the nanoparticle with higher degree of radio-opacity per unit volume, thereby imparting more efficient performance as a contrast agent.

In another embodiment, the core comprises material that exhibits magnetic behavior, including but not limited to, super-paramagnetic behavior. The "super-paramagnetic material" as used herein refers to material that may exhibit a behavior similar to paramagnetism even when at temperatures below the Curie or the Néel temperature. In another embodiment, the magnetic or super-paramagnetic materials include but are not limited to, materials comprising one or more of iron, manganese, copper, cobalt, or nickel. In one embodiment, the super-paramagnetic material comprises super-paramagnetic iron oxide. In some embodiments, the nanoparticles of the present invention may be used as magnetic resonance (MR) contrast agents. These nanoparticles may yield a T2*, T2, or T1 magnetic resonance signals/signal contrast enhancement upon exposure to a magnetic field. In one or more embodiments, the core of the nanoparticle comprises super-paramagnetic iron oxide.

In one embodiment, the nanoparticle comprises a shell that entirely covers the core. This shell may serve to stabilize the core, i.e., the shell may prevent one core from contacting an adjacent core, thereby preventing a plurality of such nanoparticle from aggregating or agglomerating as described herein, or by preventing leaching of metal or metal oxide, for instance, on the time scale of in-vivo imaging experiments. In one embodiment, the shell may be of a sufficient thickness to stabilize the core and prevent such contact. In one embodiment, the shell comprises a high concentration of Cerium. In one embodiment, such a high concentration of Cerium within the shell was surprisingly obtained according to the processes and methods as described herein.

In some embodiments, the shell facilitates improved water solubility, reduces aggregate formation, reduce agglomerate formation, prevents oxidation of nanoparticles, maintain the uniformity of the core-shell entity, provides biocompatibility for the nanoparticles, or any combination thereof. In another embodiment, the material or materials within the shell may further comprise other materials that are tailored for a particular application, such as, but not limited to, diagnostic applications and/or therapeutic applications.

In another embodiment, the core comprises any metal oxide known to one of skill in the art. In another embodiment, the metal oxide is a ferromagnetic metal oxide for example but not limited to, magnetite ($Fe_3O_4$) or maghemite (gamma-$Fe_2O_3$).

In another embodiment, the cerium is present only in the shell. In another embodiment, the core is devoid of cerium. In another embodiment, the weight ratio refers only to the metal oxide within the core and to the cerium within the shell. In another embodiment, the cerium is an outer surface, outer coating, outer layer, outer membrane, outer envelope, outer sleeve, outer casing, shell of the nanoparticle.

In another embodiment, the metal oxide is in the center, interior, middle, or nucleus portion of the nanoparticle. In another embodiment, the metal oxide is partially or fully encapsulated or surrounded by the cerium. In another embodiment, the shell is uniform or substantially uniform. In another embodiment, the shell has a uniform charge throughout the shell's surface. In another embodiment, the shell is non-uniform. In another embodiment, the shell is a continuous outer-layer. In another embodiment, the shell is non-uniform. In another embodiment, the shell is a continuous outer-layer of Cerium. In another embodiment, the shell is continuous, non-continuous and/or provides complete or incomplete coverage of the core. In another embodiment, the core is continuous or non-continuous.

In another embodiment, the weight ratio of the cerium within the shell to the metal oxide within the core is about 1% to 15%. In another embodiment, the weight ratio is about 3% to 15%. In another embodiment, the weight ratio is about 3% to 12%. In another embodiment, the weight ratio is about 5% to 12%. In another embodiment, the weight ratio is about 5% to 10%. In another embodiment, the weight ratio is about 1.6%. In another embodiment, the weight ratio is about 2.9%. In another embodiment, the weight ratio is about 9.5%. In another embodiment, the term "about" is deviation of 10% or 5%.

In another embodiment, the metal oxide core has a diameter of about 10 to 50 nm. In another embodiment, the metal oxide core has a diameter of about 20 to 50 nm. In another embodiment, the metal oxide core has a diameter of about 20 to 40 nm. In another embodiment, the metal oxide core has a diameter of about 20 to 35 nm. In another embodiment, the metal oxide core has a diameter of about 25 to 35 nm. In another embodiment, the metal oxide core has a diameter of about 30 nm.

In another embodiment, the nanoparticle has a diameter of 3 to 100 nm. In another embodiment, the nanoparticle has a diameter of about 10 to 100 nm. In another embodiment, the nanoparticle has a diameter of about 10 to 90 nm. In another embodiment, the nanoparticle has a diameter of about 20 to 90 nm. In another embodiment, the nanoparticle has a diameter of about 20 to 80 nm. In another embodiment, the nanoparticle has a diameter of about 30 to 80 nm.

In one embodiment, the nanoparticle has a positive charge of at least +30.0 mV. In another embodiment, the nanoparticle has a positive charge of at least about +30 mV to +50 mV. In another embodiment, the nanoparticle has a positive charge of at least about +35 mV to +50 mV. In another embodiment, the nanoparticle has a positive charge of at least about +35 mV to +45 mV. In another embodiment, the nanoparticle has a positive charge of at least about +40 mV to +45 mV. In another embodiment, the nanoparticle has a positive charge of at least about +35 mV.

In another embodiment, the nanoparticle has a positive charge of at least +44 mV. In another embodiment, the nanoparticle has a positive charge of at least about +44 mV to +65 mV. In another embodiment, the nanoparticle has a positive charge of at least about +50 mV to +65 mV. In another embodiment, the nanoparticle has a positive charge of at least about +50 mV to +60 mV. In another embodiment, the nanoparticle has a positive charge of at least about +55 mV to +60 mV. In another embodiment, the nanoparticle has a positive charge of at least about +56.3 mV.

In one embodiment, the nanoparticle further comprises a ligand. In another embodiment, the ligand is a polymer. In another embodiment, the ligand is an organic molecule. In another embodiment, the ligand is polycationic. In another embodiment, the nanoparticle comprises a ligand that is mono or polydentate or that can be chemically modified by means such as but not limited to oxidation when attached onto the nanoparticle surface. In another embodiment, the ligand is a small molecule. In another embodiment, the ligand bound to the shell. In another embodiment, the core is devoid of a ligand. In another embodiment, the ligand is bound primarily to the shell.

In another embodiment, the ligand is a targeting ligand. In another embodiment, the targeting ligand is a molecule or a structure that provides targeting of the nanoparticle to a desired organ, tissue, cell receptor, or cell. In another embodiment, the ligand includes, but is not limited to, proteins, peptides, antibodies, nucleic acids, sugar derivatives, or combinations thereof. In some embodiments, the nanoparticle further comprises targeting agents such that, when used as contrast agents, the particles can be targeted to specific diseased areas of the subject's body. In some embodiments, the nanoparticles may be used as blood pool agents.

In another embodiment, the nanoparticle comprises a binding material bound to the ligand. In another embodiment, the binding material includes, but is not limited to, proteins, peptides, antibodies, antigens or other suitable materials known in the art.

In another embodiment, the nanoparticle is bound to an affinity ligand, the nature of which is selected based on its affinity for a particular analyte whose presence or absence in a sample is to be ascertained. In another embodiment, the affinity ligand comprises any molecule capable of being linked to a nanoparticle which is also capable of specific recognition of a particular analyte. In another embodiment, the affinity ligand includes, but is not limited to: monoclonal antibodies, polyclonal antibodies, antibody fragments, nucleic acid molecules, oligonucleotides, proteins, oligopeptides, polysaccharides, sugars, peptides, peptide encoding nucleic acid molecules, antigens, drugs, mimetics and other ligands.

In another embodiment, the targeting ligand targets a targeting material. In another embodiment, a target material is of biological or synthetic origin. In another embodiment, the ligand includes, but is not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, acid molecules and derivatised nucleic acids, DNA, RNA, natural or synthetic drugs, mimetics, receptors, virus particles, bacterial particles, virus components, cells, cellular components, and natural or synthetic lipid vesicles.

In another embodiment, the use of the term "ligand" is one ligand or a combination of two or more ligands. In another embodiment, the ligand is composed of at least two mixed ligands with or without any additional post-nanoparticle attachment chemical modification.

In another embodiment, the ligand is a biologically active molecule. In another embodiment, the ligand is a cytokine. In another embodiment, the ligand is a protein. In another embodiment, the ligand is a nucleic acid molecule such as but not limited to siRNA, RNAi, dsRNA, DNA, or any combination thereof. In another embodiment, the ligand is an organic molecule. In another embodiment, the ligand is a cell permeation molecule. In another embodiment, the ligand is an antibody. In another embodiment, the ligand has a biological activity such as but not limited to a drug.

In another embodiment, the ligand is attached by way of covalent bonding, hydrogen bonding, adsorption, metallic bonding, Van der Waals forces, ionic bonding, or any combination thereof to the nanoparticle. In another embodiment, the ligand is covalently bound to the cerium within the shell. In another embodiment, the ligand is coordinatively bound to the cerium within the shell.

In another embodiment, the ligand comprises a positively charged, negatively charged, or a neutral organic moiety.

In another embodiment, the organic moiety comprises at least one Lewis basic heteroatom selected from the group consisting of: N, O, and S or any combination of N, O, and S.

In another embodiment, the ligand is a polymer. In another embodiment, the ligand is a Polyethylenimine polymer (PEI). In another embodiment, the ligand is a Polyethylenimine polymer that is linear. In another embodiment, the ligand is a Polyethylenimine polymer that is branched. In another embodiment, the ligand is a Polyethylenimine polymer that has a MW of 2,000 to 80,000. In another embodiment, the ligand is a Polyethylenimine polymer that has a MW of 4,000 to 25,000. In another embodiment, the ligand is a Polyethylenimine polymer that has a MW of 25,000 to 40,000.

In another embodiment, the ligand is a polycationic polymer. In another embodiment, the ligand is a Polyethylenimine type cationic polymer and effective substitutes. In another embodiment, the ligand is a Polyethylenimine type cationic polymer or effective substitutes.

In another embodiment, the ligand is Chitosan. In another embodiment, the ligand is Poly-L-lysine. In another embodiment, the ligand is Lysozyme. In another embodiment, the ligand is Diethylaminoethyl-dextran (DEAE-dextran). In another embodiment, the ligand is Polyornithine. In another embodiment, the ligand is Histone. In another embodiment, the ligand is Hexadimethrine bromide. In another embodiment, the ligand is Polyarginine. In another embodiment, the ligand is Protamine.

In another embodiment, the ligand is a nucleic acid molecule. In another embodiment, the nucleic acid molecule is DNA. In another embodiment, the nucleic acid molecule is RNA. In another embodiment, the nucleic acid molecule is siRNA. In another embodiment, the nucleic acid molecule is microRNA. In another embodiment, the nucleic acid molecule is a double-stranded RNA (dsRNA). In another embodiment, the nucleic acid molecule is a single-stranded RNA.

In another embodiment, the ligand is a marker. In another embodiment, the ligand is an imaging agent. In another embodiment, the ligand is a biomarker. In an additional embodiment the ligand is a radioactive isotope. In another embodiment, the ligand is a protein. In another embodiment, the ligand is a fluorophore. In another embodiment, the ligand is a cell-death facilitating agent.

In another embodiment, the nanoparticles such as magnetic NPs have the potential to be used in imaging and analytical detection assays. For example, in a Surfaced Enhanced Raman Spectroscopy (SERS)-based assay, increasing analyte concentration in solution or local analyte concentration at an assay surface can significantly improve the limits of detection of different analytes, especially of large biomolecules such as bacteria and viruses. Such a system could be used to bind a target forming a nanoparticle-target complex. Application of a magnetic field will allow immobilization of the nanoparticle-target complex. Alternatively, through the application of a magnetic field, the nanoparticle-target complex can be concentrated at the site of an assay surface allowing for detection or improvement of the limits of detection. During recent years, there has been in increase in interest regarding the use of magnetic nanoparticles as contrast agents for use in conjunction with magnetic resonance imaging (MRI) techniques (Ito et al., J. Biosci. Bioeng. 100:1-11 (2005), which is hereby incorporated by reference in its entirety). Magnetic nanoparticles have also been proposed for use in direct sensing methods for diagnosis of cancer (Suzuki et al., Brain Tumor Pathol. 13:127 (1996), which is hereby incorporated by reference in its entirety) and for novel tissue engineering methodologies utilizing magnetic force and functionalized magnetic nanoparticles to manipulate cells (Ito et al., J. Biosci. Bioeng. 100:1-11 (2005), which is hereby incorporated by reference in its entirety).

In another embodiment, the invention further provides that the nanoparticles are utilized as an imaging agent in applications such as but not limited to: radiology. In another embodiment, the invention further provides that a ligand comprises or is a dye or a contrast agent. In another embodiment, the invention further provides a method of imaging comprising the step of irradiating the NP-dye or the NP-contrast agent.

In another embodiment, the ligand is a dye. In another embodiment, a "dye" includes a contrast agent. In another embodiment, a contrast agent is a radioactive compound or isotopes. In another embodiment, a "dye" is a photosensitive compound. In another embodiment, a "dye" is a metal. In another embodiment, the dye is selected from cyanines, phthalocyanines, chlorines, porphyrins, benzoporphyrins, psoralens, purpurins, fluoron dyes and any other agent that absorbs and emits in the range of 500-1200 nm. In another embodiment, a dye is bound directly, via an ester, an amide, an anhydride, an ether, an amine, a thioether, a disulfide, a sulfonyl ester, a sulfonamide, or any other means as disclosed herein or known to one of skill in the art to the NP's shell.

In combination with any of the above-described embodiments, some embodiments relate to a method for making a diagnostic agent composition for X-ray/computed tomography and/or MRI. The diagnostic agent composition comprises a plurality of nanoparticles. It will be understood that according to some embodiments, the particle size of the plurality of nanoparticles may be selected so as to render the nanoparticle substantially clearable by a mammalian kidney, such as a human kidney, in particulate form.

In some embodiments, the present invention is directed to a method of use of the diagnostic agent composition comprising a plurality of the nanoparticles described herein. In some embodiments, the method comprises the in-vivo or in-vitro administration of the diagnostic agent composition to a subject, which in some instances may be a live subject, such as a mammal, and subsequent image generation of the subject with an X-ray/CT device. The nanoparticles, as described above, comprise a core and a shell. The nanoparticle may be introduced to the subject by a variety of known methods. Non-limiting examples for introducing the nanoparticle to the subject include intravenous, intra-arterial or oral administration, dermal application, or direct injection into muscle, skin, the peritoneal cavity or other tissues or bodily compartments.

In another embodiment, the method comprises administering the diagnostic agent composition to a subject, and imaging the subject with a diagnostic device. The diagnostic device employs an imaging method, examples of which include, but are not limited to, MRI, optical imaging, optical coherence tomography, X-ray, computed tomography, positron emission tomography, or combinations thereof. The diagnostic agent composition, as described above, comprises a plurality of the nanoparticles.

In one embodiment, the methods described above for use of the diagnostic contrast agent further comprise monitoring delivery of the diagnostic agent composition to the subject with the diagnostic device, and diagnosing the subject; in this method data may be compiled and analyzed generally in keeping with common operation of medical diagnostic imaging equipment. The diagnostic agent composition may be an X-ray or CT contrast agent, for example, such as a composition comprising a tantalum oxide core. The diagnosing agent composition may provide for a CT signal in a range from about 100 Hounsfield to about 5000 Hounsfield units. In another example, the diagnostic agent composition may be a MRI contrast agent, such as but not limited to, an agent comprising a super-paramagnetic iron oxide core.

One embodiment of the invention provides a method for determination of the extent to which the nanoparticles described herein, such as nanoparticles having tantalum oxide or iron oxide cores, are distributed within a subject. In one embodiment, the term "distributed" includes or can be replaced with the term "bio-distributed". The subject may be a mammal or a biological material comprising a tissue sample or a cell. The method may be an in-vivo or in-vitro method. The nanoparticle may be introduced to the subject by a variety of known methods. Non-limiting examples for introducing the nanoparticle to the subject include any of the known methods described above. In one embodiment, the method comprises (a) introducing the nanoparticles into the subject, and (b) determining the distribution of the nanoparticles in the subject. Distribution within a subject may be determined using a diagnostic imaging technique such as those mentioned previously. Alternatively, the distribution of the nanoparticle in the biological material may be determined by elemental analysis. In one embodiment, Inductively Coupled Plasma Mass Spectroscopy (ICP-MS) may be used to determine the concentration of the nanoparticle in the biological material.

In another embodiment, in therapeutic applications, for example, application of a magnetic field to the patient may serve to target drug-carrying magnetic particles to a desired body site. In many cases, the dose of systemically administered chemotherapeutics is limited by the toxicity and negative side effects of the drug. Therapeutically sufficient concentrations of the drugs in the respective tissues often need to be quite high. Magnetic carrier systems should allow targeted drug delivery to achieve such high local concentrations in the targeted tissues, thereby minimizing the general distribution throughout the body. Special magnetic guidance systems can direct, accumulate, and hold the particles in the targeted area, for example, a tumor region (Alexiou et al., J. Nanosci. Nanotechnol. 6:2762 (2006), which is hereby incorporated by reference in its entirety).

In some embodiments, for instance, a compound is a drug, a therapeutic compound, a steroid, a nucleic acid based material, a protein, or derivatives, analogues, or combinations thereof, in their native form or derivatized with hydrophobic or charged moieties to enhance incorporation or adsorption to a nanoparticle. In another embodiment such compounds are water soluble or hydrophobic. Non-limiting examples of compounds include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anticoagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. In certain embodiments, a compound is an aptamer, or a nucleic acid derivative, such as peptide nucleic acid (PNA) or locked nucleic acid (LNA).

In one embodiment, the composition comprises the nanoparticle and a carrier. In another embodiment, the carrier is a buffer. In another embodiment, the carrier is a cell culture medium. In another embodiment, the carrier is a pharmaceutical carrier. In another embodiment, the carrier is chosen according to the desired application in utilizing the nanoparticles as described herein.

In one embodiment, the present invention provides a method or a process for delivering a ligand into a cell, comprising the step of contacting the cell with the nanoparticle. In another embodiment, the present invention provides a method or a process for delivering a ligand to the cell's membrane. In another embodiment, delivering is transportation of a ligand to a desired cell or any cell. The ligand can be delivered to the cell surface, cell membrane, cell endosome, within the cell membrane, nucleus or within the nucleus, or any other desired area of the cell.

In another embodiment, the present invention provides a method or a process for delivering a ligand into cells, tissues, organs or organisms. In one embodiment, the present invention provides a method or a process for delivering a compound into a cell. In another embodiment, the present invention provides a method or a process for transfecting a cell.

In another embodiment, the ligand is a Polyethylenimine polymer and a nucleic acid molecule and delivering is transfecting the cell. In a further embodiment, this invention provides a process for making a nanoparticle, comprising the steps of: Sonicating an aqueous composition comprising Ceric ammonium Nitrate (CAN) and a prefabricated nanoparticle suspension, thus obtaining a mixture; and adding a polycationic polymer to the mixture. In another embodiment, the prefabricated nanoparticle suspension comprises nanoparticles consisting iron oxide. In another embodiment, the prefabricated nanoparticle suspension comprises nanoparticles devoid of cerium.

In another embodiment, the nanoparticle may be subjected to one or more sizing operations, such as centrifugation. Magnetic separation techniques are commonly used for the purification, quantification, or identification of various substances (see Ito et al., J. Biosci. Bioeng. 100(1): 1-11 (2005); Alexiou et al., J. Nanosci. Nanotechnol., 6:2762 (2006); and Risoen et al., Protein Expr. Purif. 6(3):272-7 (1995), which are hereby incorporated by reference in their entirety). Thus, the magnetic nanoparticles are magnetically displaceable but are not necessarily permanently magnetizable. Methods for the determination of analytes using magnetic particles are described, for example, in U.S. Pat. No. 4,554,088, which is hereby incorporated by reference in its entirety.

In one embodiment, the invention provides a suspension comprising iron oxide and cerium as described herein. In one embodiment, the prefabricated nanoparticle suspension is obtained by adding Iron(II) Chloride tetrahydrate ($FeCl_2 \cdot 4H_2O$) to Iron(III) chloride hexahydrate ($FeCl_3 \cdot 6H_2O$) and sonicating and then adding in one step aqueous Ammonium hydroxide ($NH_4OH$) and sonicating the mixture again until a suspension is obtained.

In another embodiment, the Iron(III) chloride hexahydrate $FeCl_3 \cdot 6H_2O$ solution is obtained by dissolving, about 150 to 350 mg, or about 175 to 350 mg, or about 175 to 325 mg, or about 200 to 325 mg, or about 200 to 300 mg, or about 225 to 300 mg, or about 225 to 275 mg, or about 225 to 250 mg, or about 240 mg of Iron(III) chloride hexahydrate ($FeCl_3 \cdot 6H_2O$) in about 2 to 9 mL, or about 3 to 9 mL, or about 3 to 8 mL, or about 4 to 8 mL, or about 4 to 7 mL, or about 4 to 6 mL, or about 4.5 mL of deoxygenated purified water.

In another embodiment, Iron(II) Chloride tetrahydrate ($FeCl_2 \cdot 4H_2O$) in solution is obtained by dissolving, about 10 to 200 mg, or about 25 to 175 mg, or about 50 to 150 mg, or about 75 to 125 mg, or about 97.5 mg of Iron(III) chloride hexahydrate ($FeCl_3 \cdot 6H_2O$) in about 2 to 9 mL, or about 3 to 9 mL, or about 3 to 8 mL, or about 4 to 8 mL, or about 4 to 7 mL, or about 4 to 6 mL, or about 4.5 mL of water. In another embodiment, in deoxygenated purified water.

In another embodiment, a process or a method such as described herein further comprises sonication of Iron(II) Chloride tetrahydrate ($FeCl_2 \cdot 4H_2O$) and Iron(III) chloride hexahydrate ($FeCl_3 \cdot 6H_2O$) under $N_2$ at room temperature for about 2 to 20 minutes. In another embodiment, the Iron(II) Chloride tetrahydrate ($FeCl_2 \cdot 4H_2O$) and Iron(III) chloride hexahydrate ($FeCl_3 \cdot 6H_2O$) mixture is sonicated for about 5 to 20 minutes. In another embodiment, the mixture is sonicated for about 5 to 17 minutes. In another embodiment, the mixture is sonicated for about 7 to 17 minutes. In another embodiment, the mixture is sonicated for about 7 to 15 minutes. In another embodiment, the mixture is sonicated for about 10 to 15 minutes. In another embodiment, the mixture is sonicated for about 5 to 10 minutes.

In another embodiment, sonicating is employing an ultrasonic cleaner bath (Sonics, 42 KHz at full power). In another embodiment, the sonicator is any sonicator known to one of skill in the art. In another embodiment, the sonicator is a probe sonicator. In another embodiment, the sonicator is a cup horn sonicator. In another embodiment, the sonicator is a microtiter plate horn sonifier. In another embodiment, the sonicator is a sonic tabletop bath or cleaner. In another embodiment, the duration and magnitude of sonication can be readily determined by one of average skill in the art according to the sonicator and the sample.

In another embodiment, a process or a method such as described herein further comprises adding 15% to 35% weight aqueous ammonium hydroxide ($NH_4OH$) to the Iron(II) Chloride tetrahydrate ($FeCl_2 \cdot 4H_2O$) and Iron(III) chloride hexahydrate ($FeCl_3 \cdot 6H_2O$) mixture. In another embodiment, about 17% to 35% weight aqueous ammonium hydroxide ($NH_4OH$) is added to the mixture. In another embodiment, about 17% to 33% weight aqueous Ammonium hydroxide ($NH_4OH$) is added to the mixture. In another embodiment, about 15% to 33% weight aqueous Ammonium hydroxide ($NH_4OH$) is added to the mixture. In another embodiment, about 15% to 30% weight aqueous ammonium hydroxide ($NH_4OH$) is added to the mixture. In another embodiment, about 17% to 30% weight aqueous ammonium hydroxide ($NH_4OH$) is added to the mixture. In another embodiment, about 17% to 27% weight aqueous ammonium hydroxide ($NH_4OH$) is added to the mixture. In another embodiment, about 20% to 27% weight aqueous Ammonium hydroxide ($NH_4OH$) is added to the mixture. In another embodiment, about 20% to 25% weight aqueous ammonium hydroxide ($NH_4OH$) is added to the mixture. In another embodiment, about 24% weight aqueous ammonium hydroxide ($NH_4OH$) is added to the mixture.

In another embodiment, a process or a method such as described herein further comprises sonicating aqueous ammonium hydroxide ($NH_4OH$) with the Iron(II) Chloride tetrahydrate ($FeCl_2 \cdot 4H_2O$) and the Iron(III) chloride hexahydrate ($FeCl_3 \cdot 6H_2O$) mixture for about 5 to 20 minutes. In another embodiment, aqueous ammonium hydroxide ($NH_4OH$) is sonicated with the mixture for about 7 to 20 minutes. In another embodiment, aqueous ammonium hydroxide ($NH_4OH$) is sonicated with the mixture for about 7 to 17 minutes. In another embodiment, aqueous ammonium hydroxide ($NH_4OH$) is sonicated with the mixture for about 7 to 15 minutes. In another embodiment, aqueous ammonium hydroxide ($NH_4OH$) is sonicated with the mixture for about 7 to 12 minutes. In another embodiment, aqueous ammonium hydroxide ($NH_4OH$) is sonicated with the mixture for about 12 to 17 minutes. In another embodiment, aqueous ammonium hydroxide ($NH_4OH$) is sonicated with the mixture for about 10 minutes.

In another embodiment, a process or a method such as described herein further comprises washing the prefabricated nanoparticle suspension with distilled water about 1 to 6 times. In another embodiment, the prefabricated nanoparticle suspension is washed about 2 to 6 times. In another embodiment, the prefabricated nanoparticle suspension is washed about 2 to 5 times. In another embodiment, the prefabricated nanoparticle suspension is washed about 3 times.

In another embodiment, the prefabricated nanoparticle suspension is washed with about 20 to 60 mL each time. In another embodiment, the prefabricated nanoparticle suspension is washed with about 30 to 60 mL each time. In another embodiment, the prefabricated nanoparticle suspension is washed with about 30 to 50 mL each time. In another embodiment, the prefabricated nanoparticle suspension is washed with about 40 mL each time.

In another embodiment, a process or a method such as described herein further comprises employing filter tips. In another embodiment, the filter tips have a cut-off size of about 50 to 150 KDa. In another embodiment, the filter tips have a cut-off size of about 75 to 150 KDa. In another embodiment, the filter tips have a cut-off size of about 75 to 125 KDa. In another embodiment, the filter tips have a cut-off size of about 100 to 125 KDa. In another embodiment, the filter tips have a cut-off size of about 100 KDa.

In another embodiment, a process or a method such as described herein further comprises storing the nanoparticle in distilled water for about 5 to 15 hours. In another embodiment, the nanoparticle is stored in distilled water for about 7 to 15 hours. In another embodiment, the nanoparticle is stored in distilled water for about 7 to 13 hours. In another embodiment, the nanoparticle is stored in distilled water for about 9 to 13 hours. In another embodiment, the nanoparticle is stored in distilled water for about 10 hours.

In another embodiment, a process or a method such as described herein further comprises storing the nanoparticle at room temperature.

In another embodiment, the prefabricated nanoparticle suspension is an aqueous magnetite suspension.

In another embodiment, the medium comprising prefabricated nanoparticle suspension is about 10 to 60 mL. In another embodiment, the medium is about 10 to 50 mL. In another embodiment, the medium is about 10 to 40 mL. In another embodiment, the medium is about 20 to 40 mL. In another embodiment, the medium is about 30 mL.

In another embodiment, a process or a method such as described herein further comprises separating the prefabricated nanoparticle suspension from its storage phase. In another embodiment, separating is decanting. In another embodiment, separating is magnetically separating. In another embodiment, separating is manually separating. In another embodiment, separating is automatically separating.

In another embodiment, a process or a method such as described herein further comprises adding Ceric ammonium Nitrate (CAN, $(NH_4)_2Ce(IV)(NO_3)_6$) solution to the nanoparticle.

In one embodiment, the term "Ceric ammonium Nitrate and nanoparticle combination" includes or can be replaced with the term "combination". In one embodiment, the term "Ceric ammonium Nitrate and nanoparticle combination" includes or can be replaced with the term "Ceric ammonium Nitrate and nanoparticle mixture". In one embodiment, the term "Ceric ammonium Nitrate and nanoparticle mixture" includes or can be replaced with the term "Ceric ammonium Nitrate and nanoparticle combination". In one embodiment, the term "Ceric ammonium Nitrate and nanoparticle combination" includes or can be replaced with the term "mixture". In one embodiment, the term "combination" includes or can be replaced with the term "mixture". In one embodiment, the term "mixture" includes or can be replaced with the term "combination".

In another embodiment, the Ceric Ammonium Nitrate (CAN), $(NH_4)_2Ce(IV)(NO_3)_6$ solution is obtained by dissolving, about 100 to 500 mg, or about 150 to 500 mg, or about 150 to 450 mg, or about 200 to 450 mg, or about 200 to 400 mg, or about 250 to 400 mg, or about 250 to 350 mg, or about 300 mg, Ceric ammonium Nitrate in about 1 to 24 mL, or about 3 to 24 mL, or about 3 to 21 mL, or about 6 to 21 mL, or about 6 to 19 mL, or about 9 to 19 mL, or about 9 to 17 mL, or about 9 to 15 mL, or about 12 mL of MeCOMe.

In another embodiment, a process or a method such as described herein further comprises adding water to Ceric Ammonium Nitrate (CAN) and nanoparticle combination. In another embodiment, purified water is added to the combination. In another embodiment, degassed water is added to the combination. In another embodiment, degassed purified water is added to the combination. In another embodiment, about 1 to 24 mL, or about 3 to 24 mL, or about 3 to 21 mL, or about 6 to 21 mL, or about 6 to 19 mL, or about 9 to 19 mL, or about 9 to 17 mL, or about 9 to 15 mL, or about 12 mL of water is added to the combination.

In another embodiment, Ceric Ammonium Nitrate (CAN) and nanoparticle combination is obtained by adding water and sonicating the combination. In another embodiment, sonication lasts for 30 to 120 minutes. In another embodiment, sonication lasts for 30 to 90 minutes. In another embodiment, sonication lasts for 50 to 70 minutes. In another embodiment, sonication lasts for about 60 minutes.

In another embodiment, the combination is sonicated at about −10 to 10 degrees Celsius. In another embodiment, the combination is sonicated at about −5 to 5 degrees Celsius. In another embodiment, the combination is sonicated at about 0 degrees Celsius.

In another embodiment, the combination is sonicated under an inert atmosphere. In another embodiment, the combination is sonicated under an inert nitrogen atmosphere. In another embodiment, the combination is sonicated under an inert argon atmosphere.

In another embodiment, sonicating is employing a direct immersion of titanium horn (Sonics, 750 Watt, power modulator set-up at 25%). In another embodiment, the sonicator is any sonicator known to one of skill in the art. In another embodiment, the sonicator is a probe sonicator. In another embodiment, the sonicator is a cup horn sonicator. In another embodiment, the sonicator is a microtiter plate horn sonicator. In another embodiment, the sonicator is a sonic tabletop bath or cleaner.

In another embodiment, a process or a method such as described herein further comprises washing the nanoparticle with distilled water about 1 to 6 times. In another embodiment, the prefabricated nanoparticle suspension is washed about 2 to 6 times. In another embodiment, the prefabricated nanoparticle suspension is washed about 2 to 5 times. In another embodiment, the prefabricated nanoparticle suspension is washed about 3 times.

In another embodiment, the prefabricated nanoparticle suspension is washed with about 5 to 20 mL each time. In another embodiment, the prefabricated nanoparticle suspension is washed with about 5 to 15 mL each time. In another embodiment, the prefabricated nanoparticle suspension is washed with about 10 mL each time.

In another embodiment, the prefabricated nanoparticle suspension is washed with a filtering device. In another embodiment, the prefabricated nanoparticle suspension is washed with a centrifugal filtering device (100K; processed at 4,000 rpm). In another embodiment, the filtration device is any filtration device known to one of skill in the art. In another embodiment, filtration is employed for about 3 to 10 minutes. In another embodiment, filtration is employed for about 5 to 6 minutes. In another embodiment, filtration is employed at room temperature. In another embodiment, filtration is employed at about 15 to 25 degrees Celsius. In another embodiment, filtration is employed at about 18 degrees Celsius. In another embodiment, the nanoparticle is stored in water. In another embodiment, the nanoparticle is stored in distilled water.

In another embodiment, the nanoparticle has a Transmission Electron Microscopy (TEM) diameter of about 5 to 15 nm. In another embodiment, the nanoparticle has a TEM diameter of about 5 to 12 nm. In another embodiment, the nanoparticle has a TEM diameter of about 5 to 12 nm. In another embodiment, the nanoparticle has a TEM diameter of about 5 to 10 nm. In another embodiment, the nanoparticle has a TEM diameter of about 5.28 nm. In another embodiment, the nanoparticle has a TEM diameter of about 7.61 nm. In another embodiment, the nanoparticle has a TEM diameter of about 9.94 nm.

In another embodiment, the nanoparticle has a Dynamic light scattering (DLS) Hydrodynamic diameter of about 20 to 70 nm. In another embodiment, the nanoparticle has a DLS Hydrodynamic diameter of about 25 to 70 nm. In another embodiment, the nanoparticle has a DLS Hydrodynamic diameter of about 25 to 65 nm. In another embodiment, the nanoparticle has a DLS Hydrodynamic diameter of about 30 to 65 nm. In another embodiment, the nanoparticle has a DLS Hydrodynamic diameter of about 35 to 60 nm. In another embodiment, the nanoparticle has a DLS Hydrodynamic diameter of about 37 nm. In another embodiment, the nanoparticle has a DLS Hydrodynamic diameter of about 55 nm.

In another embodiment, the nanoparticle has a Polydispersity Index (PDI) value of about 0.1 to 0.2. In another embodiment, the nanoparticle has a PDI value of about 0.11 to 0.2. In another embodiment, the nanoparticle has a PDI value of about 0.105 to 0.9. In another embodiment, the nanoparticle has a PDI value of about 0.1 to 0.7. In another embodiment, the nanoparticle has a PDI value of about 0.1 to 0.5. In another embodiment, the nanoparticle has a PDI value of about 0.1 to 0.2. In another embodiment, the nanoparticle has a PDI value of about 0.118. In another embodiment, the nanoparticle has a PDI value of about 0.149.

In another embodiment, a nanoparticle as described herein is obtained by adding a polycationic polymer while the aqueous ammonium hydroxide ($NH_4OH$) and the prefabricated nanoparticle suspension are being sonicated.

In another embodiment, the nanoparticle has a Transmission Electron Microscopy (TEM) diameter of about 3 to 15 nm. In another embodiment, the nanoparticle has a TEM diameter of about 3 to 13 nm. In another embodiment, the nanoparticle has a TEM diameter of about 4 to 13 nm. In another embodiment, the nanoparticle has a TEM diameter of about 4 to 11 nm. In another embodiment, the nanoparticle has a TEM diameter of about 5 nm. In another embodiment, the nanoparticle has a TEM diameter of about 7.65 nm. In another embodiment, the nanoparticle has a TEM diameter of about 10.3 nm.

In another embodiment, the nanoparticle has a Dynamic light scattering (DLS) Hydrodynamic diameter of about 30 to 100 nm. In another embodiment, the nanoparticle has a DLS Hydrodynamic diameter of about 30 to 90 nm. In another embodiment, the nanoparticle has a DLS Hydrodynamic diameter of about 40 to 90 nm. In another embodiment, the nanoparticle has a DLS Hydrodynamic diameter of about 50 to 90 nm. In another embodiment, the nanoparticle has a DLS Hydrodynamic diameter of about 50 to 80 nm. In another embodiment, the nanoparticle has a DLS Hydrodynamic diameter of about 50 to 70 nm. In another embodiment, the nanoparticle has a DLS Hydrodynamic diameter of about 58 nm. In another embodiment, the nanoparticle has a DLS Hydrodynamic diameter of about 62 nm.

In another embodiment, the nanoparticle has a Polydispersity Index (PDI) value of about 0.05 to 0.4. In another embodiment, the nanoparticle has a PDI value of about 0.1 to 0.4. In another embodiment, the nanoparticle has a PDI value of about 0.1 to 0.3. In another embodiment, the nanoparticle has a PDI value of about 0.18.

In another embodiment, a nanoparticle as described herein is obtained by adding a polycationic polymer to the mixture after the mixture has been obtained.

In another embodiment, the polycationic polymer is Polyethylenimine (PEI).

In another embodiment, the added PEI has a molecular weight of about 10 to 50 KDa. In another embodiment, the added PEI has a molecular weight of about 10 to 45 KDa. In another embodiment, the added PEI has a molecular weight of about 15 to 45 KDa. In another embodiment, the added PEI has a molecular weight of about 15 to 40 KDa. In another embodiment, the added PEI has a molecular weight of about 20 to 40 KDa. In another embodiment, the added PEI has a molecular weight of about 20 to 35 KDa. In another embodiment, the added PEI has a molecular weight of about 20 to 30 KDa. In another embodiment, the added PEI has a molecular weight of about 25 KDa.

In another embodiment, the added PEI has a weight ratio of about 2 to 10 to the metal oxide. In another embodiment, the added PEI has a weight ratio of about 2 to 8. In another embodiment, the added PEI has a weight ratio of about 4 to 8. In another embodiment, the added PEI has a weight ratio of about 4 to 6. In another embodiment, the added PEI has a weight ratio of about 5.25.

In another embodiment, the obtained nanoparticle has a cerium to metal oxide ratio molar mass of about 0.01 to 0.05. In another embodiment, the obtained nanoparticle has a cerium to metal oxide ratio molar mass of about 0.01 to 0.04. In another embodiment, the obtained nanoparticle has a cerium to metal oxide ratio molar mass of about 0.02 to 0.04 In another embodiment, the obtained nanoparticle has a cerium to metal oxide ratio molar mass of about 0.02 to 0.03. In another embodiment, the obtained nanoparticle has a cerium to metal oxide ratio molar mass of about 0.0204.

In another embodiment, the nanoparticle has a Transmission Electron Microscopy (TEM) diameter of about 2 to 15 nm. In another embodiment, the nanoparticle has a TEM diameter of about 2 to 12 nm. In another embodiment, the nanoparticle has a TEM diameter of about 4 to 12 nm. In another embodiment, the nanoparticle has a TEM diameter of about 4 to 10 nm. In another embodiment, the nanoparticle has a TEM diameter of about 4.35 nm. In another embodiment, the nanoparticle has a TEM diameter of about 6.5 nm. In another embodiment, the nanoparticle has a TEM diameter of about 8.65 nm.

In another embodiment, the nanoparticle has a Dynamic light scattering (DLS) Hydrodynamic diameter of about 30 to 100 nm. In another embodiment, the nanoparticle has a DLS Hydrodynamic diameter of about 30 to 90 nm. In another embodiment, the nanoparticle has a DLS Hydrodynamic diameter of about 40 to 90 nm. In another embodiment, the nanoparticle has a DLS Hydrodynamic diameter of about 50 to 90 nm. In another embodiment, the nanoparticle has a DLS Hydrodynamic diameter of about 50 to 80 nm. In another embodiment, the nanoparticle has a DLS Hydrodynamic diameter of about 65 nm. In another embodiment, the nanoparticle has a DLS Hydrodynamic diameter of about 78 nm.

In another embodiment, the nanoparticle has a Polydispersity Index (PDI) value of about 0.05 to 0.4. In another embodiment, the nanoparticle has a PDI value of about 0.1 to 0.4. In another embodiment, the nanoparticle has a PDI value of about 0.1 to 0.3. In another embodiment, the nanoparticle has a PDI value of about 0.18. In another embodiment, the nanoparticle has a PDI value of about 0.207.

In another embodiment, the product of the mixture is a composition of a polymer and organic matter.

In another embodiment, the product of the mixture is a mixed PEI-organic matter polyCOOH/$[Ce^{3/4+}L_n]$ complex adlayer.

In one embodiment, the present invention provides that the composition is a "pharmaceutical composition". In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the ligand of interest, which is accountable for the biological effect.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the carrier is a physiologically acceptable carrier. In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, PA, latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Various embodiments of dosage ranges are contemplated by this invention.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Per-oral compositions, in some embodiments, comprise liquid solutions, emulsions, suspensions, and the like. In some embodiments, pharmaceutically-acceptable carriers suitable for preparation of such compositions are well known in the art.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables of the invention are formulated in aqueous solutions. In one embodiment, injectables of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulphite and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in the context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulphite and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically acceptable carrier to be used in conjunction with the compound is basically determined by the way the compound is to be administered. If the subject compound is to be injected, in one embodiment, the pharmaceutically acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration, and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, it will be appreciated that the nanoparticle of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

In another embodiment, the present invention provides a method or a process for obtaining hydrophilic spherical, positively charged super-paramagnetic maghemite (gamma-$Fe_2O_3$) nanoparticles that are doped by controlled amounts of surface [$Ce^{3/4+}L_n$] complexes/$Ce^{3/4+}$ lanthanide metal cations for NP aggregation control (charge repulsion). In another embodiment, the present invention provides a method or a process for obtaining an ultrasound-deposited polycarboxylated (polyCOOH) organic shell.

In another embodiment, provided herein a nanofabrication process using a specific [$Ce^{3/4+}L_n$] complex coordination chemistry of any Lewis base ligand (N/O/S-containing organic species/polymers (two-steps). In another embodiment, provided herein a nanofabrication process using an injection process where the PEI phase is attached onto the surface of CAN-maghemite nanoparticles (one-step). In another embodiment, the resulting NPs of the invention show very high-level capabilities for siRNA/miRNA electrostatic capture and corresponding delivery/gene silencing at very low loading levels (much better than the well-known lipofectamine transfection lipidic reagents). In another embodiment, the current unique nanoparticulate systems based on $Ce^{3/4+}$ cation-doped maghemite NPs possess orthogonal surface multifunctionality for $2^{nd}$ step ligand attachment, i.e., via chemical manipulation of surface [$Ce^{3/4+}L_n$] complexes (coordination chemistry), of their oxidatively/ultrasonically grown polyCOOH organic matter and via their surface PEI-based polyamine shells. In another embodiment, functional CAN-maghemite nanoparticles have been successfully functionalized (contact process) using polycationic (25 kDa branched PEI, Chi, PLL and corresponding mixtures) and selected polyanionic polymers (alginic & hyaluronic acids) for nanocarrier toxicity mitigation with effective gene silencing features. In another embodiment, controlled $H_2O_2$-based oxidative process of the endosomolytic 25 kDa branched PEI component within corresponding nanocarriers/NPs (NCs) resulted in significant toxicity reduction of corresponding NCs/NPs while securing effective gene silencing capabilities. In another embodiment, provided herein NPs with dual capability MRI ($T_2$ contrast agent) and siRNA/miRNA delivery nanoscale systems for both in vitro and in vivo applications.

EXAMPLES

Example 1: Nanoparticle (NP) Doping Process

A former low-level $Ce^{3/4+}$ cation doping protocol (Haviv, Greneche et al. 2010) has been significantly modified with the following modified protocol: (i) the introduction of a minimal 2 hours (h)-long ageing period at the fabrication level of starting MASSART magnetite NPs before the Ce-doping reaction, (ii) the use of significantly more concentrated reagents (CAN for example)/NP suspensions used for the doping step, and (iii) since relating the use of a different time-saving NP cleaning/NP washing procedure (the monodispersity feature of final CAN-gamma-$Fe_2O_3$ NPs), i.e, using commercially available centrifuge filter tips possessing a 100 KDa cut-off instead of the former time-ineffective month-long magnetism-based NP cleaning/washing method (powerful external magnet).

A1. fabrication—Starting neat neutral magnetite ($Fe_3O_4$) nanoparticles ($Fe_3O_4$ NPs, basic Massart hydrolytic method). A solution of $FeCl_3 \cdot 6H_2O$ (240.0 mg, 0.9 mmol) dissolved in deoxygenated milliQ purified $H_2O$ (4.5 mL) was mixed with an aqueous solution of $FeCl_2 \cdot 4H_2O$ (97.5 mg, 0.45 mmol, 4.5 mL $H_2O$). This solution was kept under $N_2$ and ultrasonicated (Bransonic® ultrasonic cleaner bath, 2510E MTH model, 42 KHz at full power) for 5-10 min at room temperature. Then, a concentrated 24% weight aqueous $NH_4OH$ (0.75 mL) was introduced in one shot, resulting in an immediate black precipitation of magnetite ($Fe_3O_4$) NPs. Sonication was continued for 10 additional minutes. Resulting $Fe_3O_4$ NPs were transferred into a glass bottle (100 mL), magnetically decanted (using a strong external magnet), and washed with dd$H_2O$ (3×40 mL) until neutrality. Then, brilliant black free flowing magnetite NPs were stored as a 30 mL NP suspension in dd$H_2O$ before any further processing. Then, an ageing process was executed for a minimum storage time of 2 h in these conditions (room temperature).

Initially, the former aqueous magnetite NP suspension (30 mL) was magnetically decanted to separate the magnetite NPs from its aqueous storage phase. Ceric ammonium Nitrate (CAN, $(NH_4)_2Ce(IV)(NO_3)_6$, 300.0 mg, 0.547 mmol) dissolved in 12.0 mL MeCOMe was introduced onto decanted magnetite NPs, followed by the addition of degassed milliQ purified $H_2O$ (12.0 mL). The corresponding mixture was ultrasonicated using a high-power sonicator (Sonics®, Vibra cell, 750 Watt, power modulator set-up at 25%) equipped with a titanium horn (1 h, 0° C.) under an inert argon atmosphere.

Figure 3A:
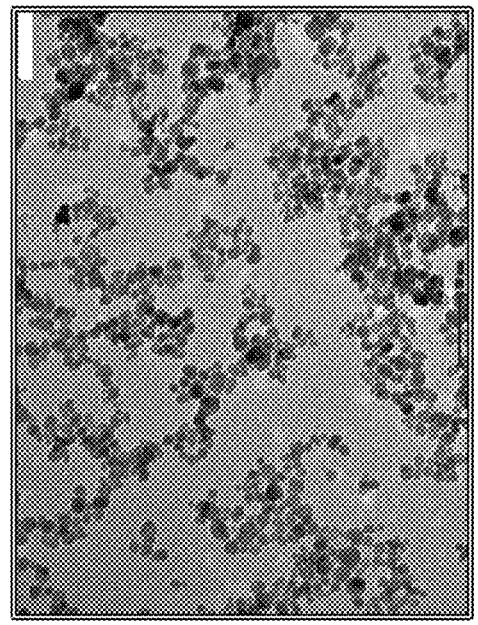
FIGS. 3a-c. includes: TEM microphotographs (FIG. 3a-b, wide and zoomed in, respectively) and a graph (FIG. 3c) showing the size distribution of ultra-small 7.61±2.33 nm-sized CAN-gamma-$Fe_2O_3$ NPs.
Figure 3B:
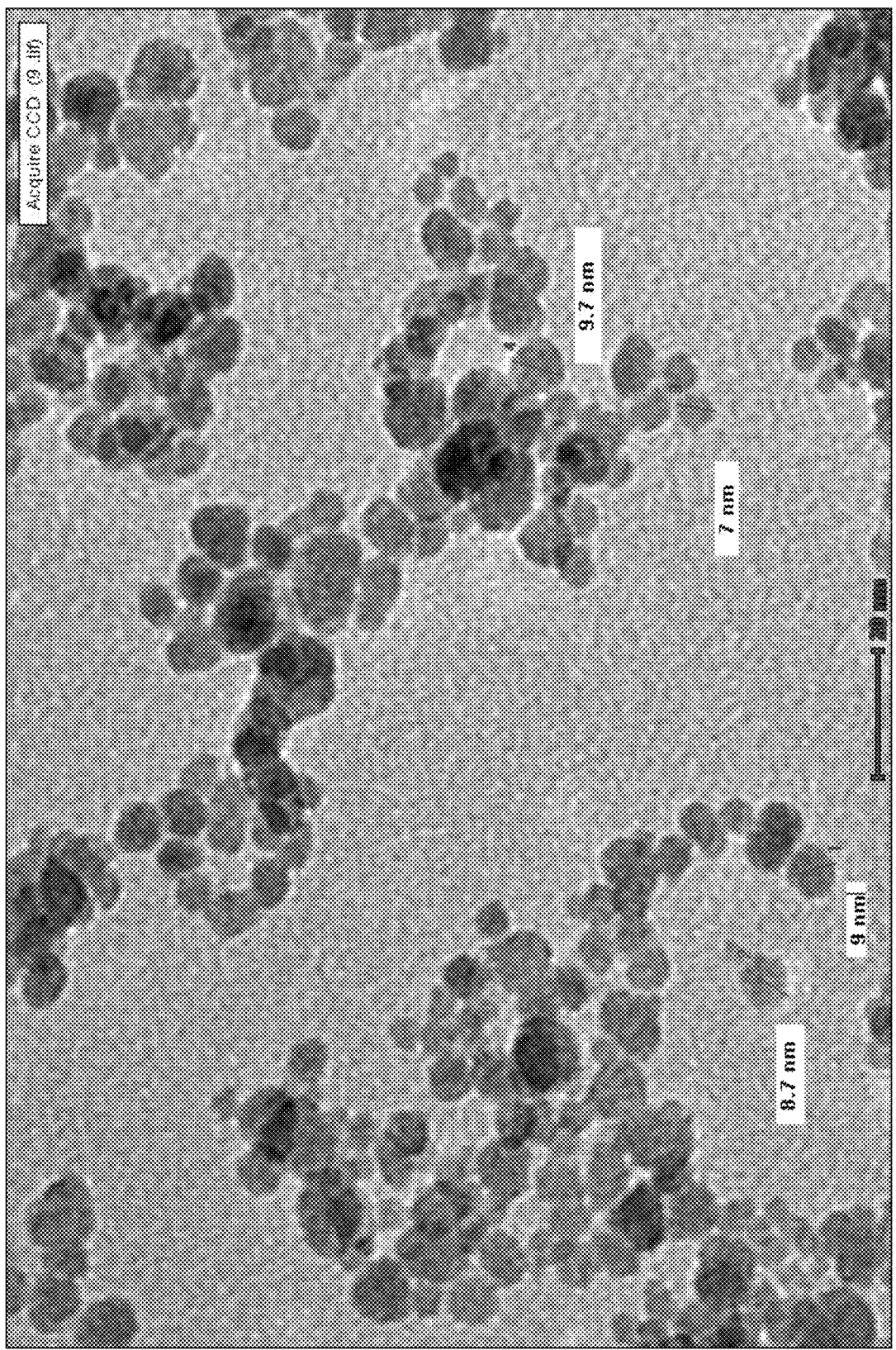
Figure 3C:
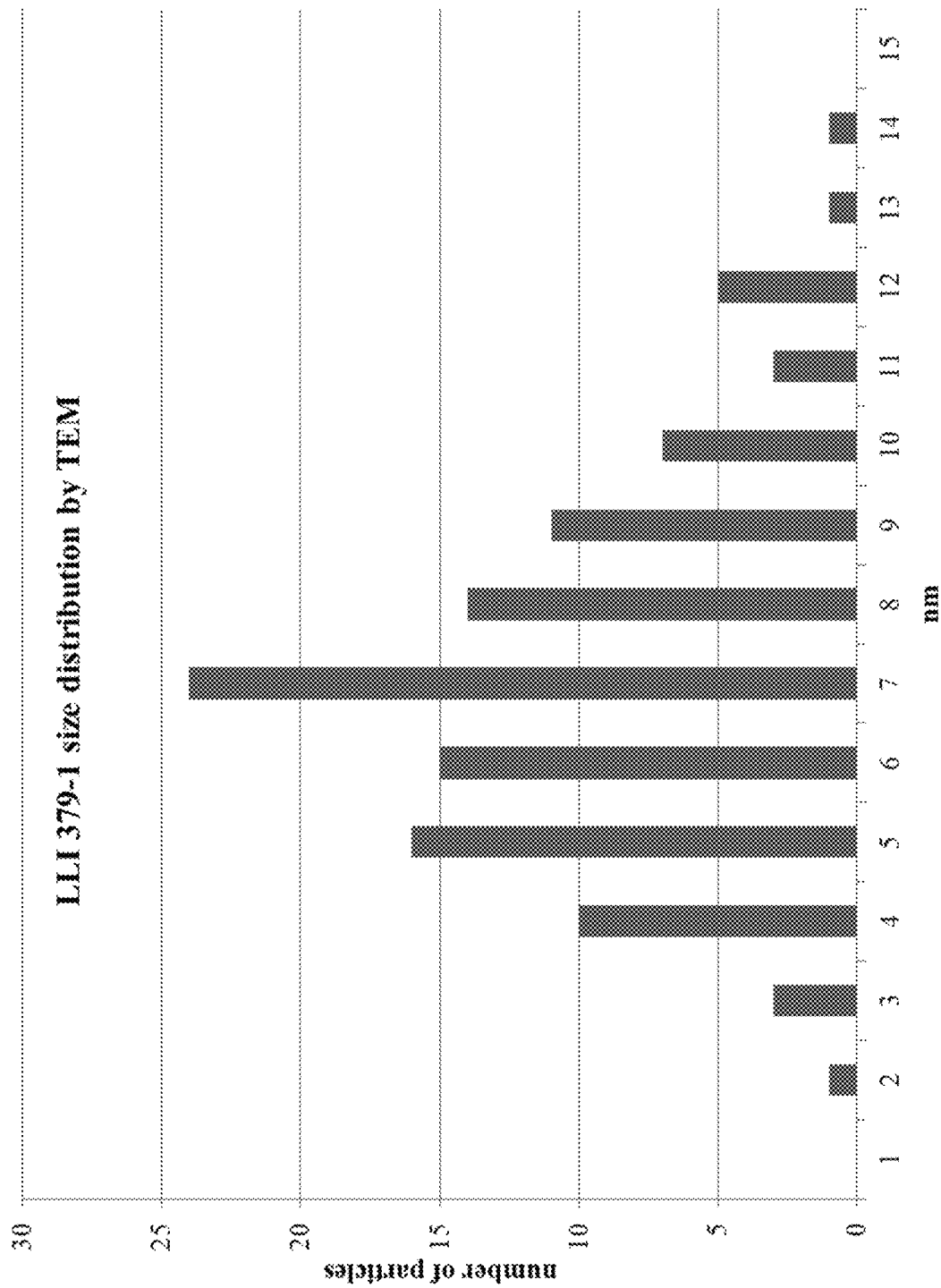
Figure 4A:
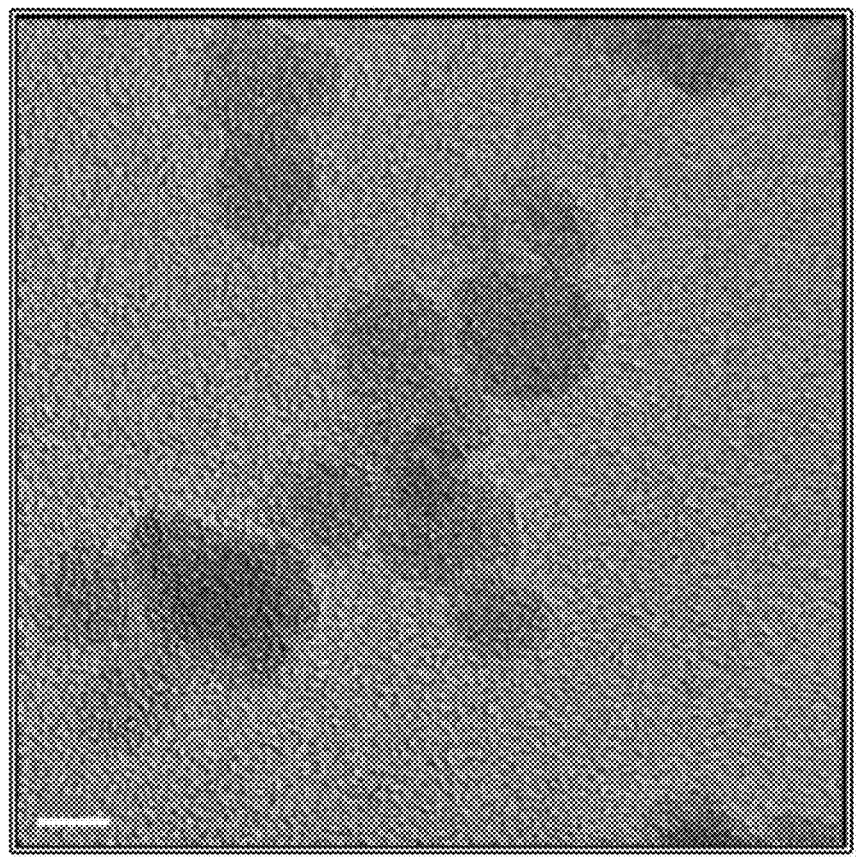
FIGS. 4a-b. includes: a HR-TEM microphotograph and a graph, showing ultra-small CAN-gamma-$Fe_2O_3$ NPs (FIG. 4a) and the compositional EDAX analysis (presence of Fe, C, O, & C elements) (FIG. 4b).

At this stage, the resulting highly stabilized hydrophilic CAN-gamma-$Fe_2O_3$ NPs were purified [washing with dd$H_2O$ (3×10 mL) using an Amicon® Ultra-15 centrifugal filter devices (100K) processed at 4,000 rpm during 5-6 min (rt, 18° C.) and re-dispersed in dd$H_2O$ (15 mL)] or alternatively processed for PEI (branched PEI polymer, 25.0 kDa) functionalization/decoration using (i) mild aqueous contacting and/or (ii) ultrasonication-assisted injection (see corresponding detailed experimental protocols mentioned below). TEM (FIGS. 3a and 4a)/HR-TEM analysis (FIGS. 3 and 4) provided an average diameter of 7.61±2.33 nm (TEM) and of 37.0-55.0 nm (DLS, PDI: 0.118-0.149) for resulting cleaned CAN-gamma-$Fe_2O_3$ NPs (average NP concentration: 5.0-6.0 mg/mL) before any further processing was done.

Figure 4B:
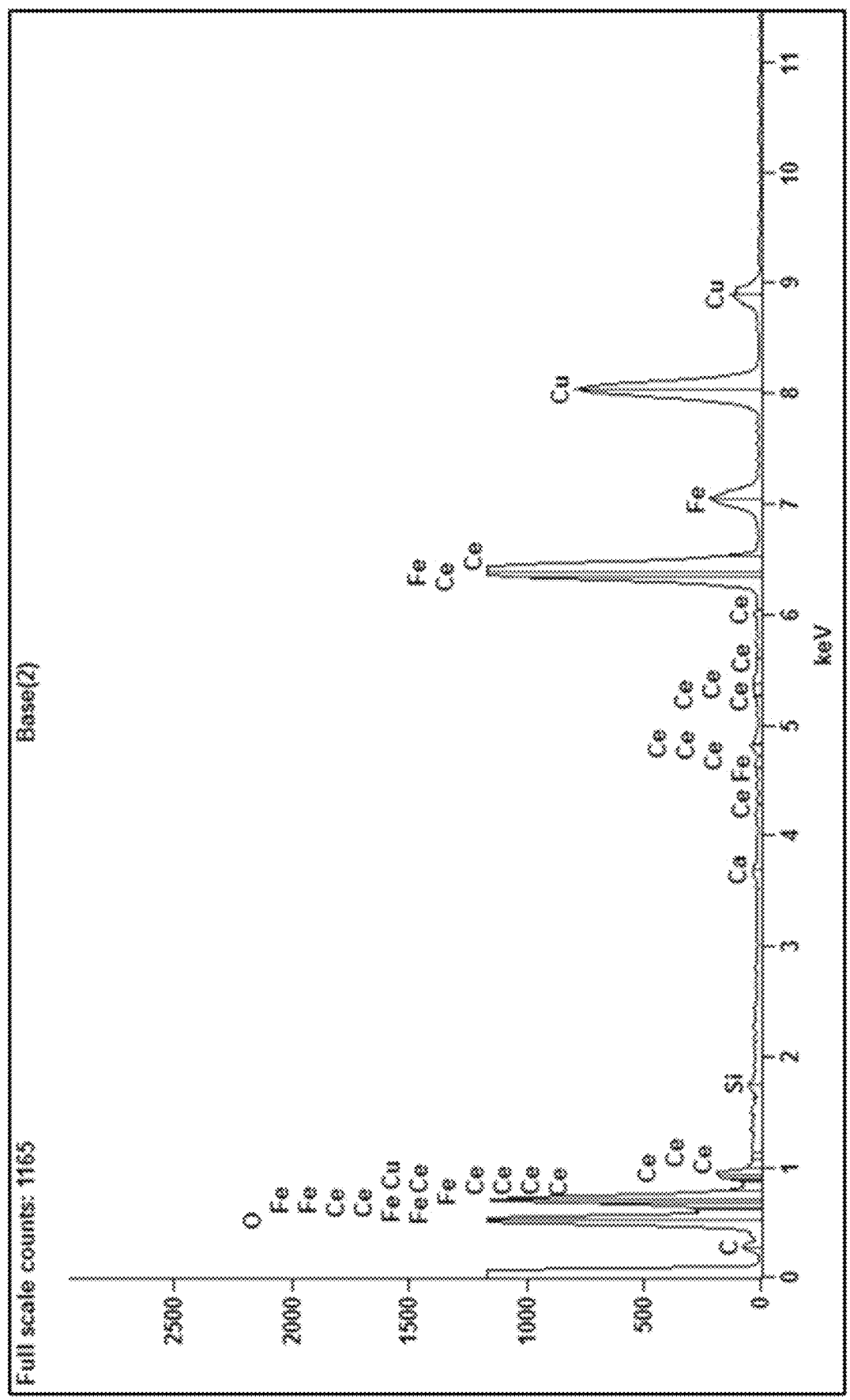
Figure 5:
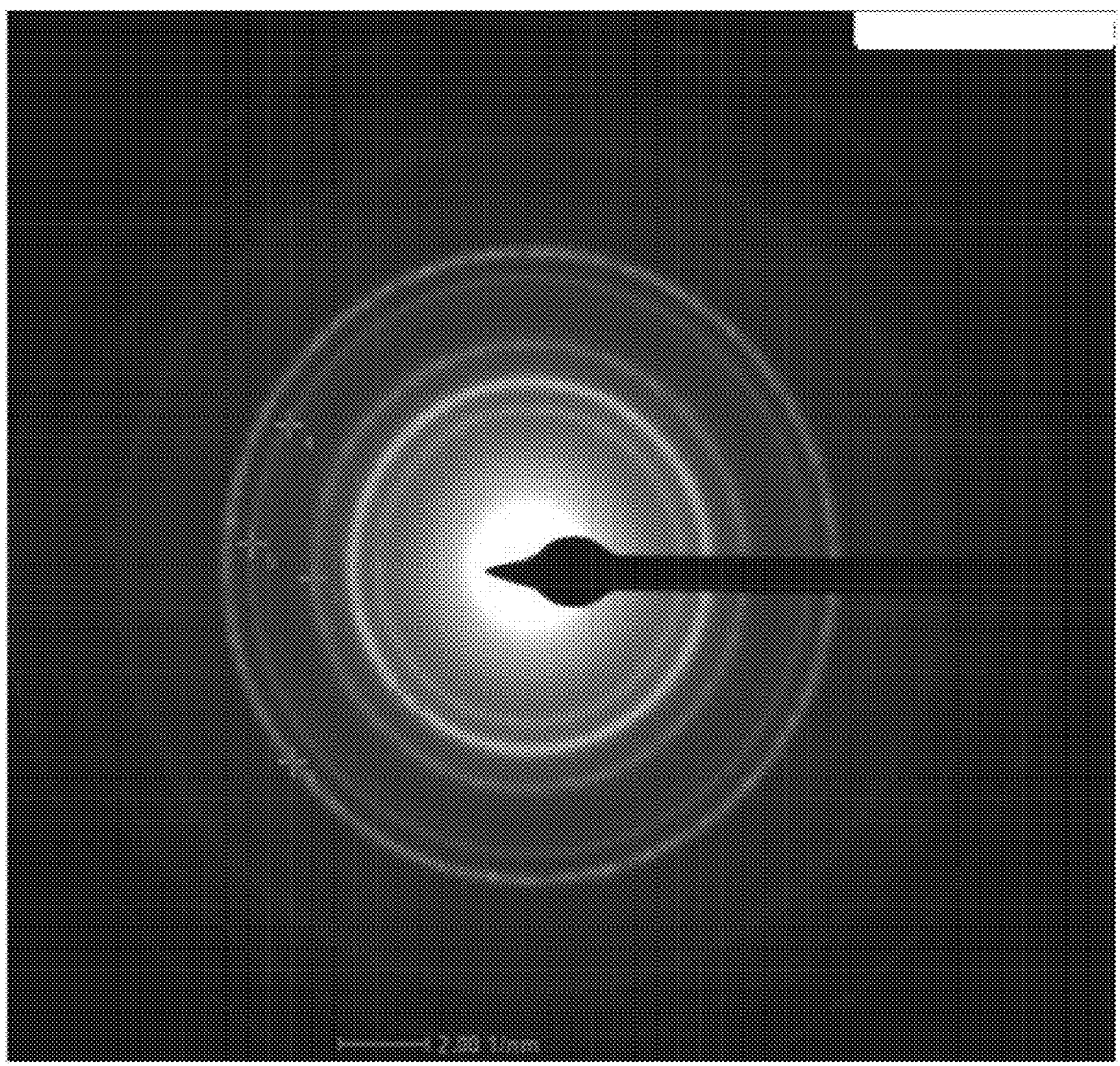
FIG. 5. is a photograph showing the TEM/Selected Area Electron Diffraction (SAED) patterns of ultra-small CAN-gamma-$Fe_2O_3$ NPs: #1 (plane 220), #2 (plane 311), #3 (plane 400), & #6 (plane 440).
Figure 6:
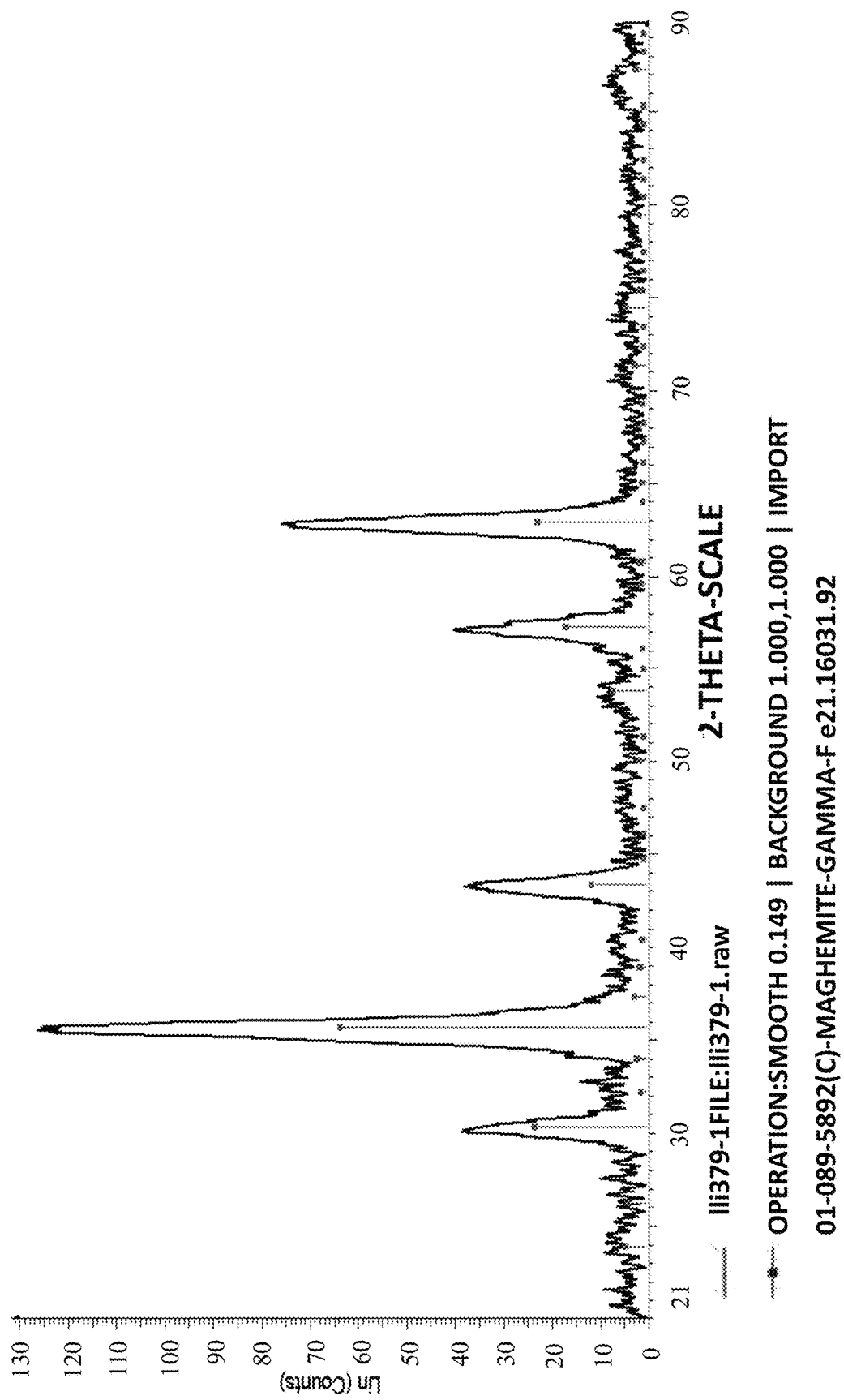
FIG. 6. is a graph showing the XRD spectrum of ultra-small CAN-gamma-$Fe_2O_3$ NPs—2θ=30.266 (plane 2,2,0), 35.651 (plane 3,1,1), 43.332 (plane 4,0,0), 53.766 (plane 4,2,2), 57.319 (plane 5,1,1), and 62.949 (plane 4,4,0).
Figure 7A:
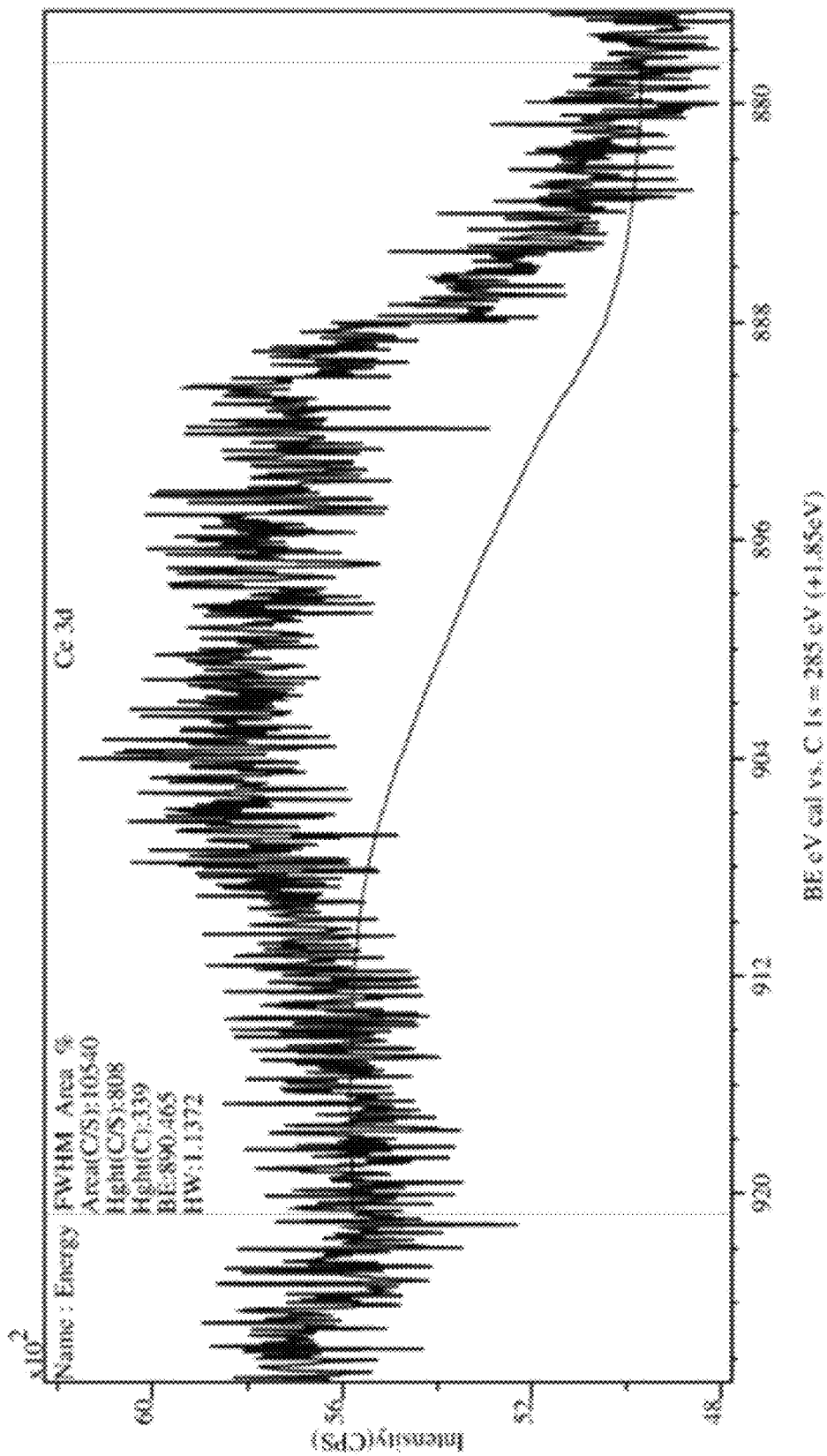
FIGS. 7a-d. is a graph showing the XPS spectroscopy of ultra-small CAN-gamma-$Fe_2O_3$ NPs—Presence of characteristic Ce $3d_{5/2}$, N 1s (nitrate anion), C 1s (presence of COOH groups) & Fe $2p_{3/2}$ (clean $Fe_2O_3$ maghemite phase) peaks.
Figure 7B:
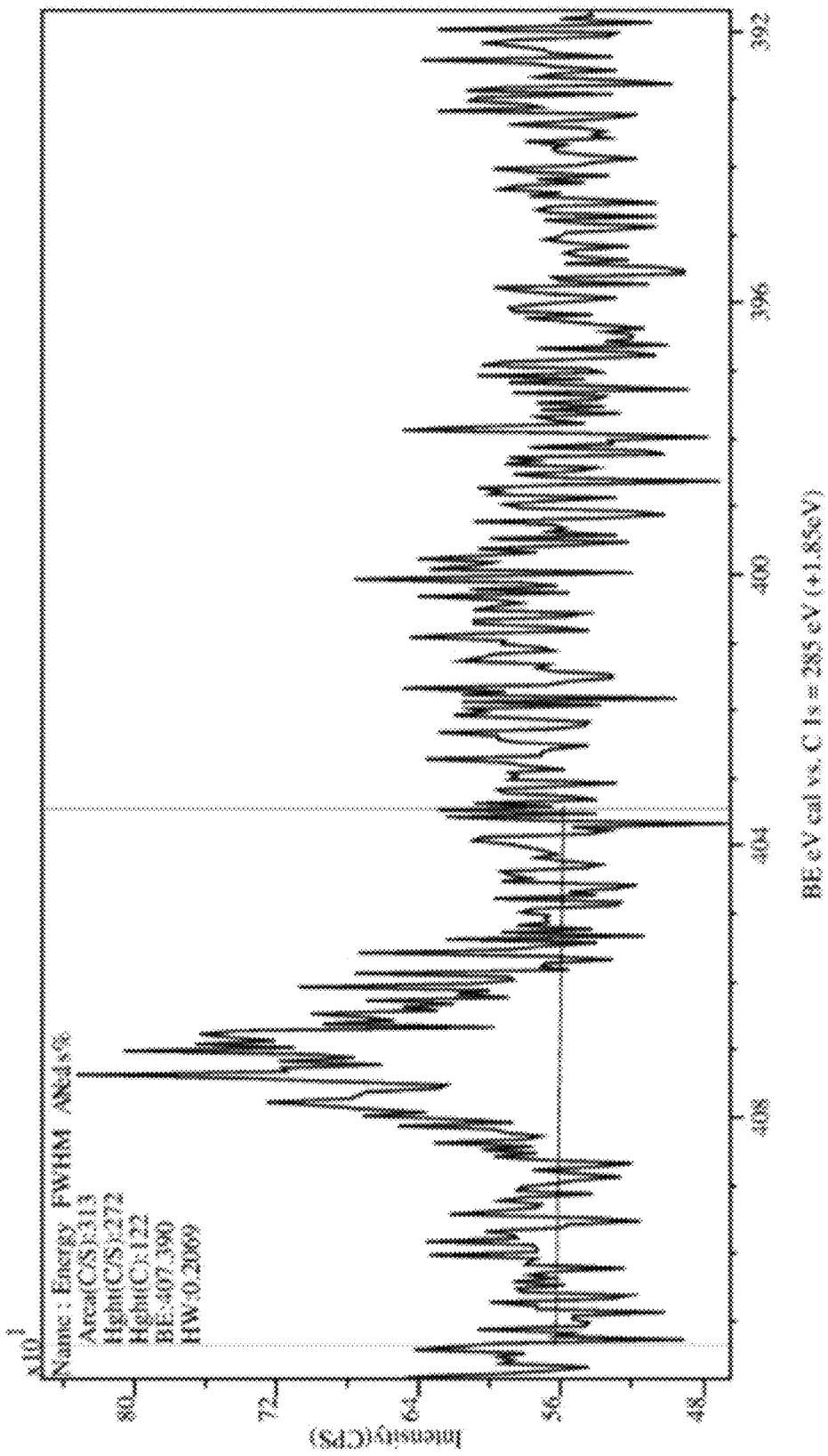
Figure 7C:
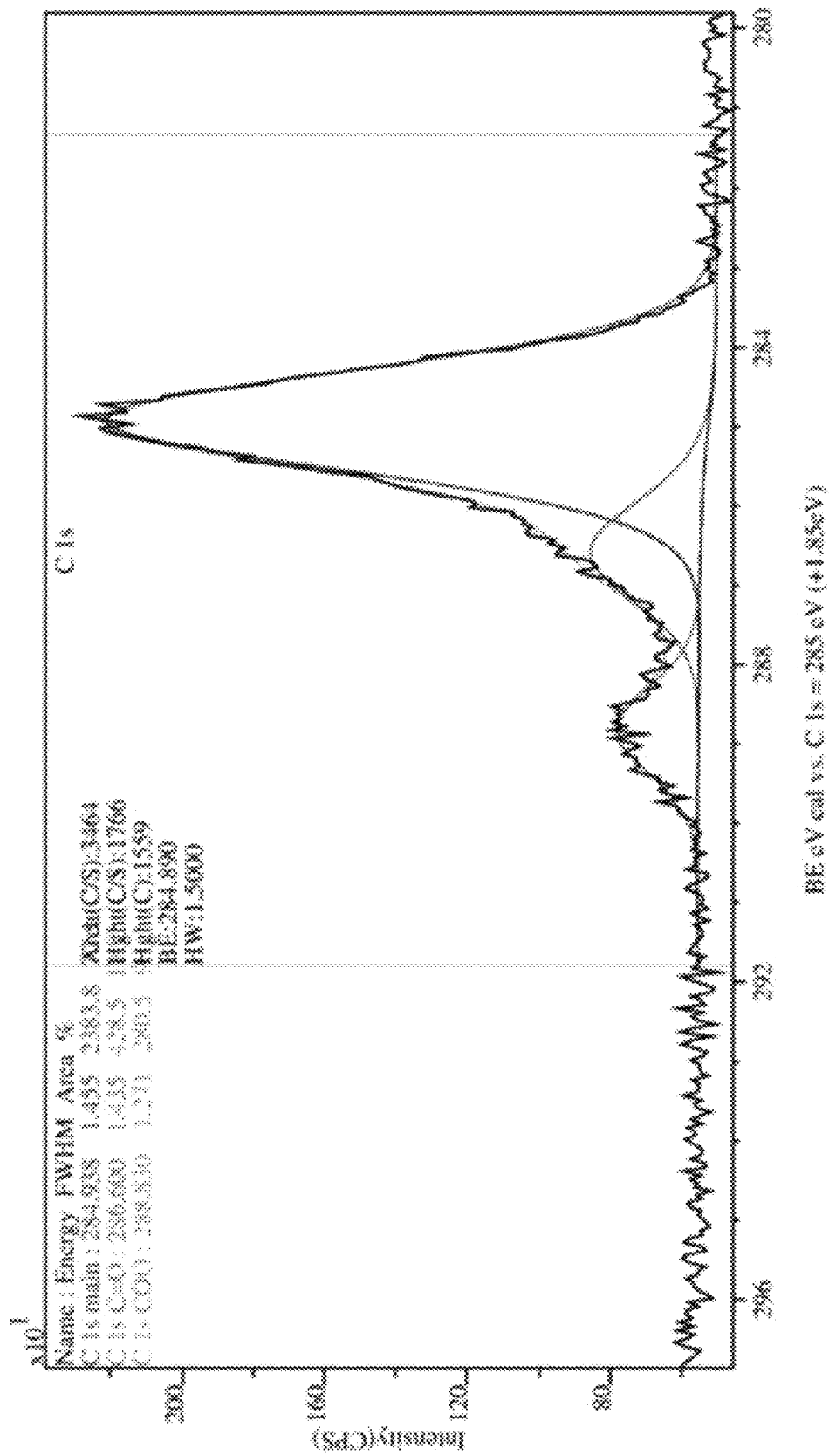
Figure 7D:
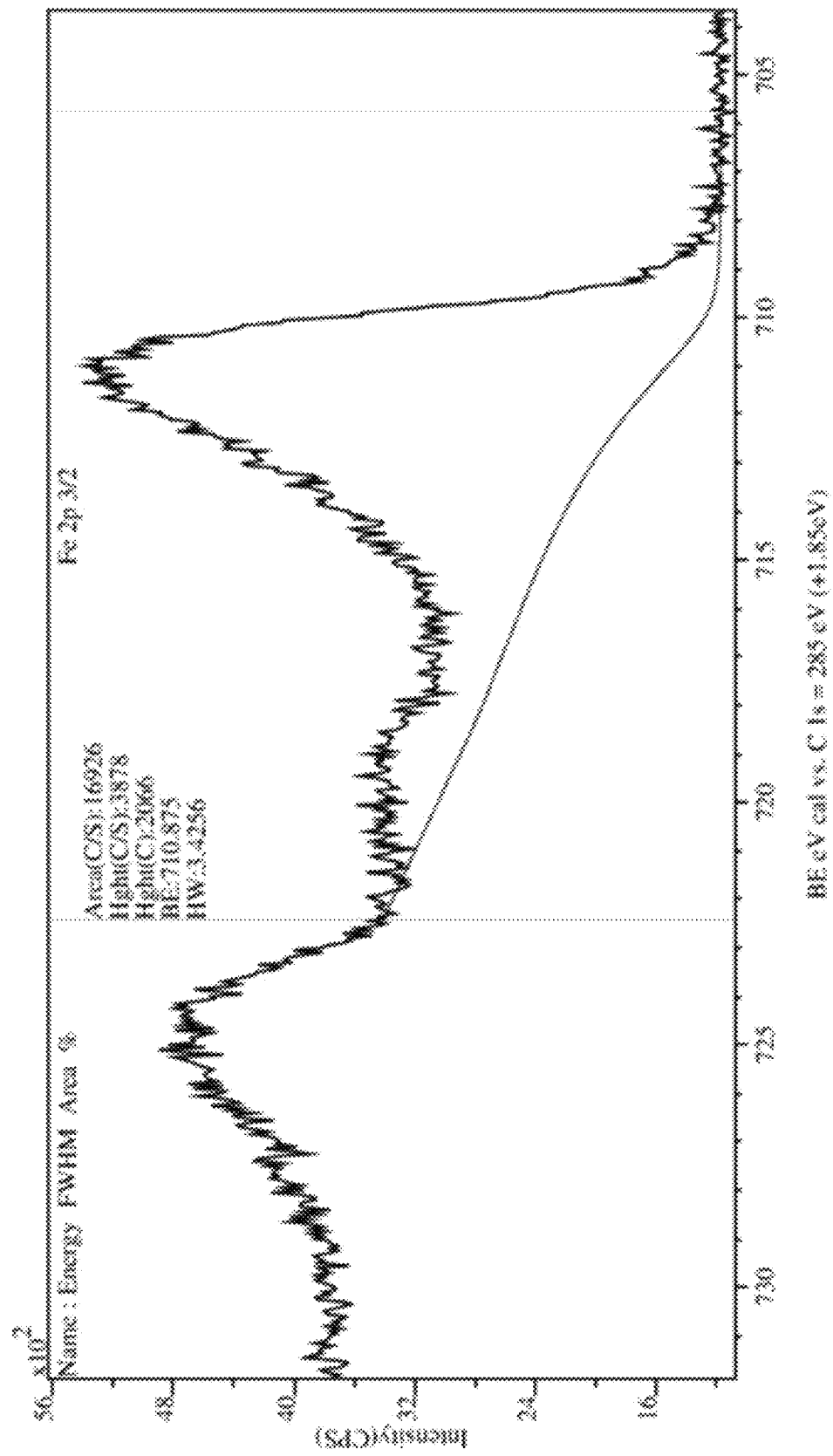
Figure 9:
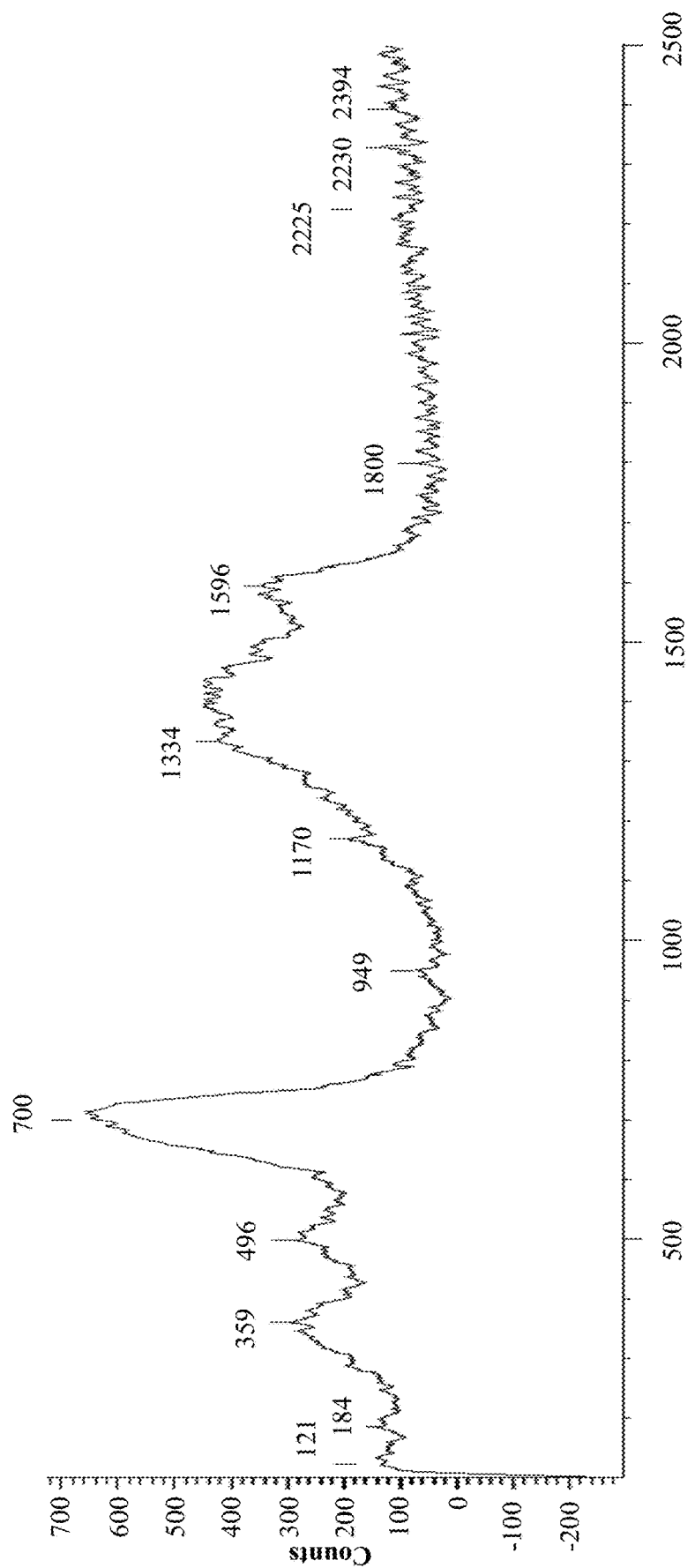
FIG. 9. is a graph showing the Raman spectrum of ultra-small CAN-gamma-$Fe_2O_3$ NPs (laser wavelength: 512 nm).

The latter improved CAN-mediated doping protocol and afforded highly positively charged (ξ potential: +43.0-53.0 mV range) non-aggregated ultra-small spherical CAN-gamma-$Fe_2O_3$ NPs that possessed a high level of surface doping $Ce^{3/4+}$ atoms/cations as measured by Inductively Coupled Plasma Atomic Emission Spectroscopy (ICP-AES, Fe & Ce=5.210 & 0.1525 mg/mL suspension, NP weight ratio Ce/Few: 0.029; Fe & Ce (molar values)=0.0933 & 0.0019 mmol/mg NPs, NP molar ratio Ce/Fem: 0.0204) and compositional TEM/energy-dispersive EDAX analyses (FIG. 4b). Particle crystallinity has been also demonstrated by HR-TEM (FIG. 4a) using Selected Area Electron Diffraction (SAED) patterns for most intense characteristic individual diffraction planes (220), (311), (400), and (440) (FIG. 5). This result has been confirmed by powder X-ray diffraction (XRD, FIG. 6) since it afforded an XRD spectrum that disclosed a six 2θ peak pattern compatible with a maghemite gamma-$Fe_2O_3$ inverse spinel structure (2θpeak values: 30.266 (plane 220), 35.651 (plane 311), 43.332 (plane 400), 53.766 (plane 422), 57.319 (plane 511), and 62.949 (plane 440), maghemite reference JCPDS card no. 39-1346—red reference peaks). Raman spectroscopy (FIG. 9) disclosed the following three Raman active phonon modes at 359.0 ($T_{2g}$), 496.5 ($E_g$), and 699.8 cm$^{-1}$ ($A_{1g}$, broad scattering peak) that are also characteristic of a maghemite phase.

Moreover and beyond former ICP and TEM-EDAX analyses mentioned above, the presence of surface doping $Ce^{3/4+}$ atoms/cations has been also confirmed by surface-sensitive X-ray photoelectron spectroscopy (XPS, FIG. 7). More specifically, the observed broad peak appearing at a binding energy (BE) of 890.47 eV could be unambiguously ascribed to Ce $3d_{5/2}$ electrons (NIST X-ray Photoelectron Spectroscopy Database/Web site: http://srdata.nist.gov/xps/Default.aspx). This same XPS analysis of CAN-gamma-$Fe_2O_3$ NPs enabled to draw additional significant observations that provided much deeper understanding/insight in the CAN-mediated NP oxidative doping process.

Figure 2:
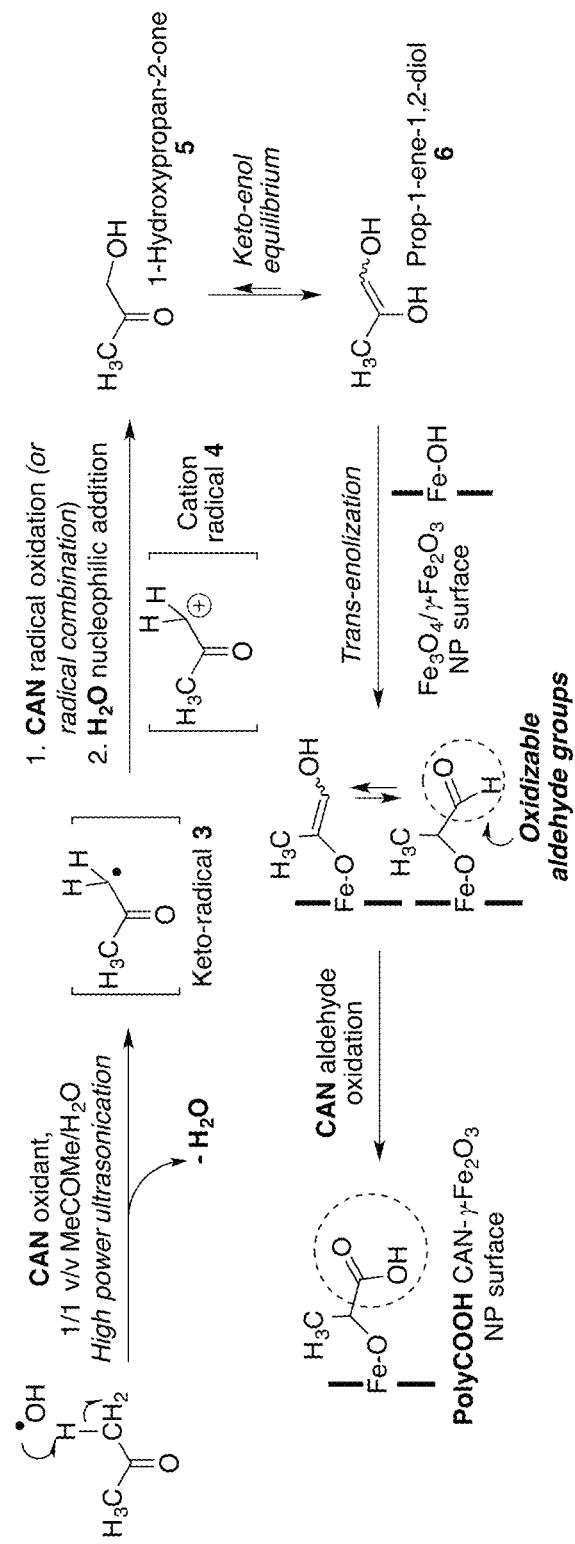
FIG. 2. is a schematic representation of the mechanistic rational for the NP surface carboxylation (via organic matter deposition) mediated by the CAN oxidant.

First, the cleanliness level and the maghemite phase nature that composed CAN-gamma-$Fe_2O_3$ NPs might be readily deduced from the observed characteristic $Fe2p_{3/2}$ electron peak (BE: 710.88 eV, FIG. 7), which confirmed former XRD data. Moreover, an intriguing C is electron peak has been also detected that characterized the presence of organic surface COOH groups (BE: 284.94 eV, FIG. 7). Considering the overall NP doping process, such COOH groups likely arose from the radical-mediated ultrasound decomposition of the sole organic component used in the process, i.e., the MeCOMe solvent. A mechanistic rational for the radical-mediated formation of corresponding COOH groups onto the NP surface has been proposed in FIG. 2. Main reaction intermediate steps involved in this aqueous oxidative process are (i) a $1^{st}$ step of H radical ($H^+$) abstraction by ultrasound-generated Fenton hydroxyl radicals ($^+OH$) (Liochev 1999; Jomova, Baros et al. 2012), (ii) the corresponding radical re-combination and/or CAN-mediated mono-electronic oxidation of keto-radicals 3 towards positively charged cation radical species 4 to afford equilibrated (keto-enol equilibrium) species 1-hydroxypropan-2-one 5 and prop-1-ene-1,2-diol 6 ($H_2O$ nucleophilic addition), and finally (iii) a trans-enolization step during which both 5 and 6 species react with surface amphoteric NP Fe(II/III)-OH groups (Schwertmann and Cornell 2000; Cheng, Su et al. 2005) to afford a NP surface chemically modified by an oxidizable polyaldehyde (polyCHO) shell.

Finally, this intermediate NP polyCHO shell being highly sensitive to the contacting strong mono-electronic CAN oxidant was readily oxidized to afford the corresponding surface-grafted polyCOOH organic shell that has been detected by surface-sensitive XPS. Alternatively, a similar direct radical generation of $FeO^+$ radical species was obtained from amphoteric Fe(II/III) groups to radically polymerize unsaturated species of the prop-1-ene-1,2-diol 6 type leading to this same XPS-detected polyCOOH organic matter that decorated the NP surface (radical polymerization of alkenes).

Figure 8:
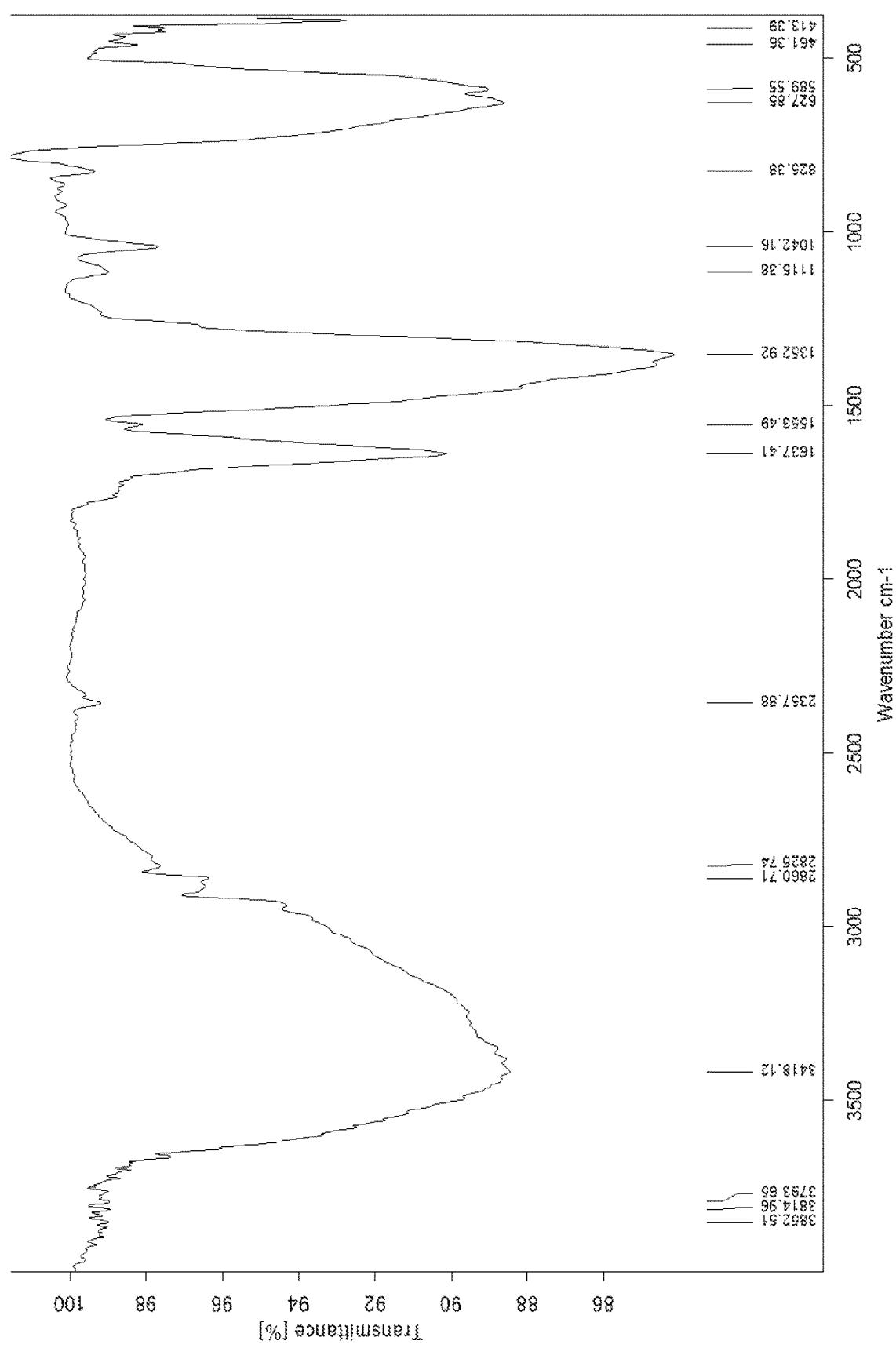
FIG. 8. is a graph showing the FT-IR spectrum of ultra-small CAN-gamma-$Fe_2O_3$ NPs.
Figure 11A:
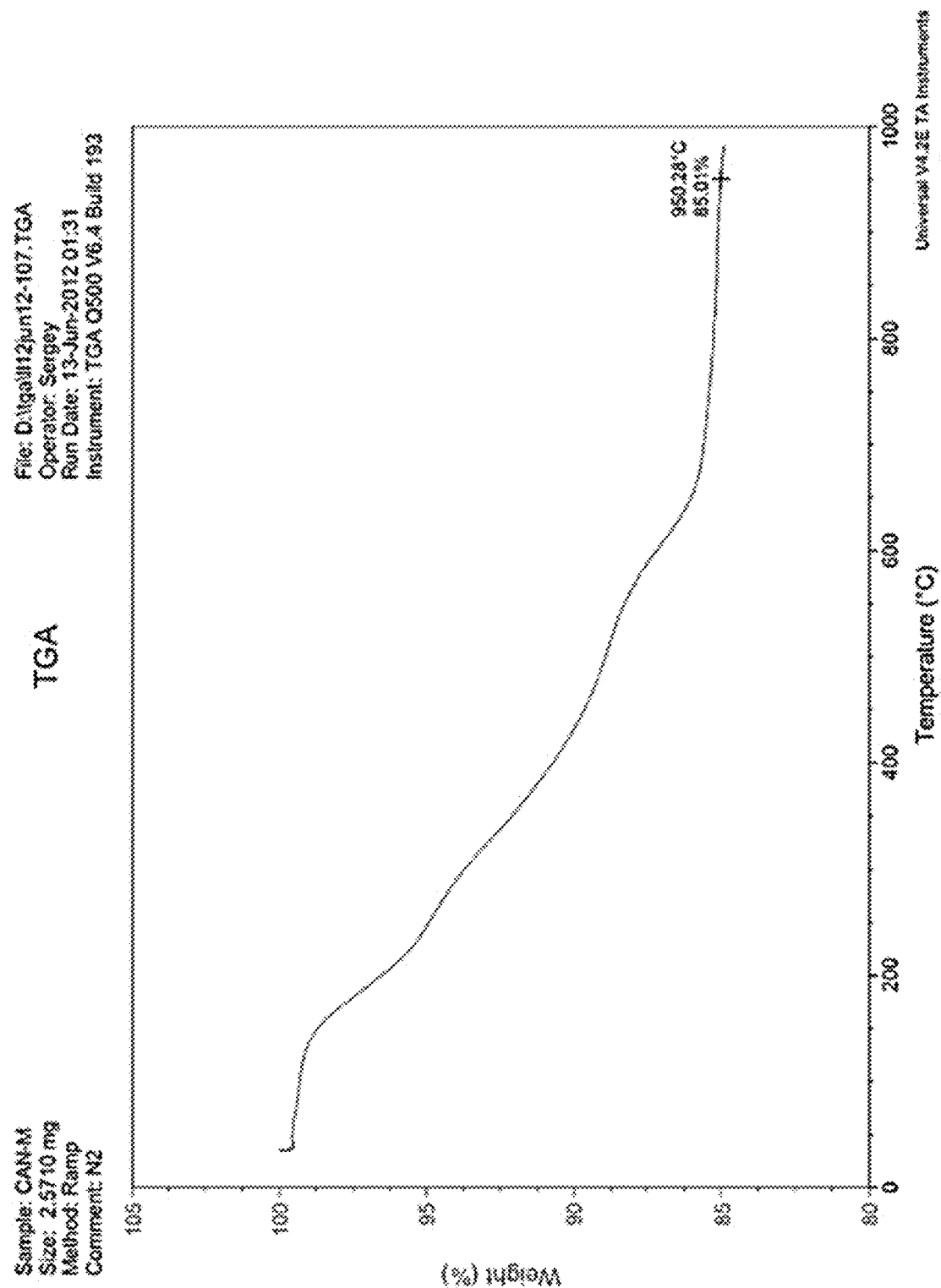
FIGS. 11a-b. are graphs showing the TGA curve of ultra-small CAN-gamma-$Fe_2O_3$ NPs ($N_2$) (Figs. a & b).
Figure 11B:
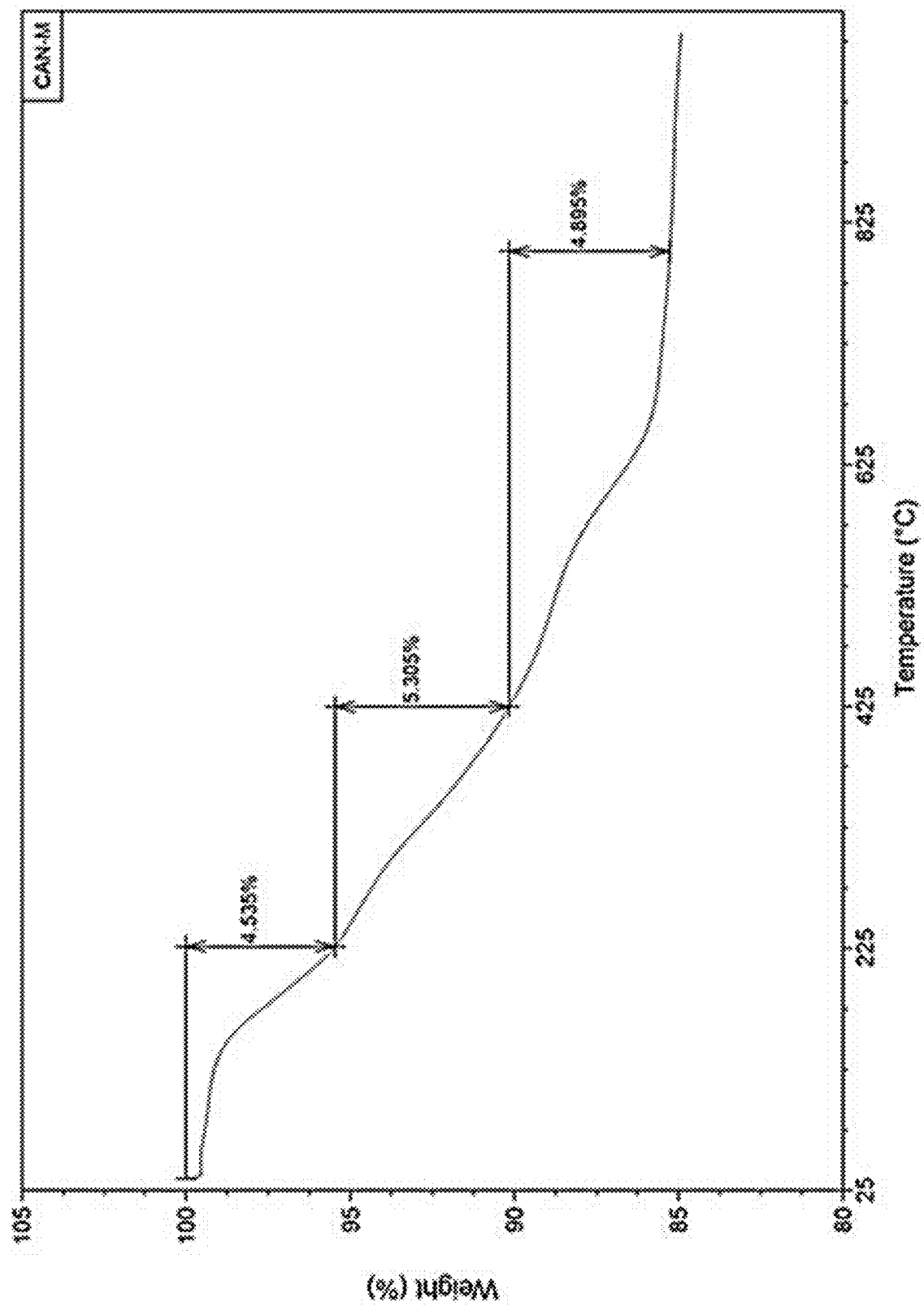
Figure 12A:
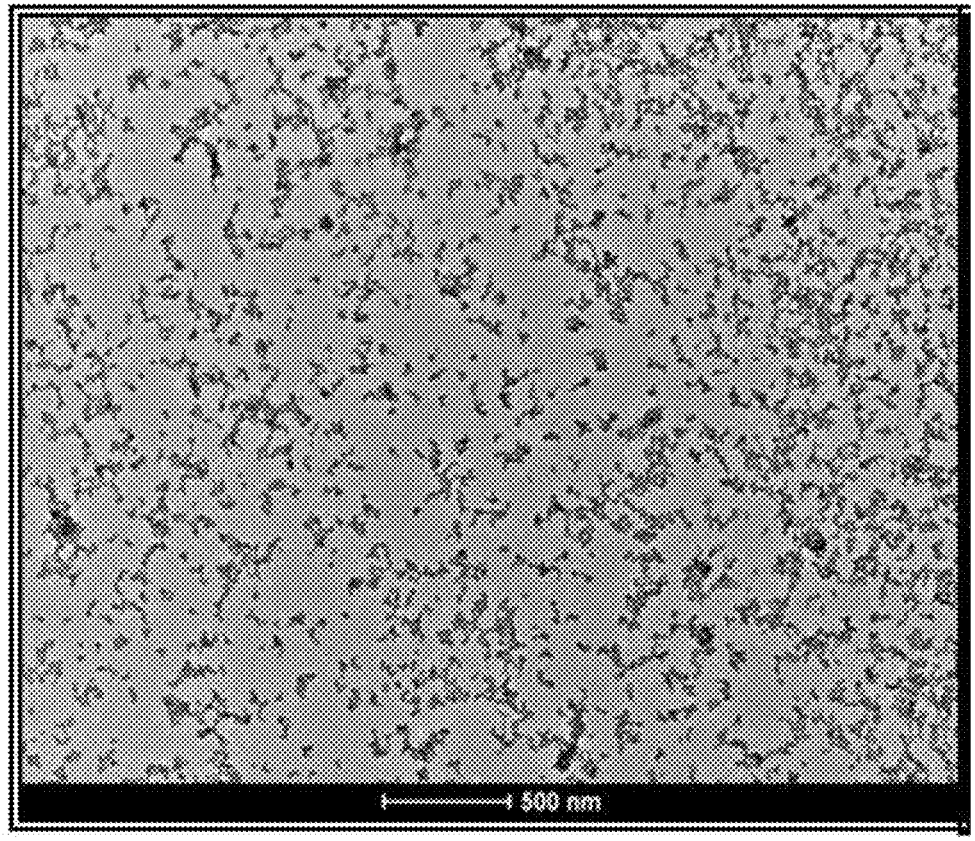
FIGS. 12 a-d. includes: TEM microphotographs (FIG. 12a) and a histogram (FIG. 12b) showing the size distribution of averaged 6.50±2.15 nm-sized $_{con}PEI_{25}$-CAN-gamma-$Fe_2O_3$ NPs (ratio: 5.25).
Figure 12B:
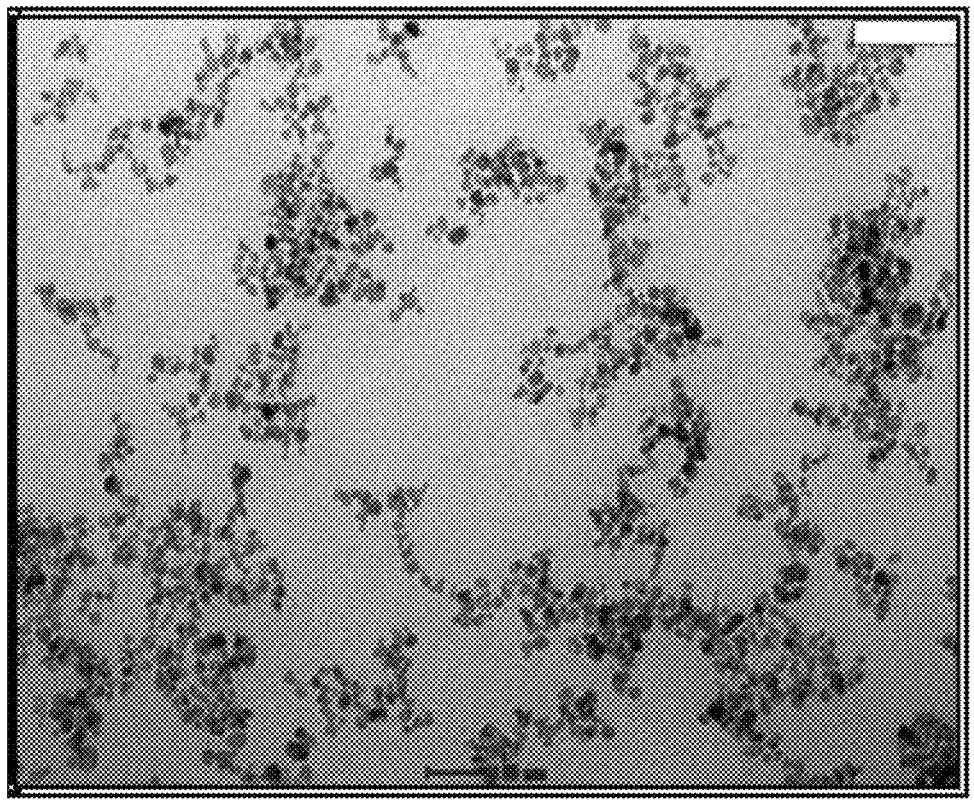
Figure 12C:
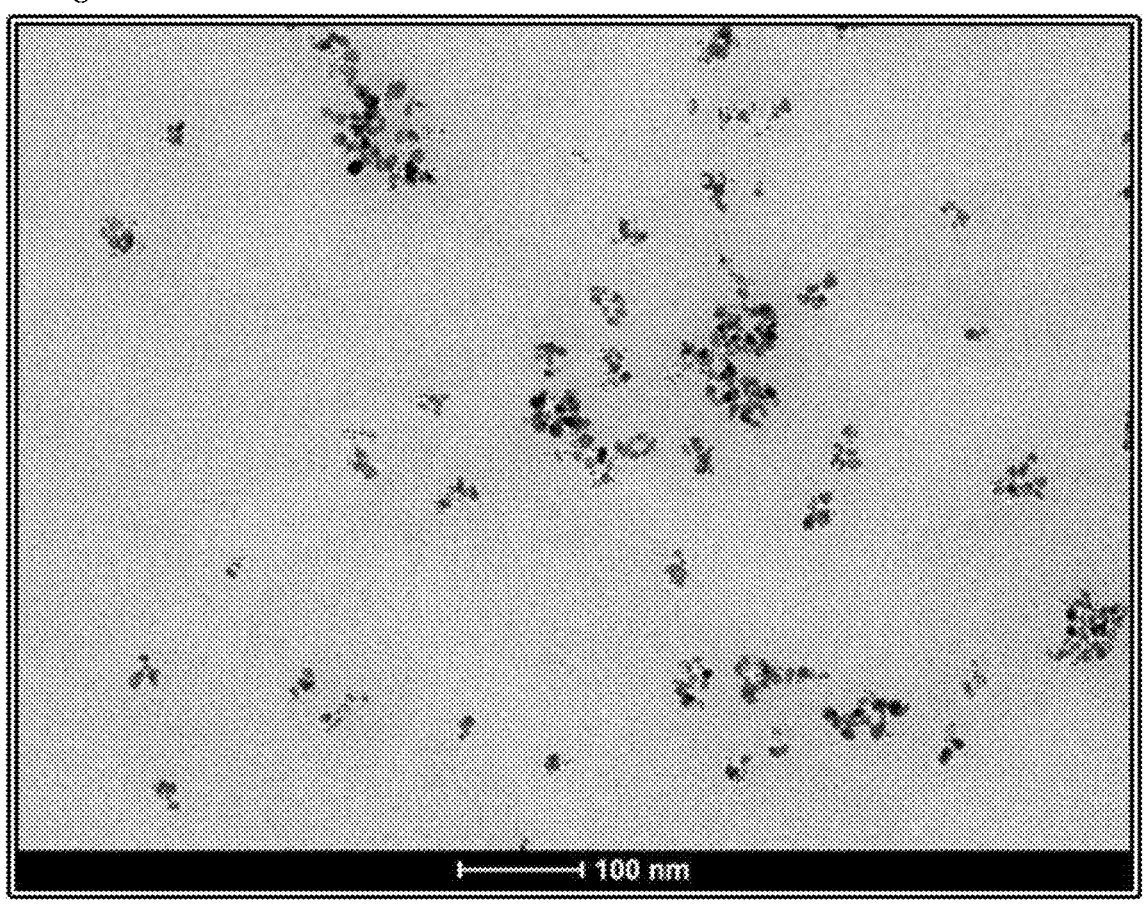
Figure 12D:
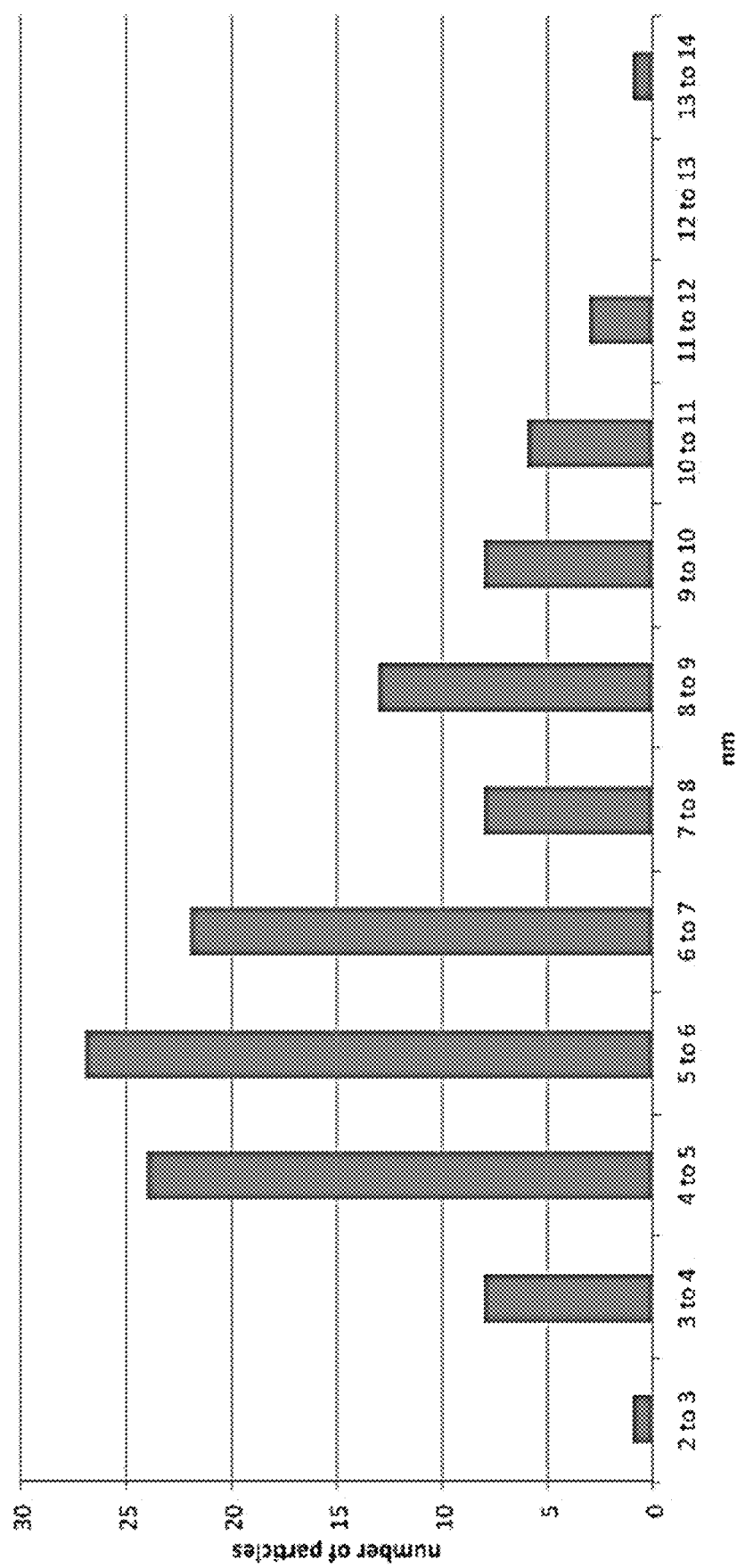

Interestingly, the presence of this organic functionality feature has been crosschecked using various analytical, spectroscopic, and chemical methods as detailed below. For example, elemental analysis of CAN-gamma-$Fe_2O_3$ NPs (sample burning temperature range: 20-1000° C.) afforded the corresponding elemental values, i.e., N=1.87 w %, C=1.73 w %, and H=1.27 w % that confirmed the presence of a carbonaceous compositional phase/adlayer. FT-IR spectroscopy (FIG. 8) also clearly showed characteristic absorption peaks that unambiguously confirmed the presence of such a C-based phase, i.e., stretching absorption peaks $v_{Csp3-H}$ and $v_{O-H}$ (wide, COOH) at 2825.74/2860.71 and 3418.12 $cm^{-1}$ respectively. FT-IR spectroscopy also provided clear evidence that both coordinating nitrate ($NO_3^-$) anions and $H_2O$ molecules were adsorbed onto the NP surface via $[Ce^{3/4+}L_n]$ complex coordination. Indeed, absorption peaks that appeared at 1352.92 and 1553.49 $cm^{-1}$ might be assigned to a $v_3$ degenerated mode of vibrations for $NO_3^-$ and solvated $NO_3^-$ anions respectively,—their $v_1$ mode of vibrations being detected at 1042.16 $cm^{-1}$ (Baltrusaitis, Schuttlefield et al. 2007). In addition, the observed strong 1637.41 $cm^{-1}$ peak related to the bending vibration mode for liganding/solvating $H_2O$ molecules. XPS analysis also confirmed the presence of same NP surface interacting $NO_3^-$ anions owing to their characteristic N 1s peak (BE: 407.39 eV, FIG. 7). Complementary thermogravimetric analysis of CAN-gamma-$Fe_2O_3$ NPs (TGA curve, $N_2$ atmosphere, 20-800° C. temperature range, heating rate 10° C./min, FIG. 11) provided a quantified insight concerning the NP organic phase composition.

Figure 10A:
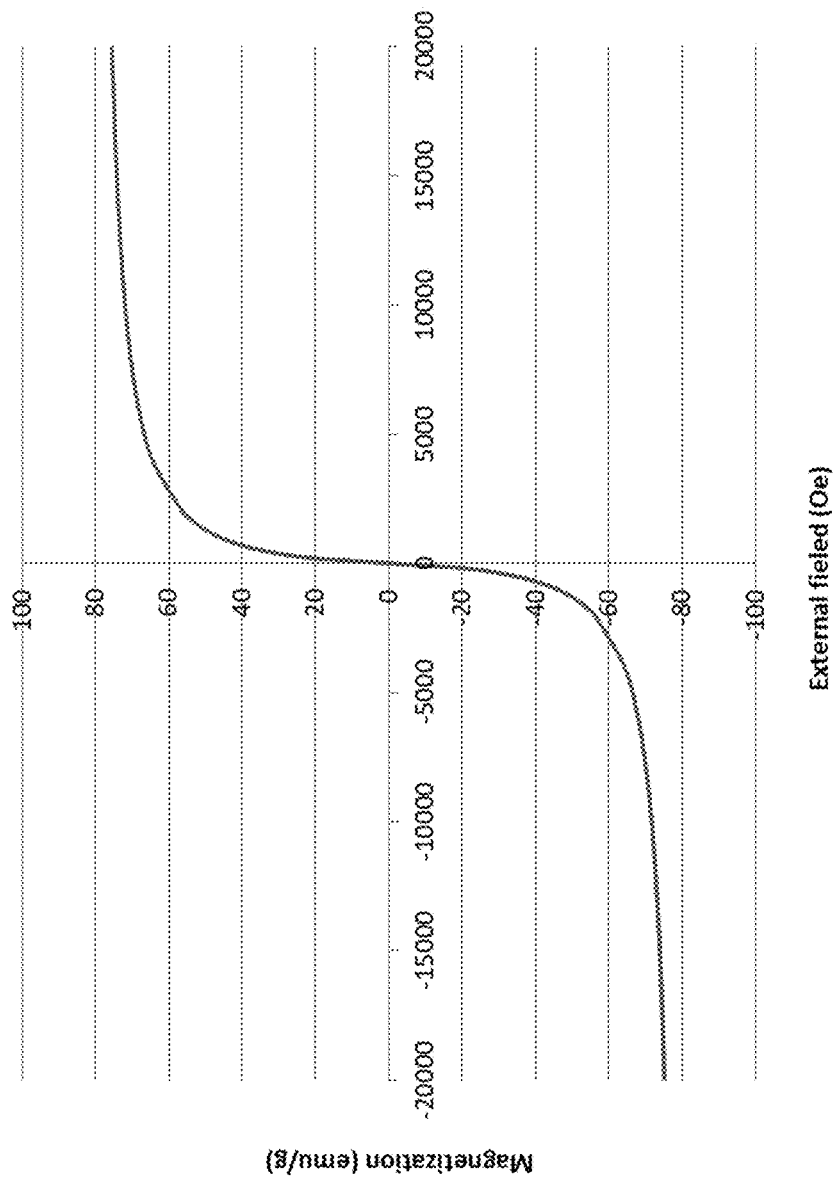
FIGS. 10a-b. are graphs showing the SQUID magnetization profile (saturation magnetization $M_s$: 75.2 emu/g) (FIG. 10a) and the ZFC/FC plots (blocking temperature $T_B$: 109-110° K, H=100 Oe) of ultra-small CAN-gamma-$Fe_2O_3$ NPs (FIG. 10b).
Figure 10B:
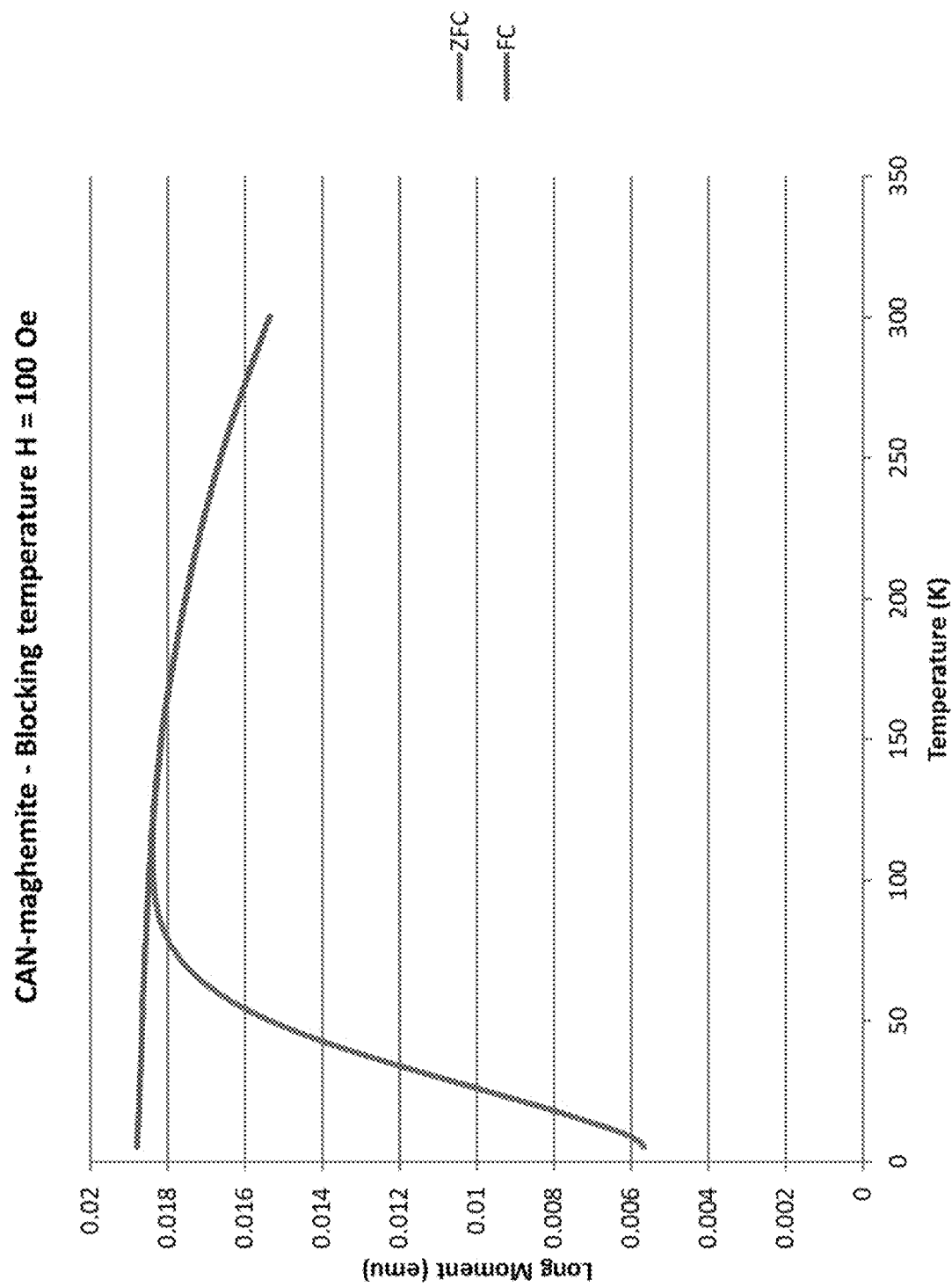

Amongst three well-defined weight looses (50-225° C.: 4.535%,—adsorbed/entrapped $H_2O$ molecules, $[Ce^{3/4+}L_n]$ complex coordinating $H_2O$ molecules, $NO_3^-$ anions with $NO_3^-$ anion solvating $H_2O$ molecules, 225-425° C.: 5.305% & 425-825° C.: 4.895%,—organic adlayer), the two last combined ones accounting for an overall 10.2% weight loose likely relating to the decomposition/evaporation of the formerly characterized polyCOOH organic shell. Interestingly, the magnetization profile of CAN-gamma-$Fe_2O_3$ NPs (SQUID saturation magnetization, 300° K, FIG. 10) provided a saturation magnetization $M_s$ of 75.2 emu/g (blocking temperature $T_B$ of 109-110° C., H=100 Oe). This 75.2 emu/g $M_s$ value is rather compatible with the TGA-measured 10.2 w % value for the organic matter shell mentioned above, meaning for a 89.8% pure maghemite phase. Indeed, calculation of the corresponding theoretical $M_s$ value for virtual 100% pure maghemite NPs afforded an $M_s$ value of 83.6 emu/g, which is very close to the 82.0 emu/g reported in the literature for such a nanoscale material (de Montferrand, Lalatonne et al. 2012). Due to lack of hysteresis phenomenon (FIG. 10), this same magnetization profile indicated that these magnetic NPs are super-paramagnetic.

Thus it is clear that the ultrasound-assisted $Ce^{3/4+}$ atom/cation doping process of pre-formed MASSART magnetite NPs using a CAN oxidant afforded fully hydrophilic functional ultra-small super-paramagnetic and non-aggregated CAN-gamma-$Fe_2O_3$ NPs enabling both types of $2^{nd}$ step NP functionalization. Indeed and as demonstrated above, NP functionality duality arose from the simultaneous presence of (i) an ultrasound-deposited polycarboxylated (polyCOOH) organic shell and of (ii) doping $[Ce^{3/4+}*L_n]$ complexes onto the NP surface. Both types of NP functionalities might be orthogonally activated as readily demonstrated by a sensitive ninhydrin-based UV spectrophotometric Kaiser test (Sarin, Kent et al. 1981) (COOH/$NH_2$ group quantification, triplicate format, see corresponding experimental protocols below for details).

First, NP derivatization using contacting 1,4-diaminobutane in excess ($H_2N$—$(CH_2)_4$—$NH_2$, overnight, 20° C.) as a typical Lewis base N-element containing species enabled coordinative complexation with Lewis acid surface doping $[Ce^{3/4+}L_n]$ complexes. The corresponding quantitative Kaiser test measurement afforded a value of 0.422 mmol accessible $NH_2$ groups/g NPs. Moreover and following same NP chemical derivatization using 1,4-diaminobutane but after NP polyCOOH shell activation by a water soluble EDC·HCl carbodiimide reagent (EDC·HCl reagent: 1-(3-dimethylaminopropyl)-3-ethylcarbodiimide hydrochloride, room temperature), a similar quantitative Kaiser test measurement afforded an expected increased value of 0.445 mmol accessible $NH_2$/COOH groups/g NPs. This observed 0.023 mmol accessible $NH_2$/COOH groups/g NPs most likely arose from quantification of orthogonally EDC-activated COOH groups belonging to the sole organic poly-COOH organic phase.

Example 2: NP Derivatization (Coordination/Contacting Mode—Absence of Activating EDC·HCl)

To 1.0 mL of an aqueous suspension of NPs (8.5 mg/mL) 0.2 mL (2.58 mmol) of 1,4-diaminobutane were added and the reaction medium was gently shaken overnight at room temperature. At reaction completion, polyNH$_2$-modified NPs were cleaned before UV Kaiser test by three sequential centrifuge precipitation-ddH$_2$O washing steps (12,500 rpm, 5° C.) for removal of the 1,4-diamine in excess.

Example 3: NP Derivatization (Organic Shell Activation Using EDC·HCl)

50.0 mg of EDC·HCl (0.26 mmol) were added to 1.0 mL of an aqueous suspension of NPs (8.5 mg/mL) and the reaction mixture was shaken for 40 min at room temperature. Then, EDC-activated NPs were cleaned from excess EDC·HCl using three sequential centrifuge precipitation-ddH$_2$O washing steps (8,000 rpm, 5° C., 8 mn). Then, the final pellet was successively added with 1.0 mL of ddH$_2$O and 0.2 mL (2.58 mmol) of 1,4-diaminobutane and the NP suspension was shaken for 1.5 h at room temperature. At reaction completion, polyNH$_2$-modified NPs were cleaned before UV Kaiser test by three sequential centrifuge precipitation-ddH$_2$O washing steps (12,500 rpm, 5° C.) for removal of the 1,4-diamine in excess.

Example 4: UV Spectroscopy Kaiser Test and polyCOOH/polyNH$_2$ Functionality Quantification Resulting polyNH$_2$ NPs were equally divided into two 13×100 mm-sized test tubes and freeze dried (lyophilization, −50° C., 0.06 mbar). Each weighed product was sequentially added with (i) 75.0 μL of an ethanol solution of phenol (PhOH, 40.0 g, 10 mL EtOH), (ii) 75.0 μL of an ethanol solution of ninhydrin (2.5 g dye, 50.0 mL EtOH) and 100.0 μL of an aqueous KCN pyridine-containing solution (65.0 mg KCN dissolved in 100.0 mL ddH$_2$O=solution A—then 2.0 mL of solution A were diluted with 100 mL of pyridine). All the test tubes were then placed on a heating block pre-adjusted to 100° C. for 10 min (ninhydrin reaction with accessible NH$_2$ groups). Each tube was then added to a 60% v/v solution of EtOH in ddH$_2$O (4.8 mL) followed by medium filtration (0.22 micrometer Millipore filter). A 0.5 mL aliquot of the filtered solution was then diluted with the former 60% v/v solution of EtOH in ddH$_2$O (4.5 mL). Finally, this diluted medium was UV tested using a UV spectrophotometer at a lambda$_{max}$ of 570 nm (ninhydrin dye) to quantify the number of accessible amine functional groups present onto the NP surface (mmol accessible NH$_2$/COOH groups/g NPs).

Example 5: NP Functionalization by a Polycationic PEI Polymer—Two (Contact) and One-Step (Injection) Decoration Methods and Main Selected Particulate Characterization Data Including Respective Optimized Fabrication Protocols Based on the unique surface chemistry developed for CAN-gamma-Fe$_2$O$_3$ NPs, the enabling endosomal-escape polycationic 25 kDa polyethyleneimine polymer (PEI) has been grafted onto the surface of CAN-gamma-Fe$_2$O$_3$ NPs of the invention using both contact and injection methods. Such nanofabrication methods afforded similarly polycationic characteristics but differently featured composite nanoparticles that disclosed high effectiveness for RNA electrostatic capture and RNA-mediated gene delivery/silencing as shown below.

Figure 13A:
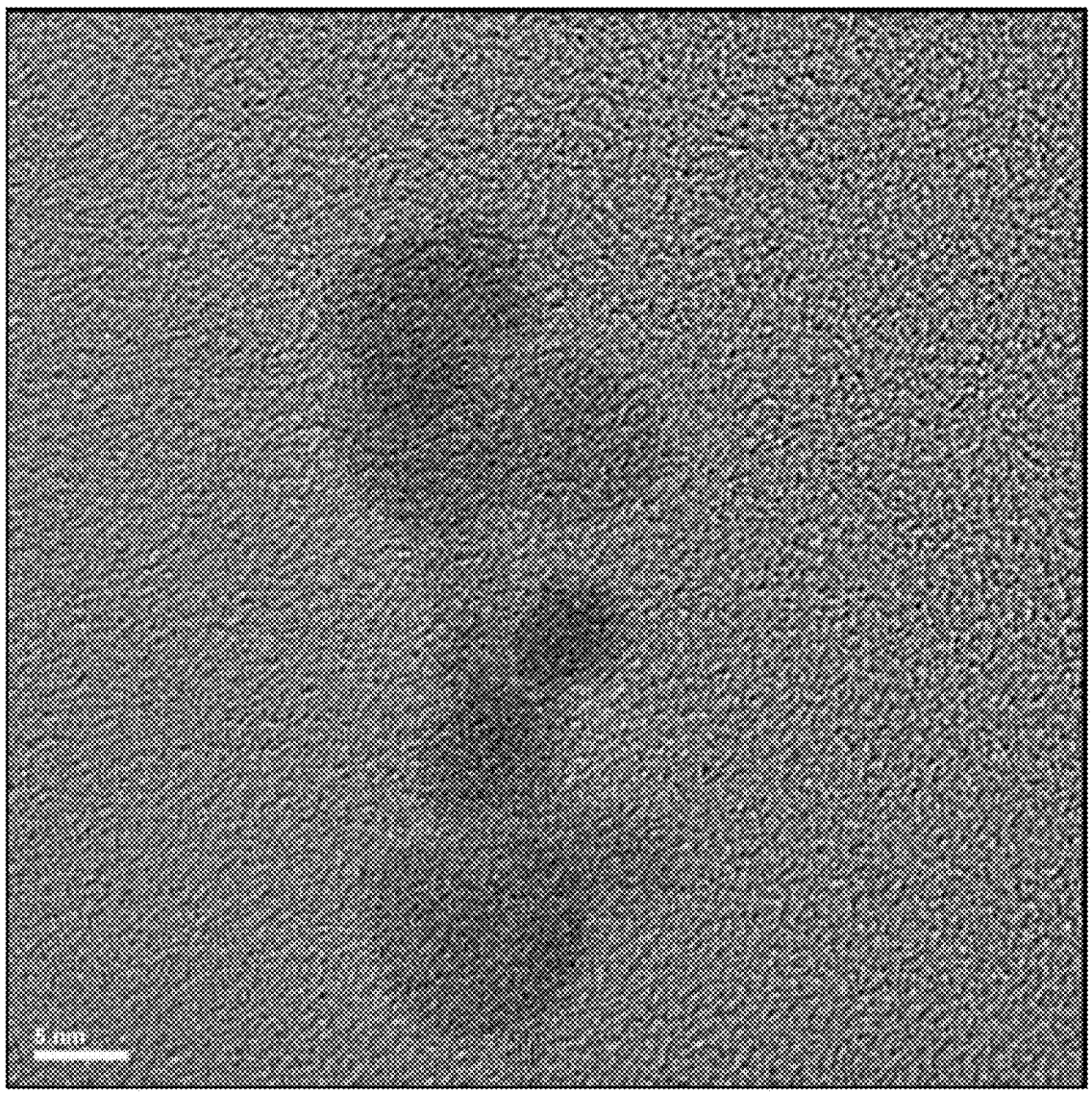
FIGS. 13a-b. includes: a microphotograph and a graph, showing the HR-TEM analysis of $_{con}PEI_{25}$-CAN-gamma-$Fe_2O_3$ NPs (ratio: 5.25) (FIG. 13a) and the compositional EDAX analysis (presence of Fe, C, O, & N elements) (FIG. 13b).
Figure 13B:
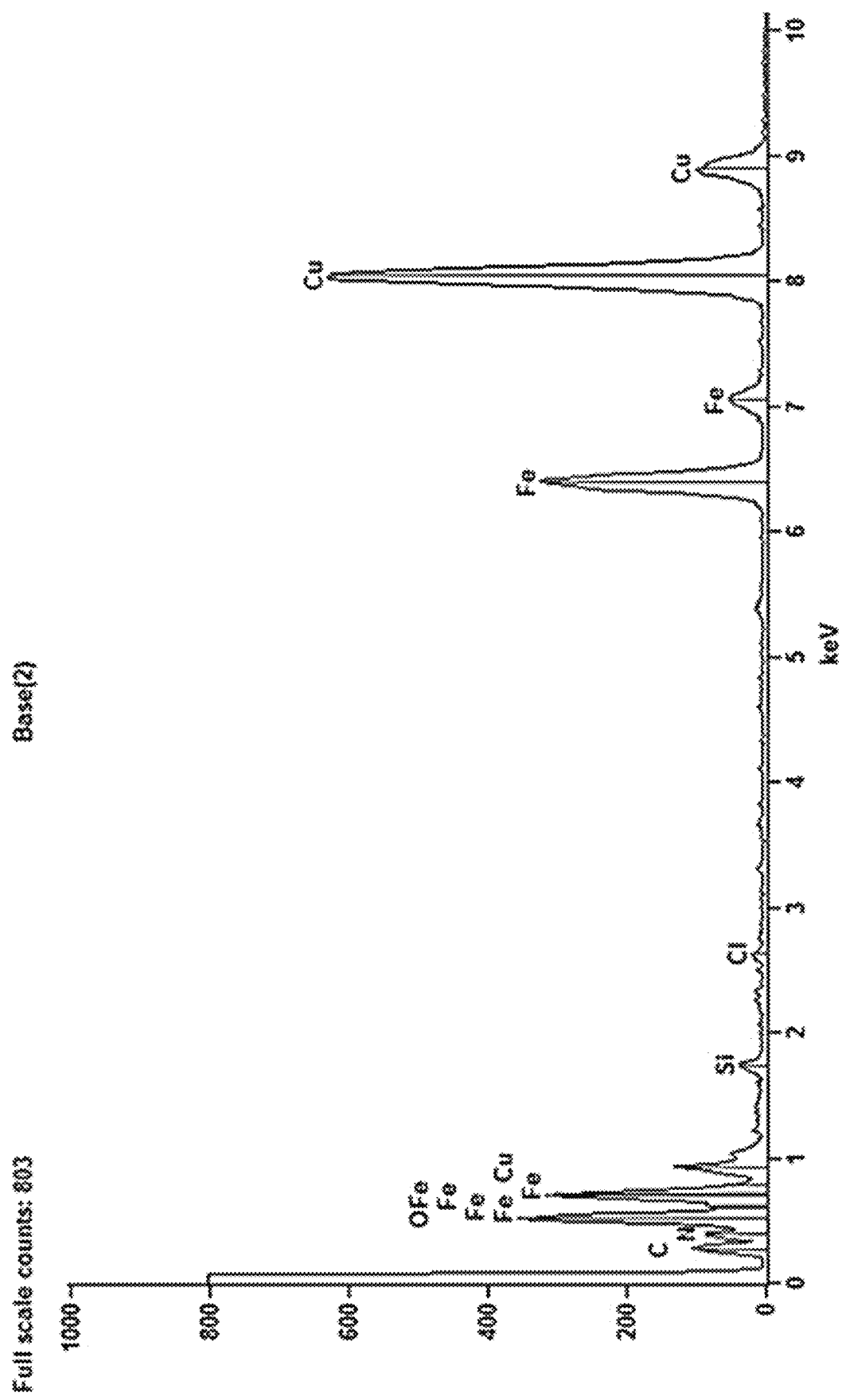
Figure 14A:
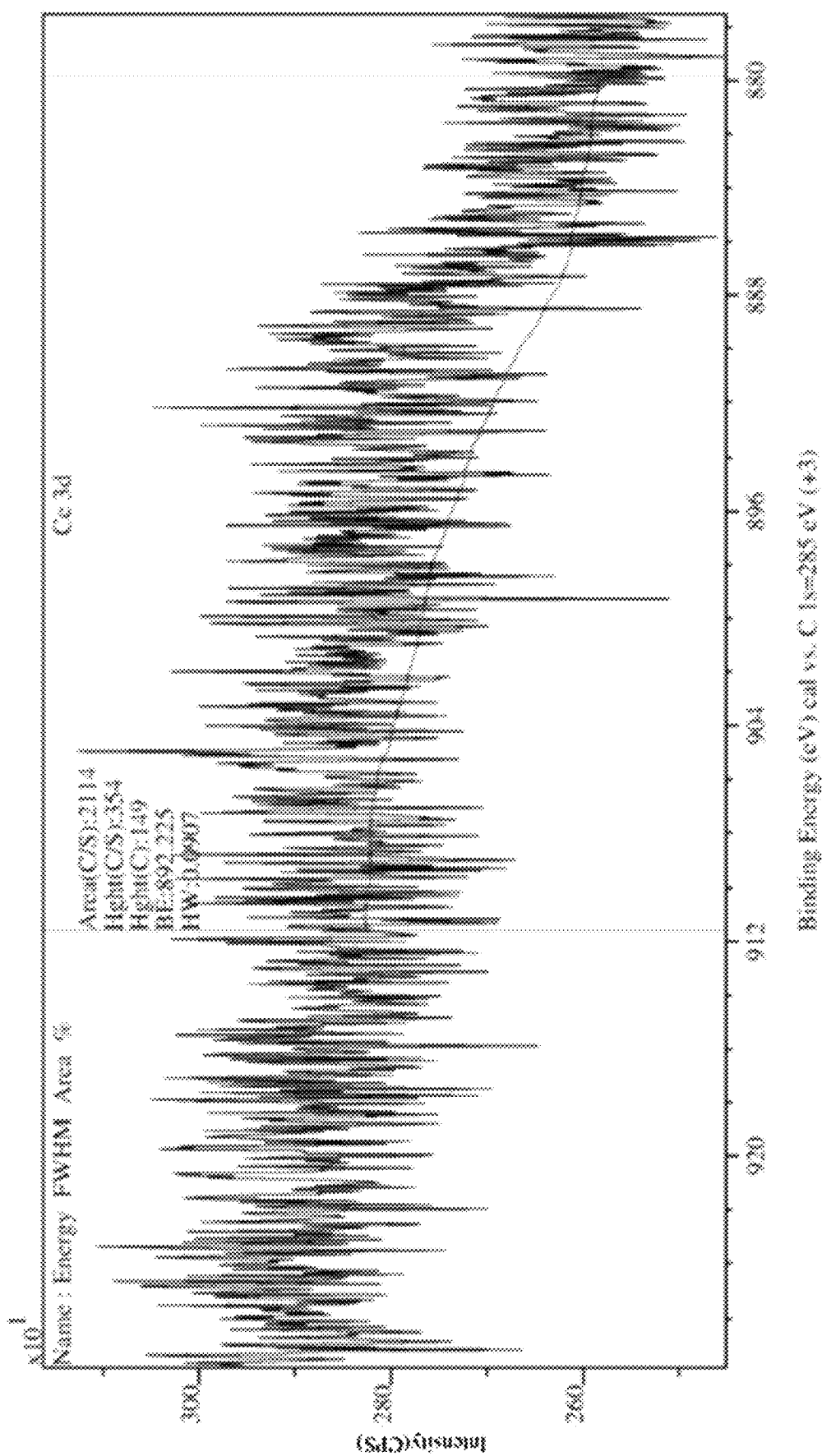
FIGS. 14a-d. is a graph showing the XPS spectroscopy of ultra-small $_{con}PEI_{25}$-CAN-gamma-$Fe_2O_3$ NPs (PEI loading: 5.25)—Ce $3d_{5/2}$ (BE: 892.23 eV) (FIG. 14a), Fe$2p_{3/2}$ (BE: 710.60 eV) (FIG. 14b), N 1s (nitrate anions & amine species, BE: 406.0-407.0 & 398.0-402.0 eV respectively) (FIG. 14c), and C 1s (BE: 285.05 eV) (FIG. 14d) peaks.
Figure 14B:
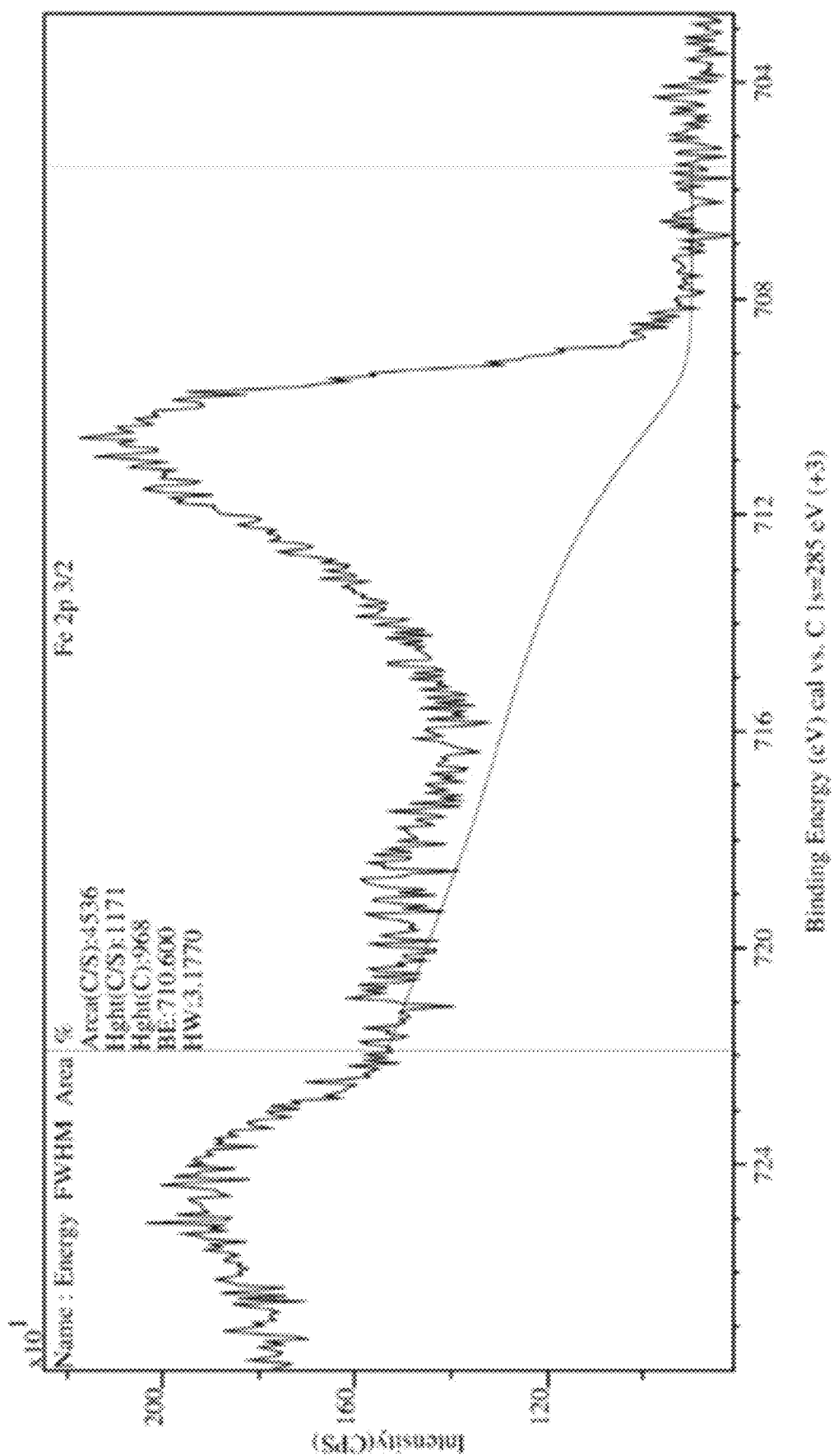
Figure 14C:
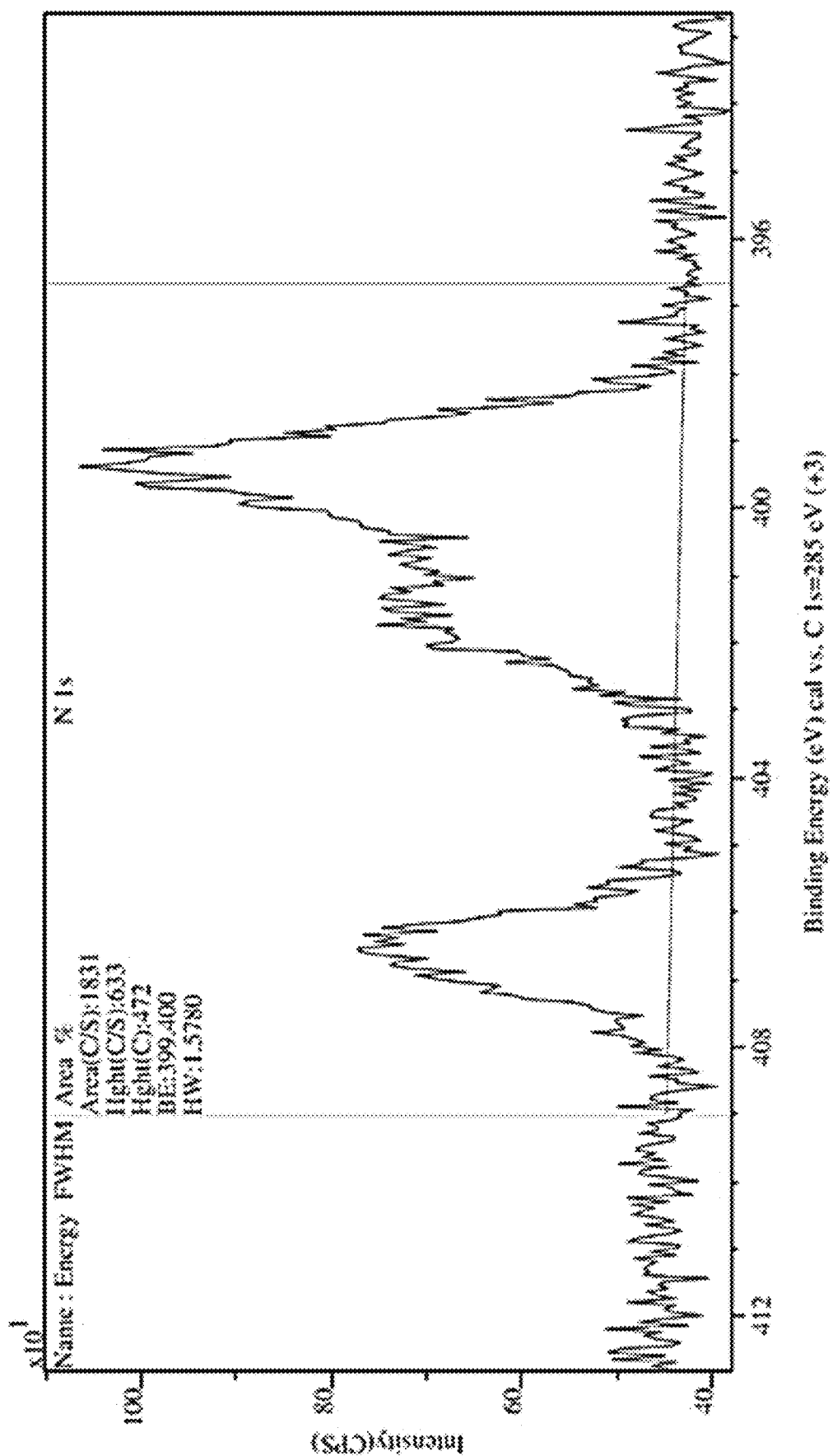
Figure 14D:
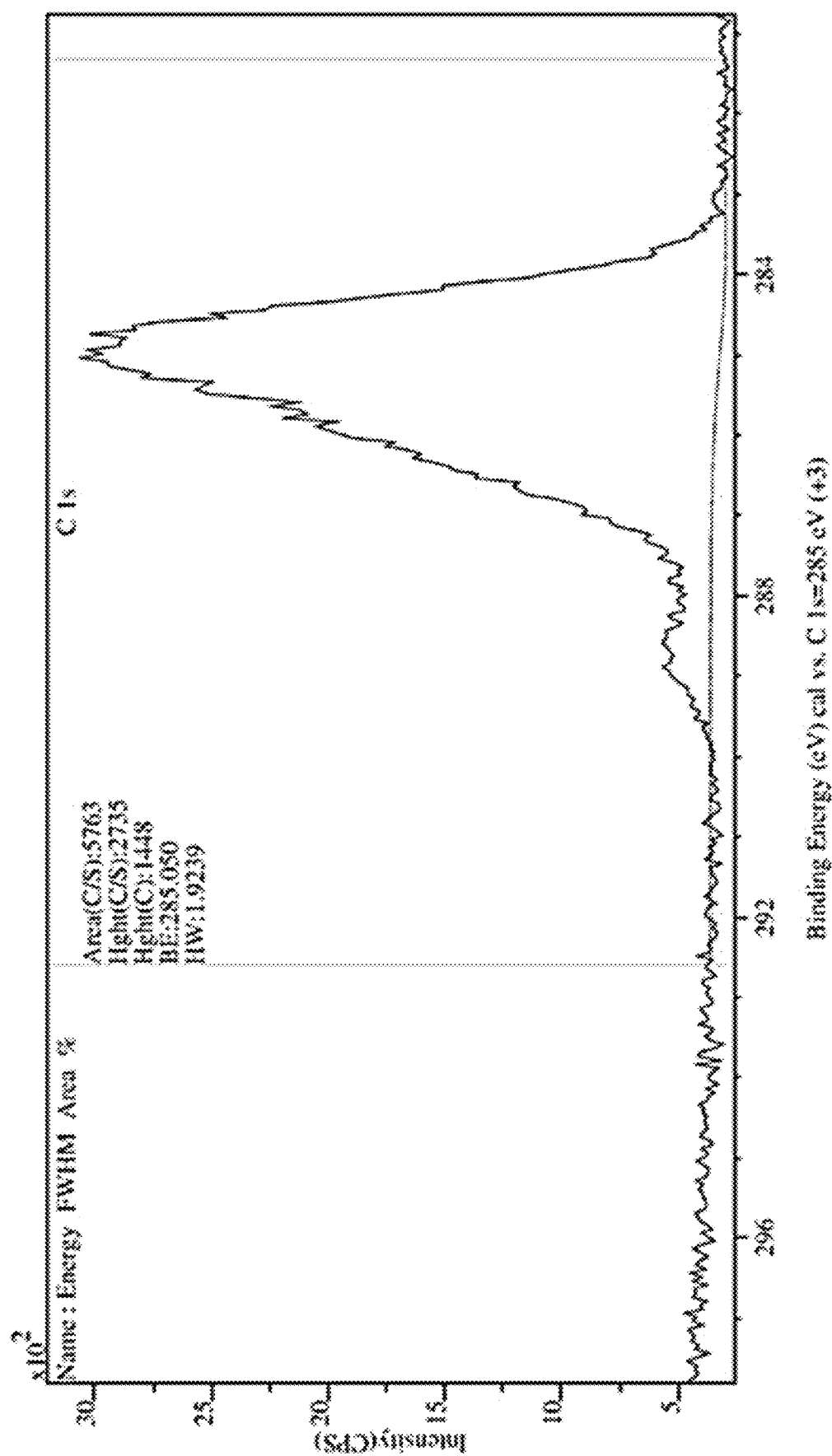

$_{con}$PEI$_{25}$-CAN-gamma-Fe$_2$O$_3$ NPs Preparation: In the 1$^{st}$ contact two-step method and as observed in the case of the small interacting 1,4-diaminobutane used in Kaiser tests mentioned above, a branched 25 kDa PEI (PEI/Fe Wt ratio: 5.25) polymers acting as a polyLewis base species (polyNH$_2$/polyNH/polyN) has been similarly reacted with former CAN-gamma-Fe$_2$O$_3$ NPs (ddH$_2$O, room temperature, overnight, coordinative complexation/L$_n$ ligand exchange involving surface doping [Ce$^{3/4+}$L$_n$] complexes) to afford corresponding highly hydrophilic non-aggregated ultra-small 6.50±2.15 nm-sized (DLS hydrodynamic diameter: 65.0-78.0 nm, PDI: 0.18-0.207) and positively charged $_{con}$PEI$_{25}$-CAN-gamma-Fe$_2$O$_3$ NPs (PEI/Fe Wt ratio: 5.25, FIGS. 12-13).

Figure 18A:
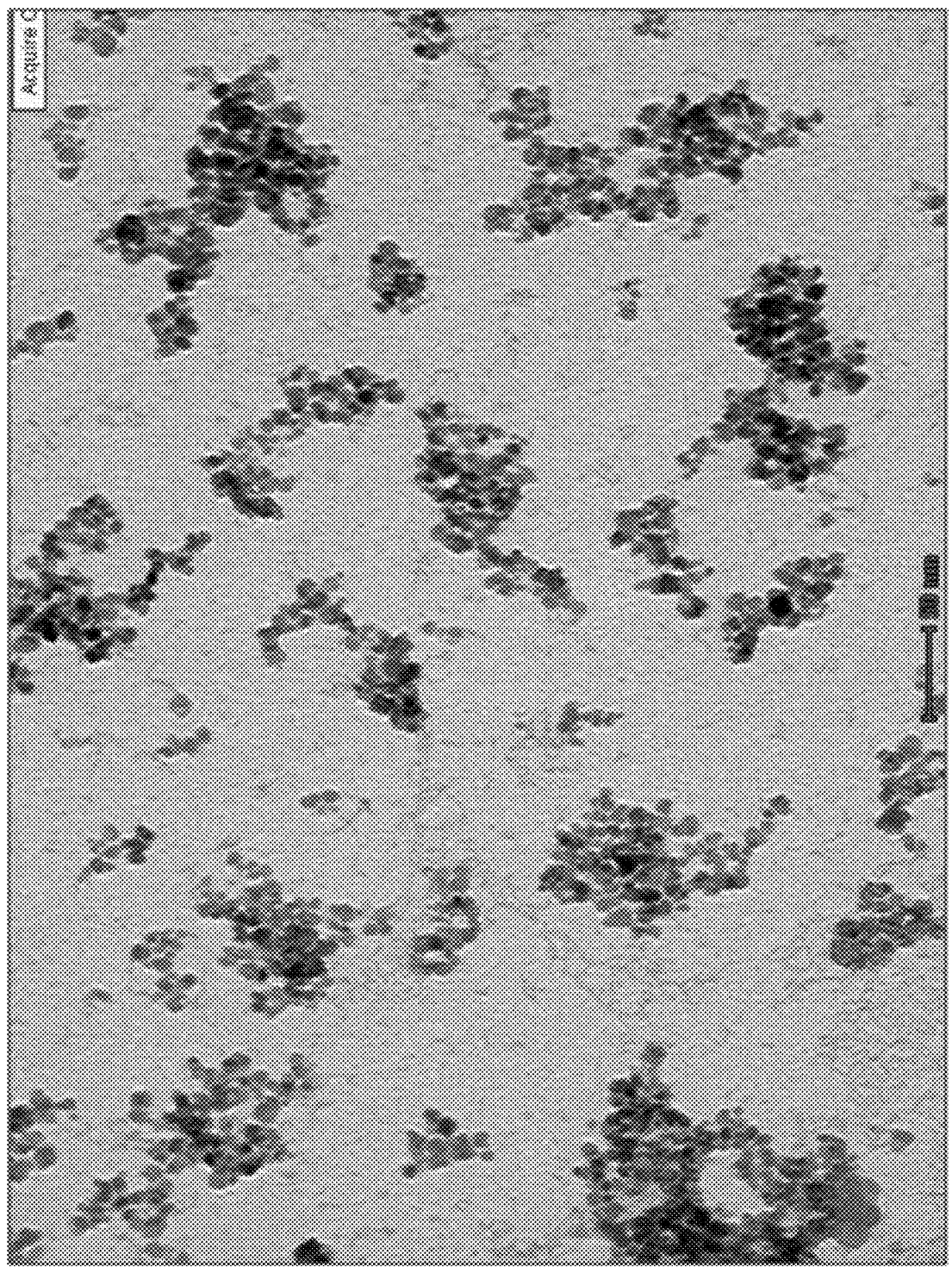
FIGS. 18 a-b. includes: a TEM microphotograph (FIG. 18a) and a histogram (FIG. 18b) showing the size distribution of ultra-small averaged 7.65±2.65 nm-sized $_{inj}$PEI$_8$-CAN-gamma-Fe$_2$O$_3$ NPs (Table 1).
Figure 18B:
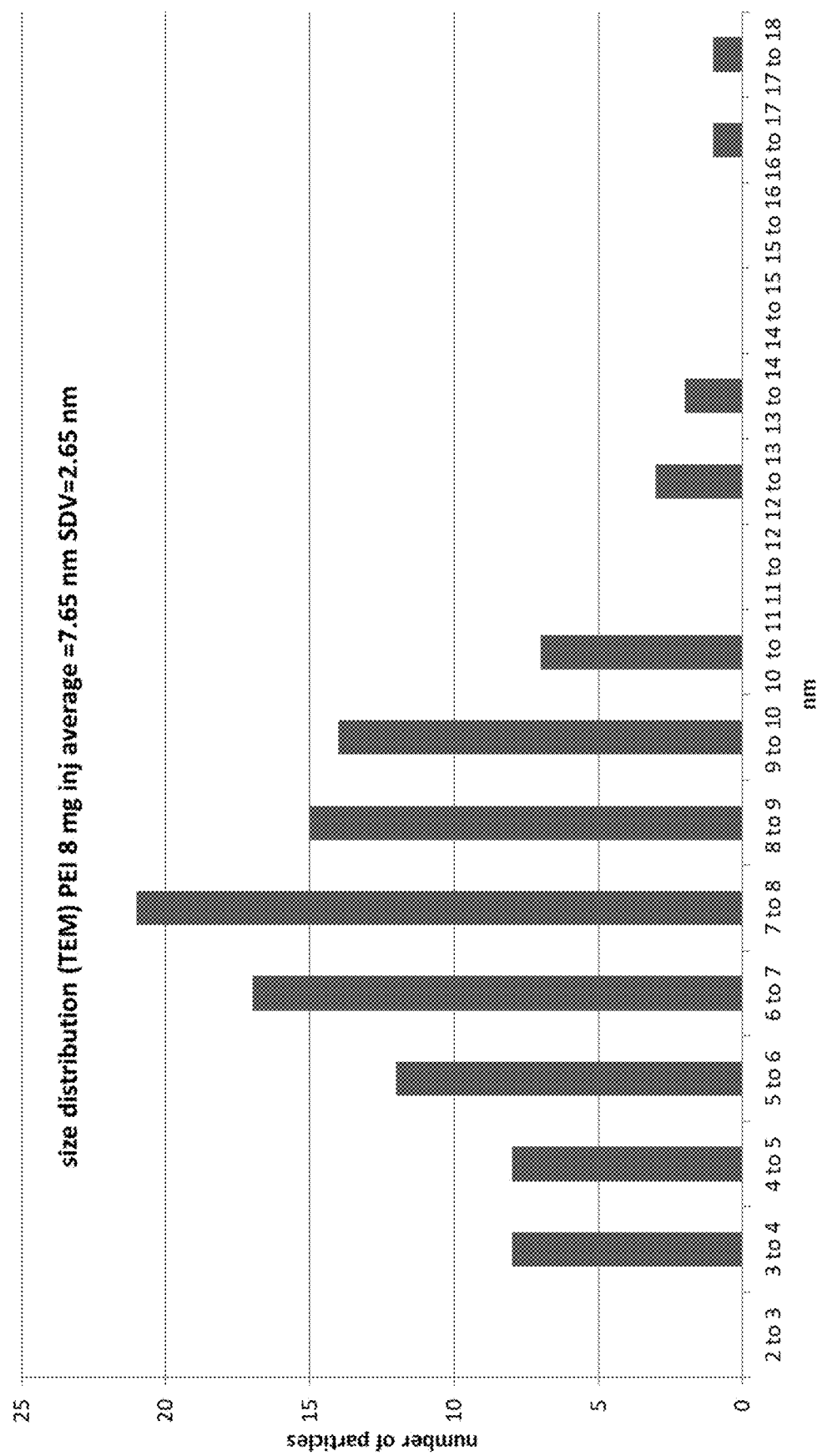
Figure 19A:
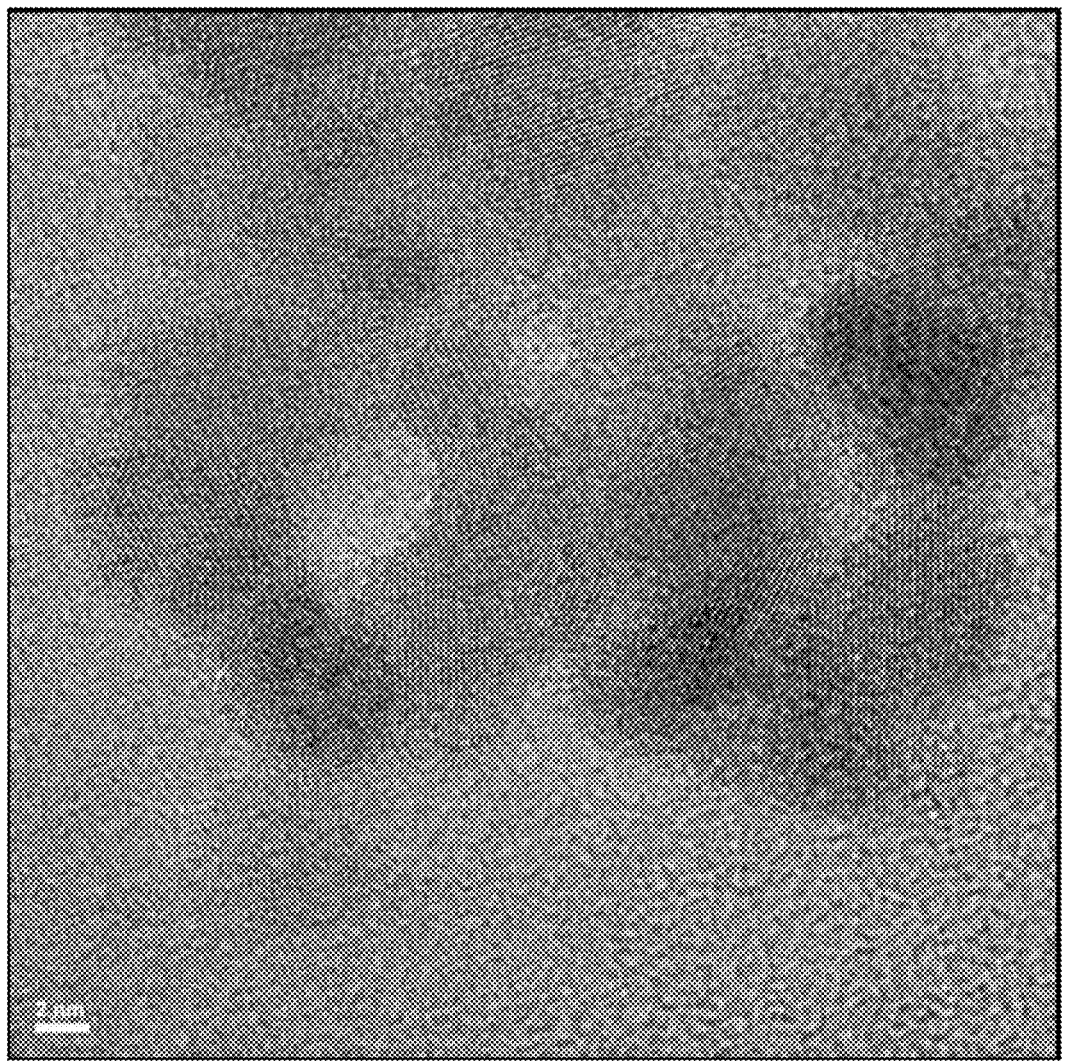
FIGS. 19 a-b: includes: a microphotograph and a graph, showing the HR-TEM analysis of ultra-small $_{inj}$PEI$_{25}$-CAN-gamma-Fe$_2$O$_3$ NPs (8.0 mg 25 KDa PEI) (FIG. 19a) and the compositional EDAX analysis (presence of Fe, C, O, & Ce elements) (FIG. 19b).
Figure 19B:
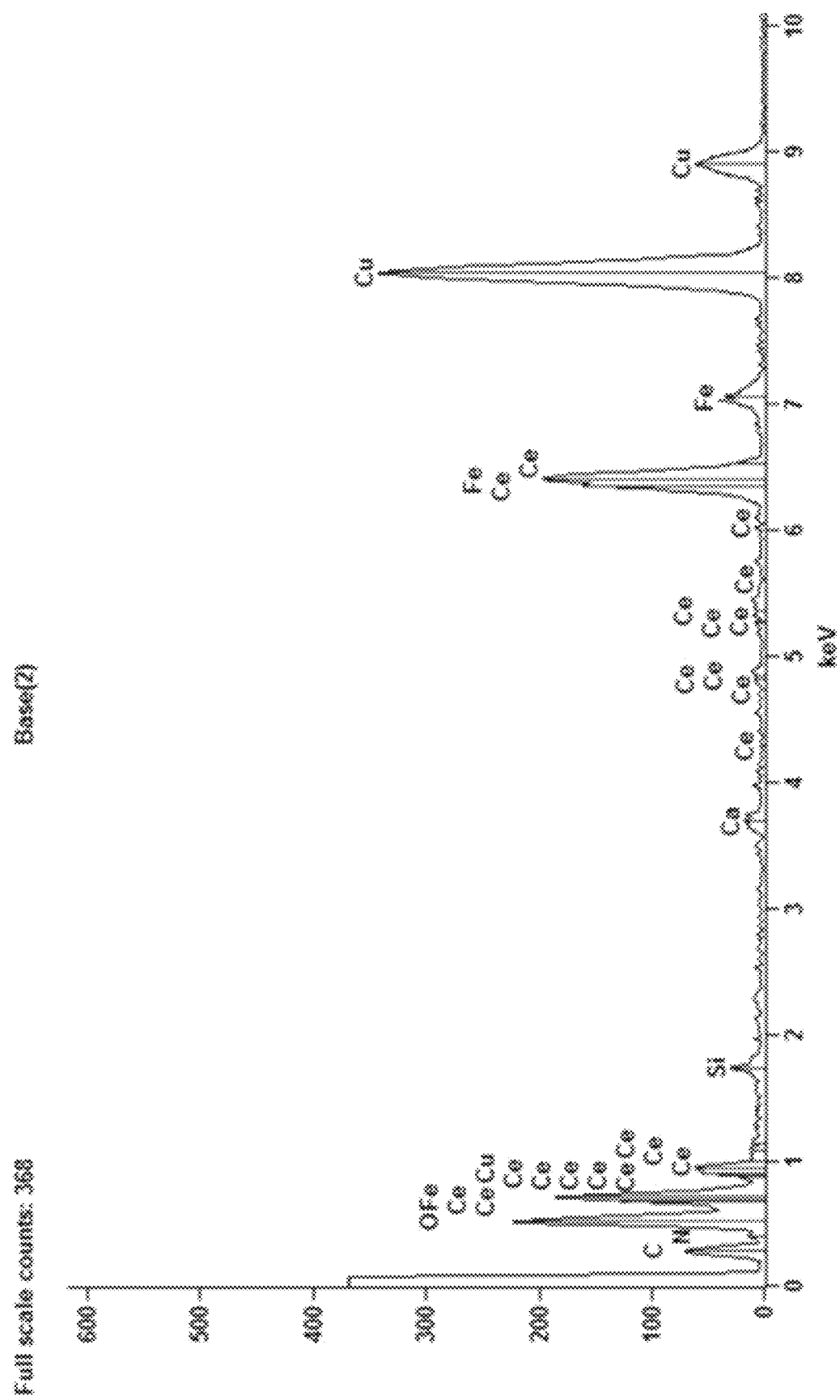
Figure 20:
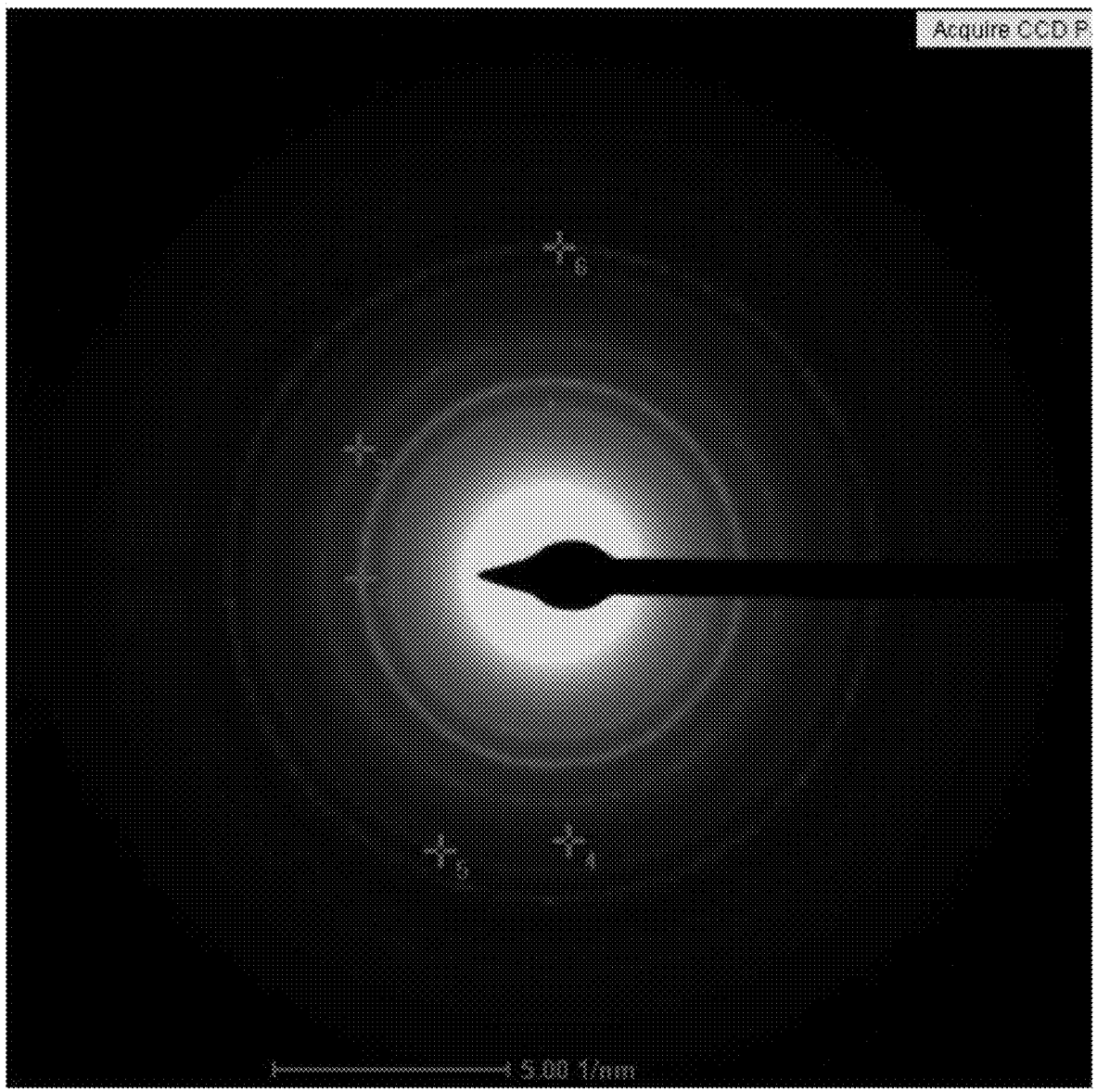
FIG. 20. is an image showing the TEM/Selected Area Electron Diffraction patterns (SAED patterns) of ultra-small $_{inj}$PEI$_{25}$-CAN-gamma-Fe$_2$O$_3$ NPs (8.0 mg 25 KDa PEI): #1 (plane 220), #2 (plane 311), #3 (plane 400) & #6 (plane 440).
Figure 21:
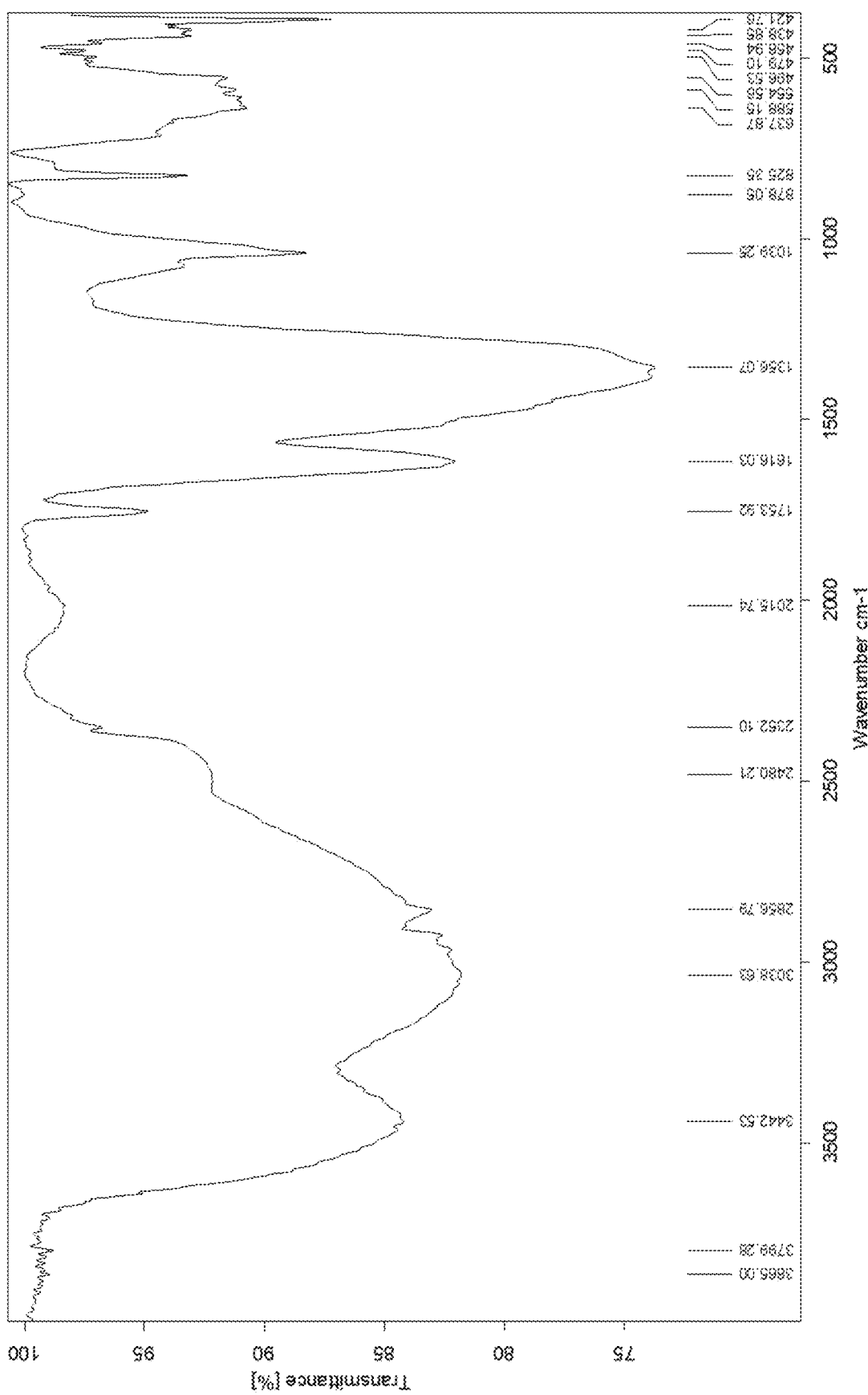
FIG. 21. is a graph showing the FT-IR spectrum of ultra-small $_{inj}$PEI$_8$-CAN-gamma-Fe$_2$O$_3$ NPs (8.0 mg 25 KDa PEI).

$_{inj}$PEI$_{25}$-CAN-gamma-Fe$_2$O$_3$ NP Preparation: In contrast and as a variant time saving protocol (one-step injection method), this same branched 25 kDa PEI might be introduced during the ultrasonic irradiation of Massart magnetite NPs in the presence of CAN to afford similar highly hydrophilic non-aggregated ultra-small 7.65±2.65 nm-sized (DLS hydrodynamic diameter: 58.0-62.0 nm, PDI: 0.18) positively charged $_{inj}$PEI$_{25}$-CAN-gamma-Fe$_2$O$_3$ NPs (FIGS. 18-19).

Interestingly both types of particles disclosed highly positive but different zeta potential values, i.e., +35.0 and +56.3 mV indicative of a different mode of PEI decoration/grafting that most likely relate to different amounts of [Ce$^{3/4+}$L$_n$] complex doping. Indeed, elemental ICP-AES analysis of both types of particles afforded highly increased elemental Ce values of 0.003615 (Wt ratio Ce/Fe: 0.09538) and 0.056 mg/mL (Wt ratio Ce/Fe: 0.0167) respectively, i.e., by a 15.5 time factor Ce amount increase for $_{inj}$PEI$_{25}$-CAN-gamma-Fe$_2$O$_3$ NPs. These data emphasized the promoting effect of the injected 25 KDa PEI phase on the doping one-step process ending with a more [Ce$^{3/4+}$L$_n$] complex-loaded more positively charged nanoparticle. Confirmation of this phenomenon also arose from surface-sensitive XPS analysis (FIGS. 14 & 24). Both types of particles disclosed peaks characterizing the presence of [Ce$^{3/4+}$L$_n$] complexes (Ce 3d$_{5/2}$ peaks, BE: 892.23 and 889.075 eV) and of the 25 KDa PEI phase (N 1s peaks for amine species, BE: 398.0-402.0 & 399.0-403.0 eV). Quite interestingly since confirming former XPS data relating to CAN-gamma-Fe$_2$O$_3$ NPs, both types of PEI-decorated nanoparticles showed characteristic peaks ascribed to the presence of nitrate anions (N 1s peaks, BE: 406.0-407.0 & 407.29 eV) involved as coordinating species of NP surface [Ce$^{3/4+}$L$_n$] complexes. Moreover, compared nanoparticulate XPS spectra enabled to even have a deeper insight on the resulting differential mode of 25 kDa PEI attachment onto the NP surface for both types of NPs. Indeed, the existence of a specific XPS peak ascribed to C 1s electrons for COOH groups was described above (organic adlayer, BE: 286.60 eV). Interestingly, this peak did not appear in the XPS spectrum of $_{con}$PEI$_{25}$-CAN-gamma-Fe$_2$O$_3$ NPs. This is due to a 25 kDa PEI layer masking effect indicative of a layered structure of the NP surface. In contrast and for $_{inj}$PEI$_{25}$-CAN-gamma-Fe$_2$O$_3$ NPs, this same characteristic XPS peak (organic COOH adlayer) is found at a BE of 286.54 eV. It means that injected 25 kDa PEI polymeric chains bound the NP surface while simultaneously mixing with the ultrasonically grown polyCOOH organic matter adlayer, which resulted in a functional heterogeneous NP surface.

The effectiveness of the coordinative chemistry based on NP surface-localized [$Ce^{3/4+}L_n$] complexes has been also readily demonstrated by the following simple experiment. Dipicolinic acid 1 (Dpic, FIG. 1) that possesses three coordinating O/S atoms is known to be a quite effective $Ce^{3/4+}$ cation complexing reagent (Prasad and Rajasekharan 2006; Katada, Seino et. al. 2008; Aghabozorg, Roshan et al. 2010). Reagent 1 (0.1 mg) has been reacted in excess with CAN-gamma-$Fe_2O_3$ NPs (saturation condition, dd$H_2O$, 0.5 ml, 3.295 mg/ml, 3 days, 20° C.) to afford Dpic-modified CAN-gamma-$Fe_2O_3$ NPs that disclosed an expected reduced zeta potential (+34.0 mV) and an increased particle size on the surface of $_{inj}$PEI$_{25}$-CAN-gamma-$Fe_2O_3$ NPs is no longer the starting pure PEI one. It might rather be a mixed PEI-organic matter polyCOOH/[$Ce^{3/4+}L_n$] complex adlayer phase that saved its overall polycationic character for RNA capture/delivery and that showed much higher thermodynamic stability during TGA combustion. Basically, TGA data have also been found coherent with related Elemental Analysis (EA) ones. $_{con}$PEI$_{25}$-CAN-gamma-$Fe_2O_3$ NPs (PEI/Fe Wt ratio: 5.25) lead to the following results, N=14.99 w %, C=27.8 w %, and H=2.1 w % (sum: 44.89 w %) while $_{inj}$PEI$_{25}$-CAN-gamma-$Fe_2O_3$ NPs (8.0 mg, Table, entry 3) afforded the following ones, N=5.13 w %, C=6.38 w %, H=1.62 w % (sum: 13.13 w %).

TABLE 1

Samples weight loss

| Entry | Sample (Graph Encoding Name) | Weight loss no 1 (%) 25-190° C. | Wt loss no 2 (%) 190-240° C. | Wt loss no 3 (%) 240-400° C. | Wt loss no 4 (%) 400-800° C. | Total Wt loss (%) |
|---|---|---|---|---|---|---|
| 1 | CAN-maghemite NPs (CAN-M) | 4.54 (25-220° C.) | | 5.31 (220-420° C.) | 4.90 (420-800° C.) | 14.74 |
| 2 | 5 mg $_{inj}$PEI$_8$-CAN-gamma-$Fe_2O_3$ NPs | 6.05 | 3.83 | 4.47 | 9.66 | 24.00 |
| 3 | 8 mg $_{inj}$PEI$_8$-CAN-gamma-$Fe_2O_3$ NPs | 11.65 | 8.77 | 6.67 | 14.34 | 41.43 |
| 4 | 20 mg PEI- CAN-gamma-$Fe_2O_3$ NPs | 13.06 | 9.75 | 7.41 | 24.34 | 54.56 |
| 5 | Branched 25 KDa PEI (PEI 25 KD) | 14.61 | | 81.36 | | 95.97 |

(DLS: 64.0 nm) when compared to starting CAN-gamma-$Fe_2O_3$ NPs. Resulting Dpic-modified CAN-gamma-$Fe_2O_3$ NPs have been then contacted with a fluorescent-labeled 25 kDa PEI polymer prepared according to ref. (Kim, Lee et al. 2007) (dd$H_2O$, 0.12 mg, overnight, 20° C.). Extensive cleaning (dd$H_2O$ washings) of the nanoparticulate phase afforded a pooled aqueous washing phase that did not show any-induced fluorescence (lambda$_{adsorption}$=498 nm). Consequently, this observation enabled to conclude that the -PEI polymer was unable to bind/functionalize Dpic-modified CAN-gamma-$Fe_2O_3$ NPs due to former Dpic-saturated [$Ce^{3/4+}$-Dpic$_n$] complexes.

Figure 17A:
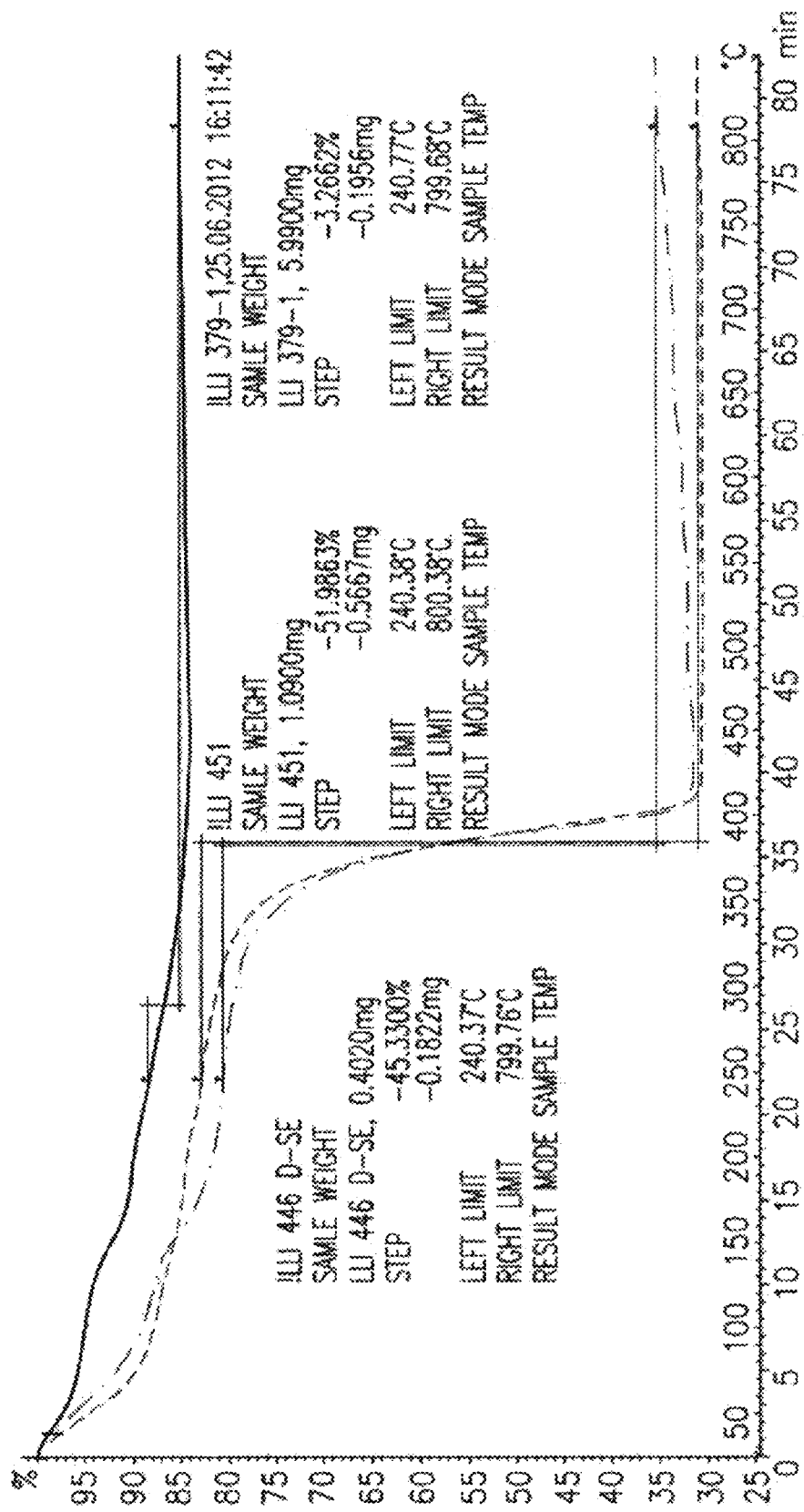
FIGS. 17a-b. are graphs showing the TGA thermogram (FIG. 17a) and the weight loss derivative function (FIG. 17b) of $_{con}PEI_{25}$-CAN-gamma-$Fe_2O_3$ NPs ((PEI ratio: 5.25)—PEI weight loss calculated from a temperature of 240° C.).
Figure 17B:
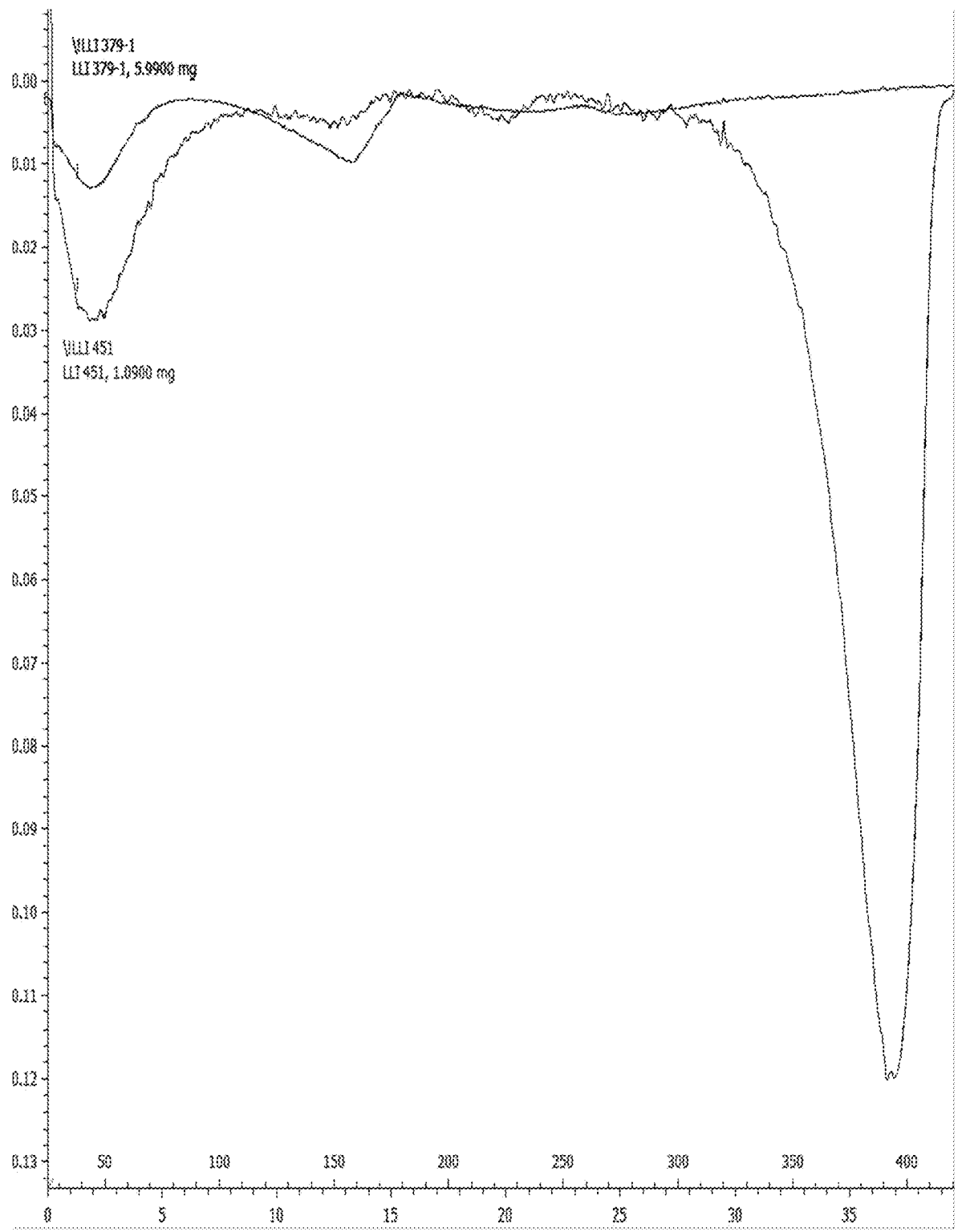
Figure 22:
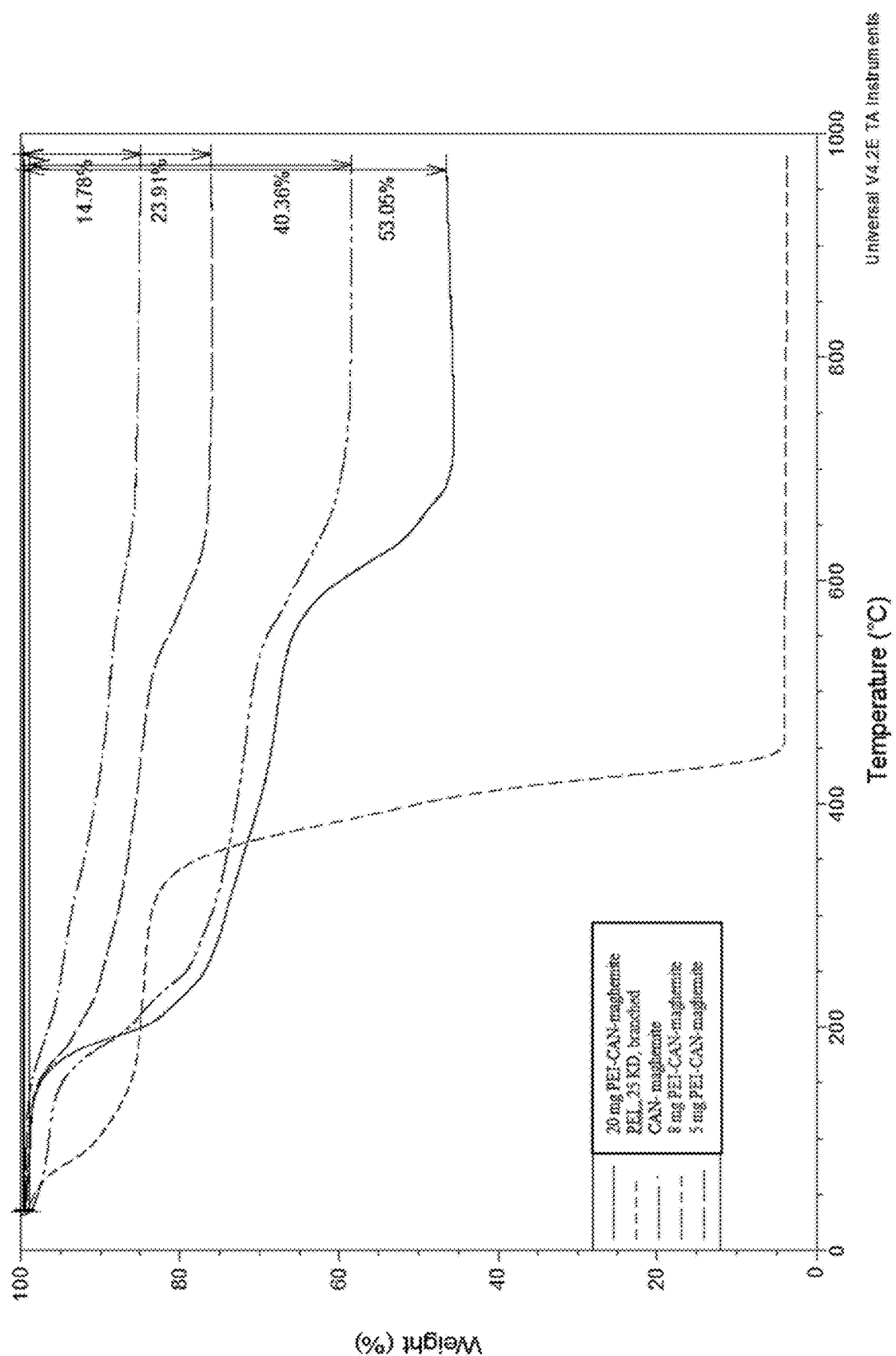
FIG. 22. is a graph showing the TGA thermogram curves of ultra-small $_{inj}$CAN-gamma-Fe$_2$O$_3$NPs at various PEI amounts (N$_2$).
Figure 23:
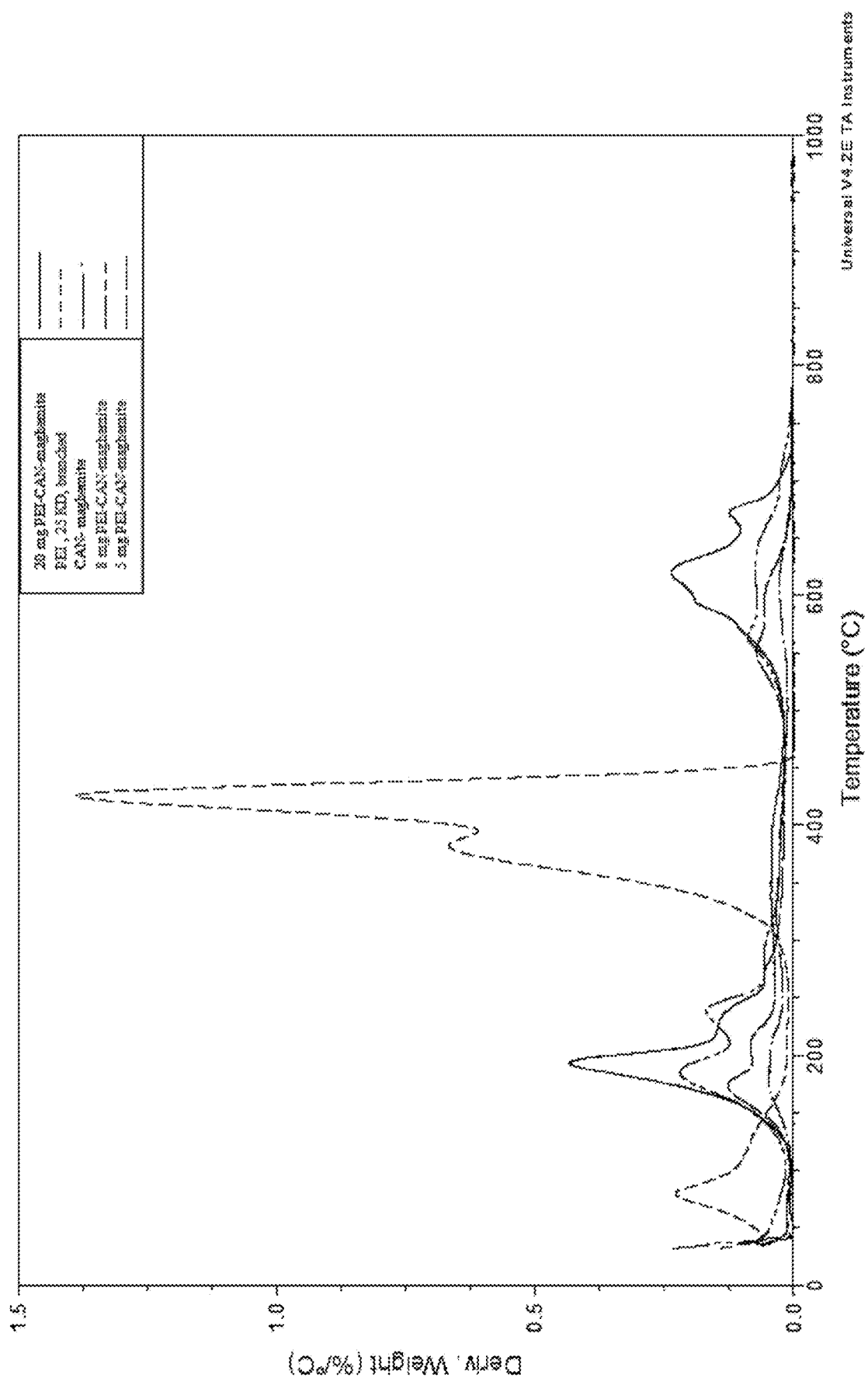
FIG. 23. are graphs showing the TGA-relating weight loss derivative function with and without 25 KDa PEI polymer at various contacting weights (25-1000° C. temperature range).
Figure 24A:
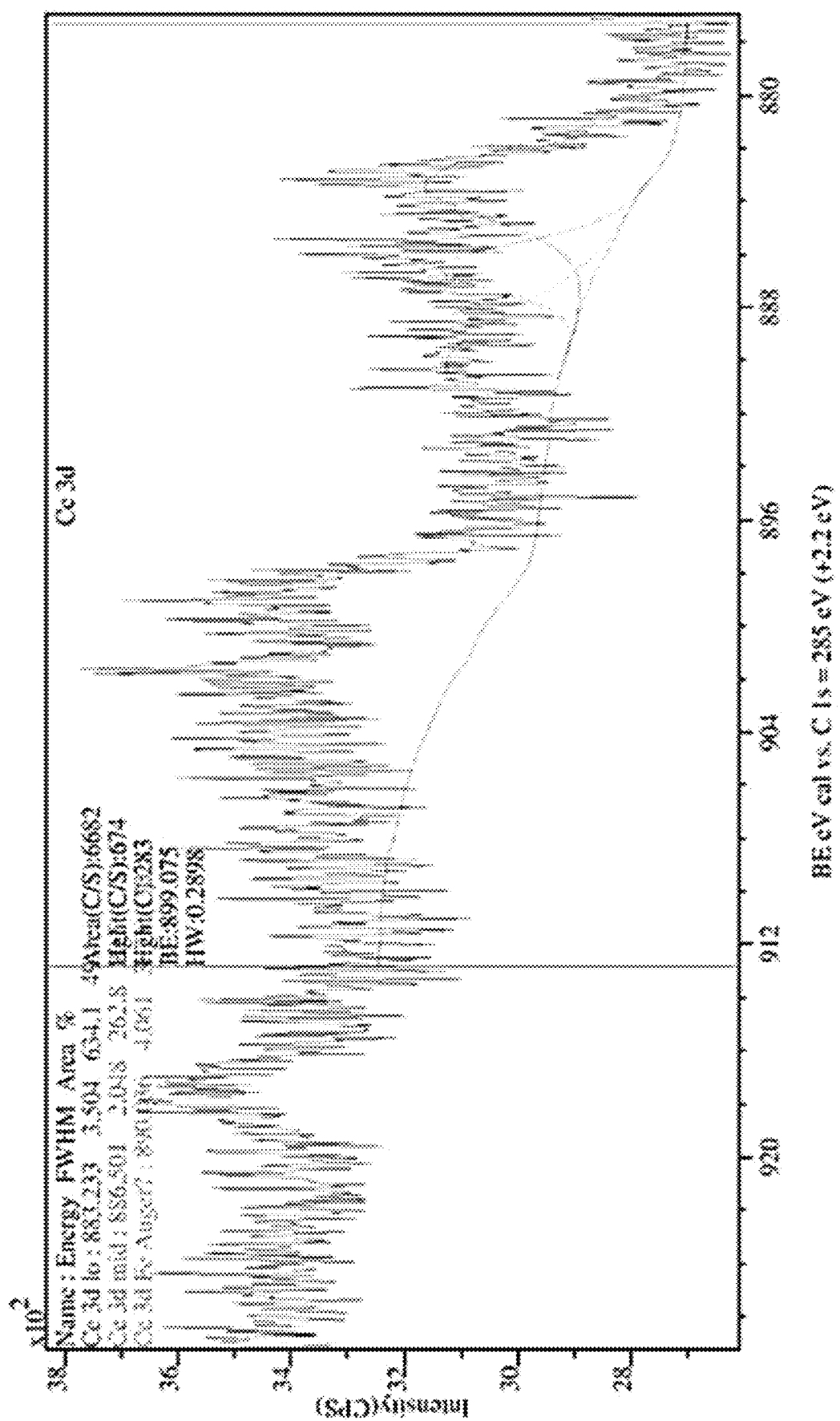
FIGS. 24 a-d. are graphs showing the XPS spectroscopy of ultra-small $_{inj}$PEI$_{10}$-CAN-gamma-Fe$_2$O$_3$ NPs (PEI loading: 10.0 mg)—Ce 3d$_{5/2}$ (BE: 899.08 eV) (FIG. 24a), Fe2p$_{3/2}$ (BE: 711.10 eV) (FIG. 24b), N 1s (nitrate anions & amine species, BE: 407.29 & 399.0-403.0 eV respectively) (FIG. 24c), and C 1s (main peak, BE: 284.89 eV & secondary deconvoluted peak, BE: =289.02 eV, characteristic of the presence of COOH groups) (FIG. 24d) peaks.
Figure 24B:
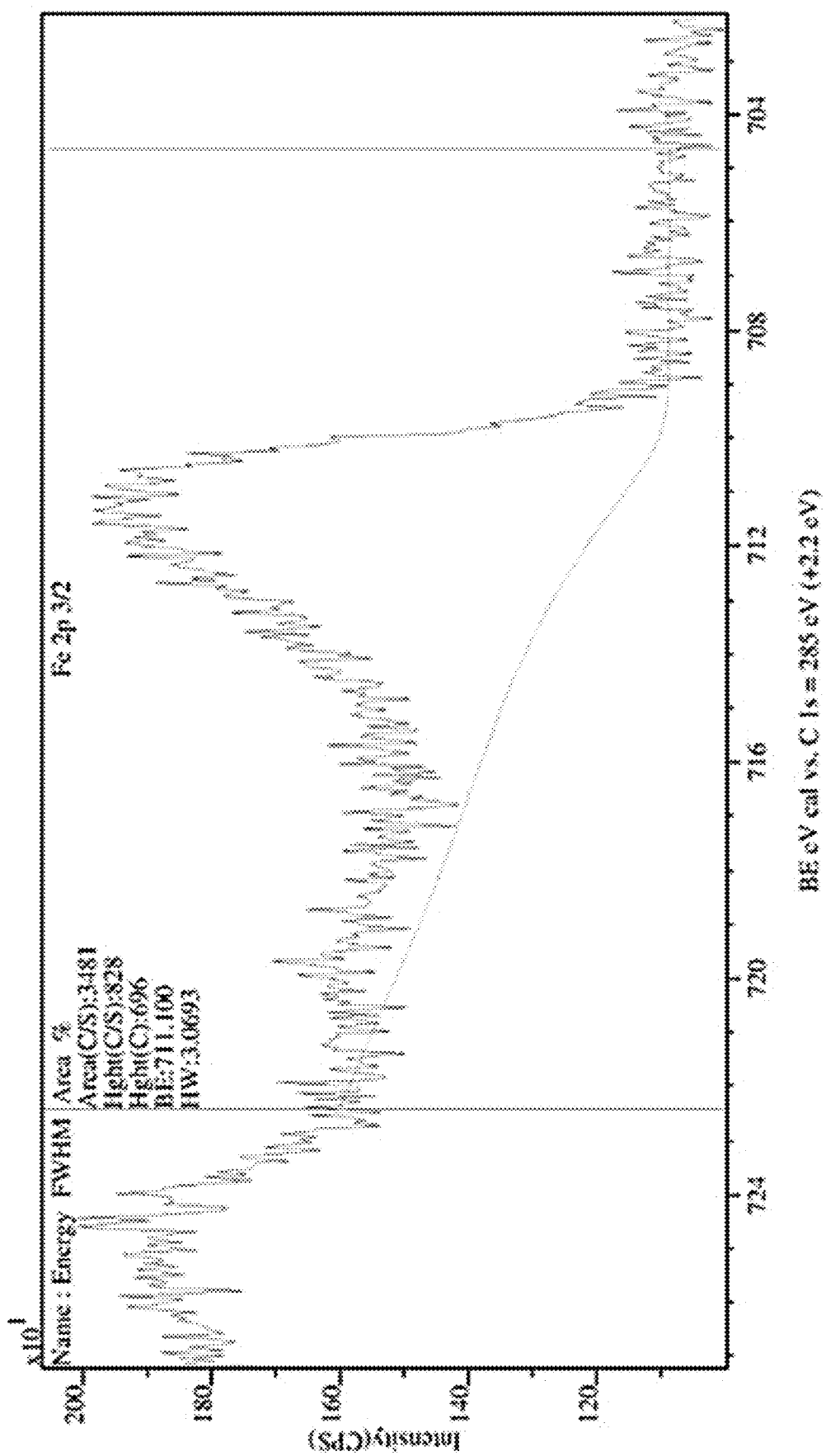
Figure 24C:
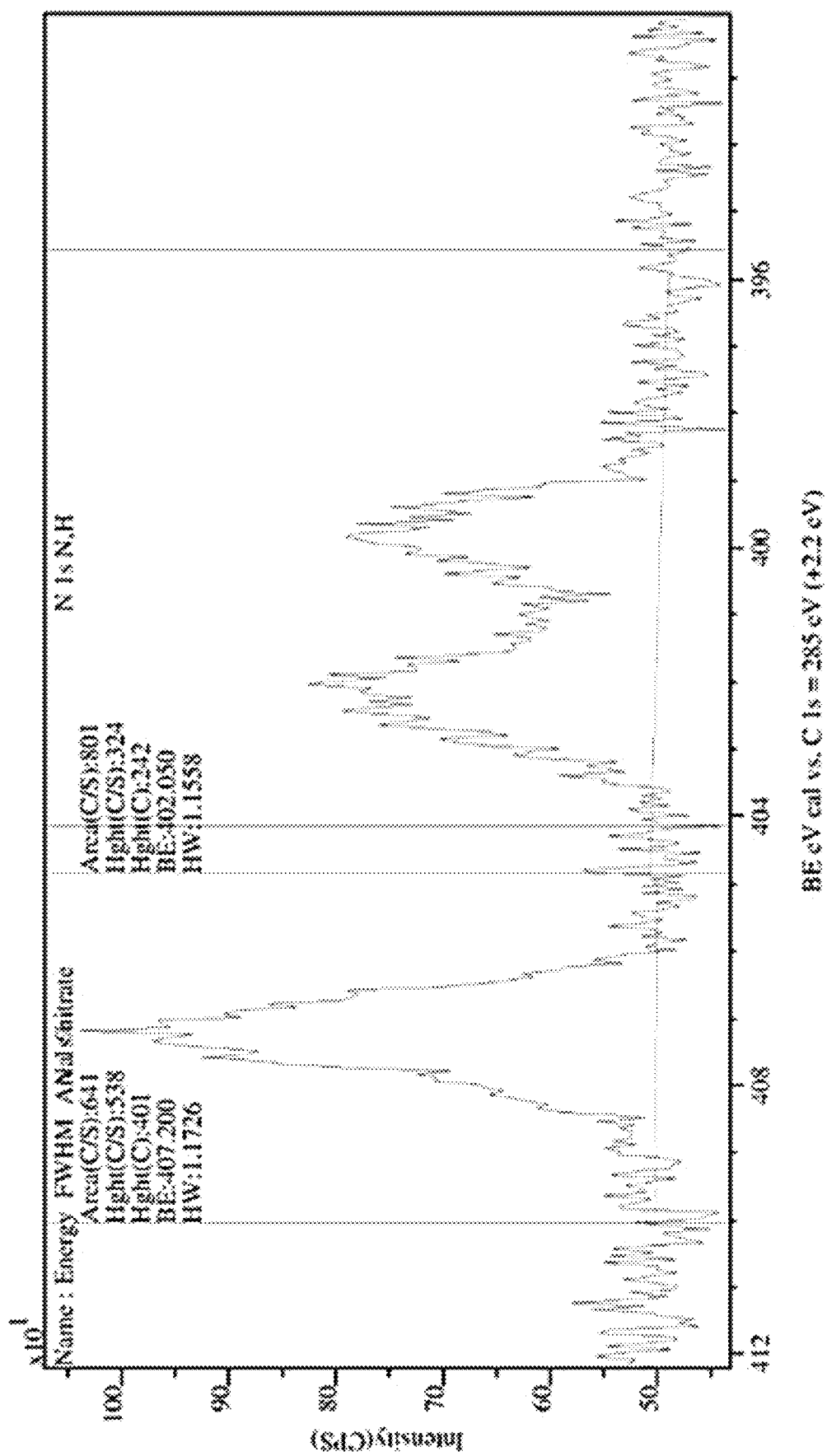
Figure 24D:
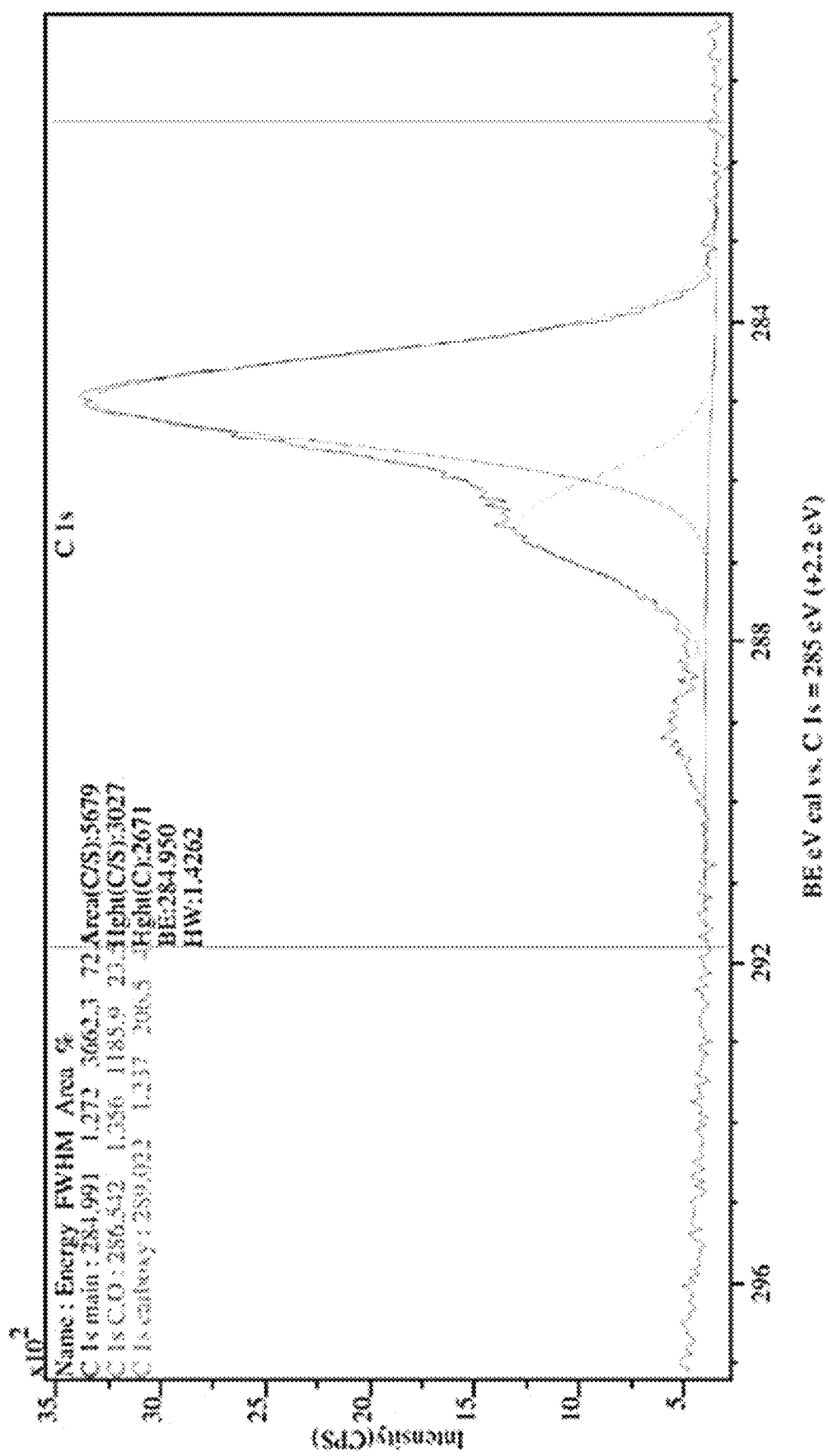

In addition and for characterization completion, both types of functional 25 kDa-decorated $_{con}$PEI$_{25}$-CAN-gamma-$Fe_2O_3$ and $_{inj}$PEI$_{25}$-CAN-gamma-$Fe_2O_3$ NPs have been also examined using thermogravimetric analysis (TGA & relating $1^{st}$ derivative graphs, $N_2$ atmosphere, 10° C./min, FIGS. 17 & 22-23). In a quite clear manner and for $_{con}$PEI$_{25}$-CAN-gamma-$Fe_2O_3$ NPs, the 25 kDa PEI weight loss can be readily identified occurring in a 240-450° C. temperature range and for a 41.27% weight loss value (FIG. 17). On the other hand, data analysis of both TGA thermograms and $1^{st}$ derivative graphs of the various $_{inj}$PEI$_{25}$-CAN-gamma-$Fe_2O_3$ NPs that have been prepared using variable increasing amounts (5-20 mg/experiment) of injected polymer (Table, entries 2-4, FIGS. 22-23) disclosed unexpected increasing amounts of PEI attached onto NPs in a 9.66-24.34% weight loss range in a 495-750° C. temperature domain. Such weight losses were significantly smaller than the one observed for $_{con}$PEI$_{25}$-CAN-gamma-$Fe_2O_3$ NPs. More importantly, they occurred at a much higher temperature domain that the one observed for the pure 25 kDa PEI polymer (Table, FIG. 23, entry 5, 240-450° C.).

These comparative results strongly suggested that the injected/ultrasonicated type of the 25 kDa PEI phase present Example 6: Functionality Characterization and Quantification of PEI-Decorated Nanoparticles Using Kaiser Test Due to the multi-phase composition of the surface of both types of PEI-decorated NPs, a deeper investigation of the overall surface functionality status and related quantification has been performed using sensitive UV spectroscopy Kaiser tests (Sarin, Kent et al. 1981) operated in different conditions. Such ninhydrin-based measurements (triplicate format) enabled quantification of both outer accessible COOH (following diamine derivatization) and/or $NH_2$ functional groups that might be quite useful for $2^{nd}$ step NP derivatization. It is worthwhile to notice that these NPs enabled three different modes of chemical derivatizations of their surface, i.e., via the (i) ultrasound-generated polyCOOH adlayer, (ii) surface-localized [$Ce^{3/4+}L_n$] complexes enabling coordination attachment chemistry of appropriate Lewis base ligands, and finally (iii) attached 25 kDa PEI/ ultrasonicated 25 KDa PEI phases.

First, direct preliminary Kaiser tests without use of 1,4-diamine afforded different values of accessible $NH_2$ groups/g NPs for both types of PEI-decorated NPs respectively, i.e., 0.847 and 0.276 mmol accessible PEI $NH_2$ groups/g NPs. As expected, $_{inj}$PEI$_{25}$-CAN-gamma-$Fe_2O_3$ NPs provided a lower surface amount of $NH_2$ groups/g NPs due to lower polymeric phase content (TGA and EA analyses). Trials aiming at quantifying the polyCOOH adlayer present in $_{con}$PEI$_{25}$-CAN-gamma-$Fe_2O_3$ NPs following EDC-mediated derivatization using 1,4-diaminobutane (1,4-$H_2N$—$(CH_2)_4$—$NH_2$) in excess were unsuccessful. Indeed, the 1,4-diamine successfully competed with the [$Ce^{3/4+}L_n$] complex-coordinated PEI phase resulting in its desorption (TGA & FT-IR tracking). In contrast, corresponding $_{inj}$-

PEI$_{25}$-CAN-gamma-Fe$_2$O$_3$ NPs operated in similar conditions, i.e., contacted with the 1,4-diamine in excess with or without EDC-activation of the polyCOOH adlayer were found stable. It afforded a 0.484 mmol accessible NH$_2$ groups/g NPs value for the polyNH$_2$ shell (1,4-diamine reaction without EDC activation). This value characterized the combined reactivity of PEI NH$_2$ groups and of [Ce$^{3/4+}$L$_n$] complex-coordinated 1,4-diamine ones with ninhydrin. When the 1,4-diamine reaction also included an EDC-activation step of the polyCOOH adlayer, an increased value of 0.883 mmol accessible NH$_2$/g NPs has been measured that characterized the polyCOOH adlayer reactivity. It means that the polyCOOH shell might be differentially quantified at a value of 0.399 mmol accessible COOH groups/g NPs. Interestingly and for the same $_{inj}$PEI$_{25}$-CAN-gamma-Fe$_2$O$_3$ NPs, both Kaiser test measurements made (i) without using the 1,4-diamine (PEI NH$_2$ groups: 0.276 mmol/g NPs) and (ii) with the 1,4-diamine but without EDC activation (combined PEI NH$_2$ and [Ce$^{3/4+}$L$_n$] complex-coordinated 1,4-diamine ones: 0.484 mmol/g NPs) enabled to quantify the neat contribution of the 1,4-diamine [Ce$^{3/4+}$L$_n$] complex coordination reactivity to a differential value of 0.208 mmol accessible NH$_2$ groups/g NPs.

In summary and solely relating to $_{inj}$PEI$_{25}$-CAN-gamma-Fe$_2$O$_3$ NPs, the separate contributions of each mode of NP chemical derivatization, i.e., the ultrasound-generated polyCOOH adlayer, the surface-localized [Ce$^{3/4+}$L$_n$] complex-based phase, and finally the 25 kDa PEI one have been found to contribute for 0.399, 0.208, and 0.276 mmol accessible NH$_2$ groups/g NPs respectively, which providing a deeper insight on the surface properties of that type of NPs. These quantified data also enabled to make one additional remark. Comparison of 25 kDa PEI contributions for $_{con}$PEI$_{25}$-CAN-gamma-Fe$_2$O$_3$ (0.847 mmol NH$_2$ groups/g NPs) and for $_{inj}$PEI$_{25}$-CAN-gamma-Fe$_2$O$_3$ NPs (0.276 mmol NH$_2$ groups/g NPs) again agreed the previously observed lower incorporation of the ultrasonicated 25 kDa PEI polymer phase for the one-step injection process of NP fabrication.

Figure 15A:
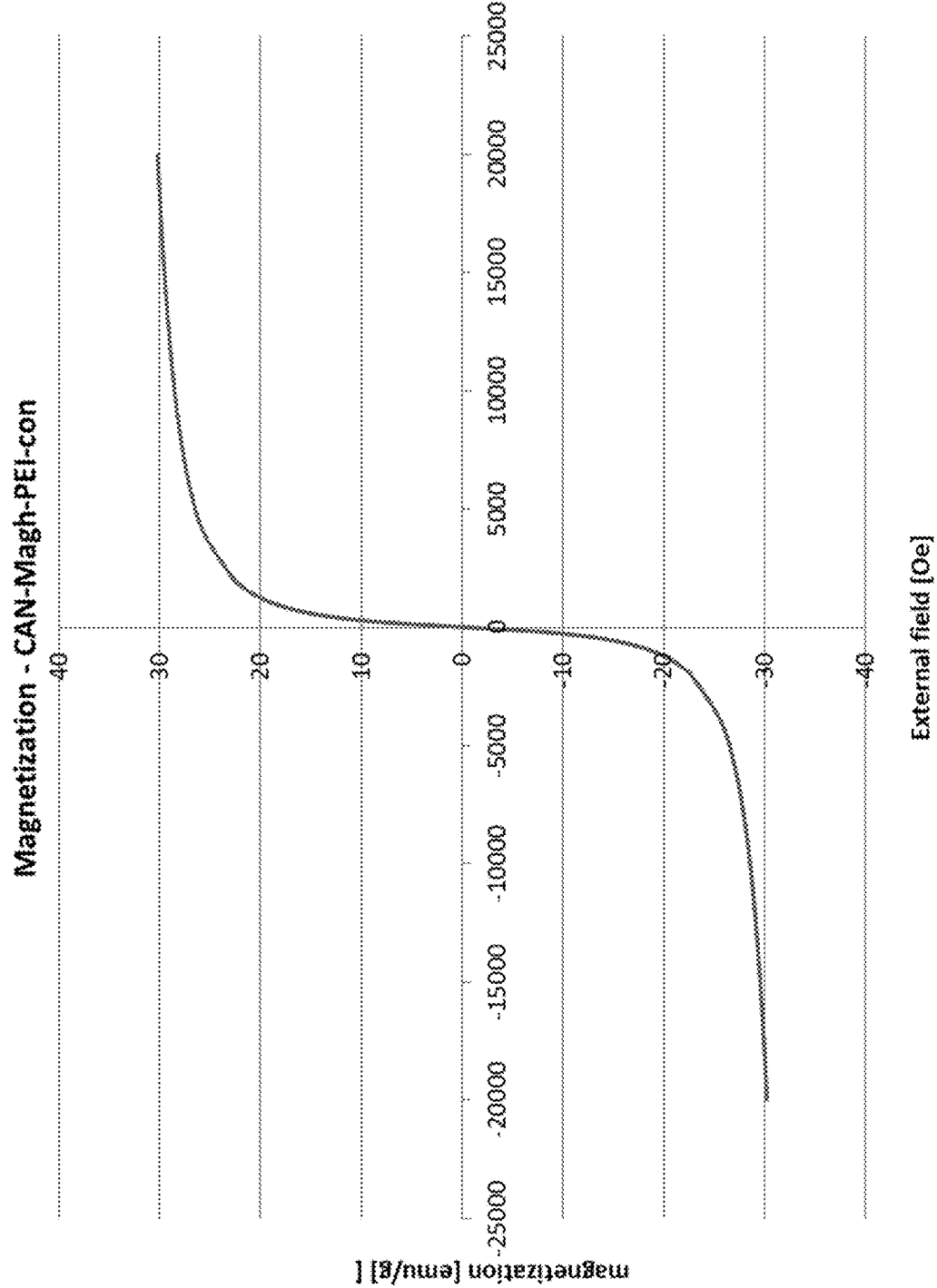
FIGS. 15a-b. are graphs showing the SQUID magnetization profile (saturation magnetization Ms: 30.2 emu/g) (FIG. 15a) and blocking temperature (ZFC and FC plots, $T_B$: 109-111° K, H=100 Oe) (FIG. 15b) of ultra-small $_{con}PEI_{25}$-CAN-gamma-$Fe_2O_3$ NPs (PEI ratio: 5.25).
Figure 15B:
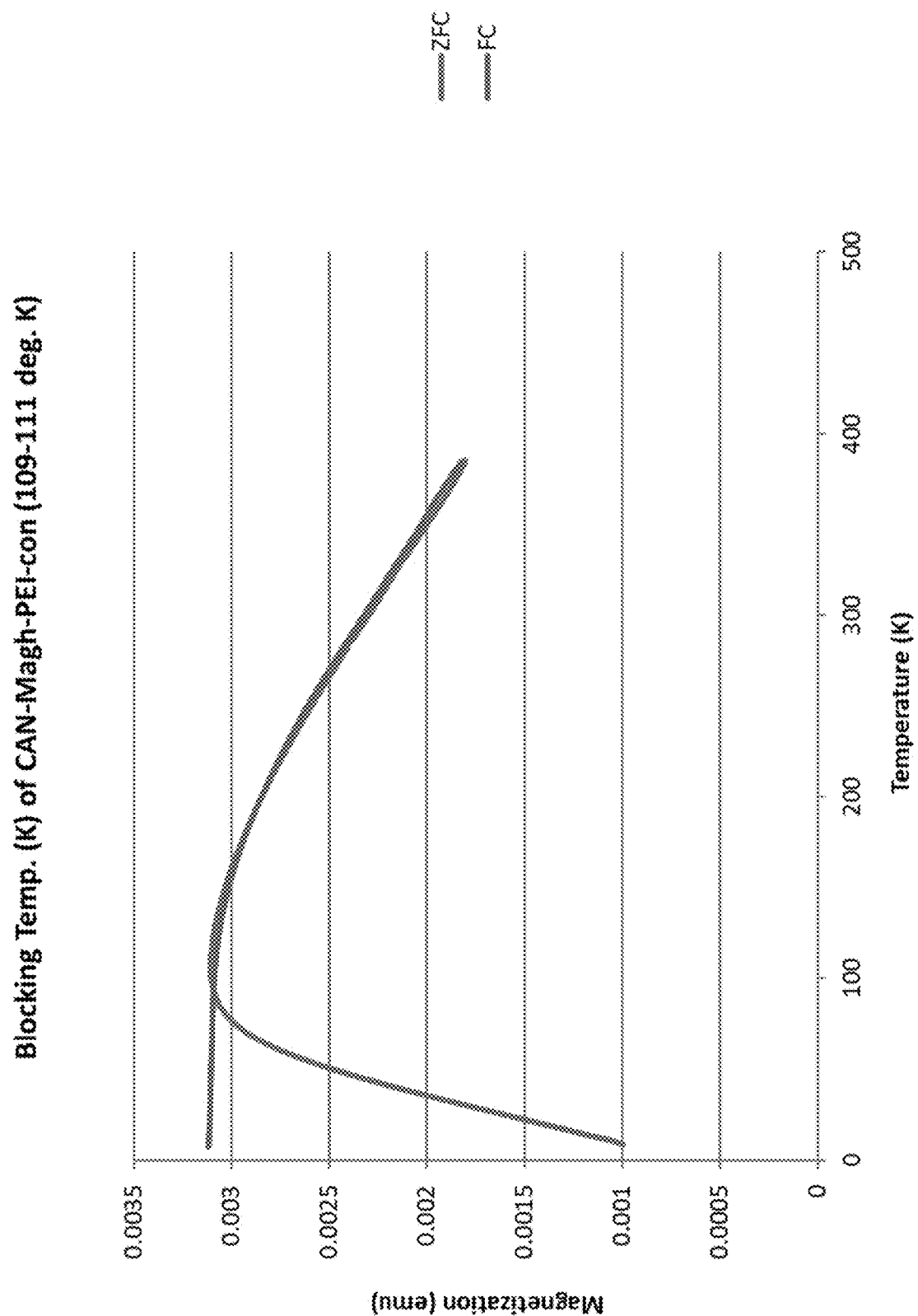
Figure 16:
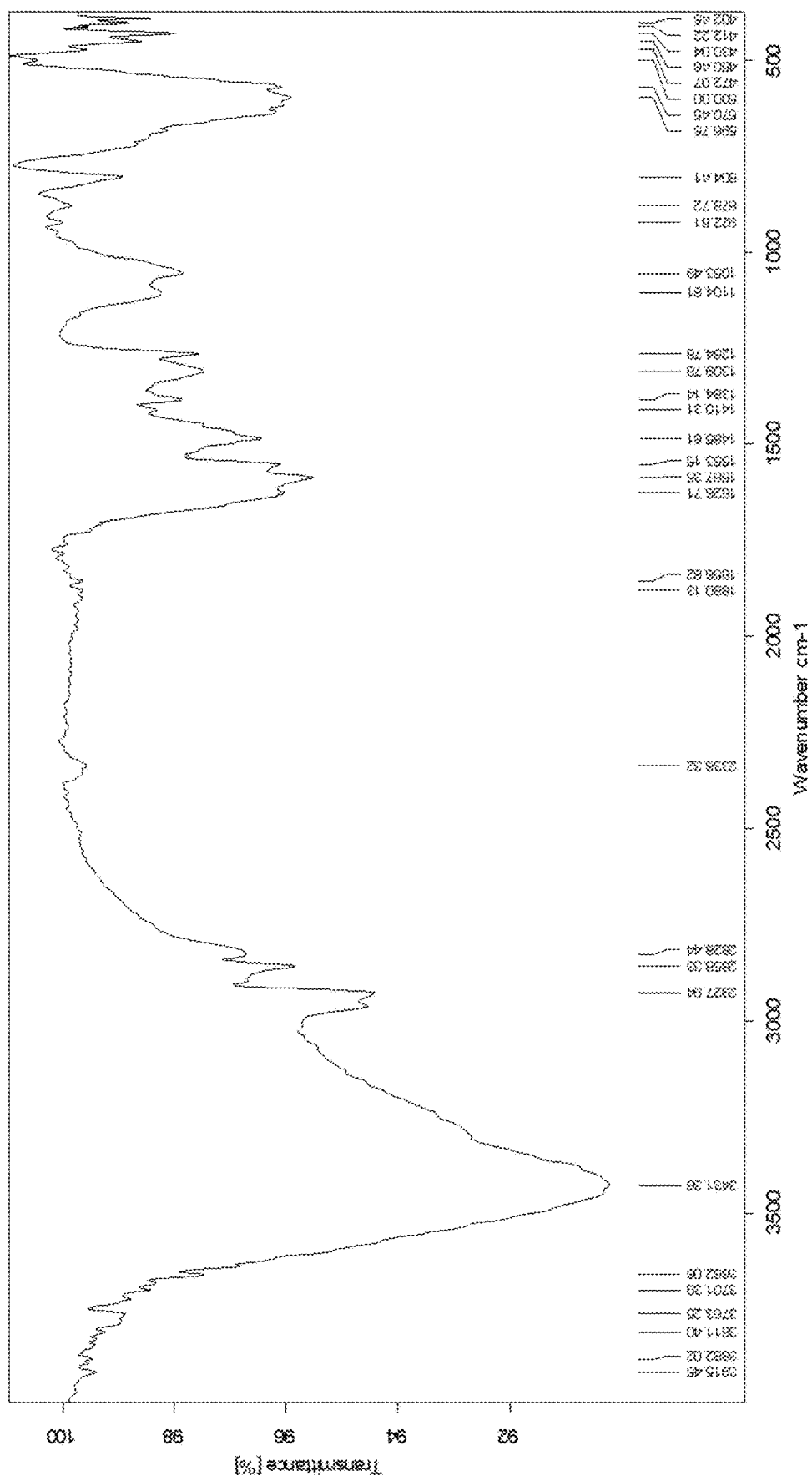
FIG. 16. is a graph showing the FT-IR spectrum of ultra-small $_{con}PEI_{25}$-CAN-gamma-$Fe_2O_3$ NPs (PEI ratio: 5.25).
Figure 25A:
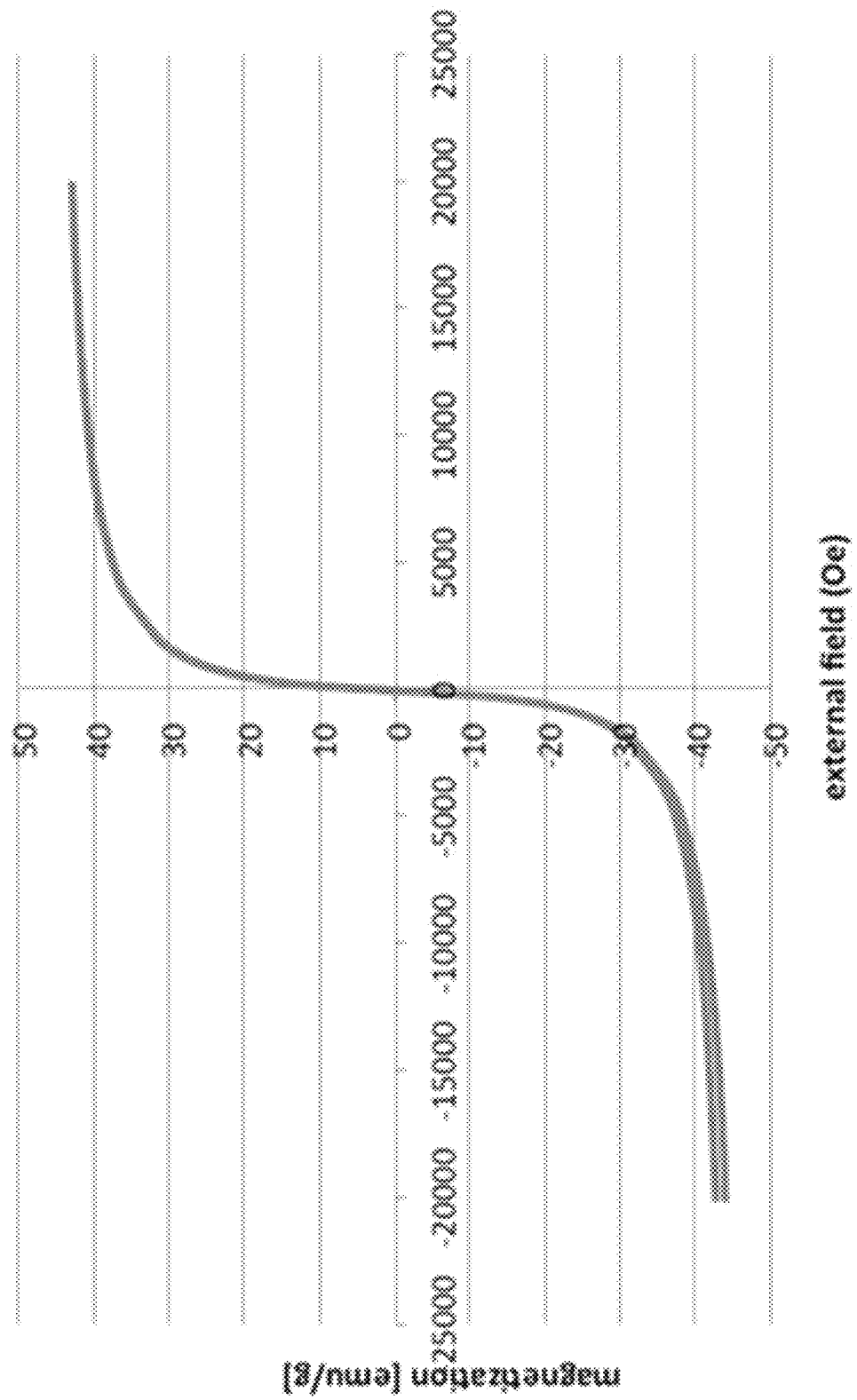
FIGS. 25 a-b. are graphs showing the SQUID magnetization profile (saturation magnetization Ms: 44.0 emu/g) (FIG. 25a) and blocking temperature (ZFC & FC plots, T$_B$: 127-129° K, H=100 Oe) (FIG. 25b) of ultra-small $_{inj}$PEI$_8$-CAN-gamma-Fe$_2$O$_3$ NPs (PEI loading: 8.0 mg).
Figure 25B:
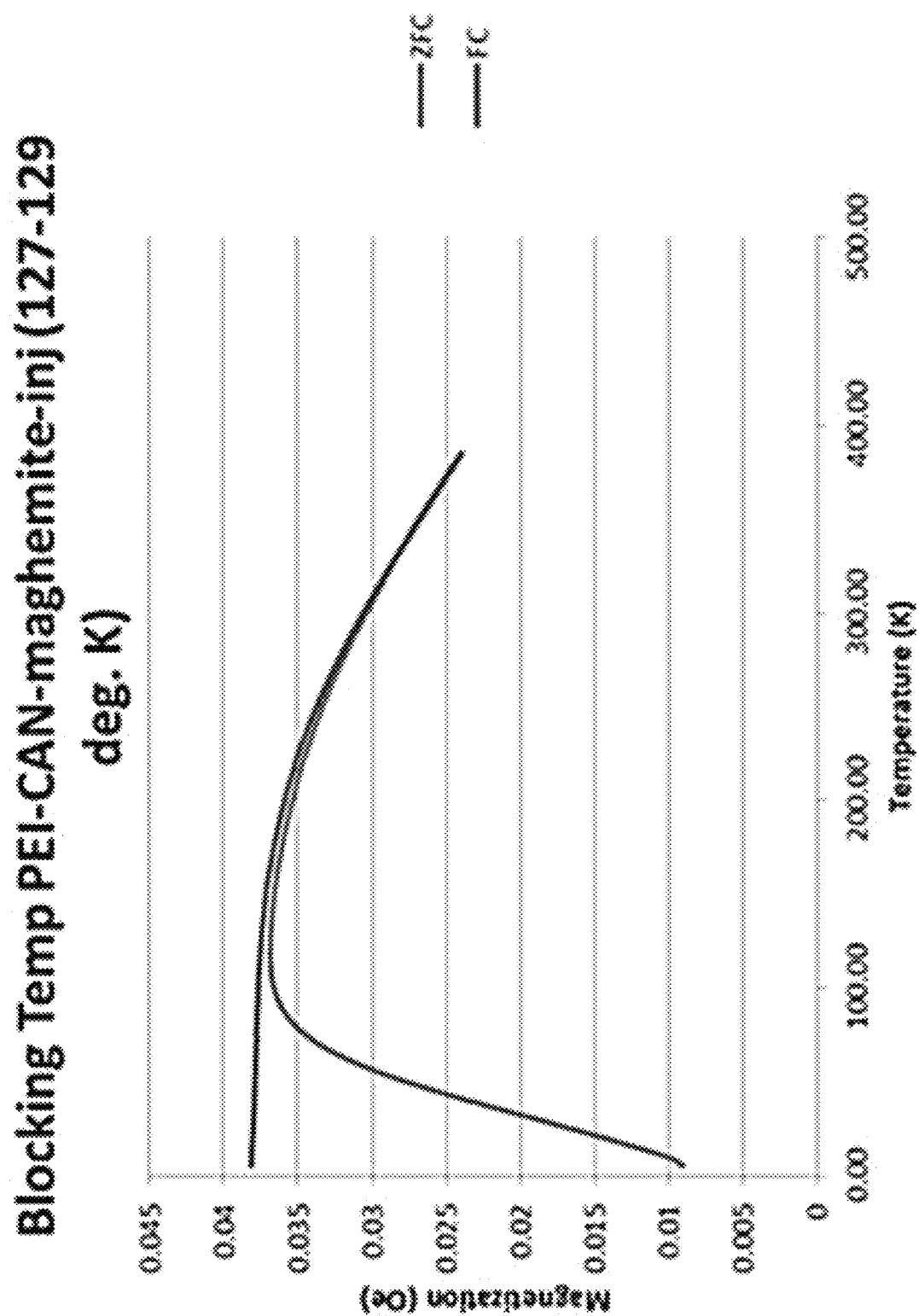

Magnetic properties of PEI-decorated NPs: FIGS. 15 & 25 reported both SQUID magnetization profiles and blocking temperatures (ZFC & FC graphs) for both ultra-small $_{con}$PEI$_{25}$-CAN-gamma-Fe$_2$O$_3$ NPs (PEI ratio: 5.25) and $_{inj}$PEI$_{8}$-CAN-gamma-Fe$_2$O$_3$ NPs (PEI loading: 8.0 mg). Clearly and similarly to former CAN-gamma-Fe$_2$O$_3$ NPs, both types of functional PEI-decorated NPs were found super-paramagnetic (hysteresis absence). They afforded corresponding Ms values of 32.2 and 44.0 emu/g as well as blocking temperatures of 109-110 & 127-129° C. respectively.

Example 7: PEI-Decorated CAN-Stabilized Maghemite Nanoparticles ($_{con}$PEI$_{25}$-CAN-Gamma-Fe$_2$O$_3$ NPs)—Optimal Aqueous PEI Contacting Process/Experimental Protocol The former corresponding NP aqueous mixture arising from CAN-mediated high power ultrasonication (Sonics®, Vibra cell, 750 Watt, power modulator set-up at 25%, Ti horn (45 min, 0° C.), dry inert argon atmosphere, 0.25 mL, Fe: 3.88 mg/mL—0.97 mg total Fe, 0.0174 mmol Fe, ICP measurement) was diluted to 1.0 mL using milliQ purified H$_2$O. Then, 5.034 mg of 25 KDa branched PEI (0.0002 mmol, PEI/Fe Wt ratio: 5.25) were added at room temperature to the NP suspension as an aqueous solution (10.0 mg PEI/mL) and the medium was shaken overnight at room temperature (orbital shaker). At completion of such a mild PEI contacting/NP surface decoration, resulting crude $_{con}$-PEI$_{25}$-CAN-gamma-Fe$_2$O$_3$ NPs (six gathered parallel processed reactions/six similarly treated batches for scale-up needs) were washed 3 times (3×10 mL ddH$_2$O) using an Amicon® Ultra-15 centrifugal filter device (100K) operated at 4,000 rpm (5 min) followed by a size exclusion process performed using centrifugation (8,000 rpm/min, 20 min, 18° C. and 7,000 rpm, 14 min, 18° C.) to afford cleaned $_{con}$PEI$_{25}$-CAN-gamma-Fe$_2$O$_3$ NPs. TEM analysis enabled to measure an averaged 6.50±2.15 nm particle diameter for cleaned ultra-small $_{con}$PEI$_{25}$-CAN-gamma-Fe$_2$O$_3$ NPs (PEI/Fe Wt ratio: 5.25).

PEI-decorated CAN-stabilized maghemite nanoparticles ($_{inj}$PEI$_{25}$-CAN-gamma-Fe$_2$O$_3$ NPs)—Optimal aqueous PEI injection process/experimental protocol: The former corresponding NP aqueous mixture arising from CAN-mediated high power ultrasonication (20 mL, Sonics®, Vibracell, 750 Watt, power modulator set-up at 25%, Ti horn (45 min, 0° C.), dry inert Ar atmosphere) was added with 8.0 mg of 25 kDa branched PEI (0.00032 mmol dissolved in 0.5 mL ddH$_2$O) via a one shot injection into the reaction medium (Ar atmosphere). High power ultrasonication was pursued for 15 additional minutes at same temperature/ultrasonication conditions. Resulting hydrophilic highly stable brown-colored $_{inj}$PEI$_{25}$-CAN-gamma-Fe$_2$O$_3$ NPs were then washed with ddH$_2$O (3×10 mL) using an Amicon® Ultra-15 centrifugal filter device (100K) operated at 4,000 rpm during 5 min (room temperature) and re-dispersed in ddH$_2$O (15 mL) for storage and/or gene silencing experiments. TEM analysis enabled to measure an averaged 7.65±2.65 nm particle diameter for cleaned ultra-small $_{inj}$PEI$_{25}$-CAN-gamma-Fe$_2$O$_3$ NPs.

Example 8: NP Functionalization Via Selected Chemical Modifications of the NP Organic Shell: Cases of (C1) NP-Supported PEI$_{25}$ Controlled Oxidation & Coordination of Specific Various Polycationic Polymers (Chitosan & Poly-L-Lysine: Chi & PLL) and/or Hybrid PEI/Polycationic Polymer Combinations—Main Selected Particulate Characterization Data with Respective Optimized (In Vitro Firefly/*Renilla* Gene Silencing)

Figure 29A:
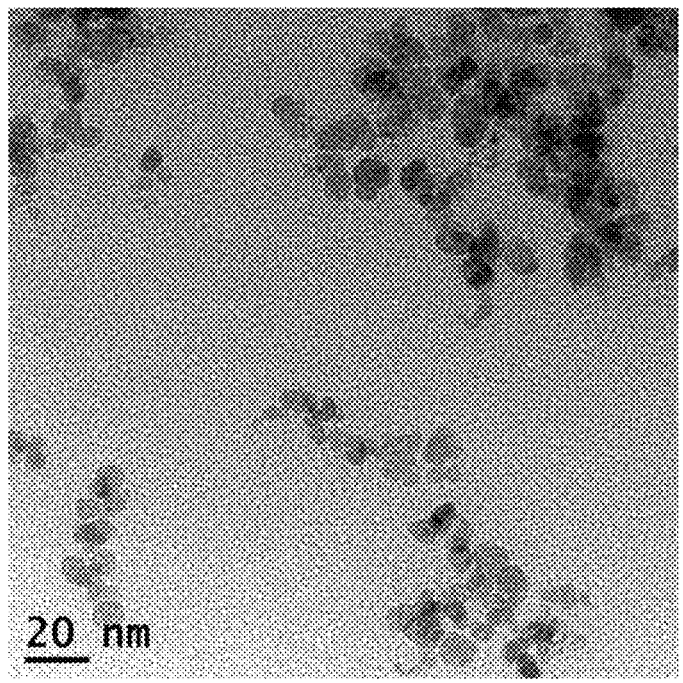
FIGS. 29a-b. includes: a TEM microphotograph (FIG. 29a) and a histogram (FIG. 29b) showing the size distribution of 6.36±2.65-sized PEI oxidized $_{con}$PEI$_{25-ox}$-CAN-gamma-Fe$_2$O$_3$ NPs.
Figure 29B:
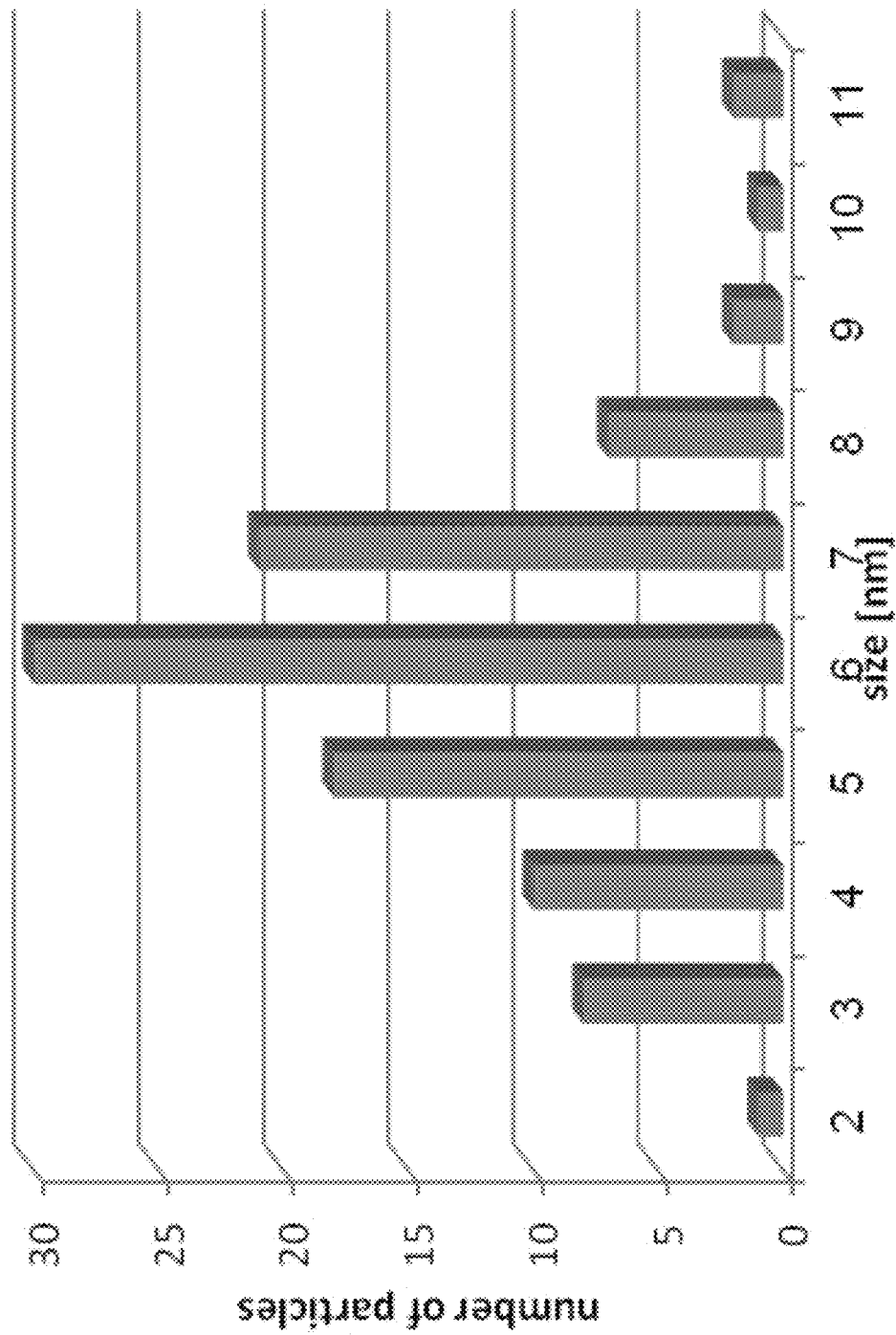
Figure 40:
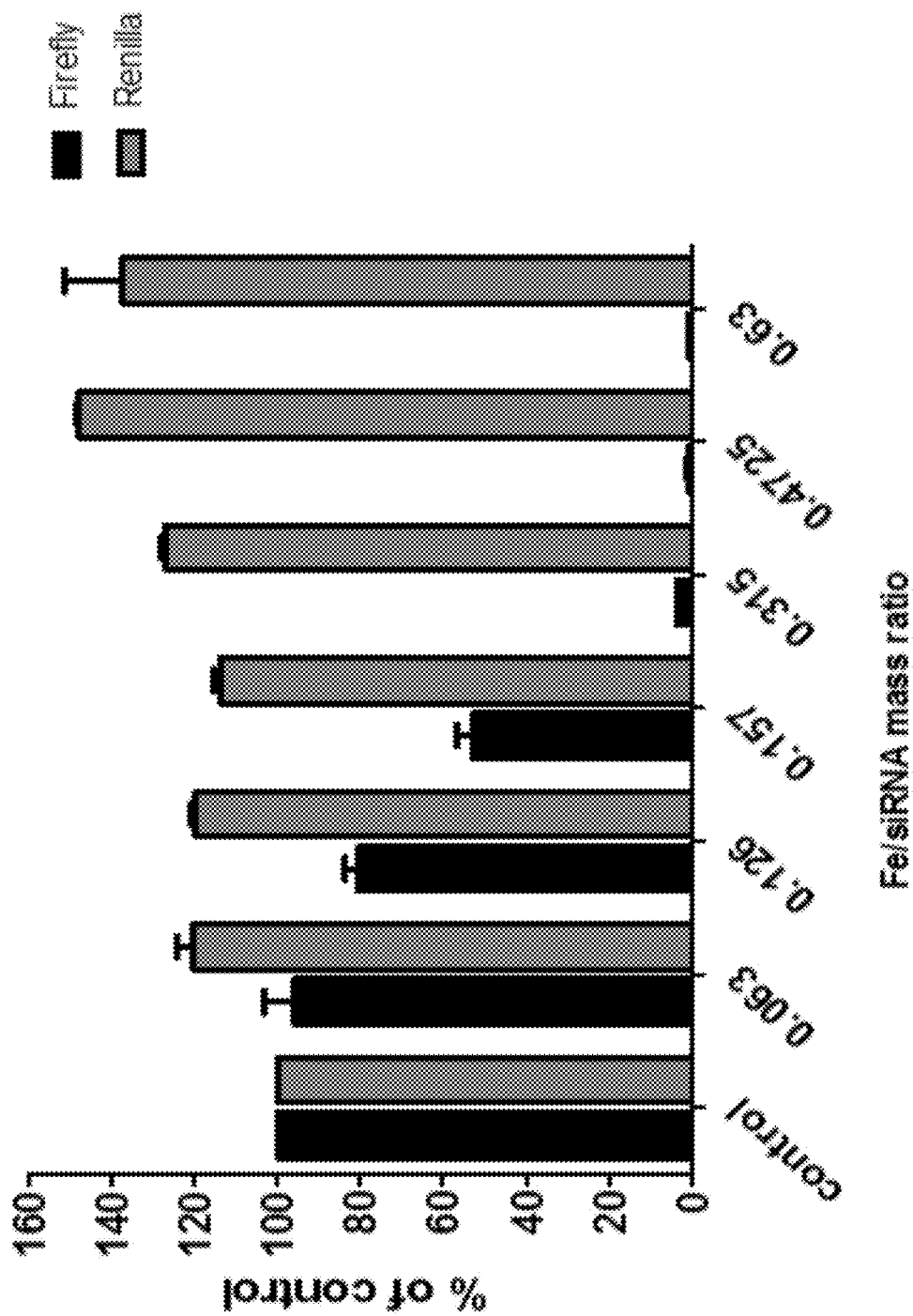
FIG. 40. is a graph showing Firefly Luciferase silencing in U2OS-Luc cells with $_{con}$PEI$_{25-ox}$-CAN-gamma-Fe$_2$O$_3$ NPs (0.1% oxidation level).

In order to provide much higher surface chemical versatility to NP design, the innovative Ce$^{3/4+}$ complex coordinative chemistry fully detailed above can have further exploited for 25 kDa PEI toxicity mitigation, i.e., using selective main group chemical modifications such as (i) controlled amine oxidation towards charge reduction of the PEI phase since PEI primary, secondary, and tertiary amines might be readily converted to corresponding mixed hydroxylamines (—NH—OH)/nitroso species (—N=O)/nitro species (—N(+)(=O)O(-)), secondary hydroxylamines (RR'—N—OH), and tertiary N-oxide [R$_3$N(=)—O(-)] respectively including (ii) use of PEI replacement alternative polycationic polymers (poly-L-lysine/Chitosan) and/or their hybrid mixtures including mixtures with polyanionic ones such as Alginic & Hyaluronic acids (Al & Hy, contact process) for NP toxicity reduction. Main fabrication protocols and selected characterization data of resulting composite particles have been mentioned below:

H$_2$O$_2$-mediated controlled PEI shell oxidation of $_{con}$PEI$_{25}$-CAN-gamma-Fe$_2$O$_3$ NPs-Optimized fabrication of corresponding PEI oxidized $_{con}$PEI$_{25\text{-}ox}$-CAN-gamma-Fe$_2$O$_3$ NPs (FIGS. 29 & 40) In a typical reaction, 3.1 mL of former aqueous $_{con}$PEI$_{25}$-CAN-gamma-Fe$_2$O$_3$ (Fe=0.41 mg/mL by ICP, Fe=1.0664 mg, NPs concentration ~4.1 mg/mL) were further diluted to 14 mL (ddH$_2$O) in a conic plastic centrifuge tube. Then, 0.341 mL of a 0.000075% wt aqueous solution of $H_2O_2$ in milliQ purified $H_2O$ is added (0.1% molar of starting NPs primary amines ($NH_2$) as measured by a Kaiser Test—0.0008 mmol $NH_2$/mg NPs). Then the reaction mixture has been shaken at 250 rpm & 10° C. overnight (cooled orbital shaker). The resulting reaction mixture was then washed by milliQ purified $H_2O$ (3×8 mL) using an Amicon® Ultra-15 centrifugal filter device (100K) operated at 4,000 rpm (centrifuge) during 5-6 min (rt, 18° C.), and then concentrated to 0.5-1 mL by water evaporation (ICP-AES, Fe=0.41 mg/mL). Selected characterization data: Average TEM & DLS sizes: 6.36±2.65 & 112.2 nm, zeta potential: +29.4 mV.

Figure 41:
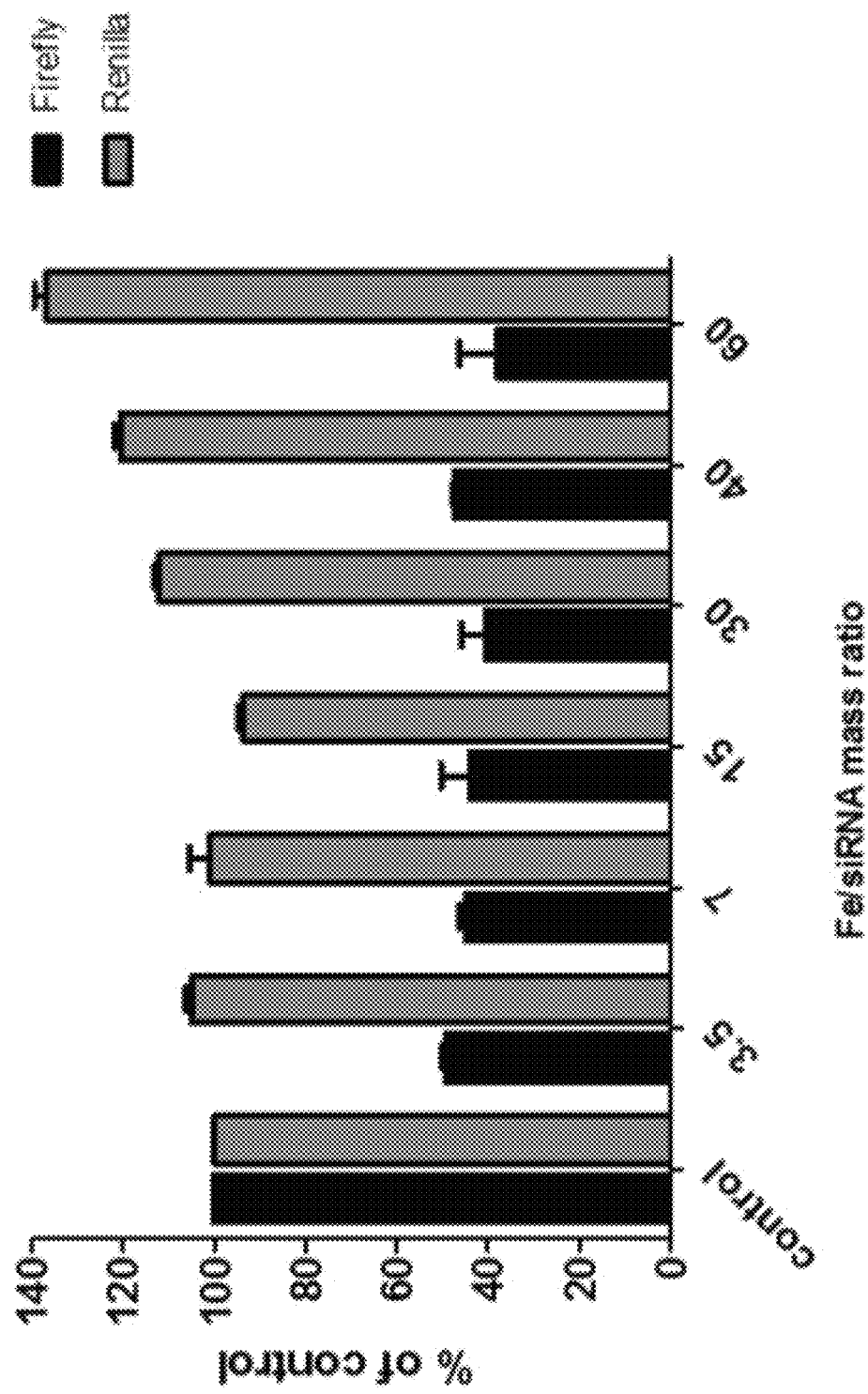
FIG. 41. is a graph showing Firefly Luciferase silencing in U2OS-Luc cells with $_{con}$Chi-CAN-gamma-Fe$_2$O$_3$ NPs (Fe/Chi w/w ratio of 1/5).

$_{con}$Chi-CAN-gamma-$Fe_2O_3$ NPs—Optimal fabrication protocol (FIG. 41): Former CAN-stabilized maghemite nanoparticles (1.0 mL aqueous suspension, 1.5 mg elemental Fe as measured by ICP-AES) were added with 22.25 mg of 50-190 KDa chitosan (Chi, $1.17 \times 10^{-4}$ mmol) dissolved in 20 mL dd$H_2O$) and incubated overnight (orbital shaker, 250 rpm, 20° C.). Resulting hydrophilic highly stable $_{con}$Chi-CAN-gamma-$Fe_2O_3$ NPs were then washed with dd$H_2O$ (3×10 mL) using an Amicon® Ultra-15 centrifugal filter device (100K) operated at 4,000 rpm (centrifuge) during 5 min (room temperature) and re-dispersed in dd$H_2O$ (1.0 mL) for storage and/or gene silencing experiments. Selected characterization data: Average TEM & DLS sizes: 7.1±1.29 & 410.4 nm, zeta potential: +52.7 mV.

Figure 42:
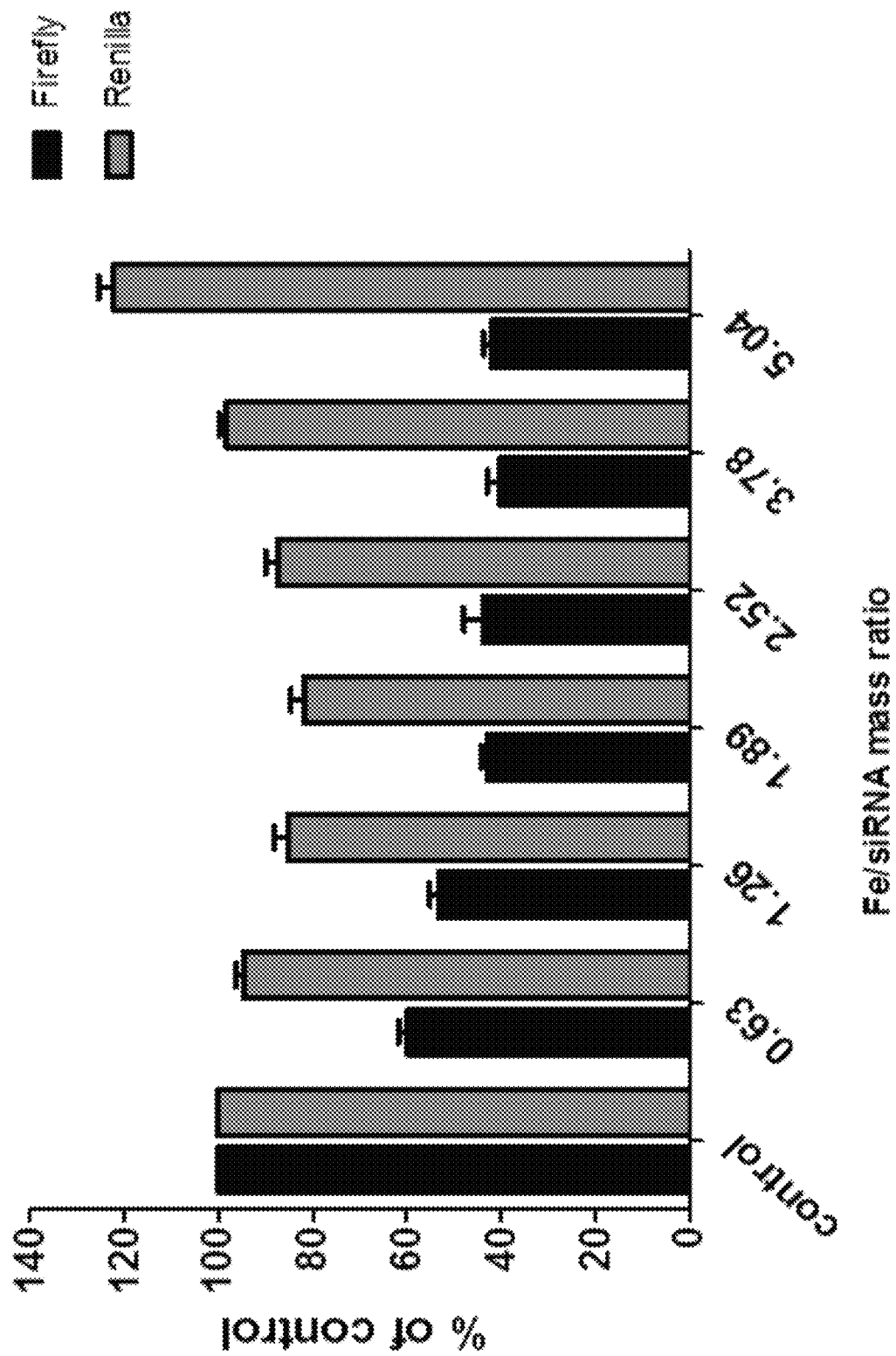
FIG. 42. is a graph showing Firefly Luciferase silencing in U2OS-Luc cells with $_{con}$PLL-CAN-gamma-Fe$_2$O$_3$ NPs (Fe/PLL w/w ratio of 1/3).

$_{con}$PLL-CAN-gamma-$Fe_2O_3$ NPs—Optimal fabrication protocol (FIG. 42): Same CAN-stabilized maghemite nanoparticles (1.0 mL aqueous suspension, 1.5 mg elemental Fe as measured by ICP-AES) were added with 13.35 mg of 15-30 KDa Poly-L-Lysine (PLL, $4.45 \times 10^{-4}$ mmol) dissolved in 20 mL dd$H_2O$) and incubated overnight (orbital shaker, 250 rpm, 20° C.). Resulting hydrophilic highly stable $_{con}$PLL-CAN-gamma-$Fe_2O_3$ NPs were then washed with dd$H_2O$ (3×10 mL) using an Amicon® Ultra-15 centrifugal filter device (100K) operated at 4,000 rpm (centrifuge) during 5 min (room temperature) and re-dispersed in dd$H_2O$ (1.0 mL) for storage and/or gene silencing experiments. Selected characterization data: Average TEM & DLS sizes: 6.4±1.35 & 84.7 nm, zeta potential: +37.0 mV.

Figure 30A:
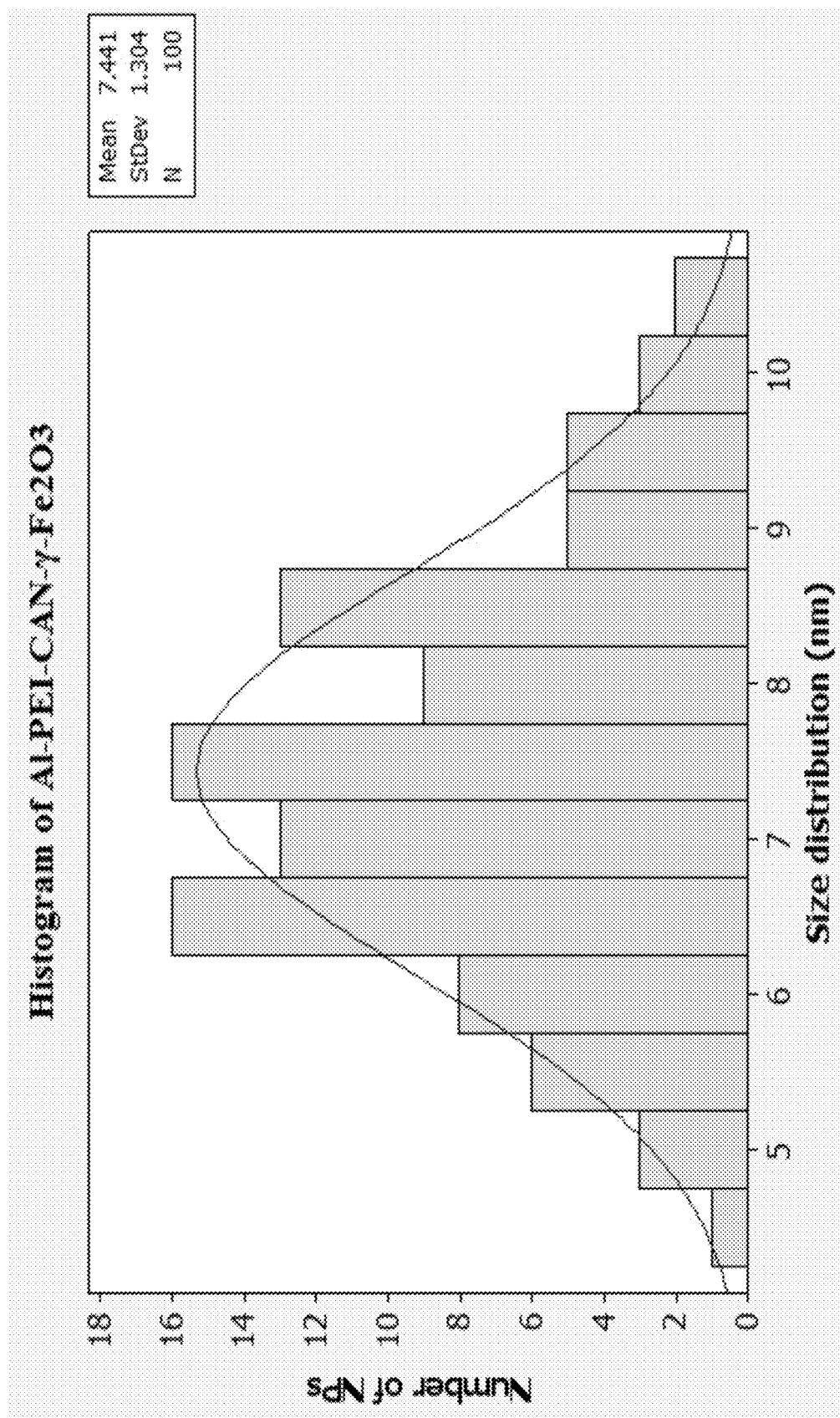
FIGS. 30a-b. includes: a TEM microphotograph (FIG. 30a) and a histogram (FIG. 30b) showing the size distribution of ultra-small averaged 7.44 nm-sized $_{con}$Al/PEI$_{25}$-CAN-gamma-Fe$_2$O$_3$ NPs.
Figure 30B:
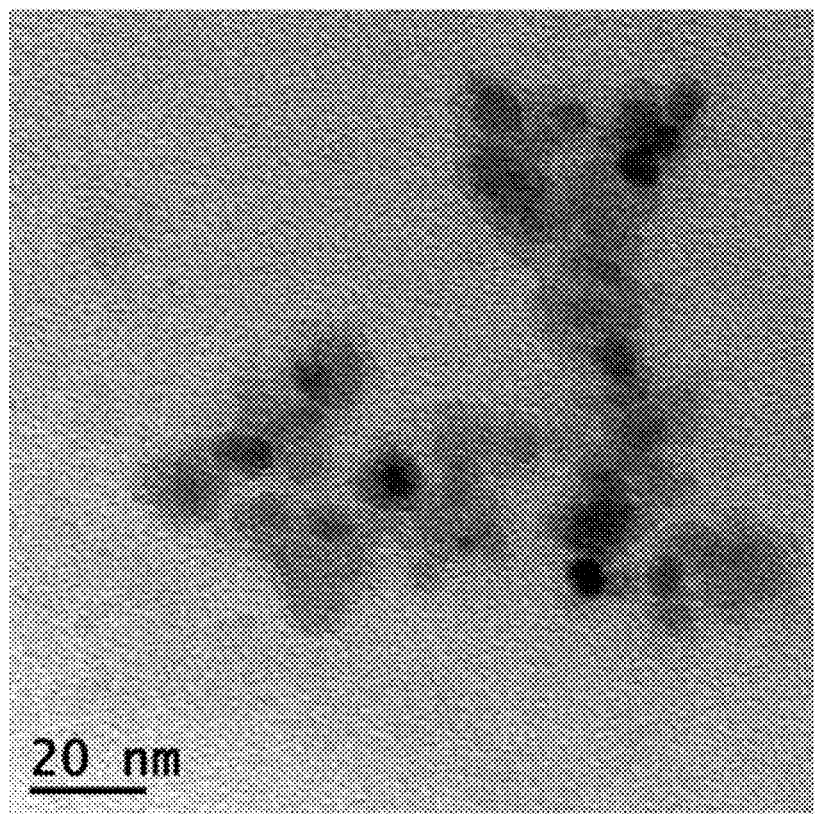
Figure 43:
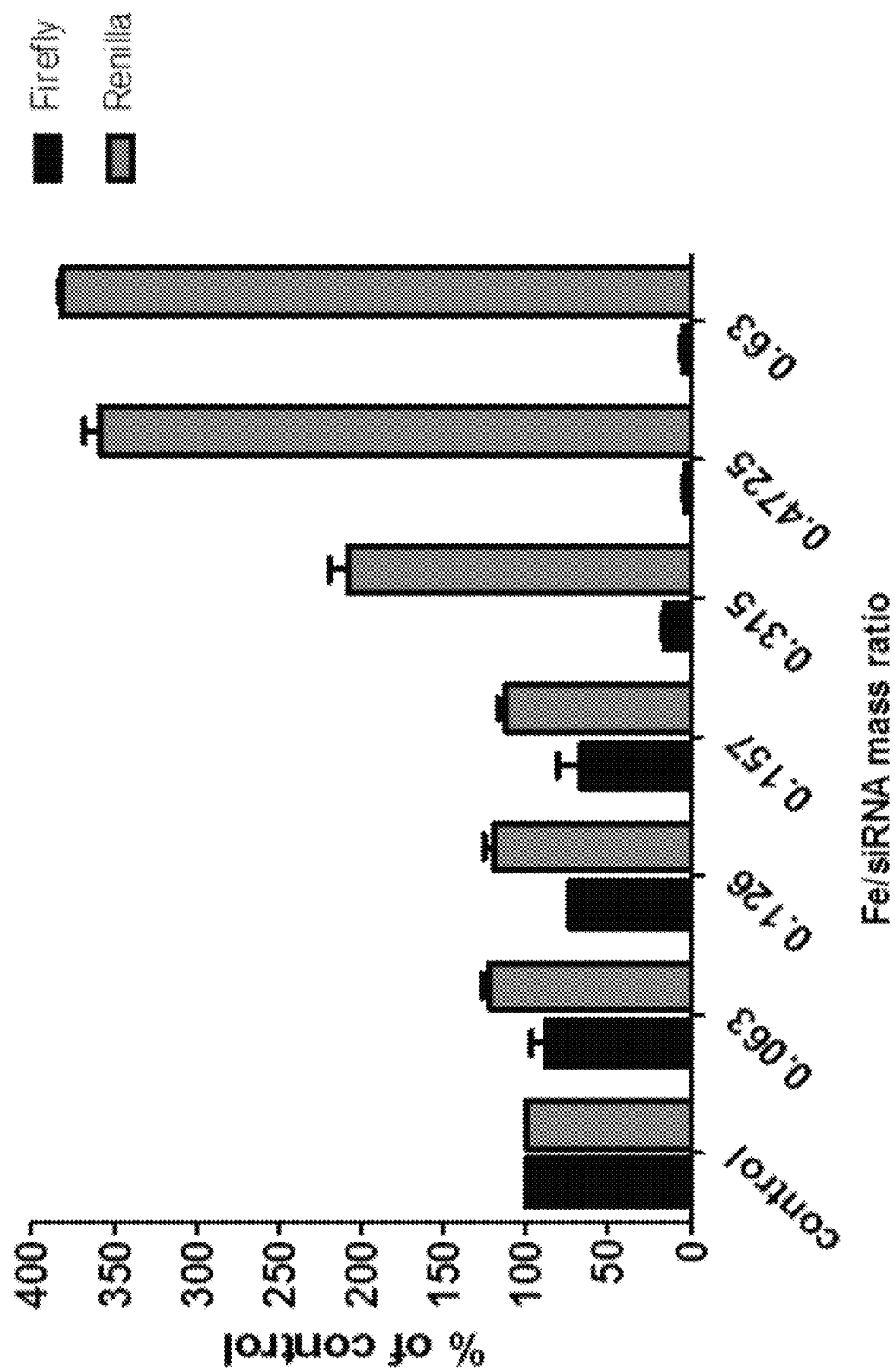
FIG. 43. is a graph showing Firefly Luciferase silencing in U2OS-Luc cells with $_{con}$Al/PEI$_{25}$-CAN-gamma-Fe$_2$O$_3$ NPs (30% w Al phase).

$_{con}$Al/PEI$_{25}$-CAN-gamma-$Fe_2O_3$ NPs (Al: Alginic acid)—Optimal fabrication protocol (FIGS. 30 & 43): These NPs have been prepared based on the concept of layer-by-layer (LbL) outer shell modification/formation when using formerly fabricated $_{con}$PEI$_{25}$-CAN-gamma-$Fe_2O_3$ NPs (see EXAMPLE 7 for details). $_{con}$PEI$_{25}$-CAN-gamma-$Fe_2O_3$ NPs contain a $Ce^{3/4+}$ cation-coordinated $_{con}$PEI$_{25}$ polymeric phase that was contacted with a polyanionic alginic acid component (Al, MW: 120-190 KDa) at various w(Fe)/w(Al) ratios for a contact non-covalent LbL electrostatic mode of attachment. Tested w(Fe)/w(Al) ratios were investigated at 1, 10, 30 and 50% of alginic acid (Al). Accordingly, the following amounts of the Al component, i.e., 0.0074 mg/$6.16 \times 10^{-8}$ mmol, 0.074 mg/$6.16 \times 10^{-7}$ mmol, 0.22 mg/$1.83 \times 10^{-6}$ mmol and 0.37 mg/$3.08 \times 10^{-6}$ mmol of alginic acid (Al) were added to 1.0 ml of $_{con}$PEI$_{25}$-CAN-gamma-$Fe_2O_3$ NPs (aqueous suspension—B1) and the medium diluted with additional 20 ml dd$H_2O$ followed by overnight incubation (orbital shaker, 250 rpm, 20° C.). Resulting hydrophilic highly stable Al-PEI-CAN-gamma-$Fe_2O_3$ NPs were then washed with dd$H_2O$ (3×10 mL) using an Amicon® Ultra-15 centrifugal filter device (100K) operated at 4,000 rpm (centrifuge) during 5 min (room temperature) and re-dispersed in dd$H_2O$ (1.0 mL) for storage and/or gene silencing experiments. Selected characterization data (NPs for an optimal 30% w/w component ratio regarding in vitro gene silencing, FIG. 30): Average TEM & DLS sizes: 7.44 & 70.0 nm, zeta potential: +35.0 mV.

Figure 31A:
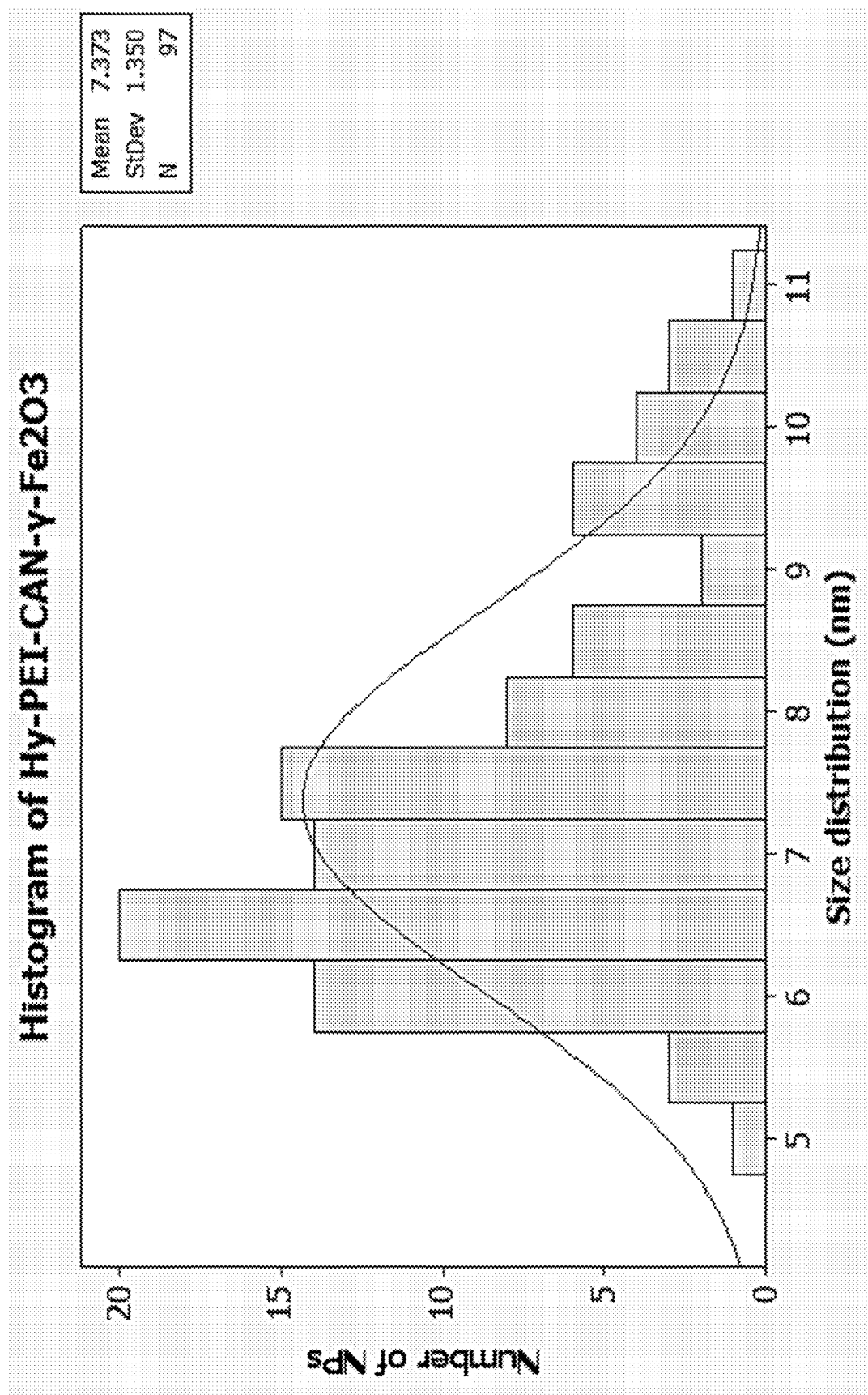
FIGS. 31a-b. includes: a TEM microphotograph (FIG. 31a) and a histogram (FIG. 31b) showing the size distribution of ultra-small averaged 7.37 nm-sized $_{con}$Hy/PEI$_{25}$-CAN-gamma-Fe$_2$O$_3$ NPs.
Figure 31B:
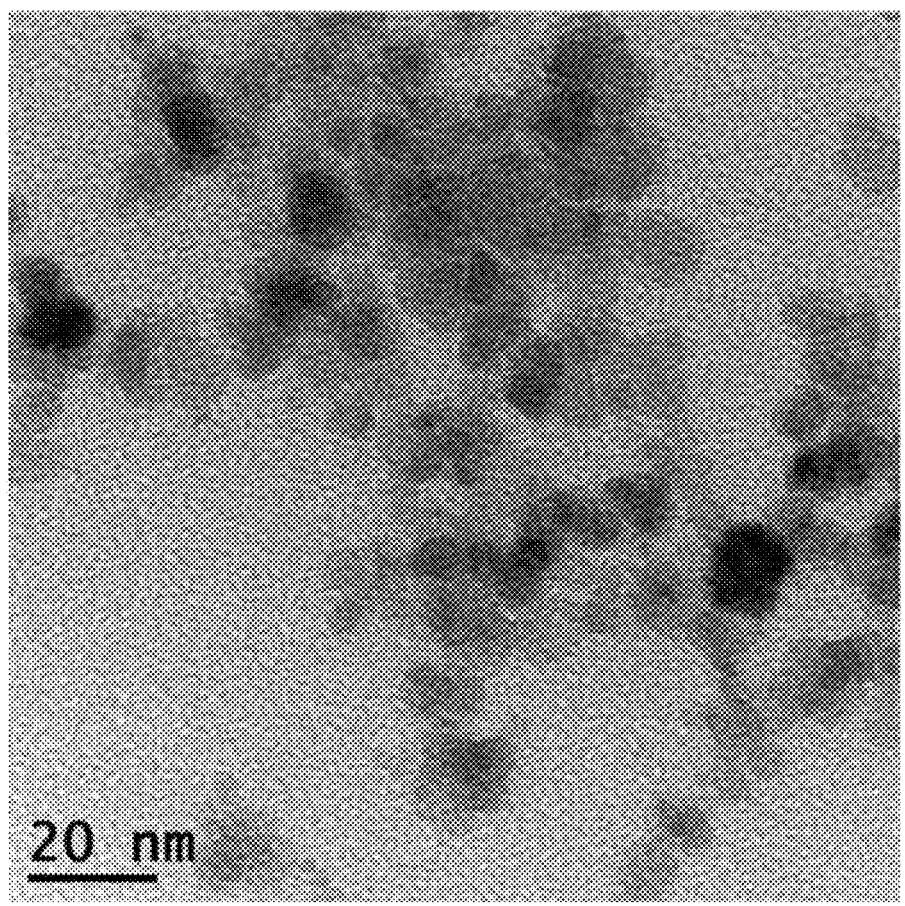
Figure 32:
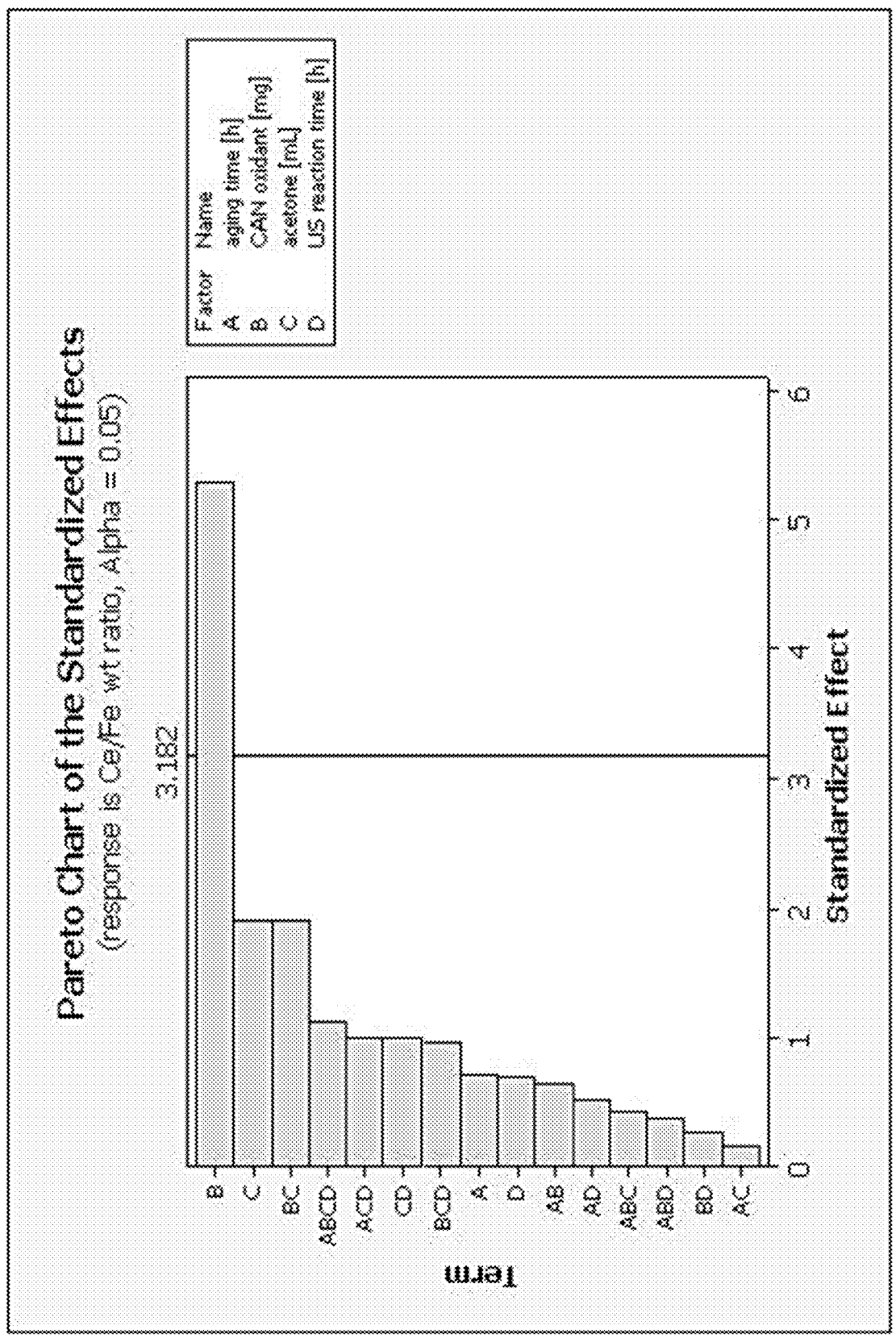
FIG. 32. is a graph showing the DOE-optimized fabrication of CAN$_{DOE}$-gamma-Fe$_2$O$_3$ NPs—Pareto chart of standardized effects for the response w/w Ce/Fe ratio.
Figure 44:
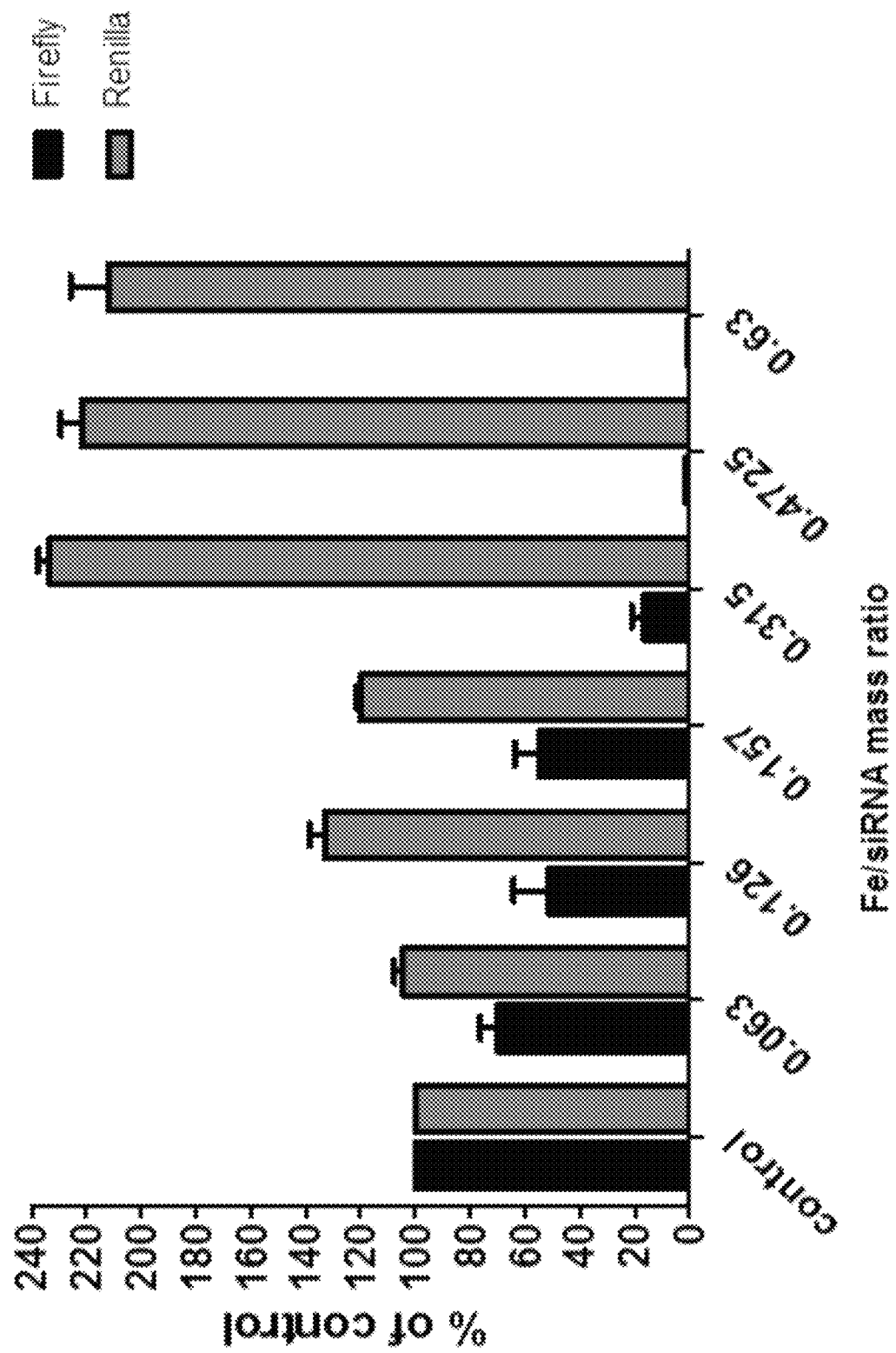
FIG. 44. is a graph showing Firefly Luciferase silencing in U2OS-Luc cells with $_{con}$Hy/PEI$_{25}$-CAN-gamma-Fe$_2$O$_3$ NPs (10% w Hy phase).

$_{con}$Hy/PEI$_{25}$-CAN-gamma-$Fe_2O_3$ NPs (Hy: hyaluronic acid)—Optimal fabrication protocol (FIGS. 31 & 44): The corresponding C4 protocol (contact process) has been similarly extended to the use of a polyanionic biodegradable biocompatible 15-30 KDa hyaluronic acid (Hy) instead of the formerly used alginic acid phase. Corresponding tested w(Fe)/w(Al) ratios were investigated at 1, 10, 30 and 50% of Hyaluronic acid (Hy, 0.0023 mg/$1.57 \times 10^{-7}$ mmol, 0.023 mg/$1.57 \times 10^{-6}$ mmol, 0.07 mg/$4.66 \times 10^{-6}$ mmol and 0.12 mg/$8 \times 10^{-6}$ mmol of the Hy acid phase) towards corresponding hydrophilic highly stable $_{con}$Hy/PEI$_{25}$-CAN-gamma-$Fe_2O_3$ NPs. Selected characterization data (NPs at an optimal 10% w/w ratio regarding in vitro gene silencing, FIGS. 31 & 44): Average TEM & DLS sizes: 7.37 & 96.3 nm, zeta potential: +38.6 mV.

Figure 45:
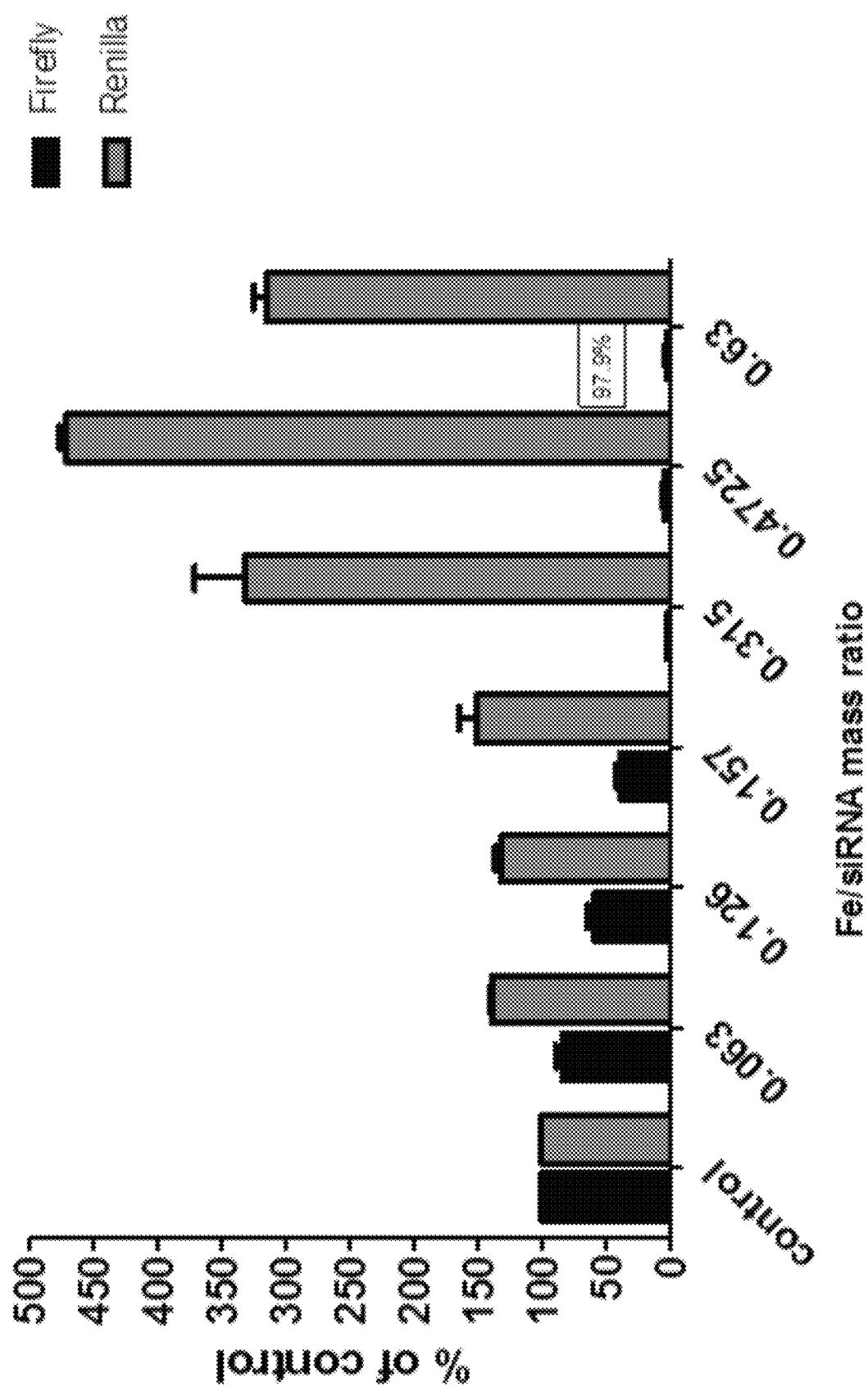
FIG. 45. is a graph showing Firefly Luciferase silencing in U2OS-Luc cells with $_{con}$Chi/PEI$_{25}$-CAN-gamma-Fe$_2$O$_3$ NPs (PEI/Chi w/w ratio: 70/30).
Figure 46:
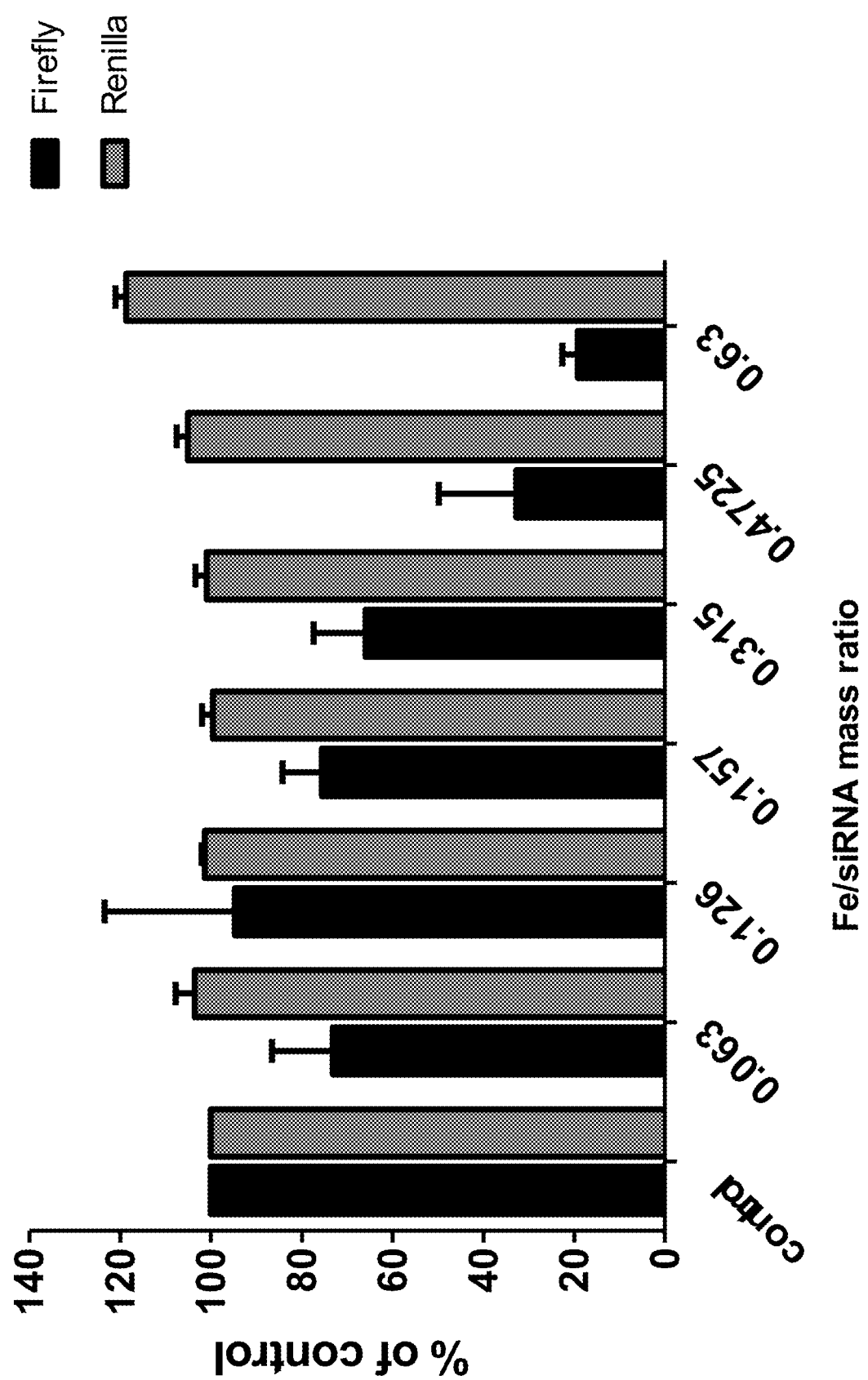
FIG. 46. is a graph showing Firefly Luciferase silencing in U2OS-Luc cells using $_{con}$PLL/PEI$_{25}$-CAN-gamma-Fe$_2$O$_3$ NPs (PEI/PLL w/w ratio: 90/10).

$_{con}$Chi/PEI$_{25}$-CAN-gamma-$Fe_2O_3$ & $_{con}$PLL/PEI$_{25}$-CAN-gamma-$Fe_2O_3$ NPs (Chi & PLL: chitosan & poly-L-lysine respectively)—Optimal fabrication protocol (FIGS. 45 & 46 respectively): This same experimental fabrication protocol as previously described has been further extended to mixtures of appropriate polycationic polymers that also contained 25 kDa branched PEI in their formulations, i.e., both Chi and PLL phases at various w/w ratios as mentioned above when used alone for interacting/attaching (coordination attachment chemistry) onto the surface of CAN-gamma-$Fe_2O_3$ NPs. Optimal gene silencing results have been reported in both FIGS. 45 & 46 respectively and for specific polymeric phase w/w ratios (Chi/PEI: 30/70 & PLL/PEI: 10:90 respectively) that were found to be most effective for gene silencing.

Example 9: Design of Experiment (DOE)-Based Improved $Ce^{3/4+}$ Cation Doping Process Towards DOE-Optimized PEI-Decorated CAN-Stabilized/ DOE Maghemite Nanoparticles ($_{con}$PEI$_{25}$-CAN$_{DOE}$-Gamma-$Fe_2O_3$ NPs) & Selected Characterization Data (FIGS. 32-39)

Since the functionalization level by doping $Ce^{3/4+}$ cations/[$Ce^{3/4+}L_n$] complexes has a so critical importance for the coordination capability of surface engineered NPs, a statistically significant Design of Experiment (DOE) (Cawse 2001) (Lendrem, Owen et al. 2001) (McKay, Hoogenraad et al. 2003) (Kenett 2013) has been successfully implemented for process global optimization (maximized reproducible level of doping by $Ce^{3/4+}$ cations/[$Ce^{3/4+}L_n$] complexes), i.e., for the obtainment of both globally optimized core CAN$_{DOE}$-gamma-$Fe_2O_3$ and related $_{con}$PEI-CAN$_{DOE}$-gamma-$Fe_2O_3$ NPs. Quite interestingly, it is worthwhile to notice that very few works have been ever reported in the field of DOE-optimized fabrication and/or functionalization of ultra-small magnetically responsive iron oxide NPs. (Forge, Roch et al. 2008; Mahmoudi, Simchi et al. 2008).

For this purpose and based on the current process, four main factors that might be significantly influential for the process were identified (Table 2). Set-up at both low and high value levels, these investigated factors are (i) the ageing time of the starting magnetite ($Fe_3O_4$) NPs (time between magnetite NP preparation and CAN-mediated ultrasound-assisted doping step, two values: 2 & 12 h), (ii) the CAN oxidant amount (two values: 150.0 & 500.0 mg), (iii) the volume of the MeCOMe solvent component at a total constant reaction volume of 24.0 mL (two values: 6.0 & 18.0 mL), and finally the high-power ultrasonication time at a fixed 25% modulator power (Sonics®, Vibra cell/Ti horn, 750 Watt; two values: 0.5 & 1.5 h). Thus, a four factor-two level full factorial design was proposed by a MINITAB® 16 DOE software (version 16.2.4, Minitab Inc.) with one factor replicate (corner points) and center points (st. order 6). That resulted in a table of 17 ($2^4$+1 center point, 1 block) experiments (Table 2) that have been randomly executed. Subsequently, investigated process responses included (i) the average DLS hydrodynamic size of resulting $CAN_{DOE}$-gamma-$Fe_2O_3$ NPs including characterization by polydispersity indexing (PDI), their average TEM size and distribution (analysis of more than 100 objects), (ii) their zeta potential, and both (iii-iv) Ce and Fe elemental weight suspension contents, and finally most significant w/w Ce/Fe ratios (Table 2).

TABLE 2

Proposed and executed statistically relevant DOE matrix of experiments towards DOE-optimized core $CAN_{DOE}$-gamma-$Fe_2O_3$

| St. Order | Ageing time (h) | CAN oxidant (mg) | Solvent component - MeCOMe volume (mL) | Ultrasonication time (h) |
|---|---|---|---|---|
| 1 | 12 | 150 | 6 | 0.5 |
| 2 | 2 | 500 | 18 | 1.5 |
| 3 | 12 | 500 | 6 | 0.5 |
| 4 | 2 | 500 | 6 | 0.5 |
| 5 | 2 | 150 | 6 | 0.5 |
| 6 | 7 | 325 | 12 | 1 |
| 7 | 12 | 500 | 6 | 1.5 |
| 8 | 12 | 500 | 18 | 0.5 |
| 9 | 2 | 500 | 18 | 0.5 |
| 10 | 2 | 150 | 6 | 1.5 |
| 11 | 12 | 150 | 18 | 0.5 |
| 12 | 12 | 150 | 6 | 1.5 |
| 13 | 2 | 150 | 18 | 1.5 |
| 14 | 2 | 500 | 6 | 1.5 |
| 15 | 12 | 500 | 18 | 1.5 |
| 16 | 12 | 150 | 18 | 1.5 |
| 17 | 2 | 150 | 18 | 0.5 |

TABLE 3

Statistically relevant DOE matrix of experiments (core $CAN_{DOE}$-gamma-$Fe_2O_3$) & corresponding process responses

| St. Order | DLS size (nm) | PDI | TEM size (nm) | zeta Potential (mV) | Ce (mg/mL) | Fe (mg/mL) | Ce/Fe w/w ratio |
|---|---|---|---|---|---|---|---|
| 1 | 49.65 | 0.172 | 7.470 | +33.0 | 0.0250 | 3.4500 | 0.00725 |
| 2 | 54.05 | 0.192 | 6.827 | +40.5 | 0.0579 | 3.6920 | 0.01568 |
| 3 | 55.56 | 0.117 | 6.989 | +52.1 | 0.2230 | 2.8900 | 0.07716 |
| 4 | 45.72 | 0.144 | 6.813 | +47.2 | 0.2050 | 3.2890 | 0.06230 |
| 5 | 49.05 | 0.187 | 6.486 | +37.6 | 0.0239 | 3.6650 | 0.00652 |
| 6 | 37.04 | 0.134 | 7.630 | +37.1 | 0.0765 | 3.4800 | 0.02198 |
| 7 | 40.81 | 0.162 | 7.852 | +33.6 | 0.1580 | 3.4200 | 0.04620 |
| 8 | 80.20 | 0.173 | 8.100 | +47.3 | 0.0868 | 3.8300 | 0.02266 |
| 9 | 56.64 | 0.175 | 7.599 | +30.9 | 0.1060 | 3.4730 | 0.03052 |
| 10 | 34.78 | 0.213 | 7.610 | +26.3 | 0.0041 | 3.4150 | 0.00120 |
| 11 | 84.08 | 0.141 | 8.001 | +34.9 | 0.0242 | 4.0900 | 0.00592 |
| 12 | 40.93 | 0.157 | 7.403 | +35.4 | 0.0230 | 4.0700 | 0.00565 |
| 13 | 58.88 | 0.172 | 6.786 | +39.9 | 0.0163 | 3.8310 | 0.00425 |
| 14 | 38.37 | 0.180 | 7.018 | +46.4 | 0.1630 | 3.2790 | 0.04971 |
| 15 | 51.80 | 0.143 | 7.711 | +50.4 | 0.2160 | 4.1100 | 0.05255 |
| 16 | 75.73 | 0.169 | 7.683 | +35.0 | 0.0115 | 3.7800 | 0.00304 |
| 17 | 65.87 | 0.134 | 7.424 | +23.2 | 0.0233 | 3.1640 | 0.00736 |

Therefore, response analyses that characterized the experimental space under investigation indicated that all the NPs obtained are strongly positively charged in a +23.2-+52.1 mV range of zeta potential values (Table 3, st. orders 17 vs. 3). These data are indicative of a successful doping process by $Ce^{3/4+}$ cations/$[Ce^{3/4+}L_n]$ complexes. Moreover and amongst all four investigated factors, the most influential one that afforded a corresponding optimal maximized w/w Ce/Fe ratio (Table 3, st. order 3, w/w Ce/Fe ratio: 0.07716) has been shown to be the CAN oxidant amount using a Pareto chart of standardized effects (FIG. 32, significance alpha-level set-up at 0.05). Interestingly, such a high-level w/w Ce/Fe ratio was found to be much higher than the one measured for former core CAN-gamma-$Fe_2O_3$ NPs (section A2) by a 266.1% factor, thus validating this DOE approach for optimization. All other primary and interactive secondary/tertiary order standardized effects have been found much less significant.

Figure 33A:
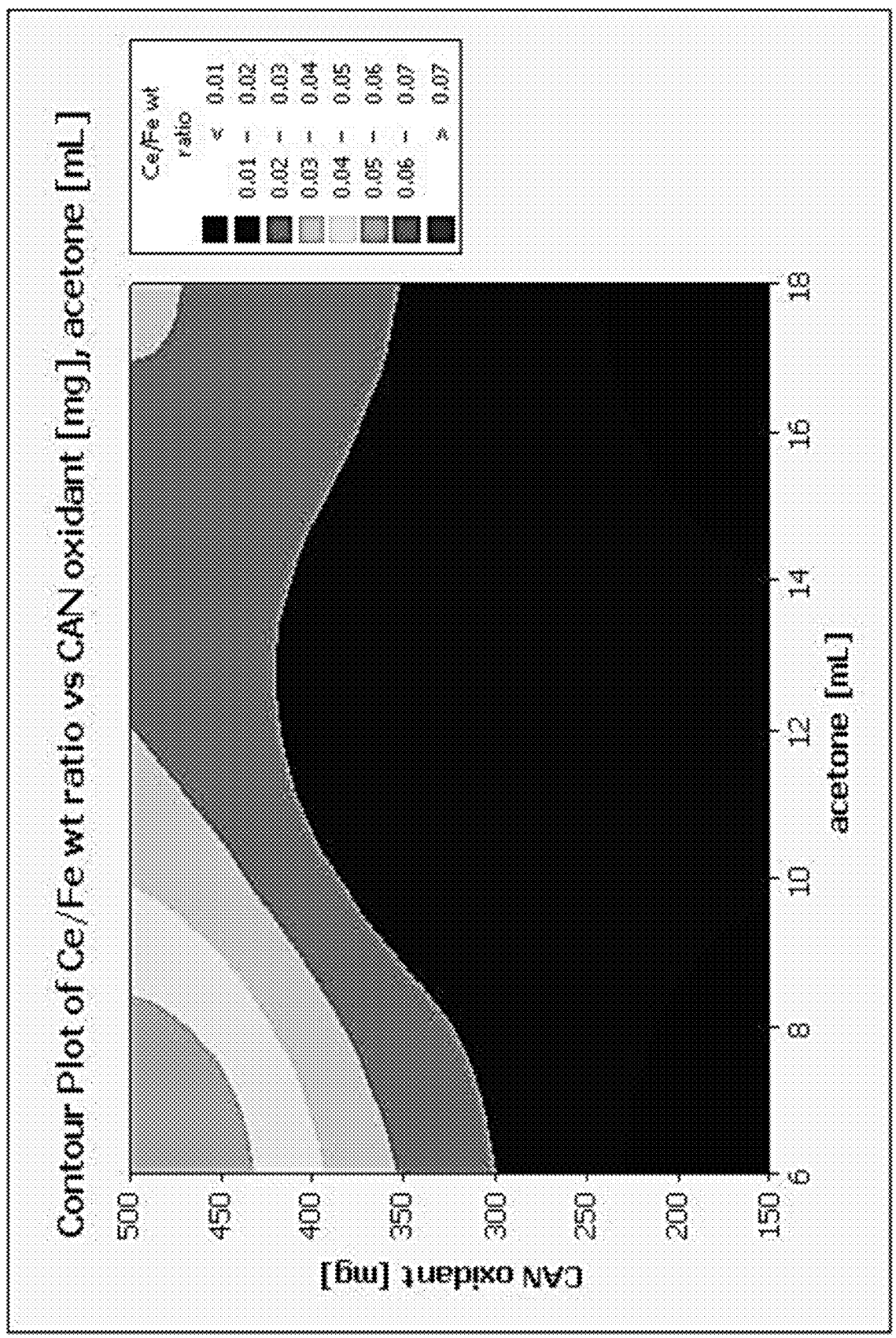
FIG. 33a. is a diagram showing the DOE-optimized fabrication of CAN$_{DOE}$-gamma-Fe$_2$O$_3$ NPs—2D Contour plot of w/w Ce/Fe ratios vs. CAN oxidant (mg) & MeCOMe (mL) amounts.
Figure 33B:
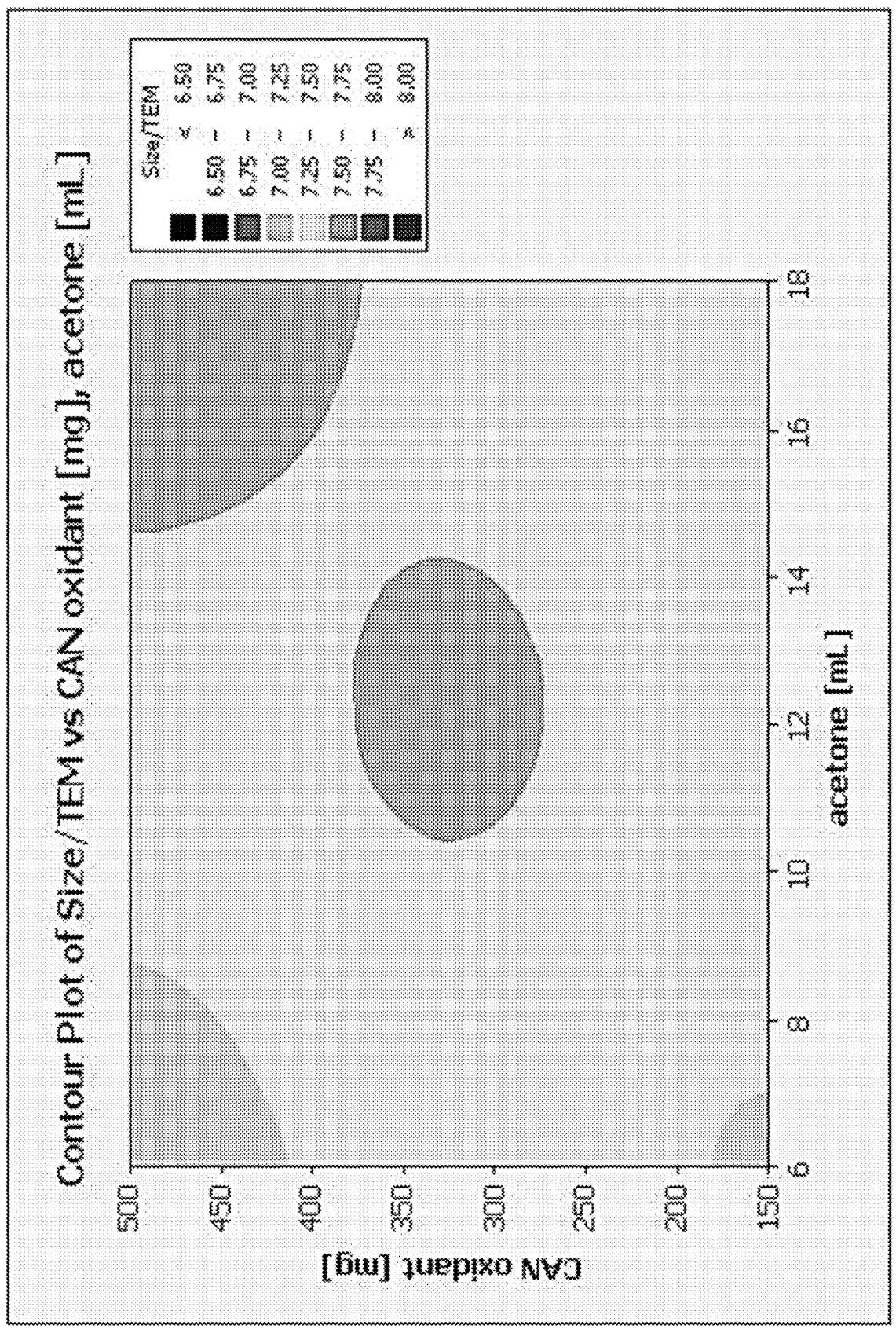
FIG. 33b. is a diagram showing the DOE-optimized fabrication of CAN$_{DOE}$-gamma-Fe$_2$O$_3$ NPs—2D Contour plot of NP TEM sizes vs. CAN oxidant (mg) & MeCOMe (mL) amounts.
Figure 33C:
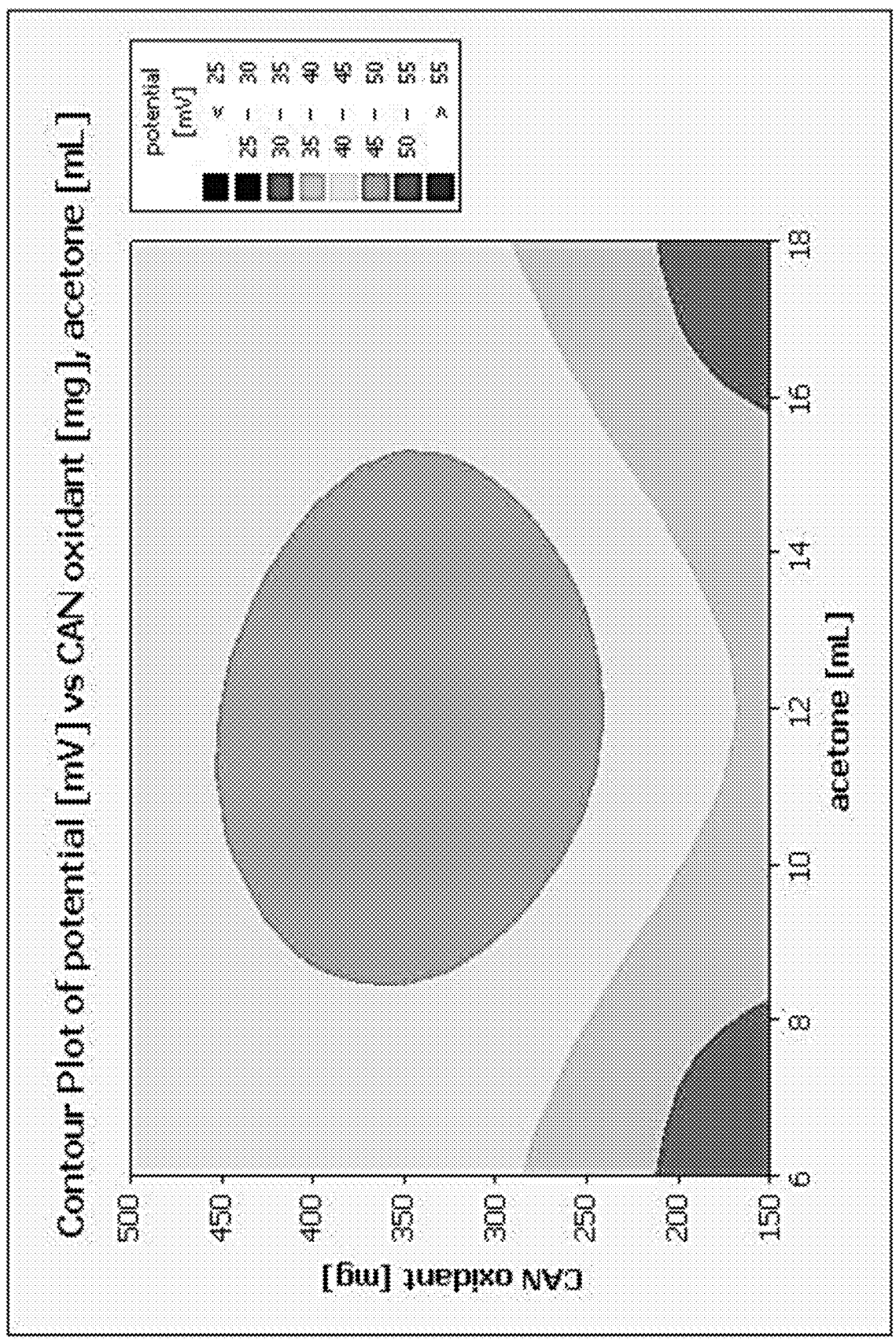
FIG. 33c. is a diagram showing the DOE-optimized fabrication of CAN$_{DOE}$-gamma-Fe$_2$O$_3$ NPs—2D Contour plot of NP zeta potential values vs. CAN oxidant (mg) & MeCOMe (mL) amounts.
Figure 33D:
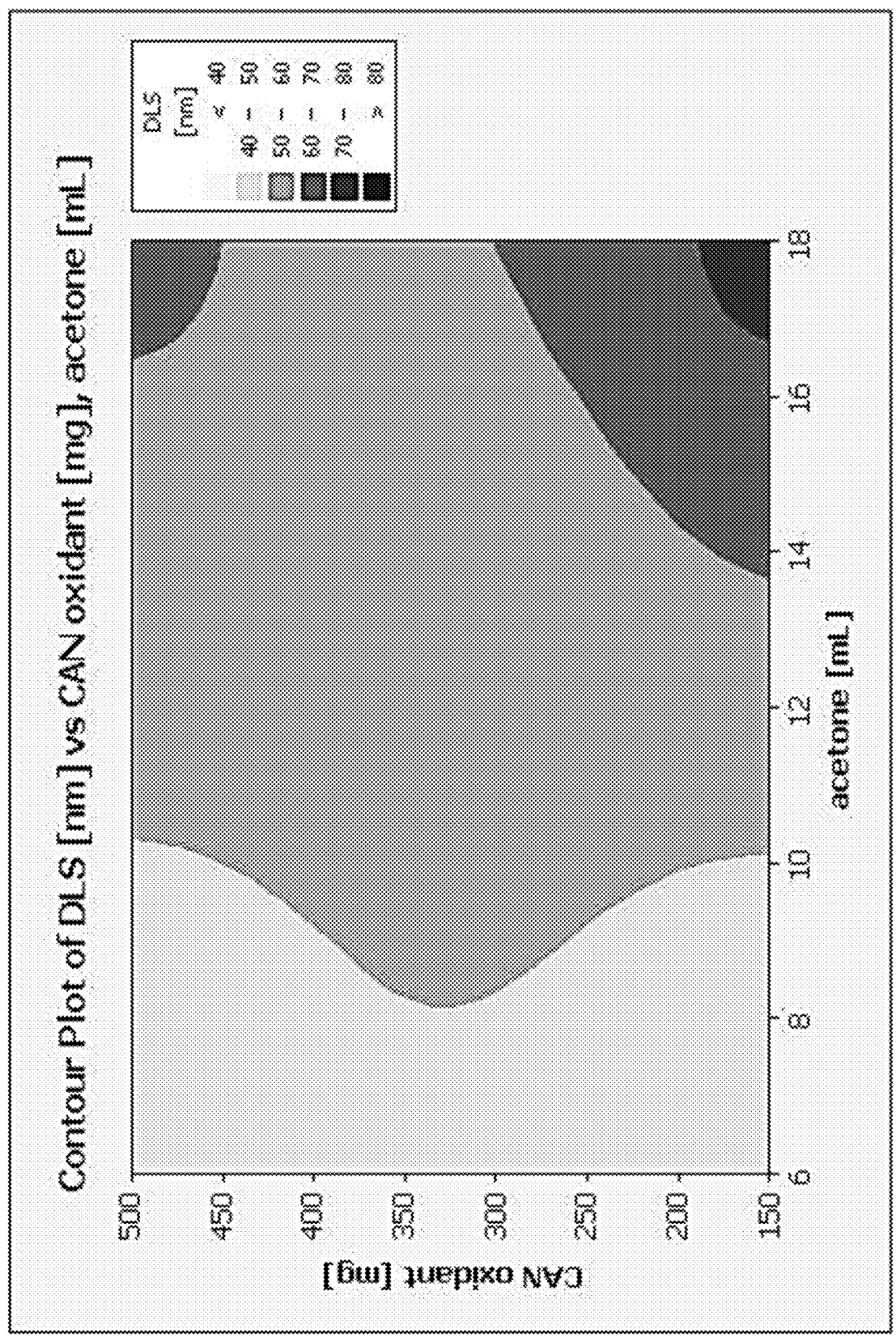
FIG. 33d. is a diagram showing the DOE-optimized fabrication of CAN$_{DOE}$-gamma-Fe$_2$O$_3$ NPs—2D Contour plot of NP hydrodynamic (DLS) size values vs. CAN oxidant (mg) & MeCOMe (mL) amounts.

Nevertheless and since both CAN oxidant (FIG. 32, secondary order BC interaction) and MeCOMe amounts (FIG. 32, primary C factor) also disclosed highest lower level magnitude effects, corresponding 2D contour plots of w/w Ce/Fe ratios and TEM NP sizes vs. both CAN oxidant and MeCOMe amounts have been reported in FIGS. 33a and 33b respectively. Interestingly, the $1^{st}$ contour plot graph (FIG. 33a) indicated that highest 0.06-0.07-ranged w/w Ce/Fe ratio values have been obtained for a (i) 6.0 mL MeCOMe volume and (ii) CAN oxidant amount greater than 430.0 mg. The $2^{nd}$ contour plot (FIG. 33b) also validated such similar CAN oxidant/MeCOMe-relating conditions in order to obtain the smallest range of NP sizes (7.0-7.25 nm domain). This same conditions set also afforded NP highest zeta potential and smallest hydrodynamic size (DLS) values (+40-45 mV & 40-50 nm domains, 2D contour plots of FIGS. 33c-d respectively).

Figure 34:
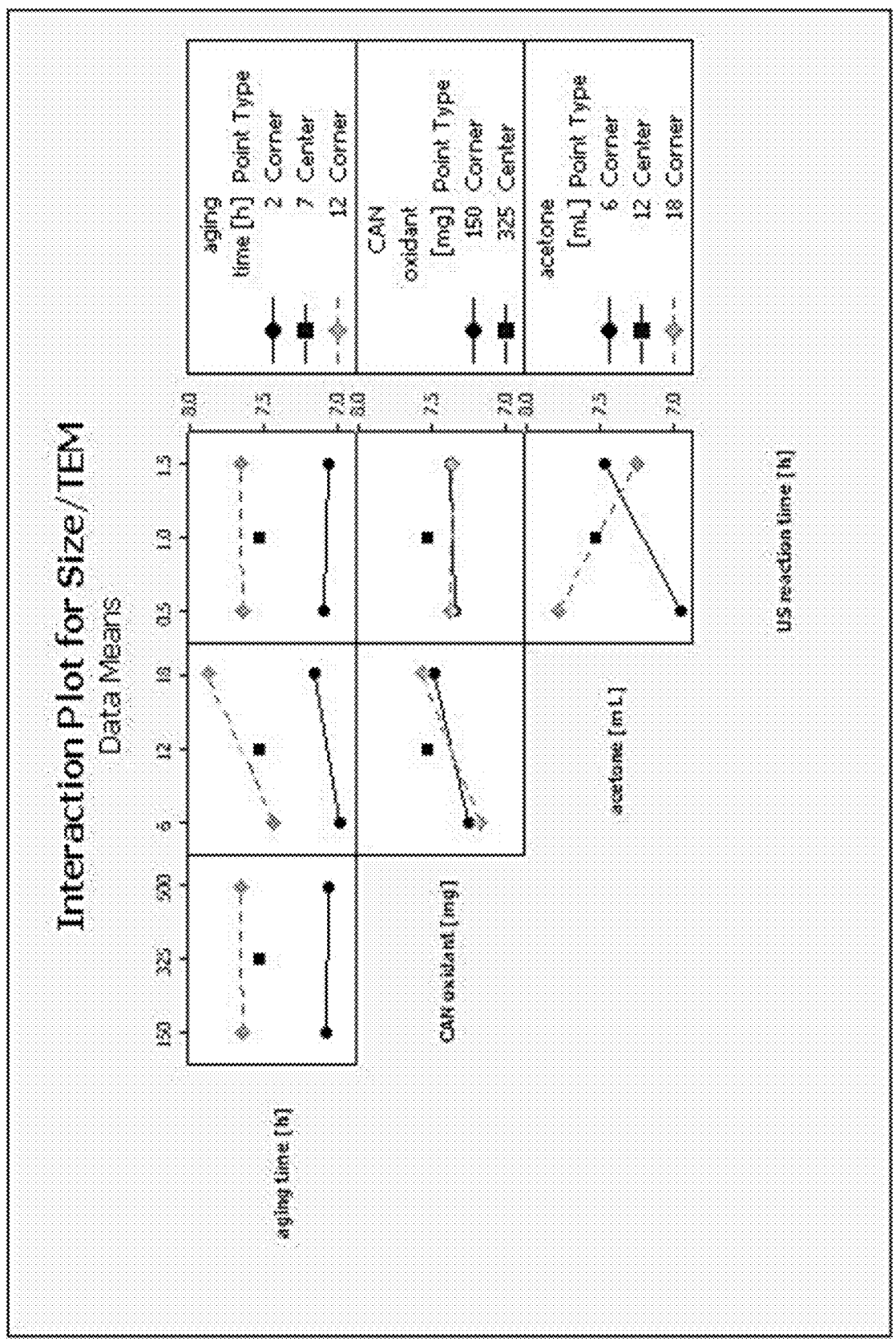
FIG. 34. are graphs showing the DOE-optimized fabrication of CAN$_{DOE}$-gamma-Fe$_2$O$_3$ NPs—Full interaction plot matrix for the NP size (TEM) size factor.
Figure 35:
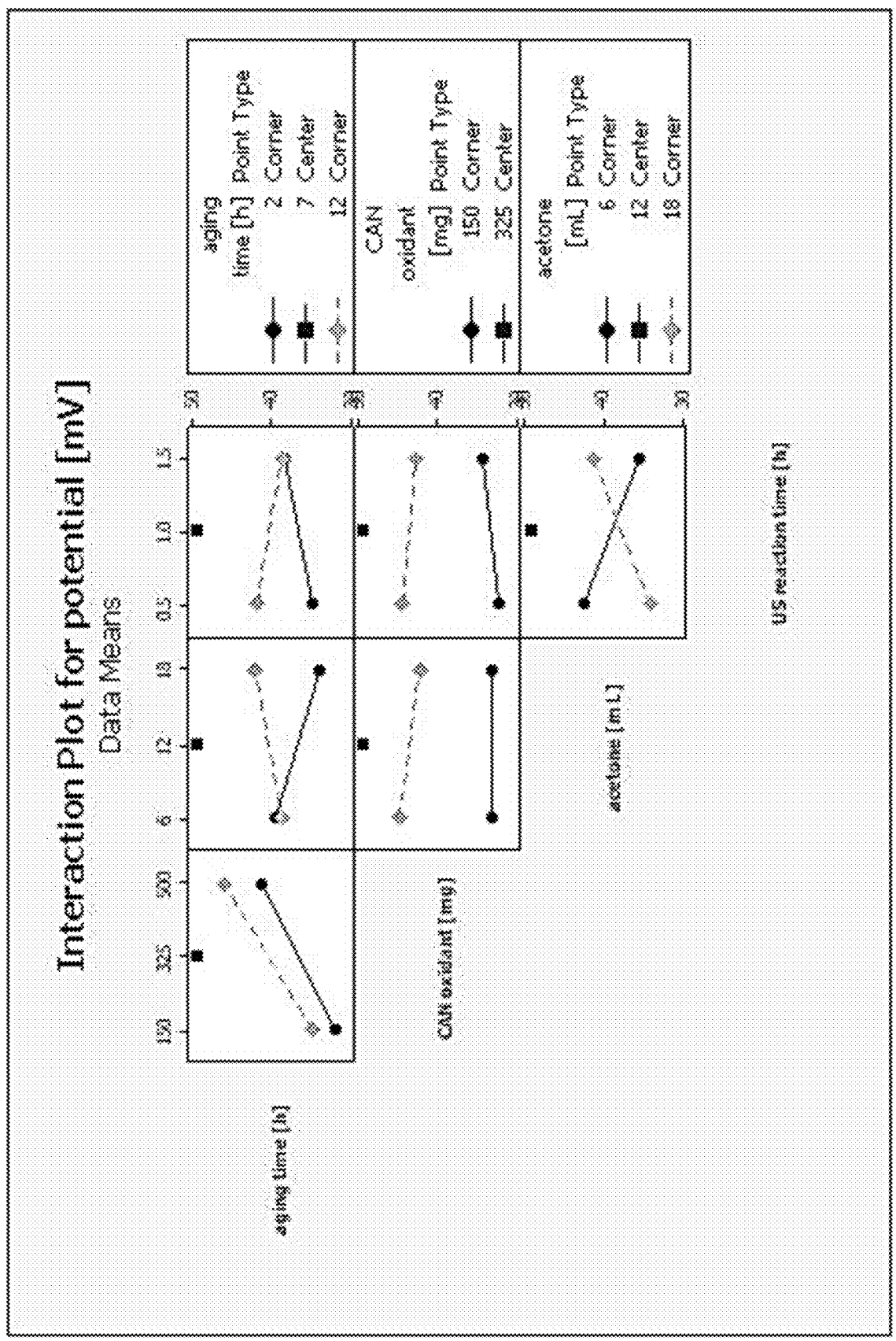
FIG. 35. are graphs showing the DOE-optimized fabrication of CAN$_{DOE}$-gamma-Fe$_2$O$_3$—Full interaction plot matrix for the NP zeta potential factor.
Figure 36:
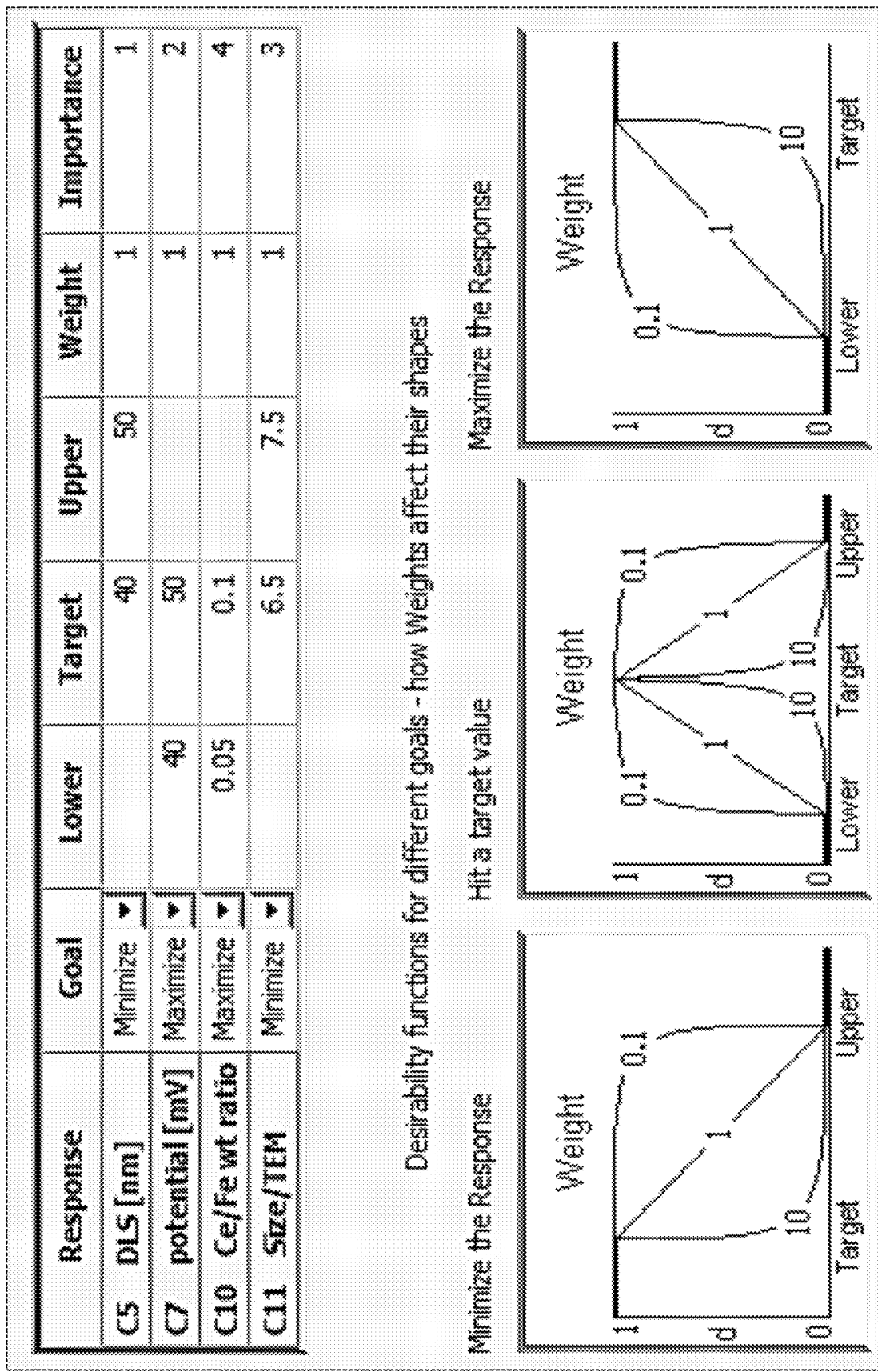
FIG. 36. are graphs showing the DOE-optimized fabrication of CAN$_{DOE}$-gamma-Fe$_2$O$_3$ NPs—NP specifications for MINITAB© 16 DOE software optimizer tool calculations.
Figure 37:
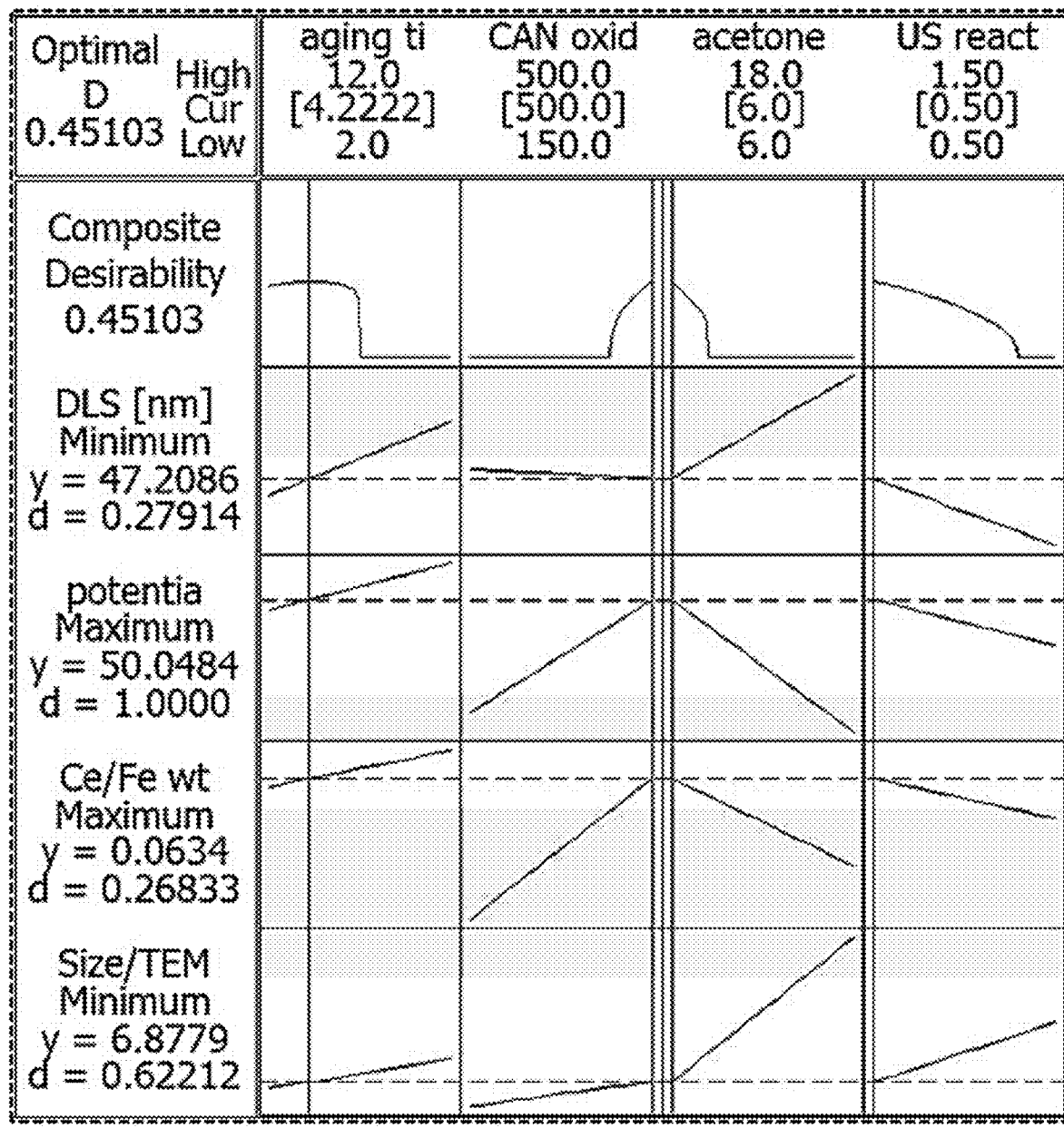
FIG. 37. is a diagram showing the DOE-optimized fabrication of CAN$_{DOE}$-gamma-Fe$_2$O$_3$ NPs—Calculated optimization plot with corresponding responses and response desirabilities.
Figure 38A:
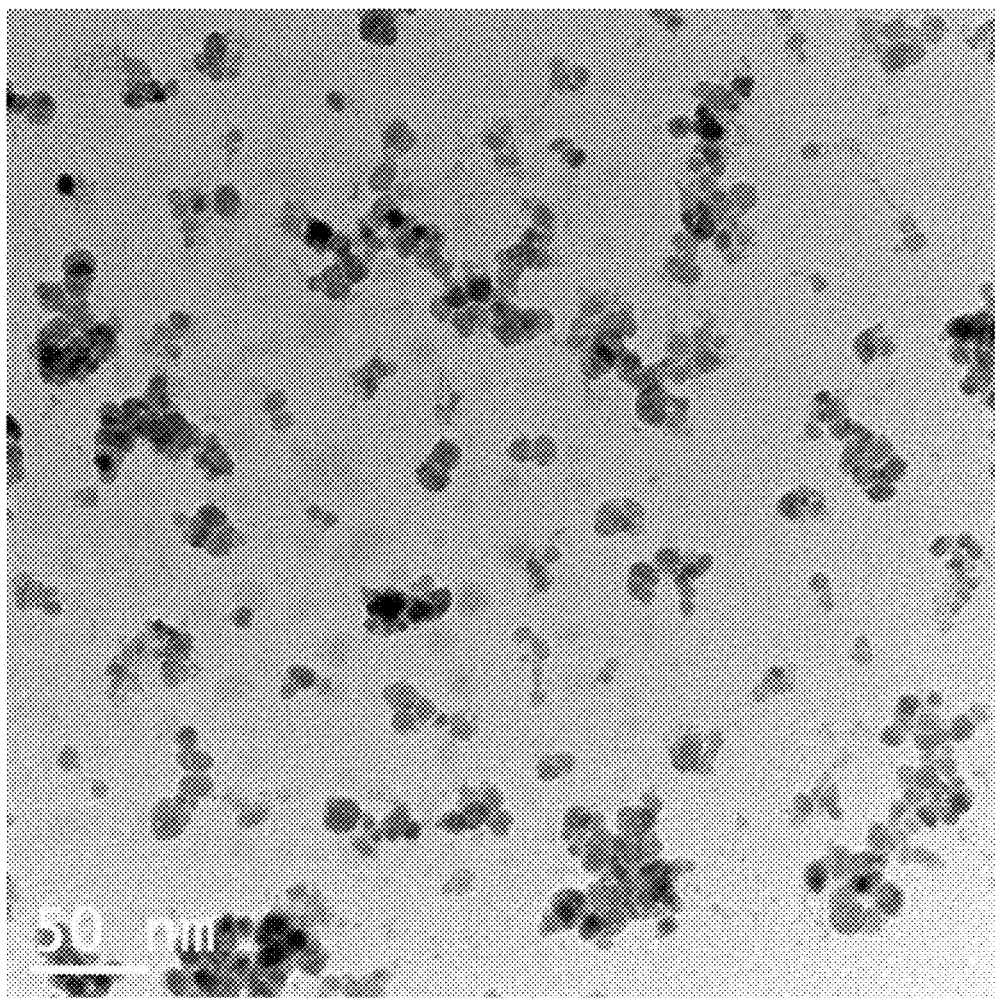
FIGS. 38a-b. includes: a TEM microphotograph (FIG. 38a) and a histogram (FIG. 38b) showing the size distribution of ultra-small averaged 6.61±2.04 nm-sized core CAN$_{DOE}$-gamma-Fe$_2$O$_3$ NPs.
Figure 38B:
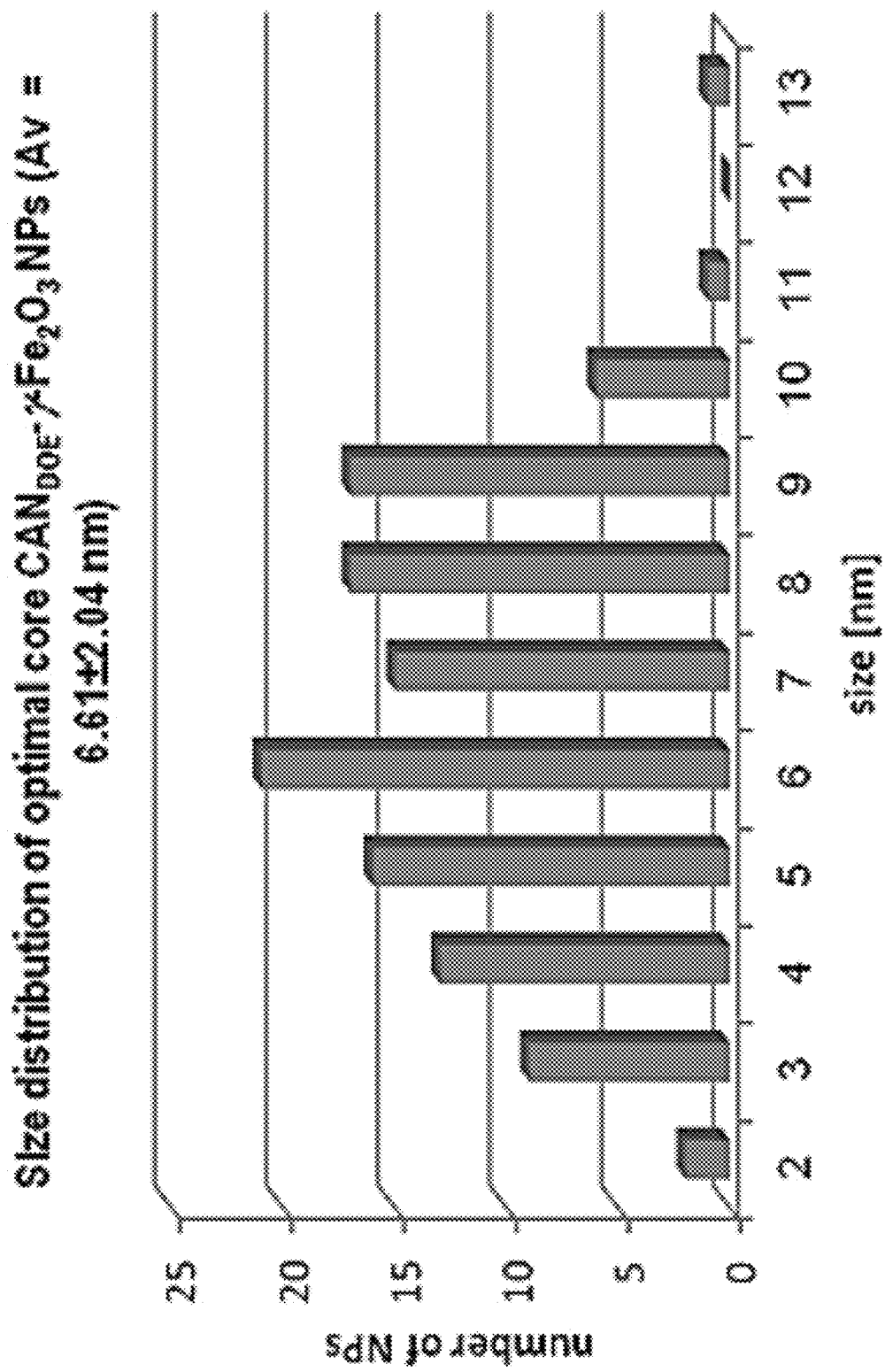
Figure 39:
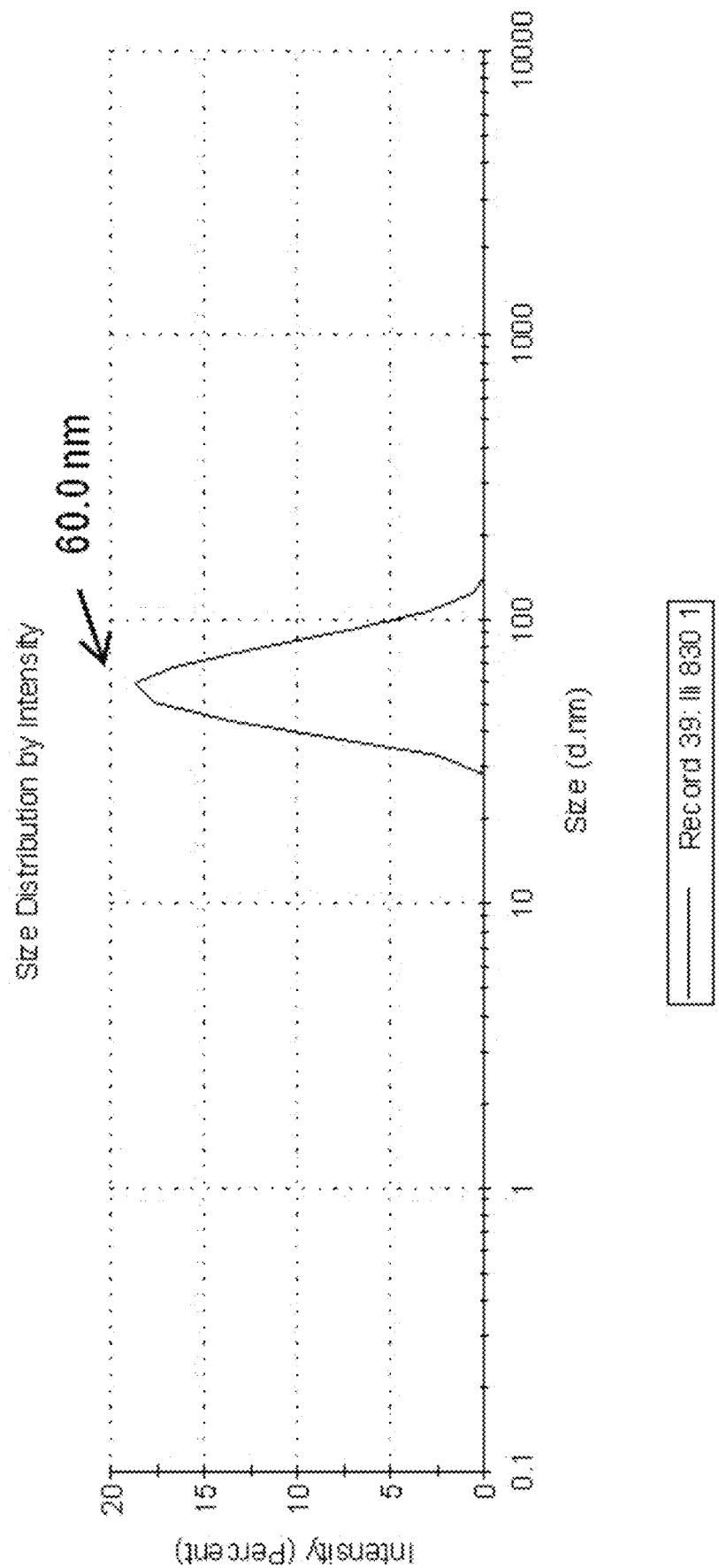
FIG. 39. is a graph showing the DLS analysis of DOE-optimized ultra-small 6.61±2.04 nm-sized core CAN$_{DOE}$-gamma-Fe$_2$O$_3$ NPs.

At this stage of the study and in order to better identify significant factor interactions, full matrices of two-way interaction plots that related to NP size (TEM) and zeta potential factors have been generated as shown in FIGS. 35 and 36 respectively. From graph examination (red spot: center point), several interesting conclusions might be drawn. For example, both MeCOMe volume and high-power ultrasonication time factors disclosed significant interactions (intersecting lines) for NP size (TEM) and zeta potential responses (FIGS. 34 & 35 respectively). On the other hand and concerning the NP size (TEM) response, the magnetite NP ageing time factor did not show any interaction with both (i) CAN oxidant amount, and (ii) high-power ultrasonication time (FIG. 34). Moreover, moderate interactions between (i) magnetite NP ageing time and MeCOMe volume factors (FIG. 34), and (ii) magnetite NP ageing time and high-power ultrasonication time factors (FIG. 35) have been also evidenced for both NP size (TEM) and zeta potential factor responses respectively.

Therefore, these calculated optimizer tool conditions have been used for the corresponding NP fabrication. They afforded corresponding DOE-optimized $CAN_{DOE}$-gamma-$Fe_2O_3$ NPs that possessed the following physico-chemical properties, i.e., (a) a NP hydrodynamic size (DLS) of 60.00 nm, (b) a positive zeta potential of +45.7 mV, (c) a w/w Ce/Fe ratio of 0.1000 that was higher that the software prediction by a 60.5% factor, and (d) a slightly smaller NP TEM size of 6.61±2.04 nm. The first two experimental NP features are quite close to corresponding software optimizer predicted values mentioned above while the two last ones have been even improved when compared to same predicted values.

Thus, the clear interacting multi-parametric character of the overall NP fabrication process necessitated to "engineer and refine" an optimal setting of input factors for the delivery of most optimized surface attachment-enabling core CAN-gamma-$Fe_2O_3$ NPs. For this purpose, the MINITAB® 16 DOE software optimizer tool has been used with the following specifications (FIG. 36): the elemental w/w Ce/Fe ratio has been selected as the most important input factor for process optimization, i.e., choosing a selected level 4 of importance with both lower and target response values of 0.05 and 0.1 respectively. Then, other input factors have been classified and adjusted according to the following order of importance,—(i) the NP size (TEM, level 3; target and upper limit values: 6.5 & 7.5 nm), (ii) the NP zeta potential (level 2, lower limit and target values: +40-+50 mV), and finally (iii) the NP hydrodynamic size (DLS, level 1, target and upper limit values: 40.0 & 50.0 nm). The corresponding calculated optimization plot has been reported in FIG. 37 and disclosed the effect of each factor (columns) on corresponding responses and response desirabilities (right column, blue data). In this case, this software optimizer tool suggested the use of a 4.22 h ageing time for starting magnetite NPs, 500.0 mg of CAN oxidant, 6.0 mL of MeCOMe, and 0.5 h high-power ultrasonication time for the obtainment of globally optimized $CAN_{DOE}$-gamma-$Fe_2O_3$ NPs that will possess the following calculated physico-chemical characteristics: (a) a minimized NP hydrodynamic size (DLS) of 47.21 nm, (b) a maximized zeta potential of +50.05 mV, (c) a maximized w/w Ce/Fe ratio of 0.0634, and (d) a minimized NP TEM size of 6.88 nm.

Selected characterization data of DOE-optimized $CAN_{DOE}$-gamma-$Fe_2O_3$ NPs (FIGS. 38-39): Average TEM & DLS sizes: 6.61 & 60.0 nm, zeta potential: +45.7 mV.

Figure 47:
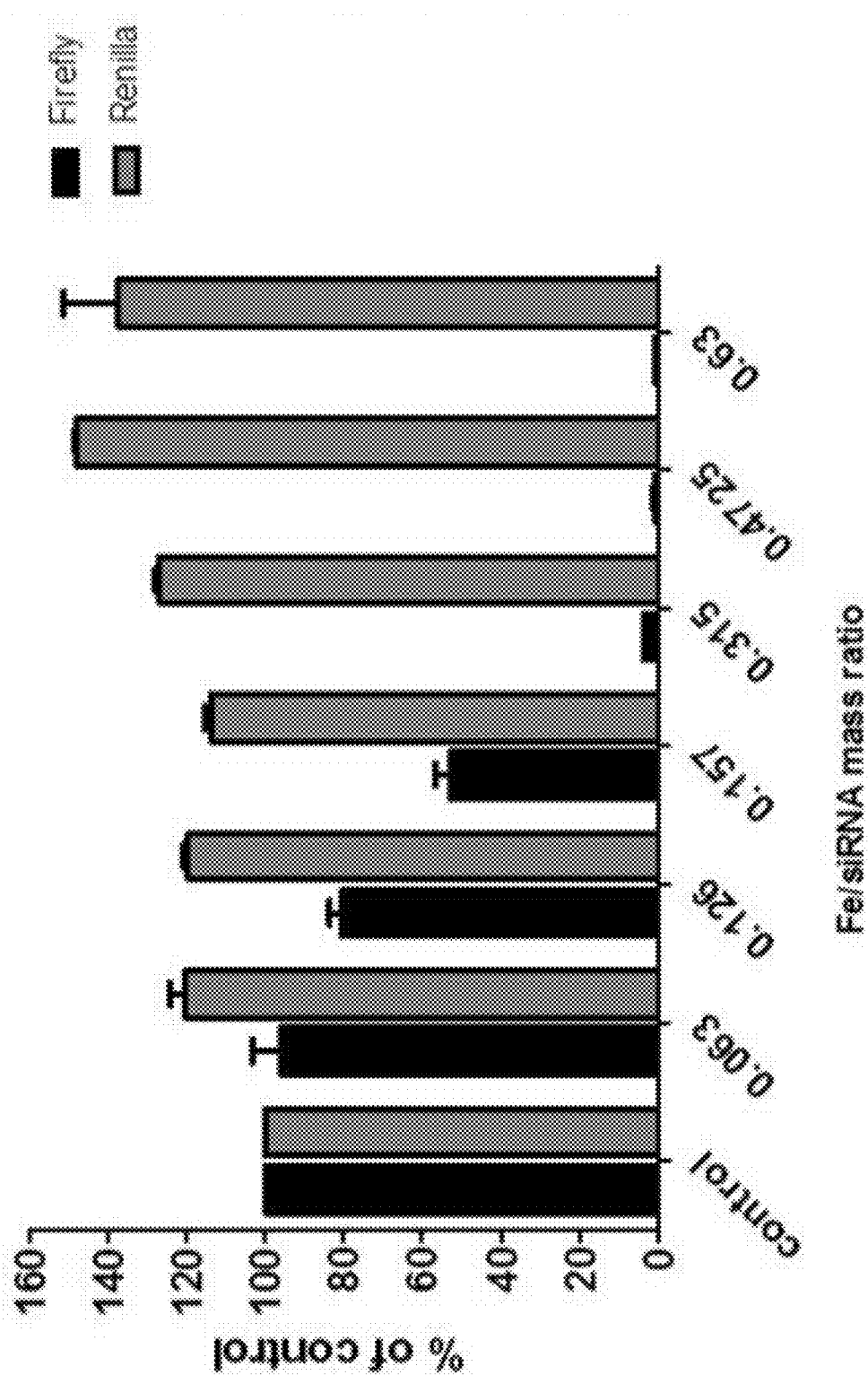
FIG. 47. is a graph showing Firefly Luciferase silencing in U2OS-Luc cells using DOE-optimized 7.35±1.56 nm-sized PEI-decorated $_{con}$PEI$_{25}$-CAN$_{DOE}$-γ-Fe2O$_3$ NPs.
Figure 48A:
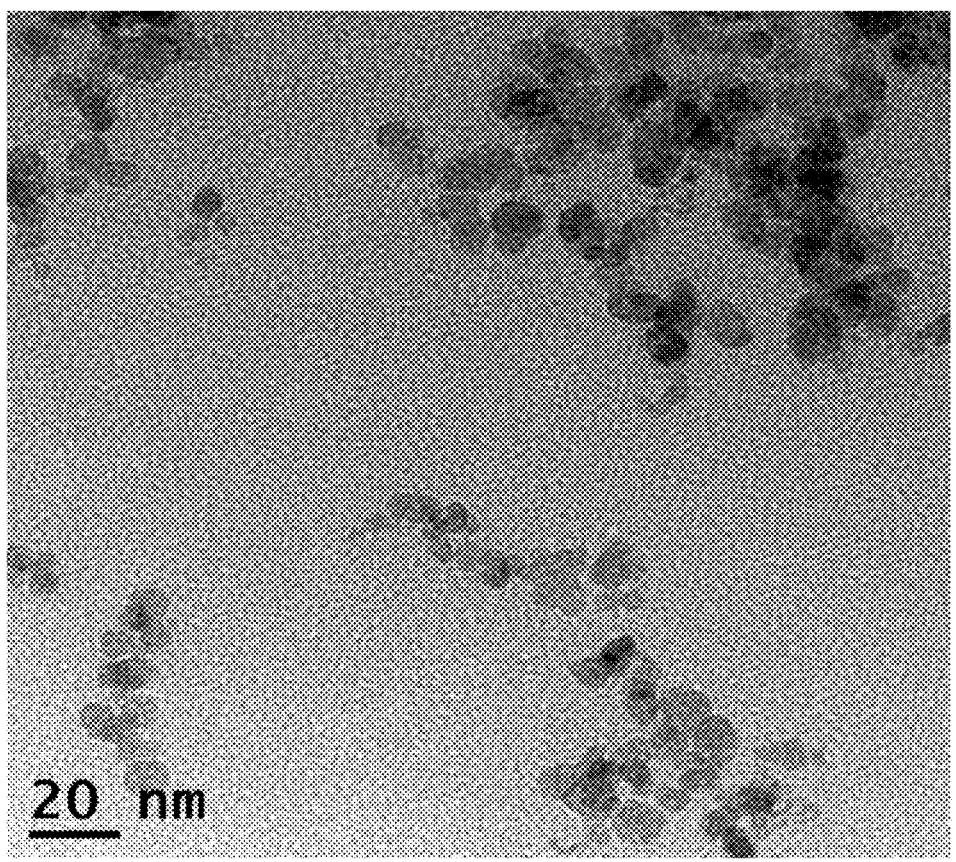
FIGS. 48a-b. includes: a TEM microphotograph (FIG. 48a) and a histogram (FIG. 48b) showing the size distribution of ultra-small averaged 7.35±1.56 nm-sized $_{con}$PEI$_{25}$-CAN$_{DOE}$-γ-Fe$_2$O$_3$ NPs.
Figure 48B:
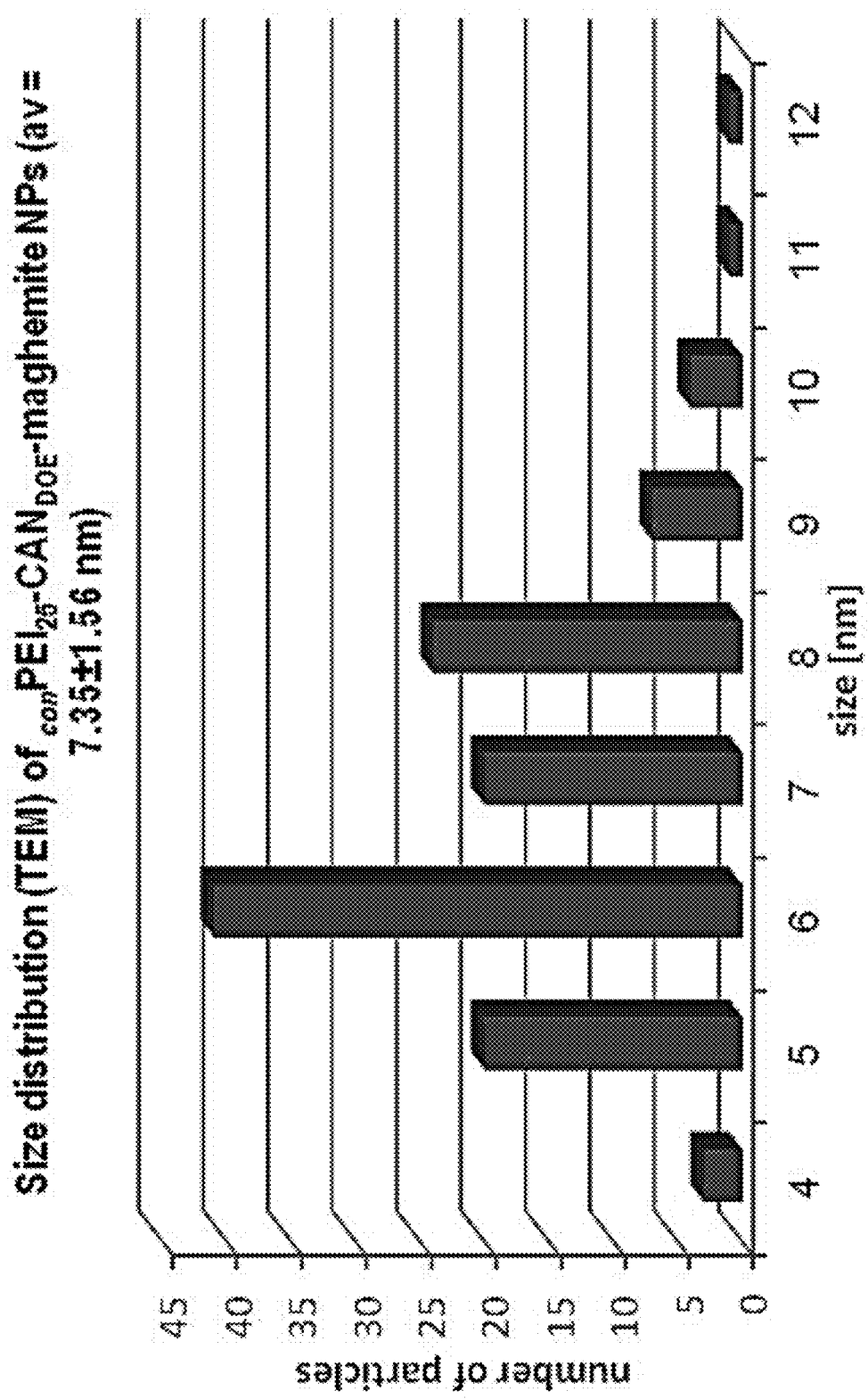
Figure 49:
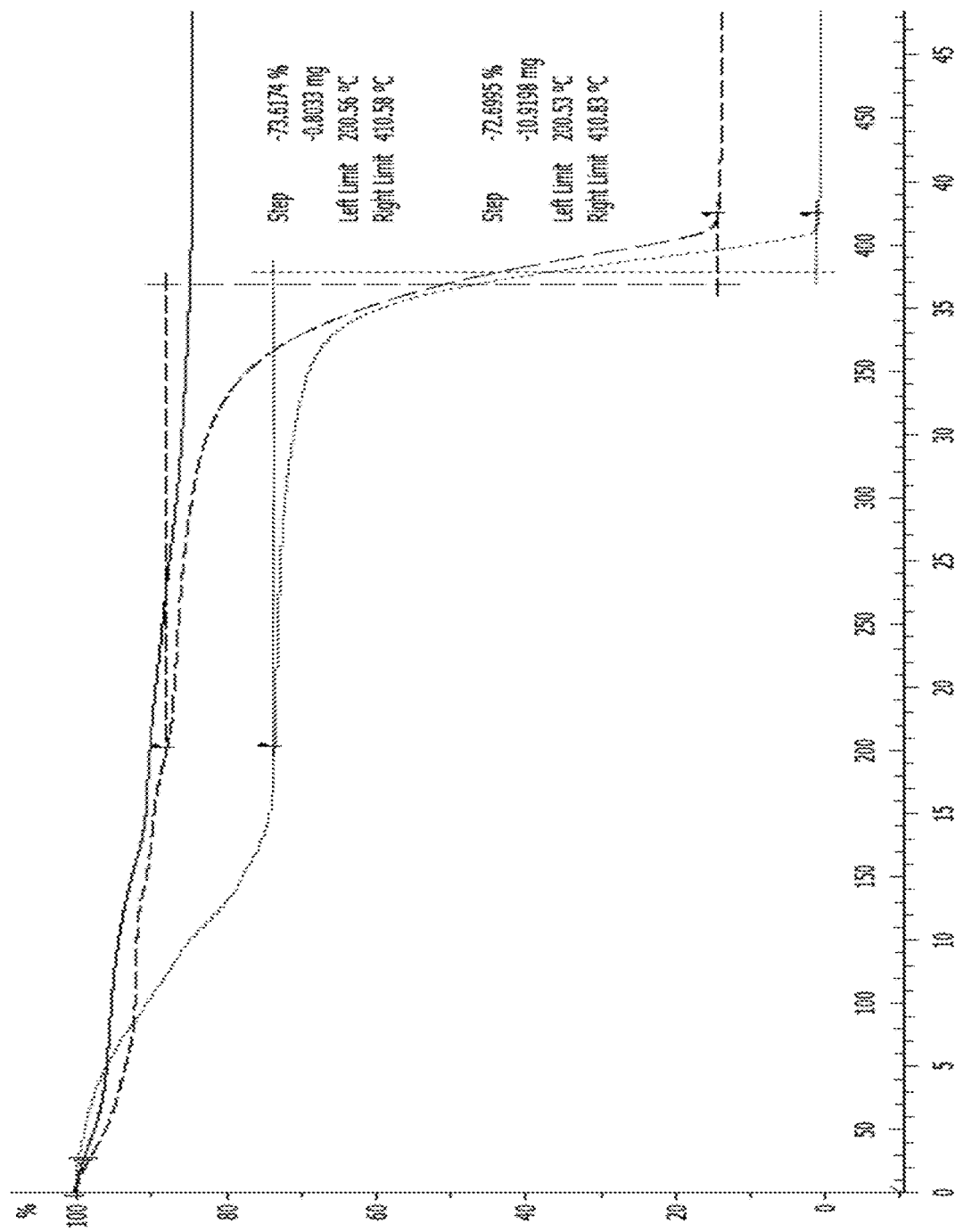
FIGS. 49a-b. are graphs showing the TGA thermogram (FIG. 49a) and the weight loss derivative function (FIG. 49b) of $_{con}$PEI$_{25}$-CAN$_{DOE}$-γ-Fe$_2$O$_3$ NPs ((PEI ratio: 5.25)—PEI weight loss (73.62%) calculated from the indicated 200.56-410.58° C. temperature range).

PEI-decorated $CAN_{DOE}$-gamma-$Fe_2O_3$ NPs ($_{con}PEI_{25}$-$CAN_{DOE}$-gamma-$Fe_2O_3$ NPs)-Optimal aqueous PEI contacting process/experimental protocol (FIGS. 47-49). For the fabrication of such corresponding DOE-optimized $_{con}PEI_{25}$-$CAN_{DOE}$-gamma-$Fe_2O_3$ NPs, the same former experimental protocol detailed in example 7 has been used with similar reagent rations, reaction time/temperature and cleaning procedure. This overall process afforded cleaned ultra-small 7.35±1.56 nm-sized $_{con}PEI_{25}$-$CAN_{DOE}$-gamma-$Fe_2O_3$ NPs.

Selected characterization data of $_{con}PEI_{25}$-$CAN_{DOE}$-gamma-$Fe_2O_3$ NPs (PEI/Fe Wt ratio: 5.25): Average TEM & DLS sizes: 7.35±1.56 & 82.9 nm (PDI: 0.195) respectively, zeta potential: +31.1 mV and TGA weight loss (200-410° C. temperature range) of 73.62%.

Figure 26A:
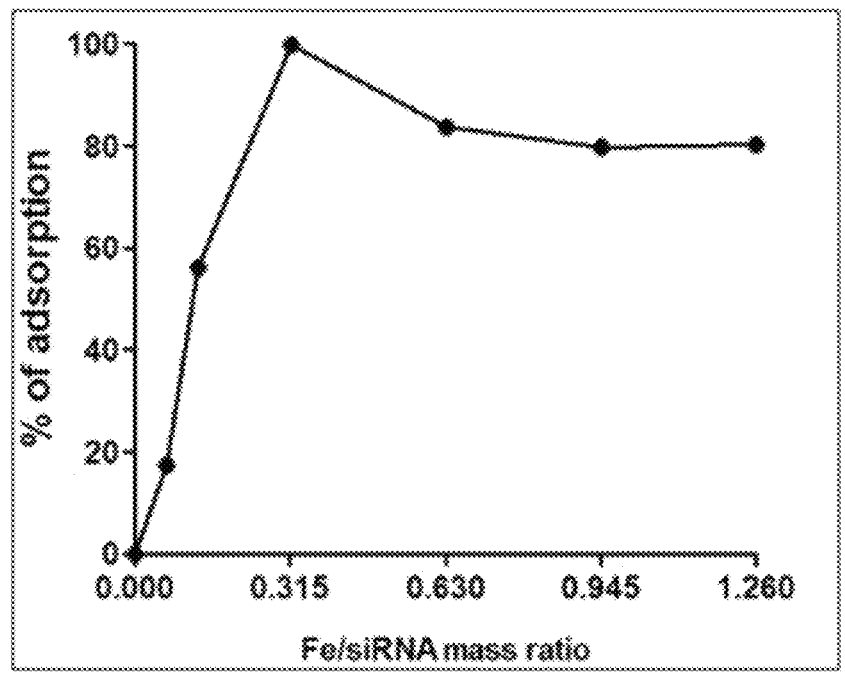
FIGS. 26a-b. are graphs showing the siRNA adsorption by $_{con}$PEI$_{25}$-CAN-gamma-Fe$_2$O$_3$ NPs (FIG. 26a) and $_{inj}$PEI$_{25}$-CAN-gamma-Fe$_2$O$_3$ NPs (FIG. 26b) respectively at various increasing Fe/siRNA weight ratios.
Figure 26B:
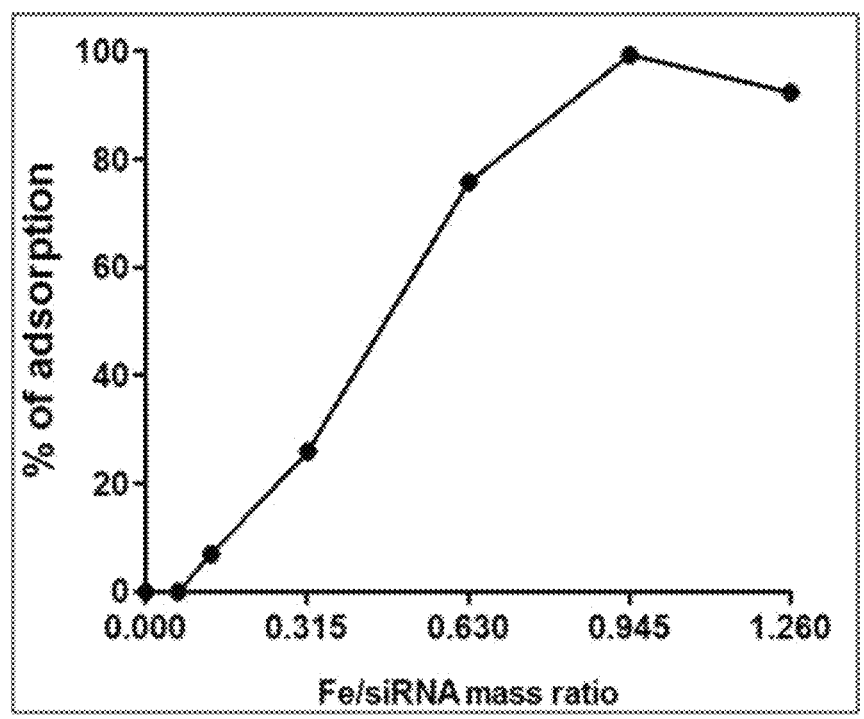

Example 10: Selected Procedures for Nanocarrier Functionalization Using Various siRNA/microRNA Species for Delivery/Gene Silencing $_{con}PEI_{25}$-CAN-gamma-$Fe_2O_3$ NPs and $_{inj}PEI_{25}$-CAN-gamma-$Fe_2O_3$ NPs suspensions were diluted in $ddH_2O$ at different concentrations to reach different Fe/siRNA mass ratios. To each nanoparticle suspension and to control tube (absence of particles), 3 µg of siRNA were added and incubated for 15 min at RT for complex formation. After 15 min of incubation, suspensions were centrifuged at 11,000 rpm for 10 min and free siRNA was measured in supernatant with a spectrophotometer (Nanodrop 1000, Fisher Scientific). The amount of free siRNA in each ratio was normalized to control tube (FIG. 26).

Cells used to examine silencing effects using siRNA and microRNA: U20S human osteosarcoma and human pancreatic cancer cell line BxPC-3 were obtained from the American Type Culture Collection (ATCC; Manassas, VA, USA). Cells were cultured in Dulbecco's Modified Eagle Medium supplemented with 10% fetal bovine serum, 100 µg/ml penicillin, 100 U/ml streptomycin, 2 mM L-glutamine and 25 mM HEPES (Biological Industries Ltd., Israel). All cells were grown at 37° C. in 5% $CO_2$.

Establishment of luciferase U2OS human osteosarcoma cell line: U2OS cells were transfected by electroporation with 5 µg psiCHECK-2 firefly and *Renilla* luciferase expression vector (Promega) and 0.25 µg pPUR puromycin resistance vector (Clontech). Plasmids were mixed with U2OS cells ($5 \times 10^6$ cells in 500 µl phosphate-buffered saline), and the mixture was incubated for 5 min at 4° C. and electropulsed with a Gene Pulser Xcell apparatus (Bio-Rad) at 170 V and 450 µF. After electroporation, cells were re-suspended in complete medium and incubated at 37° C. in 5% $CO_2$. Subsequently, cells with incorporated plasmids were selected with 1 µg/ml puromycin (Invivogen) and maintained in complete medium for several weeks. Finally, clones were isolated and maintained in a complete medium with 1 µg/ml puromycin for another several weeks.

Figure 27A:
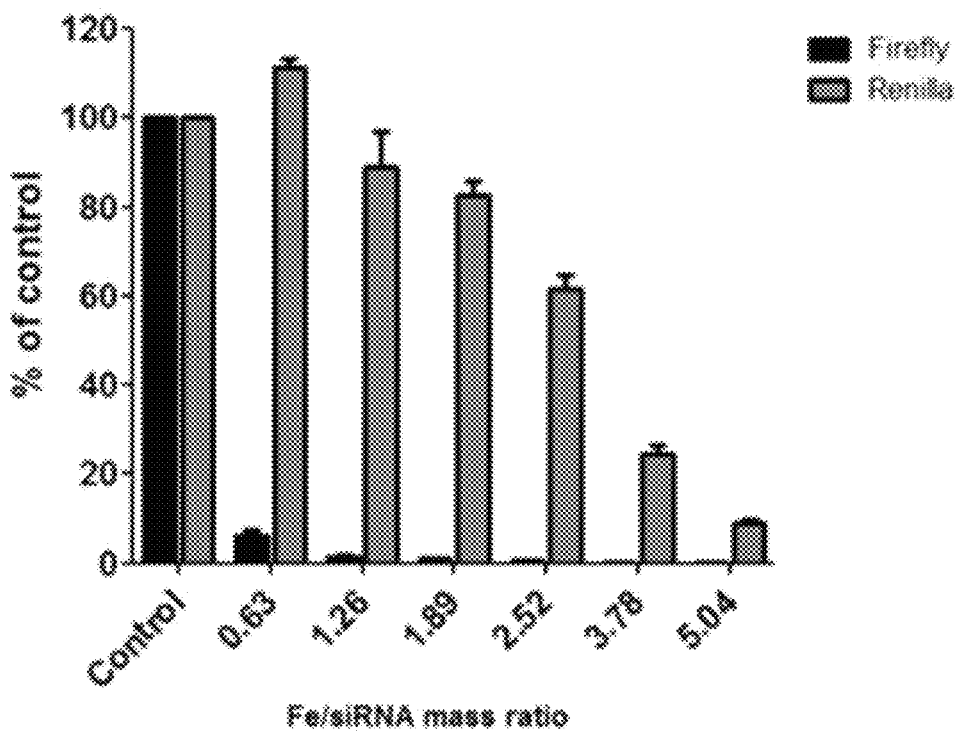
FIGS. 27 a-b. are graphs showing the Firefly Luciferase silencing in U2OS-Luc cells with $_{con}$PEI$_{25}$-CAN-gamma-Fe$_2$O$_3$ (FIG. 27a) and $_{inj}$PEI$_{25}$-CAN-gamma-Fe$_2$O$_3$ (FIG. 27b) NPs.
Figure 27B:
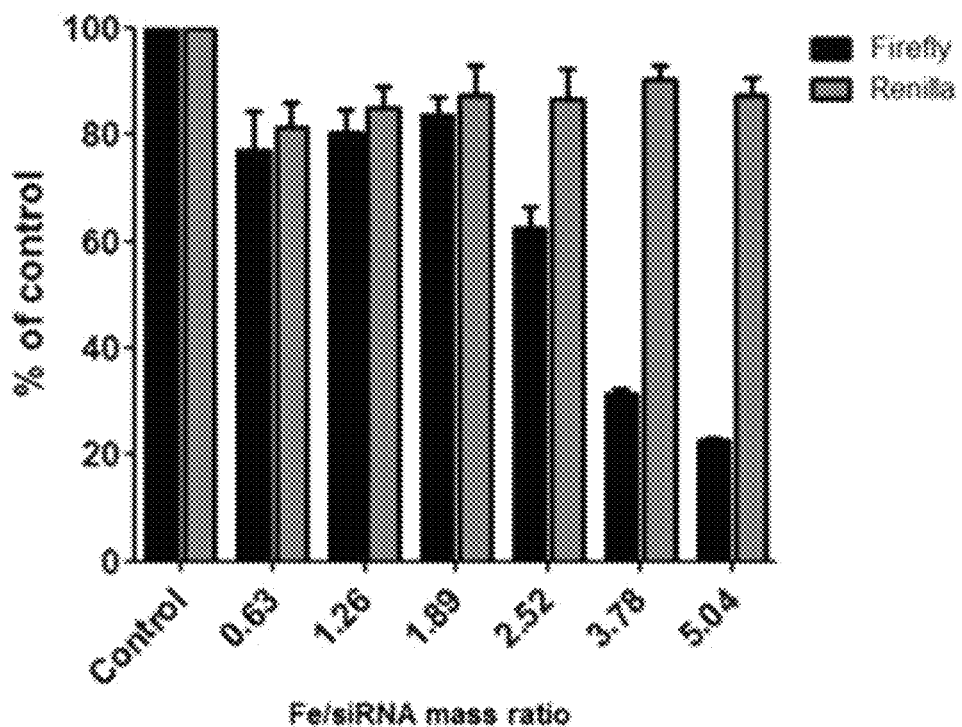

Transfection with siRNA to silence Firefly Luciferase: U2OS-Luc cells were seeded at $1 \times 10^4$ cells/well in 100p medium in a 96 well optical bottom plate (Thermo) and incubated overnight at 37° C. with 5% $CO_2$. Cells were transfected with firefly luciferase siRNA at a concentration of 100 nM (0.166 µg) mixed with $_{con}PEI_{25}$-CAN-gamma-$Fe_2O_3$ NPs (FIG. 27A) and $_{inj}PEI_{25}$-CAN-gamma-$Fe_2O_3$ NPs (FIG. 27B) at different Fe/siRNA mass ratios or without nanoparticles (control). The following oligonucleotide sequences (sense/antisense) were used: 5'-GGACAUCAC-CUAUGCCGAGUACUTC-3' (SEQ ID NO: 1), CACCU-GUAGUGGAUACGGCUCAUGAAG-3' (SEQ ID NO: 2). Forty-eight hours later, cells were assayed for both firefly and *Renilla* luciferase activities using the Dual-GLO® Luciferase Assay System (Promega). Briefly, cells were lysed and the firefly luciferase substrate added (50 µl per well Dual-GLO® Substrate/Buffer). After 10 min, firefly luciferase activity was measured using a luminometer (Synergy 4, Biotek). Next, the *Renilla* luciferase substrate was added (50 µl per well Stop & GLO® Substrate/Buffer) and the luminescence measured after additional 10 min incubation. Silencing efficacy is reflected by luciferase activities normalized to control luciferase activities.

Figure 28:
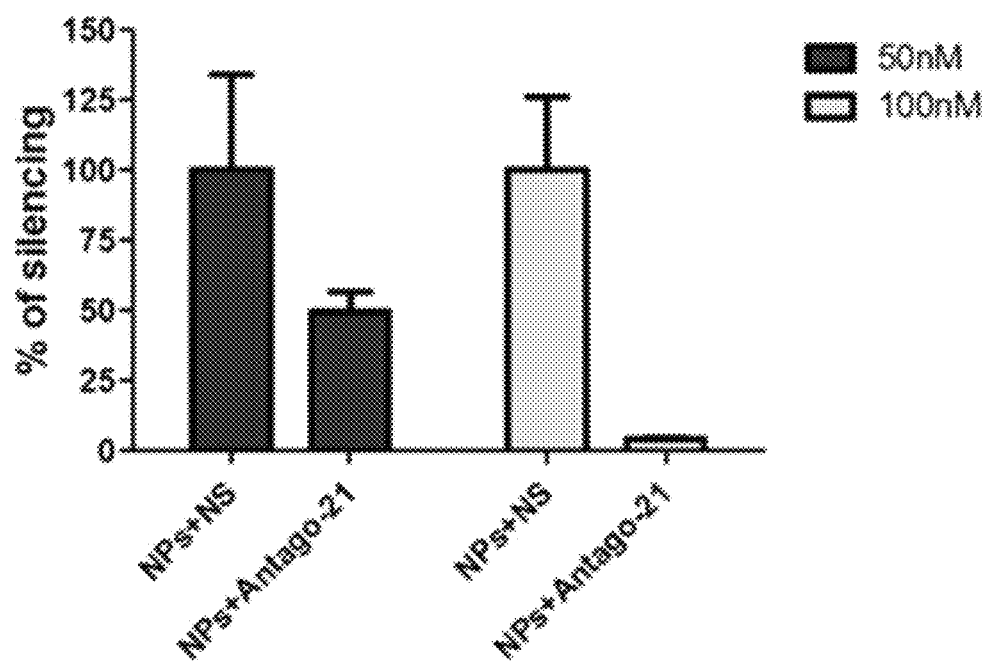
FIG. 28. is a graph showing the mir-21 silencing in BxPC-3 cells with $_{con}$PEI$_{25}$-CAN-gamma-Fe$_2$O$_3$ NPs.

Transfection to silence mir-21: BxPC-3 cells were seeded at $3 \times 10^5$ in a 12 well plate in 1 ml medium and incubated overnight at 37° C. with 5% $CO_2$. BxPC-3 cells were transfected with miRIDIAN mir-21 inhibitor or negative control (IH-300492-05 and IN-001005-01 respectively, Dharmacon) at a concentration of 50 or 100 nM (0.925 or 1.85 µg respectively) mixed with $_{con}$ $PEI_{25}$-CAN-gamma-$Fe_2O_3$ NPs at a 0.63 Fe/siRNA mass ratio. After 48 hours, total RNA was isolated using TRI reagent according to the manufacturer's protocol. RNA quality and quantity were determined with a spectrophotometer (Nanodrop 1000, Fisher Scientific). Levels of mir-21 miRNA were analyzed by real-time RT-PCR (FIG. 28).

Quantitative Estimation of miRNA by Real-Time RT-PCR: A quantitative estimation of mir-21 miRNA and RNU6B internal control expressions were performed by real-time RT-PCR using the TaqMan MicroRNA Assay and TaqMan MicroRNA RT kit (assay ID, 000397 and 001093 respectively, Applied Biosystems, Foster City, CA) according to the manufacturer's instructions. Briefly, the reaction master mix containing 10×RT buffer, 5×RT primers, Multi-Scribe reverse transcriptase, Rnase inhibitor, 100 mM dNTPs and nuclease-free water was mixed with 10 ng of total RNA. The mixtures were incubated for 30 min at 16° C., 30 min at 42° C., and 5 min. at 85° C. The PCR was performed using 10 µl of PCR master mix containing TaqMan 2×Universal PCR Master Mix, 20×TaqMan MicroRNA Assay Mix and the RT products in a volume of 20 µl. Reaction mixtures were incubated at 95° C. for 10 min, followed by 40 cycles at 95° C. for 15 s and at 60° C. for 1 min using the StepOnePlus Real-Time PCR system (Applied Biosystems). The mean Ct values of each sample were determined from triplicate reactions. The relative expression level of miRNA examined was calculated by log 2|2−ΔCt|, in which ΔCt was defined as the subtraction of the Ct value of the target miRNA from the Ct value of the internal control RNU6B.

The invention claimed is:

1. A method for delivering a ligand into a cell, comprising the step of contacting said cell with a nanoparticle, comprising cerium, a core, and an ultrasound-deposited polyCOOH organic shell, wherein said core comprises maghemite (gamma-$Fe_2O_3$), wherein the weight ratio of said cerium to said maghemite is at least 2%, said shell is a single layer and is characterized by orthogonal surface multifunctionality, said shell comprises at least one ligand being bound to said cerium within said shell, thereby delivering a ligand into a cell.

2. The method of claim 1, wherein said ligand comprises PEI polymer and a nucleic acid molecule.

3. The method of claim 2, wherein said nucleic acid molecule comprises RNA.

4. The method of claim 2, wherein said delivering a ligand into a cell, results in transfecting said cell.

5. The method of claim 2, wherein said PEI has a molecular weight of 10 to 50 KDa.

6. The method of claim 2, wherein said nanoparticle comprises an injected PEI and a functional heterogeneous surface of mixed said polyCOOH organic matter adlayer and said PEI.

7. The method of claim 2, wherein said PEI comprises branched PEI.

8. The method of claim 1, wherein said ligand comprises a cytokine, a cell permeation molecule, an antibody, a drug, or any combination thereof.

9. The method of claim 1, wherein said ligand is coordinatively or covalently bound to said cerium.

10. The method of claim 9, wherein said ligand is coordinatively bound to said cerium.

11. The method of claim 1, wherein said ligand comprises a contrast agent or a dye.

12. The method of claim 1, wherein the weight ratio of said cerium to said maghemite is at least 2.5%.

13. The method of claim 1, wherein the weight ratio of said cerium to said maghemite is at least 3%.

* * * * *

SEQUENCE LISTING

```
Sequence total quantity: 2
SEQ ID NO: 1            moltype = RNA  length = 25
FEATURE                 Location/Qualifiers
source                  1..25
                        mol_type = other RNA
                        organism = synthetic construct
SEQUENCE: 1
ggacatcacc tatgccgagt acttc                                              25

SEQ ID NO: 2            moltype = RNA  length = 27
FEATURE                 Location/Qualifiers
source                  1..27
                        mol_type = other RNA
                        organism = synthetic construct
SEQUENCE: 2
cacctgtagt ggatacggct catgaag                                            27
```